(12) United States Patent
Chen et al.

(10) Patent No.: US 7,786,108 B2
(45) Date of Patent: Aug. 31, 2010

(54) COMPOUNDS AND METHOD FOR TREATING DYSLIPIDEMIA

(75) Inventors: Xinchao Chen, Schenectady, NY (US); Todd Fields, Indianapolis, IN (US); Nathan Bryan Mantlo, Brownsburg, IN (US); Xiaodong Wang, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 693 days.

(21) Appl. No.: 11/570,542

(22) PCT Filed: Jun. 23, 2005

(86) PCT No.: PCT/US2005/022389
§ 371 (c)(1),
(2), (4) Date: Dec. 13, 2006

(87) PCT Pub. No.: WO2006/002342
PCT Pub. Date: Jan. 5, 2006

(65) Prior Publication Data
US 2007/0244095 A1  Oct. 18, 2007

Related U.S. Application Data

(60) Provisional application No. 60/582,708, filed on Jun. 24, 2004, provisional application No. 60/627,241, filed on Nov. 12, 2004, provisional application No. 60/664,862, filed on Mar. 24, 2005.

(51) Int. Cl.
| | | |
|---|---|---|
| *A61P 9/10* | (2006.01) | |
| *A61P 3/06* | (2006.01) | |
| *A61K 31/55* | (2006.01) | |
| *C07D 401/12* | (2006.01) | |
| *C07D 401/14* | (2006.01) | |
| *C07D 403/12* | (2006.01) | |
| *C07D 403/14* | (2006.01) | |
| *C07D 405/14* | (2006.01) | |
| *C07D 409/14* | (2006.01) | |
| *C07D 413/12* | (2006.01) | |
| *C07D 417/12* | (2006.01) | |
| *C07D 417/14* | (2006.01) | |
| *C07D 491/04* | (2006.01) | |

(52) U.S. Cl. .................. 514/213.01; 540/593
(58) Field of Classification Search ............ 514/213.01; 540/593
See application file for complete search history.

(56) References Cited

U.S. PATENT DOCUMENTS

| 6,140,343 | A | 10/2000 | DeNinno et al. |
| 6,147,089 | A | 11/2000 | DeNinno et al. |
| 6,197,786 | B1 | 3/2001 | DeNinno et al. |
| 6,313,142 | B1 | 11/2001 | Damon et al. |
| 6,489,478 | B1 | 12/2002 | DeNinno et al. |
| 6,689,897 | B2 | 2/2004 | Damon et al. |
| 2004/0082609 | A1 | 4/2004 | Ghosh et al. |
| 2004/0204450 | A1 | 10/2004 | Bechle et al. |
| 2005/0059810 | A1 | 3/2005 | Maeda et al. |
| 2006/0100239 | A1 | 5/2006 | Nagasaki et al. |
| 2006/0135551 | A1 | 6/2006 | Baruah et al. |

FOREIGN PATENT DOCUMENTS

| WO | WO 2005/037796 | 4/2005 |
| WO | WO 2005/097805 | 10/2005 |
| WO | WO 2005/097806 | 10/2005 |
| WO | WO 2006/012093 | 2/2006 |

OTHER PUBLICATIONS

Kazuaki Ishihara, A New Chiral BLA Promoter for Asymmetric Aza Diels—Alder and Aldol-Type Reactions of Imines, J. Am. Chem. Soc., 1994, 116. 10520-10524.
Toshio Fuchigami, Cationic Polar Cycloaddition with Anodically Prepared a-TRI- and a-Difluoromethylated N,Q-Acetals: Preparation of Fluoro-Methylated Tetra- and Dihydroquinoline Derivatives, Heterocycles, vol. 31, No. 3, 1990, p. 415.
Ishitani, Haruro, Catalytic Asymmetric Aza Diels-Alder Reactions Using a Chiral Lanthanide Lewis Acid. Entantioselective Synthesis of Tetrahydroquinoline Derivatives Using a Catalytic Amount of a Chiral Source, Tetrahedtron Lett. vol. 37 No. 41, pp. 7357-7350, 1996.
Prato, Maurizio, Evidence of a Two-Step Ionic Mechanism in the Addition of Aromatic Schiff Bases to Enol Ethers, Gazzetta Chimica Italinan 118 (1988) ;;797-798.

*Primary Examiner*—Brenda L Coleman
(74) *Attorney, Agent, or Firm*—James B. Myers

(57) ABSTRACT

Compounds of formula I

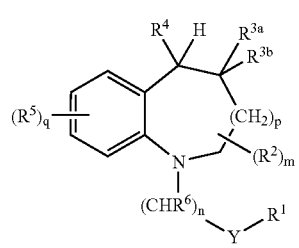

wherein n, m, p, q, Y, $R^1$ $R^2$, $R^{3a}$, $R^{3b}$, $R^4$, $R^5$, and $R^6$ are as defined herein and their pharmaceutical compositions and methods of use are disclosed.

12 Claims, No Drawings

COMPOUNDS AND METHOD FOR TREATING DYSLIPIDEMIA

REFERENCE TO RELATED APPLICATION

This application is submitted as a United States national phase entry, pursuant to 35 U.S.C. §371, of PCT/US2005/022389, filed on 23 Jun. 2005, which claims the benefit of U.S. provisional patent application Ser. Nos. 60/582,708, filed 24 Jun. 2004; 60/627,241, filed on 12 Nov. 2004 and 60/664,862 filed on 24 Mar. 2005, each of which is incorporated by reference herein.

FIELD OF THE INVENTION

The current invention relates to the fields of medicinal organic chemistry, pharmacology, and medicine. Further, the current invention relates to a group of compounds and methods for treating pathological states due to dyslipidemia

BACKGROUND OF THE INVENTION

Coronary heart disease (CHD) is one of the major causes of morbidity and mortality worldwide. Despite attempts to modify risk factors such as obesity, smoking, lack of exercise, and treatment of dyslipidemia with dietary modification or drug therapy, CHD remains the most common cause of death in the U.S. Over 50% of all CHD deaths are due to underlying atherosclerotic coronary heart disease.

Dyslipidemia is a major risk factor for CHD. Low plasma levels of high density lipoprotein (HDL) cholesterol with either normal or elevated levels of low density (LDL) cholesterol is a significant risk factor for developing atherosclerosis and associated coronary artery disease in humans. Indeed, several studies on lipoprotein profiles of CHD patients have shown that about 50% of the CHD patients have cholesterol levels that are considered to be in the normal range (<200 mg/dl). Furthermore, these studies found low HDL cholesterol in about 40% of the normo-cholesterolemic CHD patients as compared to the general population reported in the National Health and Nutrition Examination Survey. Since low levels of HDL cholesterol increase the risk of atherosclerosis, methods for elevating plasma HDL cholesterol would be therapeutically beneficial for the treatment of cardiovascular diseases including, but not limited to, atherosclerosis, CHD, stroke, and peripheral vascular disease.

Cholesterol ester transfer protein (CETP) is a 74 KD glycoprotein that facilitates the exchange of cholesterol esters in HDL for triglycerides in triglyceride-rich lipoproteins (A. R. Tall et. al., (1999) 1999 George Lyman Duss Memorial Lecture: Lipid transfer proteins, HDL metabolism and atherogenesis. *Arterio. Thromb. Vasc. Biol.* 20:1185-1188.). The net result of CETP activity is a lowering of HDL cholesterol and an increase in LDL cholesterol. This effect on lipoprotein profile is believed to be pro-atherogenic, especially in subjects whose lipid profile constitutes an increased risk for CHD. Niacin can significantly increase HDL, but has serious toleration issues that reduce compliance. Fibrates and the HMG CoA reductase inhibitors raise HDL cholesterol only modestly (~10-12%). As a result, there is a significant unmet medical need for a well-tolerated agent that can significantly elevate plasma HDL levels, thereby reversing or slowing the progression of atherosclerosis.

CETP is expressed in multiple tissues and secreted into plasma, where it associates with HDL (X. C. Jiang et al., (1991) Mammalian adipose tissue and muscle are major sources of lipid transfer protein mRNA. *J. Biol. Chem.* 266: 4631-4639). Humans and monkeys, which express CETP, have relatively low HDL cholesterol, whereas mice and rats do not express CETP and carry nearly all their cholesterol in HDL. Furthermore, transgenic expression of CETP in mice results in significantly reduced HDL cholesterol levels and developed severe atherosclerosis compared to control mice (K. R. Marotti et. al., (1993) Severe atherosclerosis in transgenic mice expressing simian cholesteryl ester transfer protein. *Nature:* 364, 73-75). Expression of human CETP in Dahl salt-sensitive hypertensive rats led to spontaneous combined hyperlipidemia, coronary heart disease and decreased survival (V. L. M. Herrera et. al., (1999) Spontaneous combined hyperlipidemia, coronary heart disease and decreased survival in Dahl salt-sensitive hypertensive rats transgenic for human cholesteryl ester transfer protein. *Nature Medicine:* 5, 1383-1389).

Antibodies either directly injected into the plasma or generated through vaccine injection can effectively inhibit CETP activity in hamsters and rabbits resulting in elevated HDL cholesterol (C. W. Rittershaus, (1999) Vaccine-induced antibodies inhibit CETP activity in vivo and reduce aortic lesions in a rabbit model of atherosclerosis. Furthermore, antibody neutralization of CETP in rabbits has been shown to be anti-atherogenic (*Arterio. Thromb. Vasc. Biol.* 20, 2106-2112; G. F. Evans et al., (1994) Inhibition of cholesteryl ester transfer protein in normocholesterolemic and hypercholesterolemic hamsters: effects on HDL subspecies, quantity, and apolipoprotein distribution. *J. Lipid Research.* 35, 1634-1645). However, antibody and/or vaccine therapy is not currently a viable option for the treatment of large populations of patients in need of treatment for dyslipidemia and resultant or associated disease state manifestations.

There have been several reports of small molecule CETP inhibitors. Barrret et al. (J. Am. Chem. Soc., 188, 7863, (1996)) and Kuo et al. (J. Am. Chem. Soc., 117, 10629, (1995)) describe cyclopropan-containing CETP inhibitors. Pietzonka et al. (Biorg. Med. Chem. Lett. 6, 1951 (1996)) describe phosphanate-containing analogs as CETP inhibitors. Coval et al. (Bioorg. Med. Chem. Lett. 5, 605, (1995)) describe Wiedendiol-A and -B related sesquiterpines as CETP inhibitors. Japanese Patent Application No. 10287662-A describes polycyclic, non-amine containing, polyhydroxylic natural compounds possessing CETP inhibition properties. Lee et al. (*J. Antibiotics,* 49, 693-96 (1996)) describe CETP inhibitors derived from an insect fungus. Busch et al. (*Lipids,* 25, 216-220 (1990)) describe cholesteryl acetyl bromide as a CETP inhibitor. Morton and Zillversmit (*J. Lipid Res.,* 35, 836-47 (1982)) describe that p-chloromercuriphenyl sulfonate, p-hydroxymercuribenzoate and ethyl mercurithiosalicylate inhibit CETP. Connolly et al. (*Biochem. Biophys. Res. Comm.* 223, 42-47 (1996)) describe other cysteine modification reagents as CETP inhibitors. Xia et al. Describe 1,3,5-triazines as CETP inhibitors (*Bioorg. Med. Chem. Lett.,* 6, 919-22 (1996)). Bisgaier et al. (*Lipids,* 29, 811-8 (1994)) describe 4-phenyl-5-tridecyl-4H-1,2,4-triazole-thiol as a CETP inhibitor. Oomura et al. disclose non-peptidic tetracyclic and hexacyclic phenols as CETP inhibitors in Japanese Patent Application No. 10287662.

U.S. Pat. No. 6,586,448 B1 describes 4-carboxamino-2-substituted-1,2,3,4-tetrahydroquinolines of the following structure:

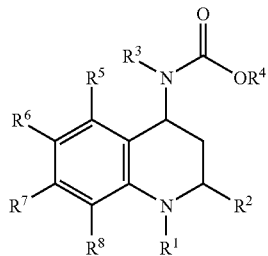

wherein $R^1$, $R^2$, $R^3$, $R^4$, $R^5$, $R^6$, $R^7$ and $R^8$ are as defined therein. Similarly, PCT patent applications WO 03/063868A1, WO 00/17164, WO 00/17165, and WO 00/17166, disclose variously, formulations, methods of preparation and methods of use of compounds tetrahydroquinoline compounds generally related to those in U.S. Pat. No. 6,586,448 B1 from which it derives as a divisional application.

European Patent Application No. 818448 by Schmidt et al. describes certain tetrahydroquinoline derivatives as cholesteryl ester transfer protein inhibitors. European Patent Application No. 818197 by Schmek et al, describe pyridines with fused heterocycles as cholesteryl ester transfer protein inhibitors. Brandes et al. in German Patent Application No. 19627430 describe bicyclic condensed pyridine derivatives as cholesteryl ester transfer protein inhibitors. In U.S. Pat. No. 6,207,671 Schmidt et al. describe substituted pyridine compounds as CETP inhibitors. In PCT Patent Applications WO 03/028727 by Müller-Gliemann et al. and WO 98/39299 by Gielen et al. certain quinoline derivatives are described as cholesteryl ester transfer protein inhibitors.

The above disclosures notwithstanding, a great need remains, particularly for affluent western societies for effective compounds useful to treat conditions caused by, associated with, or exacerbated by dyslipidemia.

SUMMARY OF THE INVENTION

The present invention provides a compound of Formula I

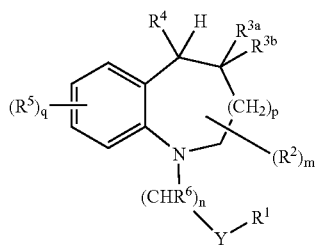

wherein n is 0, 1, 2, or 3;

m is 0, 1, 2, or 3;

p is 1 or 2;

q is 0, 1, 2, 3, or 4;

Y is a bond, C=O, or $S(O)_t$; wherein t is 0, 1, or 2;

$R^1$ is selected from a group consisting of: hydroxy, $C_1$-$C_6$ alkyl, aryl, $C_2$-$C_6$ alkenyl, $C_1$-$C_6$ haloalkyl, $C_1$-$C_6$ alkylheterocyclic, $C_3$-$C_8$ cycloalkyl, $C_1$-$C_6$ alkylcycloalkyl; $C_1$-$C_6$ alkylaryl, heterocyclyl, $C_1$-$C_6$ alkylalcohol, $C_1$-$C_6$ alkoxy, aryloxy, —$OC_2$-$C_6$ alkenyl, —$OC_1$-$C_6$ haloalkyl, —$OC_1$-$C_6$ alkylheterocyclic, —$OC_3$-$C_8$ cycloalkyl, —$OC_1$-$C_6$ alkylcycloalkyl, —$NR^7R^8$ and —$OC_1$-$C_6$ alkylaryl, —O-heterocyclic, —$OC_1$-$C_6$ alkylheterocyclic, $C_1$-$C_6$ alkyl-O—C(O)$NR^7R^8$, $C_1$-$C_6$ alkyl-$NR^7C(O)NR^7R^8$, and $C_0$-$C_6$ alkyl$COOR^{11}$; provided that $R^1$ is not hydroxy when Y is $S(O)_t$; and wherein each cycloalkyl, aryl and heterocyclic group is optionally substituted with 1 to 3 groups independently selected from oxo, hydroxy, halogen, $C_1$-$C_6$ alkyl, $C_2$-$C_6$ alkene, $C_2$-$C_6$ alkynyl, $C_1$-$C_6$ alkoxy, $C_1$-$C_6$ haloalkyl, $C_1$-$C_6$ alkylalcohol, $CONR^{11}R^{12}$, $NR^{11}SO_2R^{12}$, —$NR^{11}COR^{12}$, $C_0$-$C_3$ alkyl$NR^{11}R^{12}$, $C_1$-$C_3$ alkyl$COR^{11}$, $C_0$-$C_6$ alkyl$COOR^{11}$, cyano, $C_1$-$C_6$ alkylcycloalkyl, phenyl, —$OC_1$-$C_6$ alkylcycloalkyl, —$OC_1$-$C_6$ alkylaryl, —$OC_1$-$C_6$ alkylheterocyclic, and $C_1$-$C_6$ alkylaryl;

Each $R^2$ is bound only to a carbon atom and is or are if more than one independently selected from the group consisting of: hydrogen, hydroxy, halogen, oxo, $C_1$-$C_6$ alkyl, $C_2$-$C_6$ alkene, $C_2$-$C_6$ alkynyl, $C_1$-$C_6$ alkoxy, $C_1$-$C_6$ haloalkyl, $CONR^{11}R^{12}$, —$NR^{11}SO_2R^{12}$, —$NR^{11}COR^{12}$, $C_0$-$C_6$ alkyl$NR^{11}R^{12}$, $C_0$-$C_6$ alkyl$COR^{11}$, $C_0$-$C_6$ alkyl$COOR^{11}$, cyano, nitro, $C_0$-$C_6$ alkylcycloalkyl, phenyl, $C_0$-$C_6$ alkylaryl, heterocyclyl, $C_3$-$C_8$ cycloalkyl, and $C_1$-$C_6$ haloalkyl; and wherein two independently selected $R^2$ groups are optionally gem-disubstituted;

$R^{3a}$ and $R^{3b}$ are independently selected from the group consisting of: hydrogen, halogen, $C_1$-$C_6$ alkyl, $C_2$-$C_6$ alkene, $C_2$-$C_6$ alkynyl, $C_1$-$C_6$ alkoxy, and $C_1$-$C_6$ haloalkyl;

$R^4$ is a group represented by the formula —$NR^{4a}R^{4b}$; wherein, $R^{4a}$ is a heterocyclic, $C_1$-$C_6$ alkylheterocyclic, or $C_2$-$C_6$ alkenylheterocyclic group wherein each heterocyclic group is optionally substituted with 1 to 3 groups independently selected from the group consisting of: hydroxyl, halogen, oxo, —$NR^{11}R^{12}$, $C_1$-$C_6$ alkyl, $C_2$-$C_6$ alkenyl, $C_0$-$C_6$ alkylCN, $C_1$-$C_6$ alkoxy, $C_1$-$C_6$ alkylalcohol, $C_1$-$C_6$ haloalkyl, —OC(O)$NR^{11}R^{12}$, $C_1$-$C_6$ alkyl$NR^{11}R^{12}$ wherein the $C_1$-$C_6$ alkyl group is optionally substituted with —$OR^{10}$ or C(O)$OR^{10}$, $C_0$-$C_6$ alkyl$NO_2$, $C_0$-$C_6$ alkyl$NR^{11}SO_2R^{12}$, $C_0$-$C_6$ alkylC(O)$NR^{11}R^{12}$, $C_0$-$C_6$ alkyl$NR^{11}C(O)R^{12}$, $C_0$-$C_6$ alkyl$NR^{11}C(O)OR^{12}$, $C_0$-$C_6$ alkyl$NR^{11}C(O)NR^{10}R^{12}$, $C_0$-$C_6$ alkyl$NR^{11}CHR^{10}CO_2R^{12}$, $C_0$-$C_6$ alkylC(O)$OR^{11}$, $C_0$-$C_6$ alkyl$SO_2NR^{11}R^{12}$, $C_0$-$C_6$ alkyl$S(O)_tR^{11}$, $C_3$-$C_8$ cycloalkyl, $C_1$-$C_6$ alkylcycloalkyl, and $C_0$-$C_6$ alkylheterocyclic wherein the heterocycle of the $C_0$-$C_6$ alkylheterocyclic group is optionally substituted with halo, $C_1$-$C_6$ alkyl, oxo, —$CO_2R^{11}$ and —$NR^{11}R^{12}$; and $R^{4b}$ is selected from the group consisting of: $C_1$-$C_6$ alkylaryl, $C_2$-$C_6$ alkenylaryl, $C_2$-$C_6$ alkynylaryl, $C_1$-$C_6$ alkylheterocyclic, $C_2$-$C_6$ alkenylheterocyclic, $C_1$-$C_6$ alkylcycloalkyl, and $C_1$-$C_6$ alkyl-O—$C_1$-$C_6$ alkylaryl, wherein each cycloalkyl, aryl, or heterocyclic group is optionally substituted with 1-3 groups independently selected from the group consisting of hydroxy, oxo, —$SC_1$-$C_6$ alkyl, $C_1$-$C_6$ alkyl, $C_1$-$C_6$ alkenyl, $C_1$-$C_6$ alkynyl, $C_1$-$C_6$ haloalkyl, halogen, $C_1$-$C_6$ alkoxy, aryloxy, $C_1$-$C_6$ alkenyloxy, $C_1$-$C_6$ haloalkoxyalkyl, $C_0$-$C_6$ alkyl$NR^{11}R^{12}$, —$OC_1$-$C_6$ alkylaryl, nitro, cyano, $C_1$-$C_6$ haloalkylalcohol, and $C_1$-$C_6$ alkyl alcohol;

$R^5$ is selected from a group consisting of: hydrogen, hydroxy, halogen, $C_1$-$C_6$ alkyl, $C_2$-$C_6$ alkenyl, $C_2$-$C_6$ alkynyl, $C_1$-$C_6$ alkoxy, aryloxy, —$OC_2$-$C_6$ alkenyl, —$OC_1$-$C_6$ haloalkyl, $C_1$-$C_6$ haloalkyl, $C_3$-$C_8$ cycloalkyl, $C_1$-$C_6$ alkylaryl, $C_1$-$C_6$ alkylheterocyclic, $C_2$-$C_6$ alkenylaryl, $C_2$-$C_6$ alkenylheterocyclic, aryl, heterocyclic, cyano, nitro, $C_0$-$C_6$ alkylNR$^7$R$^8$, $C_0$-$C_6$ alkylCOR$^7$, $C_0$-$C_6$ alkylCO$_2$R$^7$, $C_0$-$C_6$ alkylCONR$^7$R$^8$, CONR$^7$SO$_2$R$^8$, —NR$^7$SO$_2$R$^8$, —NR$^7$COR$^8$, —N=CR$^7$R$^8$, —OCONR$^7$R$^8$, —S(O)$_r$R$^7$, —SO$_2$NR$^7$R$^8$, $C_0$-$C_5$CH$_2$OH, —$OC_1$-$C_6$ alkylheterocyclic, and —$OC_1$-$C_6$ alkylaryl wherein each of the alkyl, alkenyl, alkynyl, cycloalkyl, aryl and heterocyclic group or subgroup is optionally substituted with oxo, alkyloxy, aryloxy; and wherein any two R$^5$ groups may combine to form an optionally substituted 5, 6, or 7-member fused ring with the phenyl ring (A-ring) to which they are attached, wherein the 5, 6, or 7-member fused ring is saturated, partially unsaturated, or fully unsaturated and optionally contains 1, 2, or 3 heteroatoms independently selected from O, N, and S;

R$^6$ is independently selected from a group consisting of: hydrogen, $C_1$-$C_6$ alkyl, $C_2$-$C_6$ alkenyl, hydroxy, COR$^7$, $C_1$-$C_6$ alkoxy, aryloxy, —$OC_2$-$C_6$ alkenyl, —$OC_1$-$C_6$ haloalkyl, $C_1$-$C_6$ alkylNR$^7$R$^8$, $C_3$-$C_8$ cycloalkyl, heterocyclic, aryl, $C_1$-$C_6$ alkyl-O—C(O)NR$^7$R$^8$, $C_1$-$C_6$ alkyl-NR$^7$C(O)NR$^7$R$^8$ and $C_1$-$C_6$ alkylcycloalkyl;

R$^7$ and R$^8$ are each independently selected from a group consisting of: hydrogen, $C_1$-$C_6$ alkyl, $C_2$-$C_6$ alkenyl, $C_2$-$C_6$ alkynyl, —$OC_1$-$C_6$ alkyl, $C_1$-$C_6$ haloalkyl, —O-aryl, —$OC_3$-$C_8$ cycloalkyl, —O-heterocyclic, —NR$^7$R$^8$, $C_1$-$C_6$ alkylcycloalkyl, —$OC_1$-$C_6$ alkylcycloalkyl, —$OC_1$-$C_6$ alkylheterocyclic, $C_1$-$C_6$ alkylheterocyclic, —$OC_1$-$C_6$ alkylaryl, $C_3$-$C_8$ cycloalkyl, heterocyclic, aryl, and $C_1$-$C_6$ alkylaryl, wherein each alkyl, cycloalkyl, heterocyclic or aryl group is optionally substituted with 1-3 groups independently selected from hydroxy, —CN, halogen, $C_1$-$C_6$ alkyl, $C_1$-$C_6$ alkoxy, $C_1$-$C_6$ haloalkyl, and —NR$^{11}$R$^{12}$, or R$^7$ and R$^8$ combine to form a nitrogen containing heterocyclic ring which may have 0, 1, or 2 additional heteroatoms selected from oxygen, nitrogen and sulfur and wherein the nitrogen-containing heterocycle is optionally substituted with oxo, or $C_1$-$C_6$ alkyl;

R$^{10}$, R$^{11}$, and R$^{12}$ are independently selected from a group consisting of: hydrogen, $C_1$-$C_6$ alkyl, $C_1$-$C_6$ alkenyl, $C_3$-$C_8$ cycloalkyl, heterocyclic, aryl, $C_1$-$C_6$ alkylaryl, wherein each alkyl, aryl, cycloalkyl, and heterocyclic group is optionally substituted with 1-3 groups independently selected from halogen, $C_1$-$C_6$ alkylheterocyclic, and $C_1$-$C_6$ haloalkyl, or R$^{11}$ and R$^{12}$ combine to form a nitrogen containing heterocyclic ring which may have 0, 1, or 2 additional heteroatoms selected from oxygen, nitrogen or sulfur and is optionally substituted with oxo, $C_1$-$C_6$ alkyl, COR$^7$, and —SO$_2$R$^7$;

or a pharmaceutically acceptable salt, solvate, enantiomer, racemate, diastereomer or mixture of diastereomers thereof.

The present invention also provides a method for modulating CETP activity comprising the use of a compound of Formula I or a pharmaceutically acceptable salt, solvate, enantiomer, racemate, diastereomer or mixture of diastereomers thereof, for the treatment, prevention or amelioration of CETP mediated diseases.

The present invention provides a method for treating or preventing dyslipidemia comprising administering a compound of Formula I, or a pharmaceutically acceptable salt, solvate, enantiomer, racemate, diastereomer, or mixture of diastereomers, or prodrug thereof, to a patient in need thereof.

The present invention provides a method for treating or preventing CHD comprising administering a compound of Formula I, pharmaceutically acceptable salt, solvate, enantiomer, racemate, diastereomer, mixture of diastereomers, or prodrug thereof, to a patient in need thereof.

The present invention provides a method for treating and/or preventing atherosclerosis comprising administering a compound of Formula I, or a pharmaceutically acceptable salt, solvate, enantiomer, racemate diastereomer, mixture of diastereomers, or prodrug thereof, to a patient in need thereof.

The present invention provides a method for treating and/or preventing diseases related to abnormal CETP activity comprising administering a compound of Formula I, or a pharmaceutically acceptable salt, solvate, enantiomer, racemate diastereomer, mixture of diastereomers, or prodrug thereof, to a patient in need thereof.

The present invention provides a method of raising the ratio of plasma HDL-cholesterol to plasma LDL-cholesterol in a mammal comprising administering a therapeutically effective dose of a compound of Formula I, or a pharmaceutically acceptable salt, solvate, enantiomer, racemate, diastereomer, mixture of diastereomers, or prodrug thereof, to a patient in need thereof.

The present invention provides a method of raising the level of plasma HDL-cholesterol in a mammal comprising administering a therapeutically effective dose of a compound of Formula I, or a pharmaceutically acceptable salt, solvate, enantiomer, racemate, diastereomer, mixture of diastereomers, or prodrug thereof, to a patient in need thereof.

The present invention provides a method of lowering the level of plasma LDL-cholesterol in a mammal comprising administering a therapeutically effective dose of a compound of Formula I, or a pharmaceutically acceptable salt, solvate, enantiomer, racemate, diastereomer, mixture of diastereomers, or prodrug thereof, to a patient in need thereof.

The present invention also provides a pharmaceutical composition comprising a compound of Formula I or a pharmaceutically acceptable salt, solvate, enantiomer, racemate, diastereomer or mixture of diastereomers thereof, and a carrier.

The present invention also provides a method of treating and/or preventing the pathological sequelae due to low levels of plasma HDL and/or high levels of LDL-cholesterol in a mammal comprising administering an effective dose of a compound of Formula I, or a pharmaceutically acceptable salt, solvate, enantiomer, racemate, diastereomer, or mixture of diastereomers, thereof, to a patient in need thereof.

The present invention also relates to the use of a compound of Formula I for the manufacture of a medicament for treating and/or preventing atherosclerosis in a mammal comprising administering an effective dose of a compound of Formula I, or a pharmaceutically acceptable salt, solvate, enantiomer, racemate, diastereomer, mixture of diastereomers, or prodrug thereof, to a patient in need thereof.

The present invention also provides a combination therapy involving a compound of Formula I and one or more other cardio protective agents such as for example, statins, leptin, and/or other LXR, CETP, ABC A1, or lipid regulating agents useful for the treatment and/or prevention of atherosclerosis.

DETAILED DESCRIPTION OF THE INVENTION

The current invention provides novel compounds of Formula I useful in modulating CETP activity.

The term "modulation" would include, but not be limited to, up-regulation, down-regulation, inhibition, agonism, antagonism of the CETP receptor as appropriate to achieve HDL raising, or LDL lowering and the resulting biological sequelae from such intervention.

The phrase "diseases" or "diseases related to CETP modulation" or "diseases mediated by CETP activity" refers to pathological states where atherosclerosis and cardiovascular diseases are prone because of dyslipidemia and/or other risk factors and are therefore beneficially affected by down-regulation or modulation of CETP activity. These diseases include but are not limited to hyperlipidemia and its sequelae such as atherosclerosis, CHD, elevated blood pressure, CHF, stroke, hypertension, hypertriglyceremia, diabetes, obesity, inflammatory diseases including but not limited to dermatitis, arthritis, and pain, and diseases of the central nervous system including but not limited to dementia, cognitive disorders such as Alzheimer's disease.

The term "treatment" bears its usual meaning which includes prohibiting, inhibiting, ameliorating, halting, restraining, slowing or reversing the progression, or reducing the severity of a pathological symptom related to or resultant from the modulation of CETP activity, especially as related to raising plasma levels of HDL, or lowering LDL-cholesterol levels or raising the HDL/LDL ratio or controlling atherosclerosis, hyperlipidemia and/or hypercholesterolemia.

Generally, one of skill in the art is aware that valency must be conserved (complete) for all stable molecules. Therefore, the necessary implication that hydrogen atoms are necessary and available to complete valency in all structures including Formula I unless expressly indicated otherwise, is imputed to the general knowledge of one of skill in the art.

General chemical terms used in the description of compounds herein described bear their usual meanings. For example, the term "$C_{1-6}$ alkyl," or "$(C_1-C_6)$alkyl" or "$C_1-C_6$ alkyl" refers to a straight or branched aliphatic chain of 1 to 6 carbon atoms including, but not limited to, methyl, ethyl, propyl, iso-propyl, n-butyl, pentyl, and hexyl. Unless otherwise stated, the term "alkyl" means $C_1-C_6$ alkyl. Similarly, the term "$C_0-C_6$ alkyl" implies an alkyl group as indicated wherein when the term $C_0$ applies, the alkyl group is not present, and the remaining group sans carbon attach directly to the rest of the referenced molecule or group.

The terms alkenyl and alkynyl, for example, a $C_2-C_6$ alkenyl group or a $C_2-C_6$ alkynyl group as used herein mean that the respective groups can include 1, 2, or 3 double bonds or triple bonds, respectively. If more than one double or triple bond is present in the group, the double and triple bonds can be conjugated or non-conjugated.

The invention also contemplates that the term $C_1-C_6$ alkyl or $C_2-C_6$ alkenyl or similar terms also encompass the specified alkyl or alkenyl or similar group, which may be chiral, regio or steroisomeric. Such chiral or regio or stereoisomeric groups are also within the scope of the present invention.

The term alkylaryl refers to an alkyl group substituted with an aryl group. For example, $C_1-C_6$ alkylaryl indicates that an aryl group is attached to a $C_1-C_6$ alkyl group and that the resulting $C_1-C_6$ alkylaryl is attached to the rest of the referenced molecule or group via the alkyl group.

The term "substituted phenyl" or "optionally substituted phenyl" refers to a phenyl group having one or more substituents selected from the group consisting of $C_1-C_6$ alkyl, $C_1-C_6$ alkoxy, hydroxy, —$COOR^7$, $C_0-C_6$ alkyl$NR^7R^8$, nitro, chloro, fluoro, bromo, iodo, $C_1-C_6$ haloalkyl, $C_1-C_6$ haloalkoxyalkyl, $C_0-C_6$ alkylheterocyclic.

The terms "optionally substituted 5-7 member carbocyclic" or "optionally substituted 5-7 member heterocyclic" whether written in the conjunctive or disjunctive style, or in single or in compound sentences, mean a carbocyclic or heterocyclic 5-7 member ring that is optionally substituted with 1-3 groups independently selected from the group consisting of hydroxy, halogen, $C_1-C_6$ haloalkyl, $C_3-C_8$ cycloalkyl, $C_1-C_6$ alkylaryl, $C_1-C_6$ alkylheterocyclic, aryl, heterocyclic, $C_0-C_3$ alkylcyano, nitro, $C_1-C_6$ alkyl, $C_2-C_6$ alkenyl $C_1-C_6$ alkoxy, aryloxy, —$OC_2-C_6$ alkenyl, —$OC_1-C_6$ haloalkyl, $C_0-C_6$ alkyl$NR^7R^8$, $C_0-C_6$ alkyl$COR^7$, $C_0-C_6$ alkyl$CO_2R^7$, $C_0-C_6$ alkyl$CONR^7R^8$, $CONR^7SO_2R^8$, —$NR^7SO_2R^8$, —$NR^7COR^8$, —N═$CR^7R^8$, —$OCONR^7R^8$, —$S(O)_{0-2}R^7$, —$SO_2NR^7R^8$, $C_0-C_5CH_2OH$, —$OC_1-C_6$ alkylheterocyclic, and —$OC_1-C_6$ alkylaryl.

The term "optionally substituted" in general means that the subject group may be substituted, where possible, with 1-3 groups independently selected from the group consisting of hydroxy, halogen, $C_1-C_6$ haloalkyl, $C_3-C_8$ cycloalkyl, $C_1-C_6$ alkylaryl, $C_1-C_6$ alkylheterocyclic, aryl, heterocyclic, $C_0-C_3$ alkylcyano, nitro, $C_1-C_6$ alkyl, $C_2-C_6$ alkenyl $C_1-C_6$ alkoxy, aryloxy, —$OC_2-C_6$ alkenyl, —$OC_1-C_6$ haloalkyl, —$C_0-C_6$ alkyl$NR^7R^8$, $C_0-C_6$ alkyl$COR^7$, $C_0-C_6$ alkyl$CO_2R^7$, $C_0-C_6$ alkyl$CONR^7R^8$, $CONR^7SO_2R^8$, —$NR^7SO_2R^8$, —$NR^7COR^8$, —N═$CR^7R^8$, —$OCONR^7R^8$, —$S(O)_{0-2}R^7$, —$SO_2NR^7R^8$, $C_0-C_5CH_2OH$, —$OC_1-C_6$ alkylheterocyclic, and —$OC_1-C_6$ alkylaryl. Where an optionally substituted group is claimed or disclosed, it should be noticed that both the substituted and unsubstituted versions of the subject group are within the purview of the invention unless otherwise indicated.

The term "aryl" refers to a substituted or unsubstituted aromatic or heteroaromatic, or heterocyclic radical (heteroarylaryl groups are subsumed in this term). Illustrative aryl groups include but is not limited to, napthyl, quinolyl, tetrahydroquinolyl, indazolyl, pyrimidinyl, triazinyl, pyrazine, pyridazinyl, piperidyl, pyrrolidinyl, piperazinyl, morpholinyl, tetrahydrofuranyl, pyranyl, tetrazolyl, imidazolyl, 1,2,3-trazolyl, 1,2,4-triazolyl, oxadiazolyl, thiadiazolyl, thiazolyl, oxazolyl, isoxazolyl, isothiazolyl, pyrazolyl, imidazopyridine, benzimidazolyl, triazolone-yl, imidazolone-yl, imidazolidinone-yl, 2-furyl, 3-furyl, 2-thienyl 3-thienyl, 1-pyrrolyl, 2-pyrrolyl, 3-pyrrolyl, phenyl, 2-pyridyl, 3-pyridyl, 4-pyridyl, 1-naphthyl, 2-naphthyl, 2-benzofuryl, 3-benzofuryl, 4-benzofuryl, 5-benzofuryl, 6-benzofuryl, 7-benzofuryl, 2-benzothieny, 3-benzothienyl, 4-benzothienyl, 5-benzothienyl, 6-benzothienyl, 7-benzothienyl, 1-indolyl, 2-indolyl, 3-indolyl, 4-indolyl, 5-indolyl, 6-indolyl, tetrazole, imidazole, isoxazole, pyrazole, 7-indolyl, and isomers thereof. As used herein the term aryl also encompasses the benzyl group.

The term "carbocycle" as used herein refers to a cyclic group having only carbon and appropriate number of hydrogen atoms. The term encompasses groups such as cycloalkyl, cycloalkene, cycloalkylene, naphthyl, phenyl, and the like.

The term "heterocycle", "heterocyclyl", or "heterocyclic" refers to a 10 member saturated, partially unsaturated or aromatic mono-cyclic or a fused bicyclic ring containing 1-5 heteroatoms selected from N, S, or O, wherein said heterocycle is optionally substituted at carbon or nitrogen atom(s) unless otherwise specified. Most preferred heterocyclic groups include pyrrolidinyl, piperidinyl, hexamethyleneimmino, morpholino, thiomorpholino, benzthiophene, indolyl, quinolyl, isoquinolyl, tetrazolyl, and pyridinyl. As a corollary, the term "alkylheterocyclic" or "alkylheterocycle" is understood to mean that the alkyl group is attached to the heterocycle and the point of attachment to the rest of the referenced molecule or group.

The term "haloalkyl" as used herein refers to an alkyl (as noted above) substituted with one or more halo atoms selected from F, Br, Cl, and I.

The term "haloalkoxyalkyl" as used herein include for example trifluoromethoxy, pentafluoroethoxy, trifluoroethoxy ($OCH_2CF_3$), and the like.

The term "Prodrugs" describes derivatives of the compounds of the invention that have chemically or metabolically cleavable groups and become by solvolysis or under physiological conditions the compounds of the invention, which are pharmaceutically active, in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7-9, 21-24, Elsevier, Amsterdam 1985). Prodrugs include acid derivatives, such as, esters prepared by reaction of the parent acidic compound with a suitable alcohol, or amides prepared by reaction of the parent acid compound with a suitable amine. Simple aliphatic esters (e.g., methyl, ethyl, propyl, isopropyl, butyl, sec-butyl, tert-butyl) or aromatic esters derived from acidic groups pendent on the compounds of this invention are preferred prodrugs. Other preferred esters include morpholinoethyloxy, diethylglycolamide and diethylaminocarbonylmethoxy. In some cases it is desirable to prepare double ester type prodrugs, such as, (acyloxy) alkyl esters or ((alkoxycarbonyl)oxy)alkyl esters.

As used herein, the term "protecting group" refers to a group useful for masking reactive sites in a molecule to enhance the reactivity of another group or allow reaction at another desired site or sites following which the protecting group may be removed. Protecting groups are usually used to protect or mask groups including, but not limited to, —OH, —NH, and —COOH. Suitable protecting groups are known to one of skill in the art and are described in Protecting groups in Organic Synthesis, 3$^{rd}$ edition, Greene, T. W.; Wuts, P. G. M. Eds., John Wiley and Sons, New York, 1999.

As used herein, the term "solvate" is a form of the compound of the invention wherein a crystal or crystals of a compound of the invention have been formed from a stoichiometric or non-stoichiometric amount of the compound of Formula I and a solvent. Typical, non-limiting, solvating solvents include for example, water, methanol, ethanol, acetone and dimethylformamide. The term "hydrate" may be used when the solvent is water.

In those instances where a compound of the invention possesses acidic or basic functional groups, various salts may be formed which are more water soluble and/or more physiologically suitable than the parent compound. Representative pharmaceutically acceptable salts include, but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion-exchange resin.

Included within the definition of pharmaceutically acceptable salts are the relatively non-toxic, inorganic and organic base or acid addition salts of compounds of the present invention. Base addition salts include for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1-19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, hydrobromide, camsylate, carbonate, clavulanate, citrate, chloride, edetate, edisylate, estolate, esylate, fluoride, fumarate, gluceptate, gluconate, glutamate, glycolylarsanilate, hexylresorcinate, hydrochloride, hydroxynaphthoate, hydroiodide, isothionate, lactate, lactobionate, laureate, maleate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate. Preferred salts for the purpose of the invention include the hydrochloride salt, the hydrobromide salt, the bisulfate salt, the methane sulfonic acid salt, the p-toluenesulfonic acid salt, bitartrate, the acetate and the citrate salt.

A compound of the invention as illustrated by Formula I may occur as any one of its positional isomers, stereochemical isomers or regio-isomers, all of which are included within the scope of the invention. Certain compounds of the invention may possess one or more chiral centers, and thus, may exist in optically active forms. Likewise, when the compounds contain an alkenyl or alkenylene group, there exist the possibility of cis and trans isomeric forms of the compounds. The R- and S-isomers and mixtures thereof, including racemic mixtures as well as mixtures of enantiomers or cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereo-specific reactions with starting materials that contain the asymmetric centers and are already resolved. Alternatively desired stereoisomers may be prepared by methods that lead to mixtures of the stereoisomers and subsequent resolution by known methods. For example, a racemic mixture may be reacted with a single enantiomer of some other compound i.e. a chiral resolving agent. This changes the racemic form into a mixture of stereoisomers and diastereomers, because they have different melting points, different boiling points, and different solubilities and can be separated by conventional means, such as crystallization.

Preferred Embodiments of the Invention

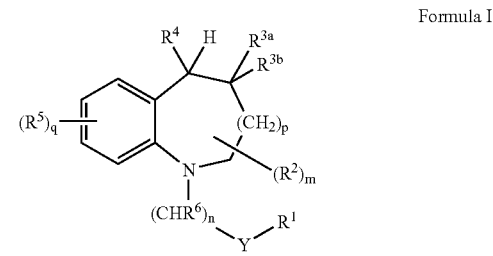

Formula I

Preferred n, m, p, and q
  Preferably n is 0, or 1. More preferably, n is 0.
  Preferably m is 0, or 1.
  Preferably p is 1 or 2.
  Preferably, q is 0, 1, 2, or 3. More preferably q is 2 or 3.
  Preferably Y is a bond or C(O), or S(O)$_t$; Where t=0, 1, or 2.

Preferred R$^1$
  A preferred R$^1$ group is selected from the group consisting of: hydroxy, hydrogen, C$_1$-C$_6$ alkyl, C$_0$-C$_6$ alkylcycloalkyl, C$_0$-C$_6$ alkylheterocyclic, C$_1$-C$_6$ haloalkyl, C$_0$-C$_6$ alkylaryl, —Oaryl, —OC$_1$-C$_6$ haloalkyl, —OC$_1$-C$_6$ alkylcycloalkyl, —OC$_3$-C$_8$ cycloalkyl, —C$_1$-C$_6$ alkylcycloalkylNR$^7$R$^8$, —OC$_1$-C$_6$ alkyl, —OC$_0$-C$_6$ alkylaryl, —OC$_1$-C$_6$alkylcyano, —OC$_1$-C$_6$ alkylCO$_2$R$^{11}$, —OC$_3$-C$_8$ cycloalkylCO$_2$R$^{11}$, —OC$_1$-C$_6$alkylhydroxy, —OC$_1$-C$_6$ alkylNR$^7$R$^8$ and —OC$_1$-C$_6$ alkylheterocyclic, provided that R$^1$ is not —OH when Y is S(O)$_t$; and wherein each alkyl, cycloalkyl, aryl, or heterocyclic is optionally substituted with 1 or 2 groups selected from halogen, $C_0$-$C_3$ alkylalcohol, $C_0$-$C_3$ alkylamine, $C_0$-$C_3$ alkyl COOH, $C_0$-$C_3$ alkylCONH$_2$, $C_0$-$C_3$ alkylcyano, and $C_0$-$C_3$ alkylC(O)OC$_1$-$C_3$ alkyl.

When p is 1, a more preferred R$^1$ group is selected from the group consisting of: hydrogen, hydroxy, $C_1$-$C_6$ alkyl, $C_0$-$C_6$ alkylaryl, $C_1$-$C_6$ alkylcycloalkyl, $C_0$-$C_6$ alkylheterocyclic, $C_3$-$C_8$cycloalkyl, —OC$_1$-$C_6$ alkyl, —OC$_1$-$C_6$ alkylcycloalkyl, —OC$_1$-$C_6$ alkylhydroxy, —OC$_1$-$C_6$ alkylNR$^7$R$^8$, and —OC$_1$-$C_6$ alkylCO$_2$R$^{11}$, provided that R$^1$ is not —OH when Y is S(O)$_t$; wherein each alkyl, cycloalkyl, heterocyclic and aryl groups are each optionally substituted as described above.

When p is 1, a still more preferred R$^1$ is a group represented by $C_1$-$C_6$ alkyl, $C_0$-$C_6$ alkylaryl, $C_0$-$C_6$ alkylheterocyclic, $C_0$-$C_6$ alkylcycloalkyl, —OC$_1$-$C_6$ alkyl and wherein each alkyl, cycloalkyl, aryl, or heterocyclic is optionally substituted with 1 or 2 groups selected from halogen, $C_0$-$C_3$ alkylalcohol, $C_0$-$C_3$ alkylamine, $C_0$-$C_3$ alkylCOOH, $C_0$-$C_{3b}$ alkylCONH$_2$, $C_0$-$C_3$ alkylcyano, and $C_0$-$C_3$ alkylC(O)OC$_1$-$C_3$ alkyl.

Preferred R$^2$

A preferred R$^2$ group is selected from the group consisting of: hydrogen, $C_1$-$C_6$ haloalkyl, $C_1$-$C_6$ alkyl, $C_1$-$C_6$ alkylcycloalkyl, $C_3$-$C_8$ cycloalkyl, $C_1$-$C_6$ alkylaryl and $C_0$-$C_6$ alkylNR$^7$R$^8$.

When p is 1, a more preferred R$^2$ group is represented by hydrogen.

Preferred R$^3$ Groups

Preferred R$^{3a}$ and R$^{3b}$ groups are independently selected from the group consisting of: hydrogen, $C_1$-$C_6$ alkyl, $C_2$-$C_6$ alkenyl, and $C_2$-$C_6$ alkynyl. More preferably, R$^{3a}$ and R$^{3b}$ are independently selected from hydrogen and $C_1$-$C_6$ alkyl.

Preferred R$^4$ Groups

A preferred R$^4$ group is NR$^{4a}$R$^{4b}$.

Also preferred, is an R$^{4a}$ group selected from the group consisting of:

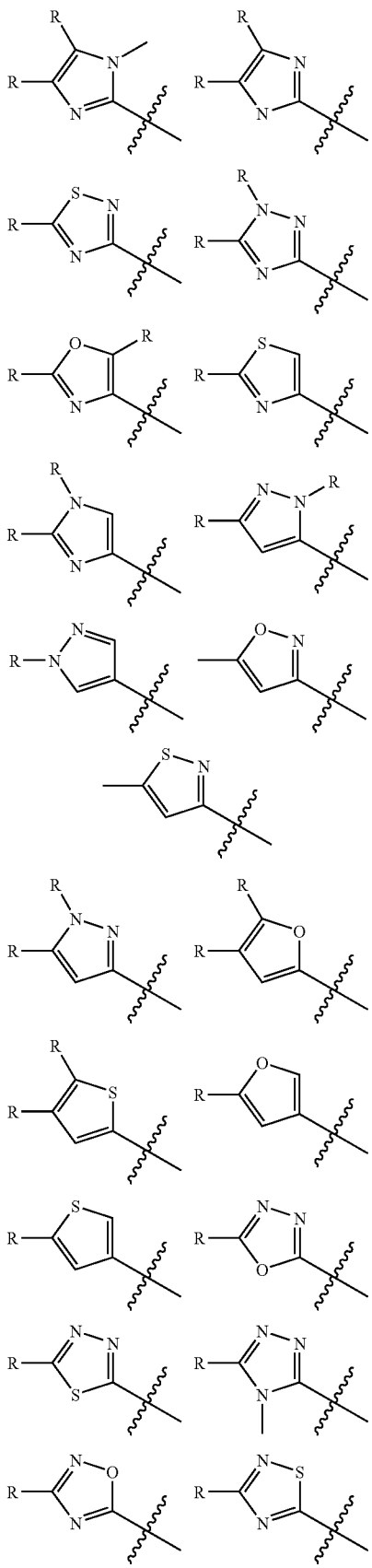

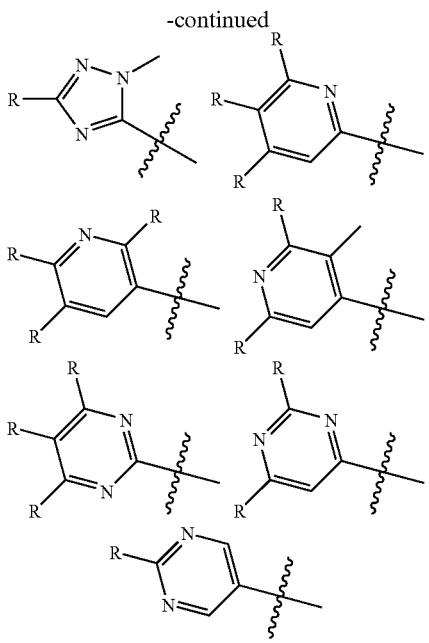

wherein R is independently selected from the group consisting of: halogen, $C_0$-$C_6$ alkylalcohol, hydrogen, $C_1$-$C_6$ alkyl, $C_1$-$C_6$ alkoxy $C_0$-$C_6$ alkylcycloalkyl, $C_0$-$C_6$ alkylheterocyclic, $C_1$-$C_6$ alkylCN, $C_1$-$C_6$ haloalkyl, $C_0$-$C_6$ alkyl$NR^{11}R^{12}$, $C_1$-$C_6$ alkylC(O)$NR^{11}R^{12}$, and $C_1$-$C_6$ alkylC(O)$OR^{11}$. Still more preferred is an R group independently selected from the group consisting of: hydrogen, $C_1$-$C_6$ alkyl, $C_2$-$C_6$ alkyl$NH_2$, and $C_2$-$C_6$ alkylalcohol.

Preferably, $R^{4b}$ is selected from $C_1$-$C_6$ alkylaryl, $C_1$-$C_6$ alkylheterocyclic, wherein the heterocyclic and aryl groups are optionally substituted with 1-3 groups selected from the group consisting of: hydroxy, oxo, cyano, —$SC_1$-$C_6$ alkyl, $C_1$-$C_6$ alkyl, $C_1$-$C_6$ alkenyl, $C_1$-$C_6$ alkynyl, $C_1$-$C_6$ haloalkyl, halogen, and —$OC_1$-$C_6$ alkyl. More preferably, $R^{4b}$ is benzyl mono or disubstituted with $C_1$-$C_6$ haloalkyl. Still more preferably $R^{4b}$ is 3,5-bistrifluorobenzyl.

Preferred $R^5$ Groups $R^5$ is preferably selected from a group consisting of: hydrogen, halogen, $C_1$-$C_6$ alkyl, $C_1$-$C_6$ haloalkyl, —$OC_1$-$C_6$ alkyl, —Oaryl, —$OC_2$-$C_6$ alkenyl, —$OC_1$-$C_6$ haloalkyl, $CH_2NR^7R^8$, —$NH_2$, —N($C_1$-$C_4$ alkyl)$_2$, —CN, and —$NO_2$. Also preferred are any two $R^5$ groups which combine to form an optionally substituted 5, 6, or 7-member ring fused with the phenyl ring to which they are attached, wherein the 5, 6, or 7-member ring is saturated, partially unsaturated, or fully unsaturated and optionally contains 1, 2, or 3 heteroatoms independently selected from O, N, and S. Optional substituents for the 5, 6, or 7-member fused ring discussed above include preferably, halogen, $C_1$-$C_6$ alkyl, $C_1$-$C_6$ haloalkyl, $C_1$-$C_6$ alkoxy, aryloxy, —$OC_2$-$C_6$ alkenyl, —$OC_1$-$C_6$ haloalkyl, —$CH_2NR^7R^8$, —$NH_2$, —N($C_1$-$C_4$ alkyl)$_2$, —CN, and —$NO_2$.

Preferred $R^6$ Groups

Preferred $R^6$ groups are independently selected from a group consisting of: hydrogen, $C_1$-$C_6$ alkyl, $C_1$-$C_6$ alkenyl, $C_3$-$C_8$ cycloalkyl, $C_1$-$C_6$ alkylhydroxy, phenyl, and $C_1$-$C_6$ alkoxy.

Preferred $R^7$ and $R^8$

Preferred $R^7$ and $R^8$ groups are independently selected from a group consisting of: hydrogen, $C_1$-$C_6$ alkyl, $C_2$-$C_6$ alkenyl, $C_1$-$C_6$ alkylaryl, and $C_1$-$C_6$ alkylheterocyclic, wherein each aryl group is optionally substituted with 1-3 groups independently selected from $C_1$-$C_6$ alkyl, halogen, and $C_1$-$C_6$ haloalkyl.

Preferred $R^{11}$ and $R^{12}$

Preferred $R^{11}$ and $R^{12}$ groups are independently selected from a group consisting of: hydrogen, $C_1$-$C_6$ alkyl, $C_2$-$C_6$ alkenyl, $C_1$-$C_6$ alkylaryl, and $C_1$-$C_6$ alkylheterocyclic, wherein each aryl group is optionally substituted with 1-3 groups independently selected from $C_1$-$C_6$ alkyl, halogen, and $C_1$-$C_6$ haloalkyl.

A particularly preferred compound of the invention is selected from the group consisting of:

(S)-(3,5-Bistrifluoromethylbenzyl)-(1-cyclopentylmethyl-7-methyl-8-trifluoromethyl-2,3,4,5-tetrahydro-1H-benzo[b]azepin-5-yl)-(2-methyl-2H-tetrazol-5-yl)amine, 5-[(3,5-Bis-trifluoromethyl-benzyl)-(1H-tetrazol-5-yl)-amino]-7-methyl-8-trifluoromethyl-2,3,4,5-tetrahydro-benzo[b]azepine-1-carboxylic acid isopropyl ester, (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid ethyl ester, (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid isopropyl ester, (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid tert-butyl ester, (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid 1-ethyl-propyl ester, (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid cyclopentyl ester, (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid 1-ethyl-2-methyl-propyl ester, (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid tetrahydro-pyran-4-yl ester, (S)-2-{5-[(3,5-Bis-trifluoromethyl-benzyl)-(1-cyclopentyl-methyl-7-methyl-8-trifluoromethyl-2,3,4,5-tetrahydro-1H-benzo[b]azepin-5-yl)-amino]-tetrazol-2-yl}-ethanol, (S)-(3,5-Bis-trifluoromethyl-benzyl)-(1-ethyl-7-methyl-8-trifluoromethyl-2,3,4,5-tetrahydro-1H-benzo[b]azepin-5-yl)-(2-methyl-2H-tetrazol-5-yl)-amine, (4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-cyclohexyl)-acetic acid, (S)-5-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-3,3-dimethyl-pentanoic acid, (S)-2-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-ethanol, (+/−)-9-[(3,5-Bis-trifluoromethyl-benzyl)-(2H-tetrazol-5-yl)-amino]-2,2-difluoro-6,7,8,9-tetrahydro-1,3-dioxa-5-aza-cyclohepta[f]indene-5-carboxylic acid isopropyl ester, (+/−)-9-[(3,5-Bis-trifluoromethyl-benzyl)-(2-methyl-2H-tetrazol-5-yl)-amino]-2,2-difluoro-6,7,8,9-tetrahydro-1,3-dioxa-5-aza-cyclohepta[f]indene-5-carboxylic acid isopropyl ester, (+/−)-Isopropyl 5-[(3,5-bistrifluoromethyl-benzyl)-(1H-tetrazol-5-yl)-amino]-8-chloro-2,3,4,5-tetrahydrobenzo[b]azepine-1-carboxylate, (+/−)-isopropyl 5-[(3,5-bistrifluoromethyl-benzyl)-(2-methyl-2H-tetrazol-5-yl)-amino]-8-chloro-2,3,4,5-tetrahydrobenzo[b]azepine-1-carboxylate, (+/−) isopropyl-6-[(3,5-bistrifluoromethyl-benzyl)-(1H-tetrazol-5-yl)-amino]-2,3,6,7,8,9-hexahydro-1H-10-aza-cyclohepta[e]indene-10-carboxylate, (+/−)-9-[(3,5-Bis-trifluoromethyl-benzyl)-(2H-tetrazol-5-yl)-amino]-2,3,6,7,8,9-hexahydro-1H-5-aza-cyclohepta[f]indene-5-carboxylic acid isopropyl ester, (+/−)-9-[(3,5-Bis-trifluoromethyl-benzyl)-(2-methyl-2H-tetrazol-5-yl)-amino]-2,3,6,7,8,9-hexahydro-1H-5-aza-cyclohepta[f]indene-5-carboxylic acid isopropyl ester, (+/−)-isopropyl 5-[(3,5-bistrifluoromethyl-benzyl)-(5-methyl-1H-pyrazol-3-yl)-amino]-8-chloro-2,3,4,5-tetrahydrobenzo[b]azepine-1-carboxylate, +/−)-isopropyl 5-[(3,5-bistrifluoromethyl-benzyl)-(5-methyl-isoxazol-5-yl)-amino]-8-chloro-2,3,4,5-tetrahydrobenzo[b]azepine-1-carboxylate, (+/−)-isopropyl 5-[(3,5-bistrifluoromethyl-benzyl)-(2-methyl-2H-tetrazol-5-yl)-amino]-9-methyl-8-trifluormethyl-2,3,4,5-tetrahydrobenzo[b]azepine-1-carboxylate, (S)-6-[(3,5-Bis-trifluoromethyl-benzyl)-(2-methyl-2H-tetrazol-5-yl)-amino]-4-methyl-2,3,6,7,8,9-hexahydro-1H-10-aza-cyclohepta[e]indene-10-carboxylic acid isopropyl ester, (S)-isopropyl 5-[(3,5-bistrifluoromethyl-benzyl)-(2-methyl-2H-tetrazol-5-yl)-amino]-8,9-dimethyl-2,3,4,5-tetrahydrobenzo[b]azepine-1-carboxylate, (S)-isopropyl 5-{(3,5-Bis-trifluoromethyl-benzyl)-[2-(2-hydroxy-ethyl)-2H-tetrazol-5-yl]-amino}-8,9-dimethyl-2,3,4,5-tetrahydrobenzo[b]azepine-1-carboxylate, (S)-9-[(3,5-Bis-trifluoromethyl-benzyl)-(2-methyl-2H-tetrazol-5-yl)-amino]-2,3,6,7,8,9-hexahydro-1H-5-aza-cyclohepta[f]indene-5-carboxylic acid tert-butyl ester, (S)-(3,5-Bis-trifluoromethyl-benzyl)-(5-cyclopentylmethyl-1,2,3,5,6,7,8,9-octahydro-5-aza-cyclohepta[f]inden-9-yl)-(2-methyl-2H-tetrazol-5-yl)-amine, (S)-(3,5-Bis-trifluoromethyl-benzyl)-(5-cyclopentylmethyl-3,5,6,7,8,9-hexahydro-1H-2-oxa-5-aza-cyclohepta[f]inden-9-yl)-(2-methyl-2H-tetrazol-5-yl)-amine, (S)-5-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-yl}-3,3-dimethyl-pentanoic acid, (S)-5-(9-{(3,5-Bis-trifluoromethyl-benzyl)-[2-(2-hydroxy-ethyl)-2H-tetrazol-5-yl]-amino}-1,3,6,7,8,9-hexahydro-2-oxa-5-aza-cyclohepta[f]inden-5-yl)-3,3-dimethyl-pentanoic acid, (S)-9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]indene-5-carboxylic acid isopropyl ester, (3,5-Bis-trifluoromethyl-benzyl)-(1-cyclopentylmethyl-2,3,4,5,7,8,9,10-octahydro-1H-naphtho[2,3-b]azepin-5-yl)-(2-methyl-2H-tetrazol-5-yl)-amine, 5-[(3,5-Bis-trifluoromethyl-benzyl)-(2-methyl-2H-tetrazol-5-yl)-amino]-2,3,4,5,7,8,9,10-octahydro-naphtho[2,3-b]azepine-1-carboxylic acid isopropyl ester, (S)-9-{(3,5-Bis-trifluoromethyl-benzyl)-[2-(2-hydroxy-ethyl)-2H-tetrazol-5-yl]-amino}-2,3,6,7,8,9-hexahydro-1H-5-aza-cyclohepta[f]indene-5-carboxylic acid isopropyl ester, (R)-9-[(3,5-Bis-trifluoromethyl-benzyl)-(2-methyl-2H-tetrazol-5-yl)-amino]-2,3,6,7,8,9-hexahydro-1H-5-aza-cyclohepta[f]indene-5-carboxylic acid isopropyl ester, (S)-9-[(3,5-Bis-trifluoromethyl-benzyl)-(2-methyl-2H-tetrazol-5-yl)-amino]-2,3,6,7,8,9-hexahydro-1H-5-aza-cyclohepta[f]indene-5-carboxylic acid isopropyl ester, (S)-6-{(3,5-Bis-trifluoromethyl-benzyl)-[2-(2-hydroxy-ethyl)-2H-tetrazol-5-yl]-amino}-2,3,6,7,8,9-hexahydro-1H-10-aza-cyclohepta[e]indene-10-carboxylic acid isopropyl ester, (S)-6-{(3,5-Bis-trifluoromethyl-benzyl)-[2-(2-hydroxy-ethyl)-2H-tetrazol-5-yl]-amino}-4-methyl-2,3,6,7,8,9-hexahydro-1H-10-aza-cyclohepta[e]indene-10-carboxylic acid isopropyl ester, (S)-9-[(3,5-Bis-trifluoromethyl-benzyl)-(2-methyl-2H-tetrazol-5-yl)-amino]-2,3,6,7,8,9-hexahydro-1H-5-aza-cyclohepta[f]indene-5-carboxylic acid 2-methoxycarbonyl-2-methyl-propyl ester, (S)-9-[(3,5-Bis-trifluoromethyl-benzyl)-(2-methyl-2H-tetrazol-5-yl)-amino]-2,3,6,7,8,9-hexahydro-1H-5-aza-cyclohepta[f]indene-5-carboxylic acid 2-carboxy-2-methyl-propyl ester, (S)-1-{5-[(3,5-Bis-trifluoromethyl-benzyl)-2-methyl-2H-tetrazol-5-yl)-amino]-7-methyl-8-trifluoromethyl-2,3,4,5-tetrahydro-benzo[b]azepin-1-yl}-3-furan-2-yl-methoxy)-propan-2-one, 2-{5-[(3,5-Bis-trifluoromethyl-benzyl)-2-methyl-2H-tetrazol-5-yl)-amino]-7-methyl-8-trifluoromethyl-2,3,4,5-tetrahydro-benzo[b]azepin-1-yl}-1-phenyl-ethanol, 2-{5-[(3,5-Bis-trifluoromethyl-benzyl)-2-methyl-2H-tetrazol-5-yl)-amino]-7-methyl-8-trifluoromethyl-2,3,4,5-tetrahydro-benzo[b]azepin-1-yl}-2-phenyl-ethanol, (S)-4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-benzoic acid methyl ester, (S)-4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-benzoic acid, (S)-3-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-benzoic acid methyl ester, (S)-3-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-benzoic acid, (S)-4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-benzoic acid, (4-{5-[(3,5-Bis-trifluoromethyl-benzyl)-(3-methyl-isoxazol-5-yl)-amino]-7-methyl-8-trifluoromethyl-2,3,4,5-tetrahydro-benzo[b]azepin-1-ylmethyl}-cyclohexyl)-acetic acid methyl ester, (4-{5-[(3,5-Bis-trifluoromethyl-benzyl)-(3-methyl-isoxazol-5-yl)-amino]-7-methyl-8-trifluoromethyl-2,3,4,5-tetrahydro-benzo[b]azepin-1-ylmethyl}-cyclohexyl)-acetic acid, (S)-(3,5-Bis-trifluoromethyl-benzyl)-(7-methyl-1-pyridin-4-ylmethyl-8-trifluoromethyl-2,3,4,5-tetrahydro-1H-benzo[b]azepin-5-yl)-(2-methyl-2H-tetrazol-5-yl)-amine, (S)-(3,5-Bis-trifluoromethyl-benzyl)-(7-methyl-1-pyridin-4-ylmethyl-8-trifluoromethyl-2,3,4,5-tetrahydro-1H-benzo[b]azepin-5-yl)-(2-methyl-2H-tetrazol-5-yl)-amine hydrochloride, (S)-(3,5-Bis-trifluoromethyl-benzyl)-(7-methyl-1-pyridin-3-ylmethyl-8-trifluoromethyl-2,3,4,5-tetrahydro-1H-benzo[b]azepin-5-yl)-(2-methyl-2H-tetrazol-5-yl)-amine, (S)-(3,5-Bis-trifluoromethyl-benzyl)-(1-cyclopropylmethyl-7-methyl-8-trifluoromethyl-2,3,4,5-tetrahydro-1H-benzo[b]azepin-5-yl)-(2-methyl-2H-tetrazol-5-yl)-amine, (S)-2-{5-[(3,5-Bis-trifluoromethyl-benzyl)-(2-methyl-2H-tetrazol-5-yl)-amino]-7-ethyl-8-trifluoromethyl-2,3,4,5-tetrahydro-benzo[b]azepin-1-yl}-ethanol, (S)-(2-{5-[(3,5-Bis-trifluoromethyl-benzyl)-(2-methyl-2H-tetrazol-5-yl)-amino]-7-ethyl-8-trifluoromethyl-2,3,4,5-tetrahydro-benzo[b]azepin-1-yl}-ethyl)-carbamic acid tert-butyl ester, (S)-4-{5-[(3,5-Bis-trifluoromethyl-benzyl)-(2-methyl-2H-tetrazol-5-yl)-amino]-7-ethyl-8-trifluoromethyl-2,3,4,5-tetrahydro-benzo[b]azepin-1-ylmethyl}-benzoic acid, (S)5-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-ylmethyl}-thiophene-2-carboxylic acid, (S)-(3,5-Bis-trifluoromethyl-benzyl)-(2-methyl-2H-tetrazol-5-yl)-(5-pyridin-4-ylmethyl-3,5,6,7,8,9-hexahydro-1H-2-oxa-5-aza-cyclohepta[f]inden-9-yl)-amine, (S)-(4-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-ylmethyl}-cyclohexyl)-acetic acid, (S)-2-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-yl}-ethanol, (S)-9-[[2-(2-Amino-ethyl)-2H-tetrazol-5-yl]-(3,5-bis-trifluoromethyl-benzyl)-amino]-1,3,6,7,8,9-hexahydro-2-oxa-5-aza-cyclohepta[f]indene-5-carboxylic acid tert-butyl ester, (S)-[2-(2-Amino-ethyl)-2H-tetrazol-5-yl]-(5-benzyl-3,5,6,7,8,9-hexahydro-1H-2-oxa-5-aza-cyclohepta[f]inden-9-yl)-(3,5-bis-trifluoromethyl-benzyl)-amine, (S)-[2-(2-Amino-ethyl)-2H-tetrazol-5-yl]-(3,5-bis-trifluoromethyl-benzyl)-[5-(3,3,3-trifluoro-propyl)-3,5,6,7,8,9-hexahydro-1H-2-oxa-5-aza-cyclohepta[f]inden-9-yl]-amine, (S)-5-{5-[(3,5-Bis-trifluoromethyl-benzyl)-(2-methyl-2H-tetrazol-5-yl)-amino]-2,3,4,5,7,8,9,10-octahydro-naphtho[2,3-b]azepin-1-yl}-3,3-dimethyl-pentanoic acid, (S)-(3,5-Bis-trifluoromethyl-benzyl)-(1-cyclopentylmethyl-11-methyl-2,3,4,5,7,8,9,10-octahydro-1H-naphtho[2,3-b]azepin-5-yl)-(2-methyl-2H-tetrazol-5-yl)-amine, (S)-5-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-thiophene-2-carboxylic acid, (S)-5-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-2-methyl-propionic acid ethyl ester, (S)-(3,5-Bis-trifluoromethyl-benzyl)-(1,7-dimethyl-8-trifluoromethyl-2,3,4,5-tetrahydro-1H-benzo[b]azepin-5-yl)-(2-methyl-2H-tetrazol-5-yl)-amine, (S)-(3,5-Bis-trifluoromethyl-benzyl)-(2-methyl-2H-tetrazol-5-yl)-(7-methyl-1-thiazol-2-ylmethyl-8-trifluoromethyl-2,3,4,5-tetrahydro-1H-benzo[b]azepin-5-yl)-amine, (S)-(3,5-Bis-trifluoromethyl-benzyl)-[7-methyl-1-(1-methyl-1H-imidazol-2-ylmethyl)-8-trifluoromethyl-2,3,4,5-tetrahydro-1H-benzo[b]azepin-5-yl]-(2-methyl-2H-tetrazol-5-yl)-amine, (S)-(1-Benzyl-7-methyl-8-trifluoromethyl-2,3,4,5-tetrahydro-1H-benzo[b]azepin-5-yl)-(3,5-bis-trifluoromethyl-benzyl)-(2-methyl-2H-tetrazol-5-yl)-amine, (S)-5-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}, (S)-(4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-phenyl)-acetic acid, (S)-4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-butyric acid, (S)-(3,5-Bis-trifluoromethyl-benzyl)-(7-methyl-1-piperidin-4-ylmethyl-8-trifluoromethyl-2,3,4,5-tetrahydro-1H-benzo[b]azepin-5-yl)-(2-methyl-2H-tetrazol-5-yl)-amine, (S)-(4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-piperidin-1-yl)-acetic acid ethyl ester, (S)-(4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-piperidin-1-yl)-acetic acid, (S)-3-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-2-methyl-propionic acid, (S)-(3,5-Bis-trifluoromethyl-benzyl)-(7-methyl-1-pyrrolidin-2-ylmethyl-8-trifluoromethyl-2,3,4,5-tetrahydro-1H-benzo[b]azepin-5-yl)-(2-methyl-2H-tetrazol-5-yl)-amine, (S)-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-acetic acid, (S)-[2-(2-Amino-ethyl)-2H-tetrazol-5-yl]-[1-(2-benzyloxy-ethyl)-7-methyl-8-trifluoromethyl-2,3,4,5-tetrahydro-1H-benzo[b]azepin-5-yl]-(3,5-bis-trifluoromethyl-benzyl)-amine, (S)-2-{5-[[2-(2-Amino-ethyl)-2H-tetrazol-5-yl]-(3,5-bis-trifluoromethyl-benzyl)-amino]-7-methyl-8-trifluoromethyl-2,3,4,5-tetrahydro-benzo[b]azepin-1-yl}-ethanol, (S)-5-[[2-(2-Amino-ethyl)-2H-tetrazol-5-yl]-(3,5-bis-trifluoromethyl-benzyl)-amino]-7-methyl-8-trifluoromethyl-2,3,4,5-tetrahydro-benzo[b]azepine-1-carboxylic acid tert-butyl ester, (S)-[2-(2-Amino-ethyl)-2H-tetrazol-5-yl]-(3,5-bis-trifluoromethyl-benzyl)-(7-methyl-1-thiazol-2-ylmethyl-8-trifluoromethyl-2,3,4,5-tetrahydro-1H-benzo[b]azepin-5-yl)-amine, (S)-(2-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-ethoxy)-acetic acid, (S)-Acetic acid 2-{5-[(3,5-bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-ethyl ester, (S)-(3,5-Bis-trifluoromethyl-benzyl)-(2-methyl-2H-tetrazol-5-yl)-[7-methyl-1-(2H-tetrazol-5-ylmethyl)-8-trifluoromethyl-2,3,4,5-tetrahydro-1H-benzo[b]azepin-5-yl]-amine, (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid 2-aminoethyl ester, (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid 2-carboxy-2-methyl-propyl ester, (S)-[2-(2-Amino-ethyl)-2H-tetrazol-5-yl]-(3,5-bis-trifluoromethyl-benzyl)-(1-cyclopropylmethyl-7-methyl-8-trifluoromethyl-2,3,4,5-tetrahydro-1H-benzo[b]azepin-5-yl)-amine, (S)-[2-(2-Amino-ethyl)-2H-tetrazol-5-yl]-(3,5-bis-trifluoromethyl-benzyl)-(1-cyclopropylmethyl-7-methyl-8-trifluoromethyl-2,3,4,5-tetrahydro-1H-benzo[b]azepin-5-yl)-amine hydrochloride, and pharmaceutically acceptable salts solvate, enantiomer, racemate, diastereomer or mixture of diastereomers thereof.

The geometric isomers associated with the double bonds and the optical isomers associated with asymmetric carbon atoms of compounds of Formula I are also contemplated to be within the scope of the current invention as useful for the treatment of diseases related to CETP modulation.

Synthesis of Compounds of the Invention

The compounds of the instant invention can be synthesized as exemplified in the following Schemes, Examples, and procedures. Anthranilate intermediates of Formula 1 can be chemically prepared, for example, by following the synthetic routes set forth in the Schemes below. However, the following discussion is not intended to limit the scope of the present invention in any way because one of skill in the art is able to extrapolate without undue experimentation from the Schemes and Examples herein to other specific compounds within the scope of the invention. Many of the reagents and starting materials can be readily obtained from commercial suppliers and are readily available to one of ordinary skill in the art. Other reagents and starting materials may be made by procedures which are selected from standard techniques of organic and heterocyclic chemistry, techniques which are analogous to the syntheses of known similar reagents or starting materials, and the procedures described in the preparations and Examples below, including any novel procedures. This includes, but is not limited to, esterification of a carboxylic acid, hydrolysis of a nitrile to a carboxylic acid, and subsequent esterification. The R, R1, R2, R3, R4, R5, R6, etc, designations used within this section for the purpose of illustrating the various methods of synthesizing compounds of the invention and/or illustrating variability of substituents at the pendent position are not necessarily synonymous in scope or meaning with similar groups used in the generic structure for compounds of Formula I. However, groups in final compounds of the schemes occupying similar positions are co-extensive in scope and meaning compared to groups occupying similar positions as defined for the generic structure of compounds of Formula I.

Intermediate Preparation Scheme 1

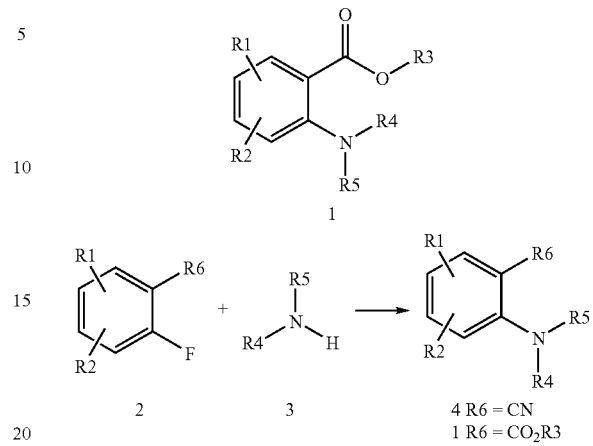

In intermediate preparation Scheme 1, the nucleophilic aromatic substitution occurs by methods known in the art, (Wells, K. M. et al. Tetrahedron Letters, 1996, 37(36), 6439-6442). The appropriately substituted amine is dissolved in a suitable solvent, such as DMF or DMSO, with a base, such as cesium carbonate, and the appropriately substituted benzonitrile or fluoro benzoate (R6=CN or $CO_2R3$). The reaction proceeds at 0° C. to elevated temperatures (up to or about 150° C.) in anywhere from ten minutes to several days depending on the stability of the starting materials and/or reaction conditions. The product of structure 4 (R6=CN) or 1 (R6=$CO_2R3$) can then be isolated by a standard aqueous workup, followed by normal phase chromatographic methods or recrystallization techniques commonly employed in the art.

Intermediate Preparation Scheme 2

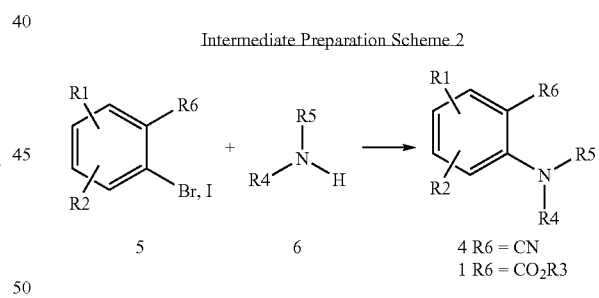

In intermediate preparation Scheme 2, the N-aryl coupling occurs by methods known in the art, (Hartwig, J. F. et al. Angew. Chem., Int. Ed. Engl. 1998, 37, 2046-2067). The appropriately substituted amine is dissolved in a suitable solvent, such as DMF, with a base, such as cesium carbonate or sodium tert-butoxide, the appropriately substituted benzonitrile or haloalkyl benzoate (R6=CN or $CO_2R3$), and a suitable catalyst complex, such as palladium acetate and diphenyl phospino ferrocene. The reaction proceeds at 0° C. to elevated temperatures in anywhere from ten minutes to several days depending on the stability of the starting materials. The product of structure 4 (R6=CN) or 1 (R6=$CO_2R3$) can then be isolated by a standard aqueous workup, followed by normal phase chromatographic methods or recrystallization techniques commonly employed in the art.

Intermediate Preparation Scheme 3

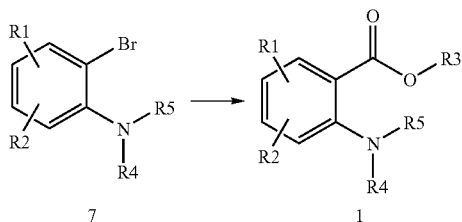

In intermediate preparation Scheme 3, the carbonylation occurs by methods known in the art, (Heck, *Palladium Reagents in Organic Synthesis*; Academic Press: New York, 1985, p. 348-358). The appropriately substituted aryl bromide is dissolved in a suitable solvent, such as DMF, with a base, such as cesium carbonate or sodium tert-butoxide, a suitable catalyst complex such as palladium acetate and diphenyl phospino ferrocene, an appropriate alcohol (R3-OH) and saturated with carbon monoxide. The reaction proceeds at 0° C. to elevated temperatures (up to or about 150° C.) in anywhere from ten minutes to several days depending on the stability of the starting materials and/or reaction conditions. The product of structure 1 may then be isolated by a standard aqueous workup, optionally followed by normal phase chromatographic methods or recrystallization techniques commonly employed in the art.

Intermediate Preparation Scheme 4

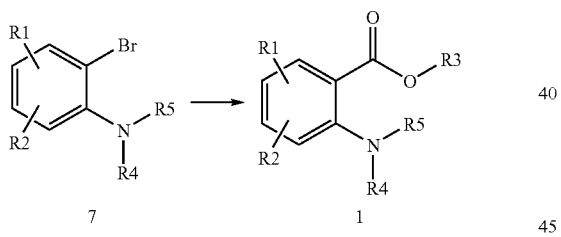

In intermediate preparation Scheme 4, the aromatic carboxylation occurs by methods known in the art, (Boger, D. L. et al, Journal of Organic Chemistry, 1994, 59(17), 4943-4949, Volpin et al, *Organomet. Reactions,* 1975, 5, 313-386). The appropriately substituted aryl bromide is dissolved in a suitable solvent, such as diethyl ether or tetrahydrofuran, with an alkyllithium, such as n-butyl lithium or tert-butyl lithium or magnesium turnings. The resulting anion is quenched with a suitable carbon dioxide source, such as dry ice, or dimethyl carbonate. The reaction proceeds at about −78° C. to about room temperature in anywhere from about five minutes to several hours depending on the stability of the starting materials. The product of structure 1 can then be isolated by a standard aqueous workup, followed by normal phase chromatographic methods or recrystallization techniques commonly employed in the art.

Intermediate Preparation Scheme 5

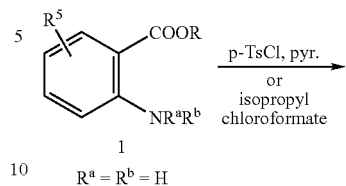

$R^a = R^b = H$

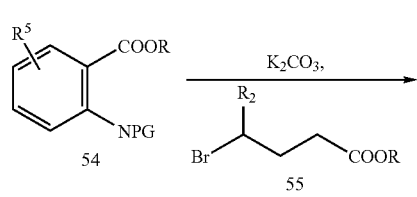

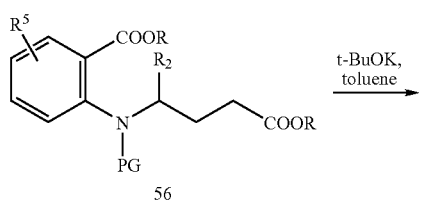

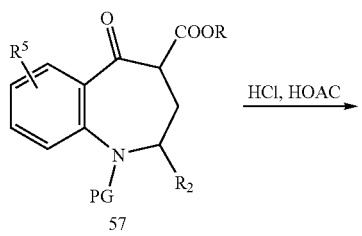

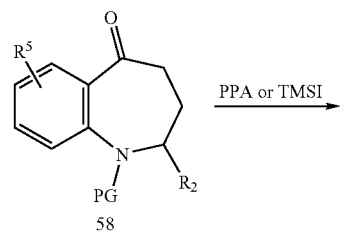

-continued

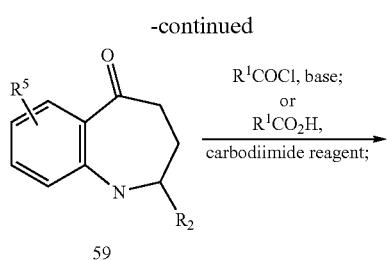

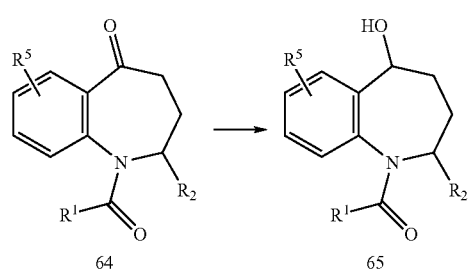

Synthetic Scheme 5 shows preparation of exemplary precursor compounds for Formula I. For example, substituted arylamino esters 1 that are either commercially available or prepared as set forth in the literature or in Schemes 1 to 4 can be protected with tosyl chloride, isopropyl chloroformate, or other suitable protecting group to provide 54. The compound 54 may in turn be alkylated with appropriately substituted, or unsubstituted 3-bromoethylesters 55 thus affording 56. Dieckmann condensation-cyclization of intermediate 56 yields N-protected benzazepinone 57, which is subjected to acid hydrolysis and decarboxylation to afford ketone derivatives 58. Removal of the protecting group, if necessary, with acid (e.g. PPA (polyphosphoric acid)), TMSI (trimethylsilyliodide), or HCl provides the intermediate 59. N-acylation of 59 by treatment with an appropriately substituted aryl or alkyl chloroformate in the presence of an organic base such as pyridine affords carbamates of structure 64. Alternatively, treatment of 59 with an acid chloride or an appropriate activated ester, affords compounds of formula 64. The intermediate benzazepin-5-ones may be reduced with a reducing agent such as sodium borohydride in an appropriate solvent, such as tetrahydrofuran or methanol, to achieve the benzylic alcohol 65 as shown in Scheme 5.

Scheme 6

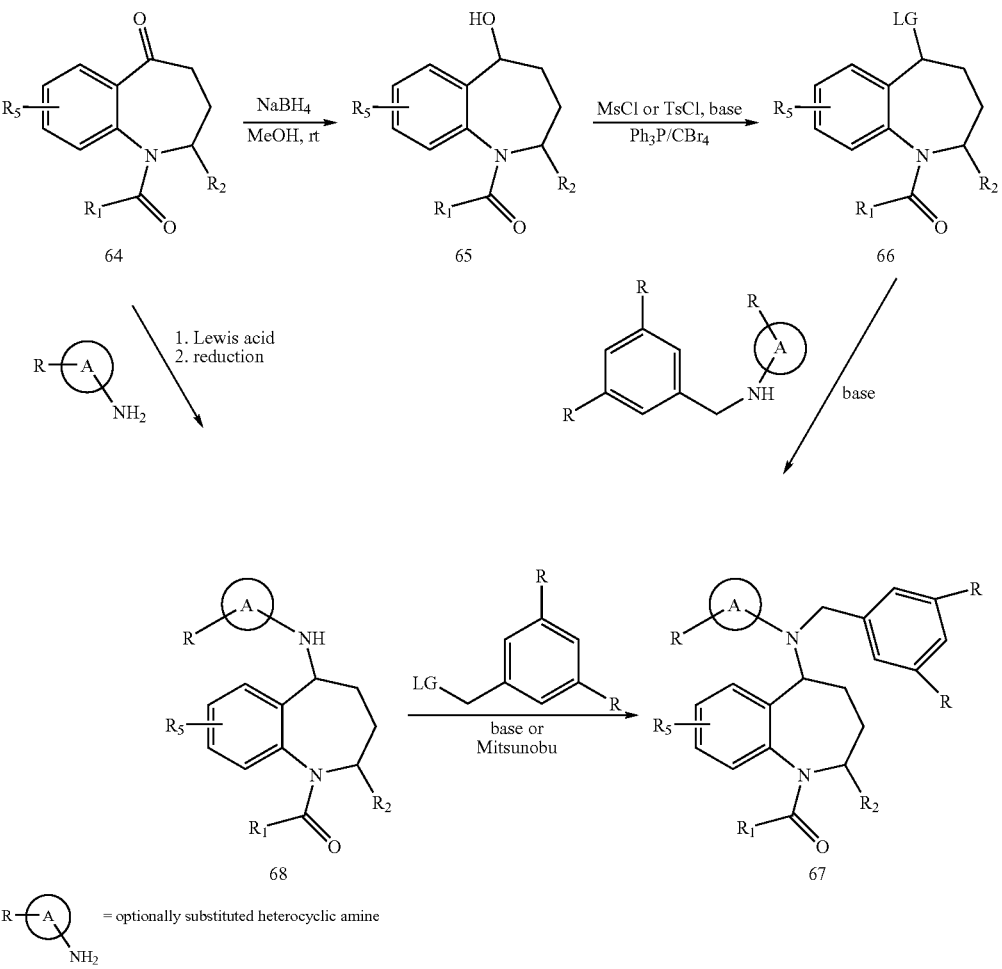

Compounds of Formula I may be prepared as shown in Schemes 6 and 7, in which reductive amination chemistry is utilized. Formation of a Schiff base of benzazepin-5-ones 64 with a heterocyclic amine is followed by treatment with a reducing agent such as sodium borohydride in an appropriate solvent, such as tetrahydrofuran or methanol, to achieve the heterocyclic amine adducts. Further elaboration by reaction with an activated benzylic reagent in the presence of base or the use of a Mitsunobu-type displacement reaction affords the corresponding product, a compound of the invention. Alternatively, the benzazepin-5-ones (64) may be reduced to the corresponding carbinol intermediate with a reducing agent such as sodium borohydride in an appropriate solvent, such as tetrahydrofuran or methanol. These adducts may be converted directly to provide disubstituted amine products using the Mitsunobu protocol, or initially converted to activated templates such as a mesylate, tosylate or bromide and displaced with the heterocyclic-substituted benzylamine to achieve trisubstituted amine products as shown in Scheme 6. A preferred group of potential heterocyclic R-A substituents has been described supra.

elaboration by reaction with an activated heterocyclic reagent in the presence of base (or alternatively, Schiff base formation with a heteroaromatic aldehyde followed by reduction) provides a secondary route to disubstituted amine products 67.

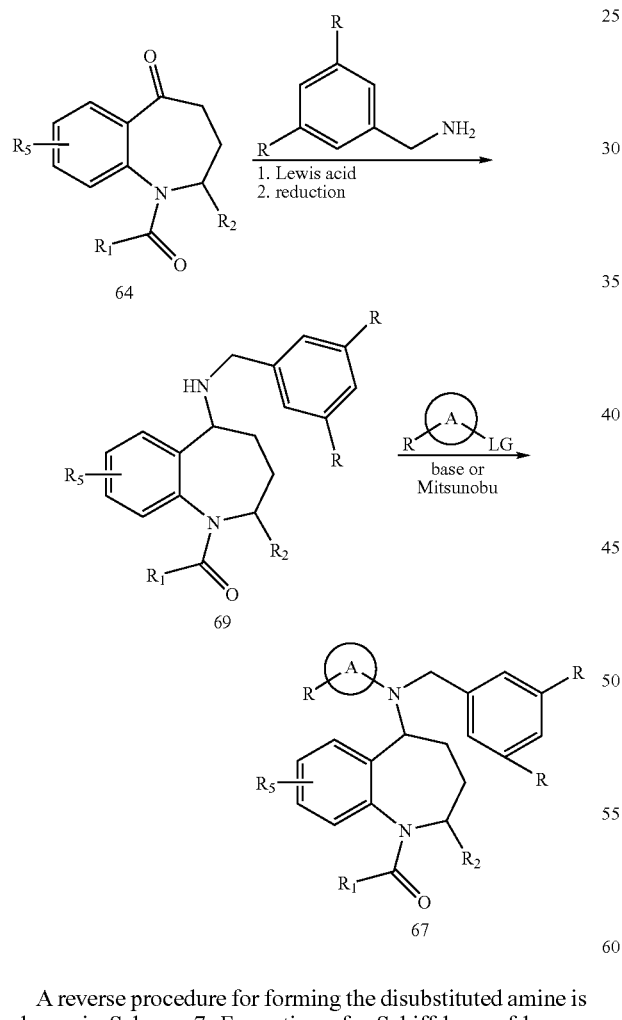

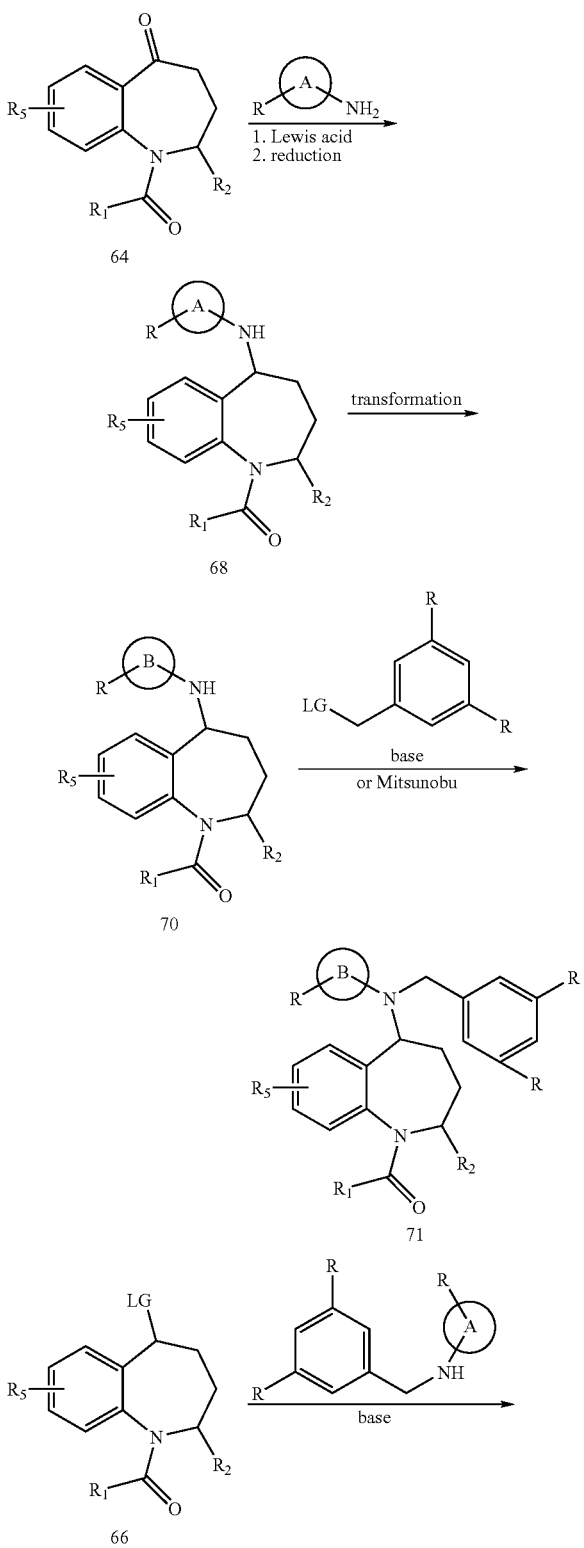

A reverse procedure for forming the disubstituted amine is shown in Scheme 7. Formation of a Schiff base of benzazepin-5-ones (64) with a benzylic amine is followed by treatment with a reducing agent such as sodium borohydride in an appropriate solvent, such as tetrahydrofuran or methanol, to achieve the disubstituted benzylic amine adduct 69. Further -continued

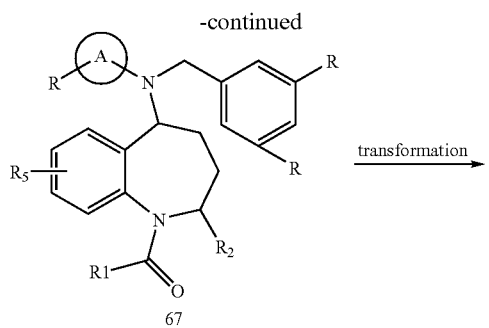

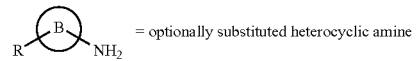

Compounds of Formula I may also be prepared by transformation of pendant functionality as shown in Scheme 8. Disubstituted amine products, such as, 68 in which the moiety R-A corresponds to reactive functionality such as cyano, carboxylate, and the like may be transformed into heterocyclic moieties such as 71 in intermediate stages of synthesis or at the end of the synthetic preparation. Also, the order of N-substitution may be reversed as shown above. Procedures for transforming pendant functionalities wherein R-A corresponds to reactive functionality such as nitrile, carboxylate, etc are known to one of skill in the art and may be found in general organic and/or heterocyclic chemistry reference text such as but not limited to *Comprehensive Organic Transformations*, $2^{nd}$, ed., by Richard Larock, Wiley-VCH, Publishers, New York.

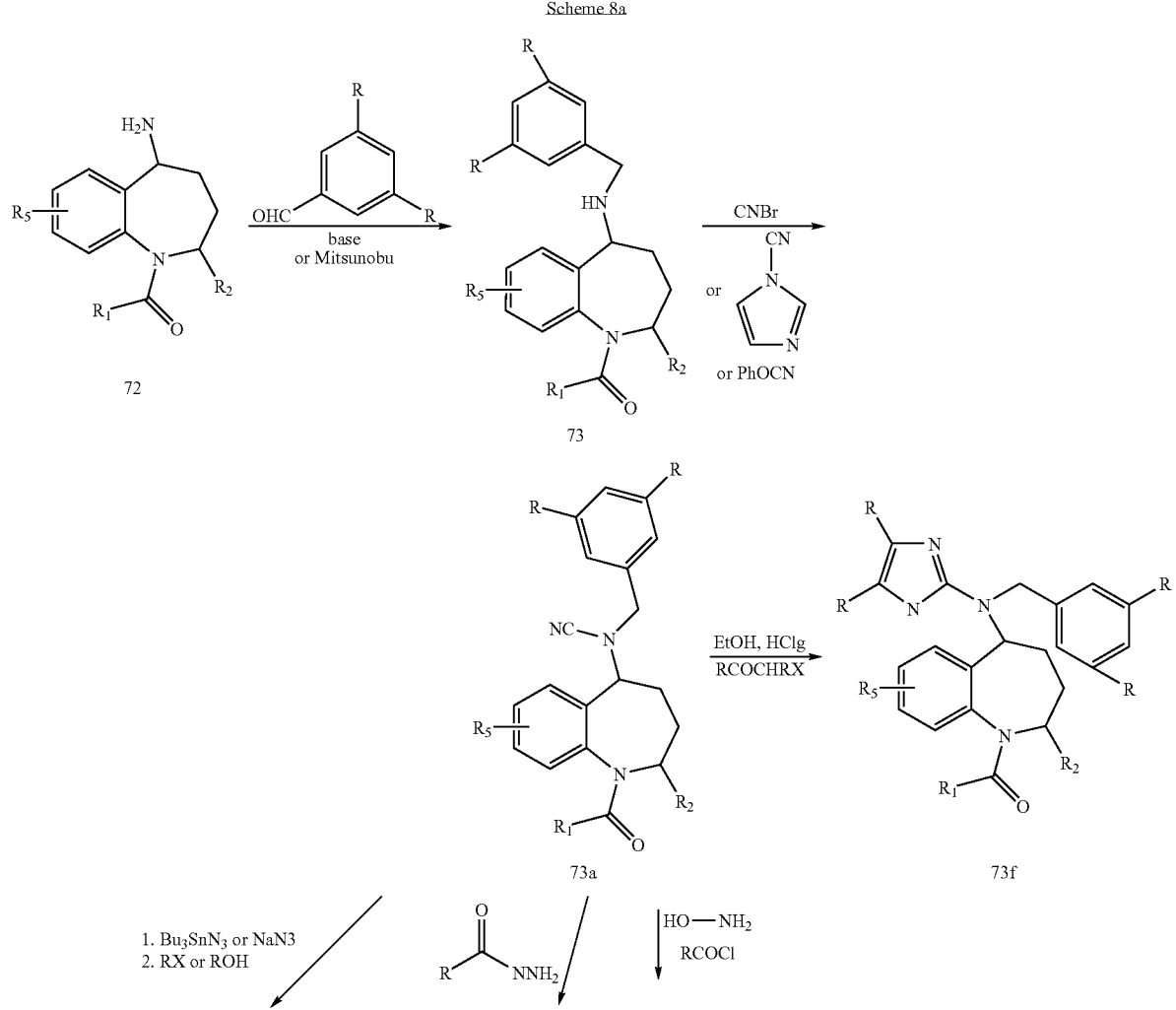

-continued
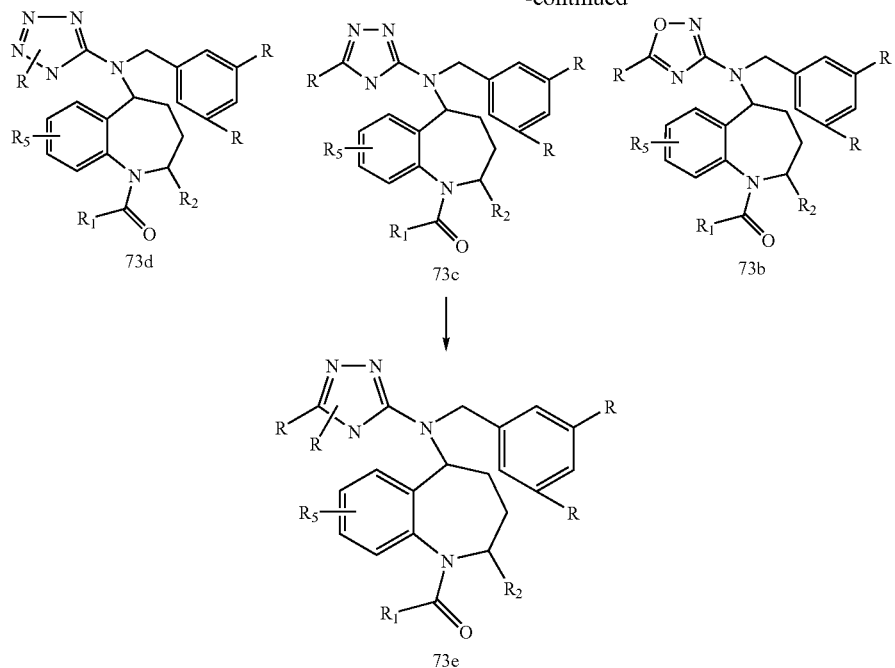
Scheme 8a shows a few examples of transformation reactions to illustrate inter-conversion of functionalities as means of preparing compounds of the invention. Detailed procedures are disclosed in the examples, known to one of skill in the art or may be readily sourced from reference sources by one of skill in the art.
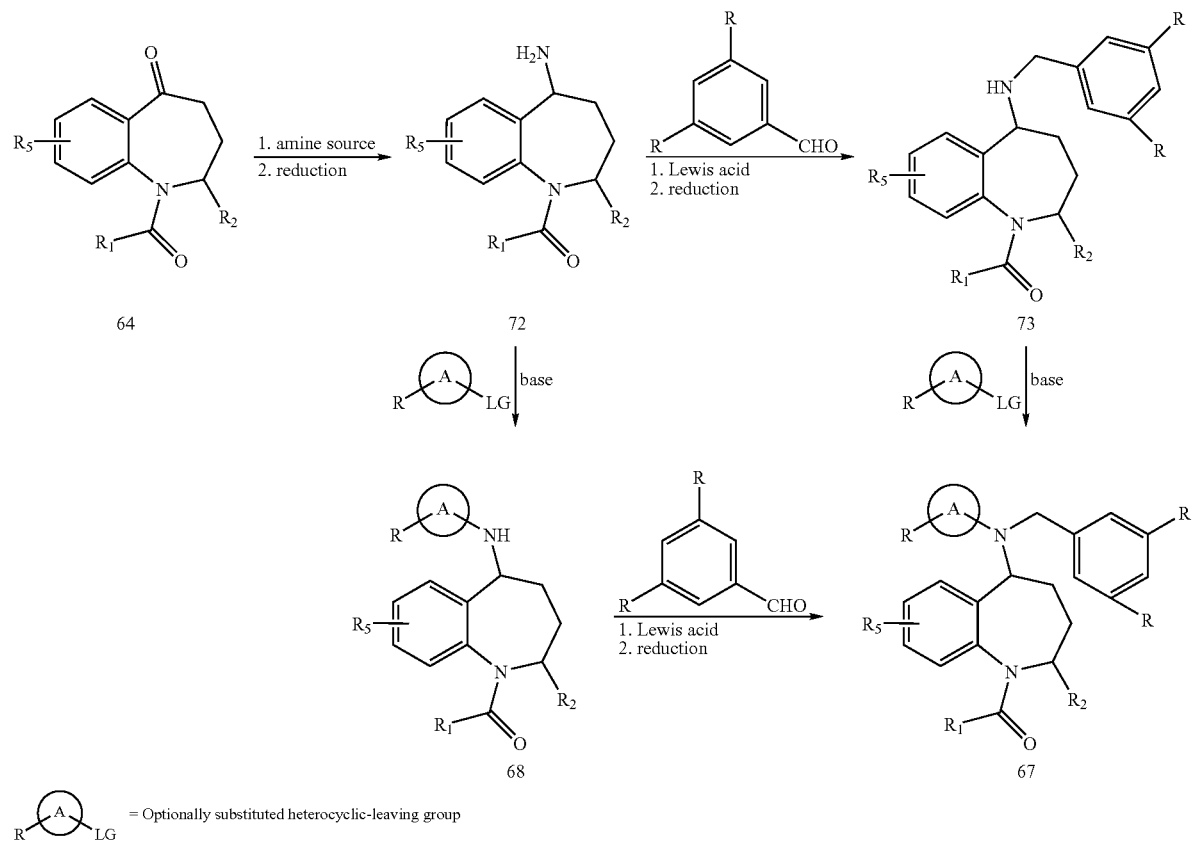

Compounds of the Formula I may also be prepared as shown in Schemes 9 and 10, in which the intermediate benzazepin-5-ones are transformed into benzylic amine adducts. This may be achieved by a number of methods, including reductive amination with a primary amine surrogate (such as, hydroxylamine, hydrazine, ammonium chloride, benzophenoneimine, among others), to provide a primary amine, as shown in Scheme 9, or may be incorporated into the ring construction sequence, as shown in Scheme 10, by chemistry known to one of ordinary skill in the art (Hadden, M.; Nieuwenhuyzen, M.; Potts, D.; Stevenson, P. J.; Thompson, N. *Tetrahedron* 2001, 57, 5615; Crousse, B.; Begue, J.-P.; Bonnet-Delpon, D. *J Org Chem* 2000, 65, 5009). Schiff base formation by treatment of the amine with a benzaldehyde is followed by treatment with a reducing agent such as sodium borohydride in an appropriate solvent, such as tetrahydrofuran or methanol, to achieve the benzylic amine adducts (or alternatively, displacement of an activated benzylic substrate, such as a mesylate, tosylate or bromide) provides the benzylamine product. This is followed by treatment with an activated heteroaryl (heterocyclic aryl) substrate, such as a mesylate, tosylate or bromide in the presence of a base to produce dibenzylic products, as shown in Scheme 9. In a reverse fashion, formation of a Schiff base of benzazepine-5-amines with a heteroaromatic aldehyde, followed by treatment with a reducing agent such as sodium borohydride in an appropriate solvent, such as tetrahydrofuran or methanol (or alternatively, displacement of an appropriately activated heteroaryl substrate, such as a mesylate, tosylate or bromide) achieves the benzylic heteroaromatic amine adduct. This is followed by treatment with an activated benzylic substrate, such as a mesylate, tosylate, or bromide, in the presence of a base to produce dibenzylic products, as shown in Scheme 9.

Scheme 10

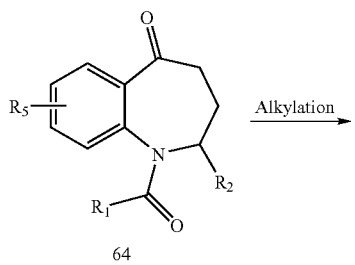

64

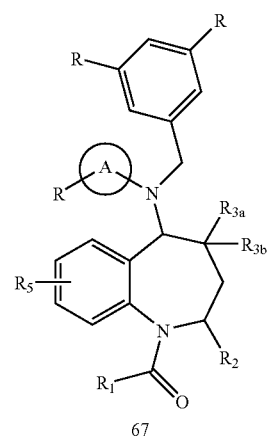

79

67

In Scheme 10, compound 64 can be treated with a base, such as sodium hydride or lithium diisopropylamide or lithium bis(trimethylsilyl)amide, in a solvent, such as DMF or tetrahydrofuran. Alkylation with the appropriately substituted halide or mesylate or tosylate may form compound 79 where R3a and R3b can be the same or different. Conversion of 79 to 67 is as described, for example in scheme 9.

Scheme 11

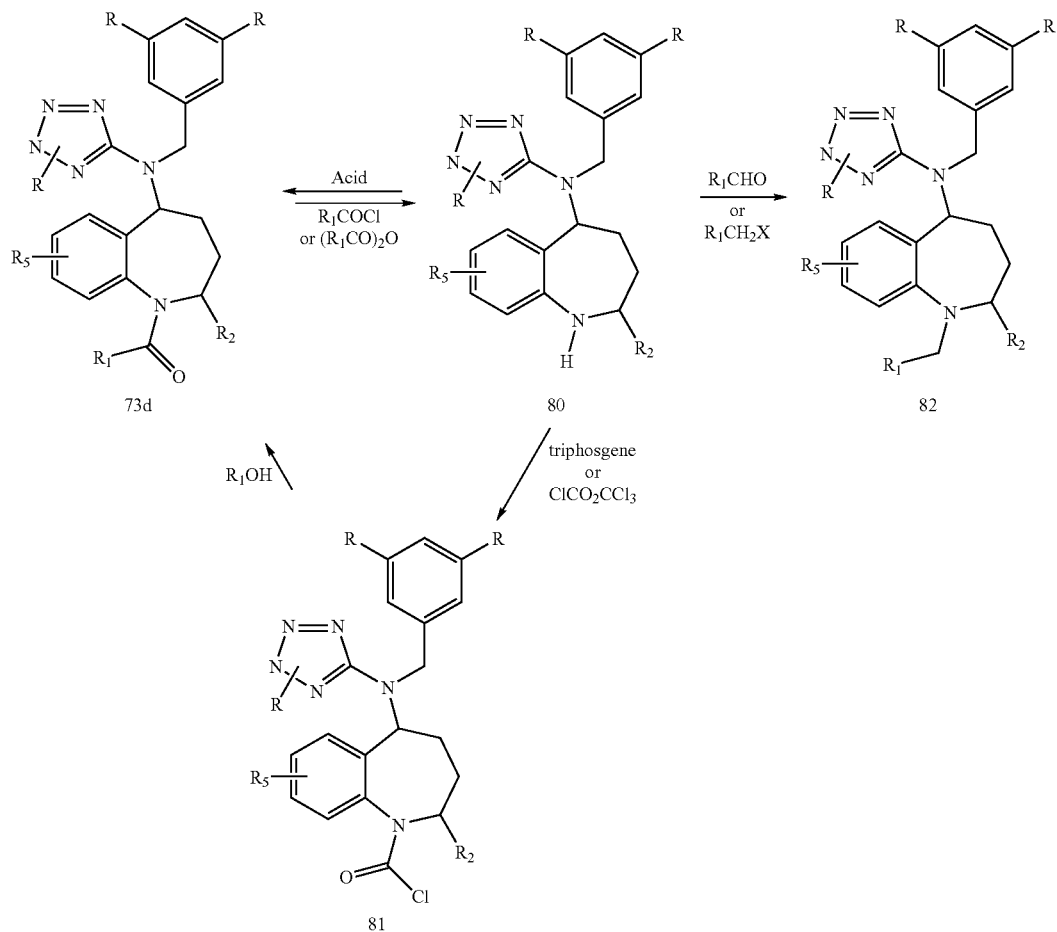

As shown in Scheme 11, compound 73d may be hydrolyzed to the corresponding amine 80, and may be further acylated using standard procedures known or determined by one skilled in the art to provide 73d. Or alternatively, 80 can be treated with triphosgene or trichloromethylchoroformate to provide 81. Compound 81 can afford compound 73d by reaction with the appropriate alcohols. Also, compound 80 can be alkylated by methods known in the art such as treating 80 with base and an alkyl halide, tosylate or the like, to afford 82. Alternatively compound 82 can be obtained using reductive amination conditions.

Scheme 12

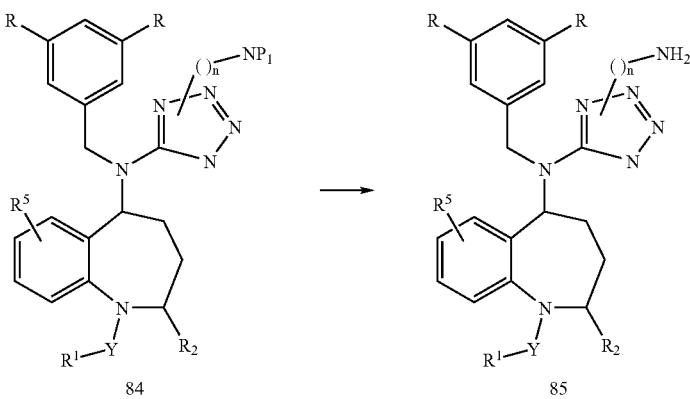

-continued

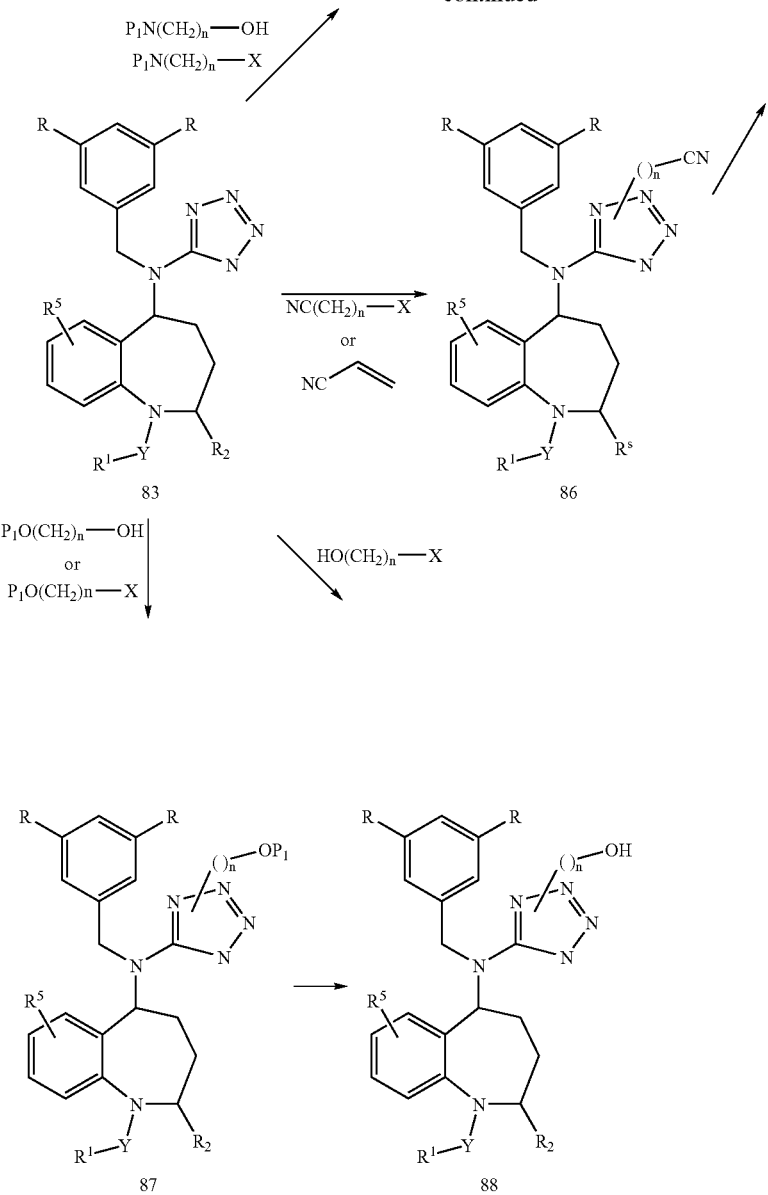

As shown in Scheme 12, tetrazole 83 can be alkylated with the appropriate protected aminoalcohol under Mitsunobu conditions or with the appropriate protected aminoalkylbromide, iodide, mesylate, or the like in the presence of base to provide a protected aminoalkyltetrazole 84. Removal of the protecting group, P1, using methods well known in the art can yield compound 85. Alternatively, tetrazole 83 can be alkylated with the appropriate alkylcyano bromide or with the appropriate acrylonitrile under Michael reaction conditions. Cyano derivative 86 can be then reduced to the corresponding amine 85. Tetrazole 83 can be alkylated using the appropriate alcohol under Mitsunobu conditions, or with the appropriate alkyl halide or the like in the presence of base to provide 87. Removal of P1 (protecting group) using methods well known in the art can yield compound 88. Alternatively hydroxyalkyltetrazole 88 can be obtained by alkylation of 83 with the corresponding halide in the presence of base.

Scheme 14

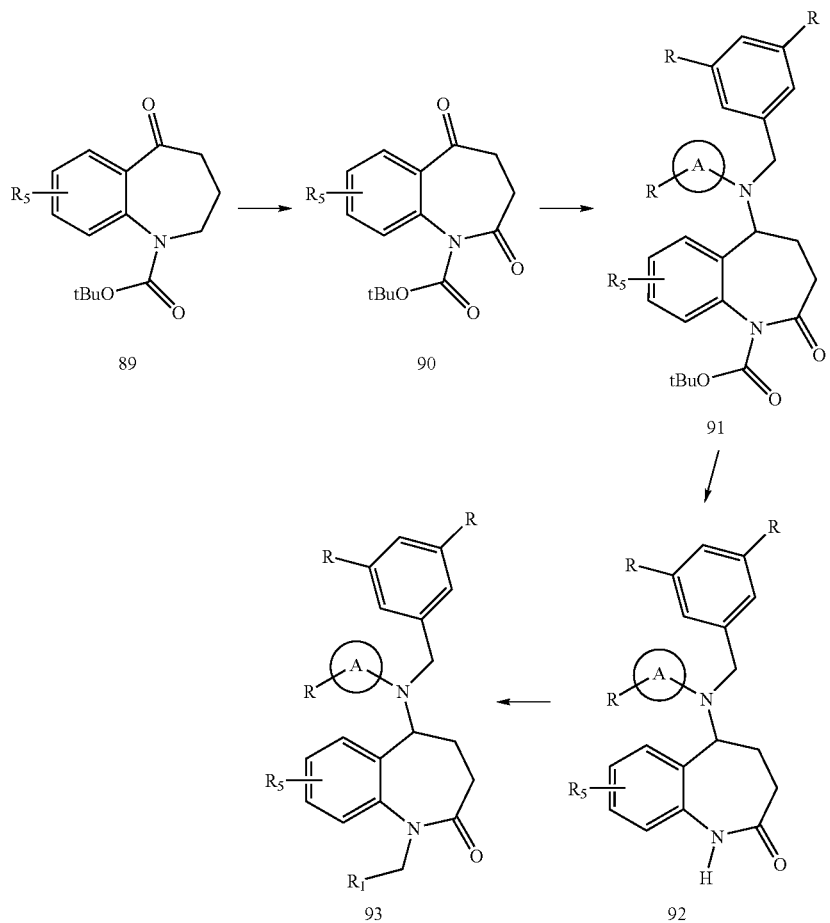

As shown in Scheme 14, compound 89 can be oxidized to compound 90 with ruthenium oxide in presence of sodium periodate. Compound 90 can be converted to 91 as is described, for example in scheme 9. Deprotection of tertbutoxycarbonyl group by methods well known in the art, can afford amide 92. Alkylation of 92 with the appropriate alkyl halide or tosylate or the like in presence of a base, can give rise compound 93.

Scheme 15

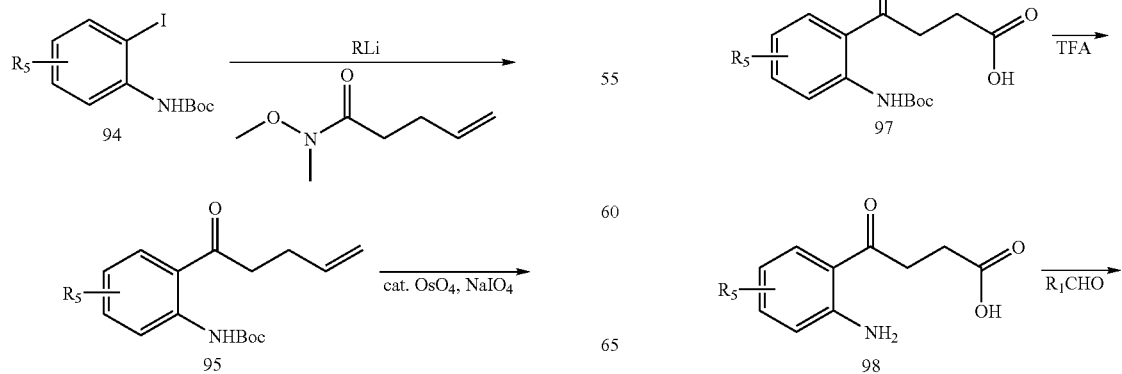

-continued

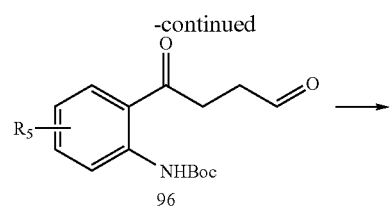

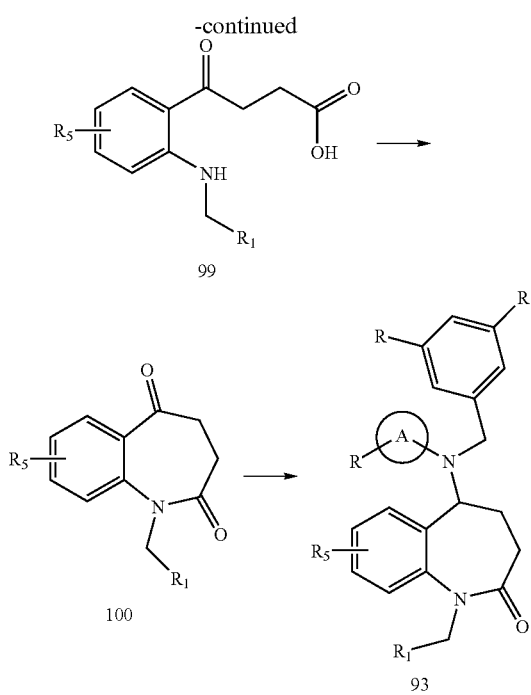

As shown in Scheme 15, iodoaryl derivative 94 can be transformed in ketone 95 by lithium exchange reaction followed by addition of a Weinreb amide. Then conversion of compound 95 in the aldehyde 96 and oxidation to the corresponding carboxylic acid can afford compound 97. Hydrolysis of amino protecting group and reductive amination reaction can give rise to compound 99, which can be cyclize to compound 100. Finally compound 93 can be obtained as is described in scheme 14.

Assay

The following assay protocol and result(s) thereof demonstrating the utility and efficacy of the compounds and/or methods of the current invention are given for the purpose of illustration and are not meant to be limiting in any way.

In Vitro CETP Inhibitor Assay: SPA ASSAY

An in vitro Scintillation Proximity Assay (SPA) has been used to evaluate the ability of compounds of this invention to inhibit the transfer of radiolabeled cholesterol esters between HDL and LDL. This assay monitors the inhibition of the transfer of [$^3$H]cholesterol esters from HDL (Amersham) to biotinylated LDL (Amersham) by a CETP source. The CETP source for this assay can be produced by AV-12 cells that have been created to express human CETP. The radiolabeled cholesterol ester is transferred in a HEPES-NaCl based buffer, after thirty minutes incubation the reaction is stopped and the biotinylated LDL is bound to streptavidin/scintillant coated SPA beads (Amersham). The radioactive signal is measured in a Packard 96-well scintillation TopCounter with window settings fully open. A decrease in radioactive signal from the LDL relative to a standard indicates the ability of compounds to inhibit the activity of CETP. Preferred compounds of the invention evaluated according to this assay protocol exhibit CETP inhibition at concentrations of less than 100 micromolar.

Alternatively, other CETP sources can be used to mediate the transfer of radiolabeled cholesterol ester in this assay. For example, endogenous CETP from human plasma, CETP from mice that express human CETP, and endogenous CETP from hamsters can be used as the CETP source in this assay.

Buffers other than HEPES-NaCl based buffer can be used in this assay, for example, human plasma, mouse plasma or a Tris-buffer that is high in albumin may be used.

It will be understood by those skilled in the art that other sources of radioactivity may be used to track the CETP activity in this assay.

Additionally, radio labeled-LDL may be used in this assay.

In Vivo Assay of CETP Activity

Syrian Golden Hamsters, which express endogenous CETP, can be used to assess the activity of the compounds in vivo. Test compounds are administered orally in selected aqueous or oil based vehicles for up to one week. At various times after dosing, ranging from 4 h to 48 h, blood/plasma can be obtained. The CETP activity can be determined by a method similar to that described above for the in vitro CETP activity assay, with the modification that plasma from the treated animals is used as the CETP source in the assay.

A strain of transgenic mice that express human CETP (Taconic, Germantown, N.Y.) can also be used to test compounds of this invention. Test compounds can be administered orally in selected aqueous or oil based vehicles for up to one week. At various times after dosing, ranging from 4 h to 48 h, blood/plasma can be obtained. The CETP activity can be determined by a method similar to that described above for the in vitro CETP activity assay, with the modification that plasma from the treated animals is used as the CETP source in the assay.

Alternatively, a strain of transgenic mice that express both human CETP and human apolipoprotein A-1 (Taconic, Germantown, N.Y.) can be used to test compounds of this invention. Test compounds can be administered orally in selected aqueous or oil based vehicles for up to one week. At various times after dosing, ranging from 4 h to 48 h, blood/plasma is obtained. CETP activity can be determined by a method similar to that described for the in vitro CETP activity assay, with the modification that plasma from the treated animals is used as the CETP source in the assay.

In Vivo Assay of Plasma Lipids

Activity of compounds of this invention in vivo can be evaluated by comparing the level of elevation of HDL cholesterol relative to a control by a given amount of a compound in a CETP-containing animal species. A strain of transgenic mice that express both human CETP and human apolipoprotein A-1 (Taconic, Germantown, N.Y.) can be used to evaluate compounds of this invention. Test compounds are administered to the animals once orally in selected aqueous or oil based vehicles. At various times after dosing, ranging from 4 h to 24 h, blood is obtained. The blood is allowed to clot, and serum is obtained from the clotted blood by centrifugation. The HDL cholesterol levels in the serum can be determined by known procedures using HDL-C plus reagents (Roche/Hitachi, Indianapolis, Ind.) with a clinical chemistry analyzer (Roche/Hitachi, Indianapolis, Ind.). Additional serum lipids can be analyzed by enzymatic methods. Lipids in the VLDL, LDL and HDL fractions are analyzed by enzymatic methods after precipitation or size exclusion chromatography. An example of the elevation of HDL cholesterol levels at 8 hr after administration are summarized in Table 1.

TABLE 1

Elevation of HDL cholesterol levels at 8 hr

| Compound of Example No. | Single Oral Dose (mg/kg) | % HDL cholesterol increase |
| --- | --- | --- |
| 3 | 30 | 71 |
| 16 | 30 | 82 |
| 17 | 30 | 73 |
| 18 | 30 | 105 |
| 20 | 30 | 72 |
| 25 | 30 | 142 |
| 27 | 30 | 128 |
| 30 | 30 | 54 |
| 31 | 30 | 114 |
| 32 | 30 | 128 |
| 33 | 30 | 354 |
| 50 | 30 | 127 |
| 73 | 30 | 374 |
| 77 | 30 | 229 |
| 89 | 30 | 186 |
| 94 | 30 | 154 |
| 129 | 30 | 92 |
| 139 | 30 | 130 |
| 141 | 30 | 74 |
| 142 | 30 | 90 |
| 148 | 30 | 224 |
| 151 | 30 | 165 |
| 153 | 30 | 165 |
| 154 | 30 | 99 |
| 165 | 30 | 177 |
| 166 | 30 | 102 |
| 170 | 30 | 95 |
| 175 | 30 | 100 |
| 178 | 30 | 128 |
| 185 | 30 | 155 |
| 187 | 30 | 124 |
| 191 | 30 | 91 |
| 192 | 30 | 102 |
| 196 | 30 | 126 |
| 200 | 30 | 153 |
| 201 | 30 | 147 |
| 202 | 30 | 206 |

The efficacy of compounds of the invention in vivo can also be evaluated utilizing Syrian Golden Hamsters. The compounds can be tested in hamsters made hypercholesterolemic by feeding a high fat high cholesterol diet for a minimum of two weeks or in non-hypercholesterolemic hamsters fed normal chow for two weeks. Test compounds can be administered orally in selected aqueous or oil based vehicles for up to 1 week. Serum from the animals can be obtained, and lipids can be analyzed by enzymatic methods. Lipids in the VLDL, LDL and HDL fractions can be analyzed by known enzymatic methods after precipitation or size exclusion chromatography.

Alternatively, a strain of transgenic mice that expresses human CETP (Taconic, Germantown, N.Y.) can be used to test the efficacy of the compounds of this invention. The hCETP mice can be made hypercholesterolemic by feeding a high fat chow diet such as TD 88051, as described by Nishina et al. (J Lipid Res., 31, 859-869 (1990)) for at least two weeks before the start of the study. Test compounds can be administered orally to the animals in selected aqueous or oil based vehicles for up to 1 week. Serum can be obtained from the animals. Lipids from the serum can be analyzed by enzymatic methods. Lipids in the VLDL, LDL and HDL fractions are analyzed by enzymatic methods after precipitation or size exclusion chromatography.

Method of Treatment

As used herein, the term "effective amount" means an amount of compound of the present invention, i.e., Formula I, which is capable of alleviating the symptoms of the various pathological conditions herein described. A specific dose of a compound administered according to this invention will, of course, be determined by the particular circumstances surrounding the case including, for example, but not limited to: the compound administered, the route of administration, the state of being of the patient, and the pathological condition being treated. A typical daily dose will contain a nontoxic dosage level of from about 0.01 mg to about 1000 mg/day of a compound of the present invention. Preferred daily doses generally will be from about 1 mg to about 250 mg/day.

The compounds of this invention may be administered by a variety of routes including oral, rectal, transdermal, subcutaneous, intravenous, intramuscular, and intranasal. These compounds preferably are formulated prior to administration, the selection of which will be decided by the attending physician. Thus, another aspect of the present invention is a pharmaceutical composition comprising an effective amount of a compound of Formula I, or a pharmaceutically acceptable salt thereof, solvate, prodrug, enantiomer or prodrug thereof, and a pharmaceutically acceptable carrier, diluent, or excipient. The total active ingredients in such formulations comprises from 0.1% to 99.9% by weight of the formulation.

The term "pharmaceutically acceptable" as used herein means that the carrier, diluent, excipients and salt are compatible with the other ingredients of the formulation and not deleterious to the recipient thereof.

Pharmaceutical formulations of the present invention may be prepared by procedures known in the art using well-known and readily available ingredients. For example, the compounds of Formula I can be formulated with common excipients, diluents, or carriers, and formed into tablets, capsules, suspensions, powders, and the like. Non limiting examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium, and magnesium stearate, and solid polyethyl glycols.

The compounds also may be formulated as elixirs or solutions for convenient oral administration or as solutions appropriate for parenteral administration, for example, by intramuscular, subcutaneous or intravenous routes. Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of Formula I, generally, will be administered in a convenient formulation as determined by the attending physician. The following formulation examples are only illustrative and are not intended to limit the scope of the present invention.

Formulations

Compounds of the invention may be formulated following one or more of the formulation examples, procedures, protocols or mixing ratios below. In the formulations which follow, the term "Active Ingredient" as used herein means a compound of Formula I, a salt, solvate, racemate, enantiomer diastereomer, mixture of diastereomers, prodrug thereof, or a combination of a compound of Formula I and other effective agents for the treatment or prevention of dyslipidemia, atherosclerosis, or other co-morbid conditions and symptoms.

Formulation 1: Gelatin Capsules

Hard gelatin capsules can be prepared according to the following:

| Ingredient | Quantity (mg/capsule) |
| --- | --- |
| Active ingredient | 0.1-1000 |
| Starch, NF | 0-650 |
| Starch flowable powder | 0-650 |
| Silicone fluid 350 centistokes | 0-15 |

The formulation above may be changed in compliance with the reasonable variations provided.

Formulation 2: Tablets

A tablet formulation, each tablet containing 2.5-1,000 mgs of active ingredient, can be prepared using the ingredients below:

| Ingredient | Quantity (mg/tablet) |
| --- | --- |
| Active ingredient | 2.5-1000 |
| Cellulose, microcrystalline | 200-650 |
| Silicon dioxide, fumed | 10-650 |
| Stearate acid | 5-15 |

The components are blended and compressed to form tablets.

Formulation 3: Tablets

Alternatively, tablets, each containing 25-1000 mg of active ingredient, can be prepared according to the following:

| Ingredient | Quantity (mg/tablet) |
| --- | --- |
| Active ingredient | 25-1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and thoroughly blended. The solution of polyvinylpyrrolidone is mixed with the blended powders. The blended powders are then passed through a No. 14 mesh U.S. sieve and pelletized or formed into granules. The granules so produced are dried at 50°-60° C. and passed through a No. 18 mesh U.S. sieve. The sodium carboxymethyl starch, magnesium stearate, and talc, previously passed through a No. 60 U.S. sieve, are then added to the granules, which after mixing, are compressed on a tablet machine to yield tablets.

Formulation 4: Suspensions

A suspensions containing 0.1-1000 mg of medicament per 5 ml dose can be prepared as follows:

| Ingredient | Quantity (mg/5 ml) |
| --- | --- |
| Active ingredient | 0.1-1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The active ingredient is passed through a No. 45 mesh U.S. sieve and then blended with the sodium carboxymethyl cellulose and syrup to form a smooth paste. The benzoic acid solution, flavor, and color are diluted with an amount of purified water and added, with stirring to the paste. Sufficient purified water is then added to provide the suspension with the desired volume (or concentration).

Formulation 5: Aerosol

An aerosol solution can be prepared as follows:

| Ingredient | Quantity (% by weight) |
| --- | --- |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The desired amount is then fed to a stainless steel container and diluted with the remaining propellant. The valve units are then fitted to the container.

Formulation 6: Intravenous Solution

A solution suitable for intravenous administration can be prepared as follows:

| Ingredient | Quantity |
| --- | --- |
| Active ingredient | 50 mg |
| Isotonic saline | 1,000 mL |

A solution comparing the above ingredients can be intravenously administered to a patient at a rate of about 1 mL per minute or as prescribed by a physician.

EXAMPLES

Compounds of the invention may be prepared following or in analogy to one or more of the Examples and procedure below.

Example 1

Synthesis of (+/−)-Isopropyl 5-[(3,5-bistrifluorom-ethylbenzyl)-(2-methyl-2H-tetrazol-5-yl)amino]-7-bromo-2,3,4,5-tetrahydrobenzo[b]azepine-1-carboxylate

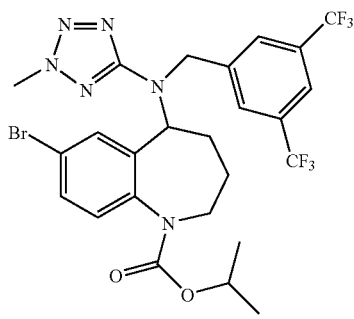

Step 1. Preparation of Methyl 5-bromo-2-isopropoxycarbonylaminobenzoate

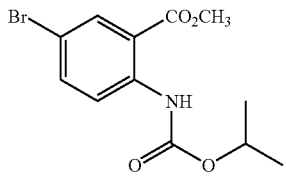

Add isopropyl chloroformate (36.9 mL, 36.9 mmol, 1.0 M in toluene) dropwise to a solution of methyl 2-amino-5-bromobenzoate (5.0 g, 24.6 mmol) and pyridine (80.0 mL, 36.9 mmol) in dichloromethane (80 mL) at room temperature under an atmosphere of nitrogen and stir for 1.5 h. Pour the reaction into water (100 mL) and separate the layers. Extract the aqueous layer with dichloromethane (2×40 mL) and combine the organic extracts and wash with 2 N hydrochloric acid, saturated sodium hydrogen carbonate, and brine (80 mL each). Dry the organic layer over anhydrous sodium sulfate, filter, and remove the solvent under reduced pressure to afford the title compound as a pale yellow solid (6.68 g, 86%). $^1$H NMR (CDCl$_3$) δ 1.31 (d, J=6.3 Hz, 6H), 3.92 (s, 3H), 5.03 (septet, J=6.3 Hz, 1H), 7.61 (dd, J=1.9, 8.5 Hz, 1H), 8.11 (d, J=1.9 Hz, 1H), 8.40 (d, J=8.5 Hz, 1H), 10.31 (br s, 1H). ESI MS m/z 316 [C$_{12}$H$_{14}$BrNO$_4$+H]$^+$.

Step 2. Preparation of Methyl 5-bromo-2-[isopropoxycarbonyl-(3-methoxycarbonylpropyl)amino]benzoate

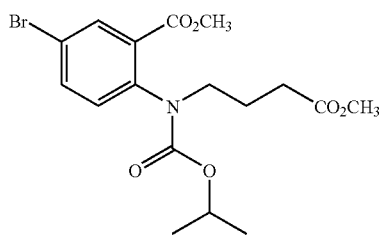

Heat a suspension of methyl 5-bromo-2-isopropoxycarbonylaminobenzoate (10.0 g, 31.6 mmol), methyl 4-bromobutyrate (22.9 g, 126 mmol) and cesium carbonate (41.6 g, 126 mmol) in N,N-dimethylformamide (150 mL) under nitrogen at 80° C. for 24 h. Cool the mixture to room temperature and pour into water (200 mL). Extract with ethyl acetate (3×100 mL) and wash the organic extracts with water (3×100 mL) and brine (100 mL). Dry the organic layer over anhydrous sodium sulfate, filter, and remove the solvent under reduced pressure. Chromatograph the residue over silica gel, eluting with hexanes/ethyl acetate (60:40), to provide the title compound as a colorless oil (11.8 g, 89%). $^1$H NMR (CDCl$_3$, 300 MHz) δ 1.05-1.07 (m, 4H), 1.30-1.32 (m, 2H), 1.89-1.94 (m, 2H), 2.38-2.44 (m, 2H), 3.46-3.60 (m, 1H), 3.65 (s, 3H), 3.68-3.79 (m, 1H), 3.86 (s, 3H), 4.85-5.01 (m, 1H), 7.12 (d, J=8.3 Hz, 1H), 7.62 (dd, J=1.7, 8.4 Hz, 1H), 8.07 (brs, 1H); ESI MS m/z 416 [C$_{17}$H$_{22}$BrNO$_6$+H]$^+$.

Step 3. Preparation of (+/−)-Isopropyl 7-bromo-5-oxo-2,3,4,5-tetrahydrobenzo[b]azepine-1-carboxylate

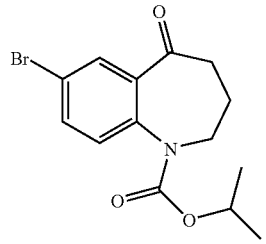

Add a solution of methyl 5-bromo-2-[methoxycarbonylpropyl)amino]benzoate (11.7 g, 28.1 mmol) in toluene (100 mL) to a suspension of potassium tert-butoxide (6.31 g, 56.2 mmol) in toluene (100 mL) at 70° C. under an atmosphere of nitrogen over a period of 30 min. After 15 min, cool the mixture to room temperature and pour the suspension into ice water (500 mL). Adjust the pH of the solution to pH=3 with 2 N hydrochloric acid (25 mL) and separate the layers. Extract the aqueous layer with ethyl acetate (3×200 mL) and combine the organic extracts. Dry the organic layer over anhydrous sodium sulfate, filter, and remove the solvent under reduced pressure to provide (+/−)-1-isopropyl-4-methyl-7-bromo-5-oxo-2,3,4,5-tetrahydrobenzo[b]azepine-1,4-dicarboxylate as an orange oil (10.5 g, 98% crude). Dissolve (+/−)-1-isopropyl-4-methyl-7-bromo-5-oxo-2,3,4,5-tetrahydrobenzo[b]azepine-1,4-dicarboxylate (10.5 g, 27.3 mmol) in glacial acetic acid (100 mL) and add water (10 mL) followed by concentrated hydrochloric acid (35 mL) and heat the resulting solution at reflux for 1 h. Cool the mixture to room temperature and pour into ice water (500 mL). Adjust the to pH=8 with potassium hydroxide (85 g) in water (200 mL), and extract the mixture with ethyl acetate (3×150 mL) and combine the organic extracts. Dry the organic layer over anhydrous sodium sulfate, filter, and remove the solvent under reduced pressure. Dissolve the crude material (12.0 g) in dichloromethane (30 mL) and cool to 0° C. To the solution add pyridine (2.0 mL, 25.5 mmol) followed by dropwise addition of 1.0 M solution of isopropyl chloroformate in toluene (19.1 mL, 19.1 mmol) and stir for 1.5 h. Pour the reaction into water (100 mL) and separate the layers. Extract the aqueous layer with dichloromethane (2×40 mL) and combine the organic extracts and wash with 2 N hydrochloric acid, saturated sodium hydrogen carbonate, and brine (80 mL each). Dry the organic layer over anhydrous sodium sulfate, filter, and remove the solvent under reduced pressure. Chromatograph the residue over silica gel eluting with hexanes/ethyl acetate (60:40), to afford the title compound as a yellow solid (3.5 g, 40% over three steps). $^1$H NMR (CDCl$_3$, 300 MHz) δ 1.30 (d, J=6.2 Hz, 6H), 2.09-2.21 (m, 2H), 2.75-2.79 (m, 2H), 3.75-3.80 (m, 2H), 5.05 (septet, J=6.2 Hz, 1H), 7.38 (m, 1H), 7.61 (dd, J=1.9, 8.5 Hz, 1H), 7.67 (m, 1H), 7.98 (d, J=8.5 Hz, 1H); ESI MS m/z 326 [C$_{14}$H$_{16}$BrNO$_3$+H]$^+$.

Step 4. Preparation of (+/−)-Isopropyl 5-(3,5-bistrifluoromethylbenzylamino)-7-bromo-2,3,4,5-tetrahydrobenzo[b]azepine-1-carboxylate

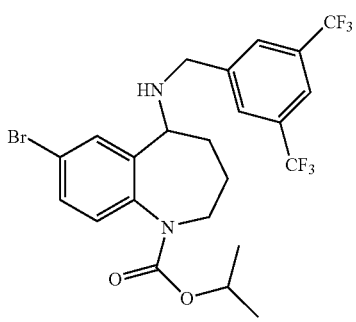

Add 3,5-bis(trifluoromethyl)benzylamine (3.23 g, 13.31 mmol) followed by titanium isopropoxide (3.69 mL, 12.35 mmol) to a solution of isopropyl 7-bromo-5-oxo-2,3,4,5-tetrahydro benzo[b]azepine-1-carboxylate (3.10 g, 9.50 mmol) in anhydrous tetrahydrofuran (30 mL) at room temperature under an atmosphere of nitrogen and stir the solution for 16 h. Dilute the solution with methanol (30 mL) and slowly add sodium borohydride (0.539 g, 14.25 mmol) over a period of 15 min, then stir at room temperature for 3.5 h. Quench the reaction with the addition of 2 N NaOH (50 mL) and water (50 mL) and stir for 30 min. Filter the mixture and wash the solids with ethyl acetate/ethanol (4:1, 3×100 mL). Separate the filtrate and wash the organic layer with 2 N NaOH, 2 N hydrochloric acid, and brine (50 mL each). Dry the organic layer over anhydrous sodium sulfate, filter, and remove the solvent under reduced pressure to afford the title compound as an orange oil (5.08 g, 96%), which is of sufficient purity to use for subsequent chemistry without additional purification.

Step 5. Preparation of (+/−)-Isopropyl 5-[(3,5-bistrifluoromethylbenzyl)cyanoamino]-7-bromo-2,3,4,5-tetrahydrobenzo[b]azepine-1-carboxylate

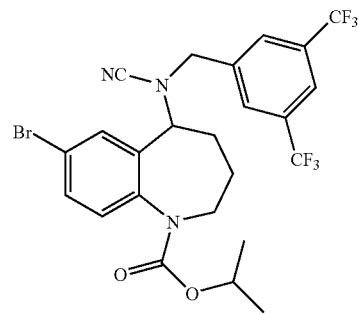

Add a solution of 1-cyanoimidazole in N,N-dimethylacetamide to a solution of isopropyl 5-(3,5-bistrifluoromethylbenzylamino)-7-bromo-2,3,4,5-tetrahydrobenzo[b]azepine-1-carboxylate in N,N-dimethylacetamide at room temperature under nitrogen and heat the mixture to 100° C. Pour the cooled mixture into water and extract with methylene chloride. Dry the organic layer over anhydrous sodium sulfate, filter, and remove the solvent under reduced pressure. Chromatograph the residue over silica gel to afford the title compound.

Step 6. Preparation of (+/−)-Isopropyl 5-[(3,5-bistrifluoromethylbenzyl)-(2H-tetrazol-5-yl)amino]-7-bromo-2,3,4,5-tetrahydrobenzo[b]azepine-1-carboxylate

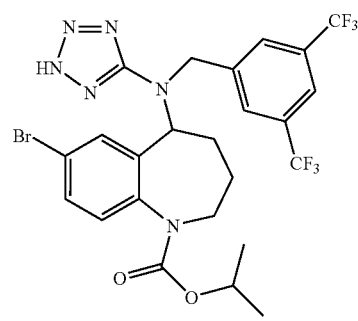

Add a solution of (+/−)-isopropyl 5-[(3,5-bistrifluoromethylbenzyl)-cyanoamino]-7-bromo-2,3,4,5-tetrahydrobenzo[b]azepine-1-carboxylate in anhydrous N,N-dimethylformamide dropwise to a stirred suspension of sodium azide and ammonium chloride in anhydrous N,N-dimethylformamide and heat the resulting yellow mixture at 110° C. under nitrogen. Dilute the cooled mixture with water and 2 N NaOH and wash with diethyl ether. Acidify with 5 N HCl, collect the precipitate and wash with water to provide the title compound.

Step 7. Preparation of (+/−)-Isopropyl 5-[(3,5-bistrifluoromethylbenzyl)-(2-methyl-2H-tetrazol-5-yl)amino]-7-bromo-2,3,4,5-tetrahydrobenzo[b]azepine-1-carboxylate

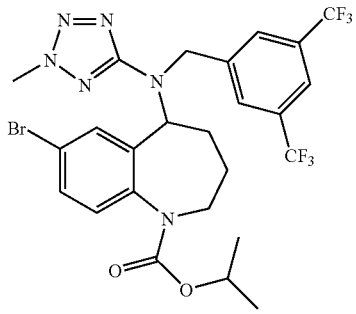

Add tri-n-butylphosphine to a solution of (+/−)-isopropyl 5-[(3,5-bistrifluoromethylbenzyl)-(2H-tetrazol-5-yl)amino]-7-bromo-2,3,4,5-tetrahydrobenzo[b]azepine-1-carboxylate, methanol and 1,1'-(azocarbonyl)dipiperidine (ADDP) in toluene at 0° C. under nitrogen and warm to room temperature. Dilute the mixture with ethyl acetate, wash with 2 N HCl and brine and dry over sodium sulfate. Remove the solvents under reduced pressure and purify the residue by flash column chromatography on silica gel to provide the title compound.

Example 2

Synthesis of (+/−)-Isopropyl 5-[(3,5-bistrifluoromethylbenzyl)-(3-methylisothiazol-5-yl)amino]-7-bromo-2,3,4,5-tetrahydrobenzo[b]azepine-1-carboxylate

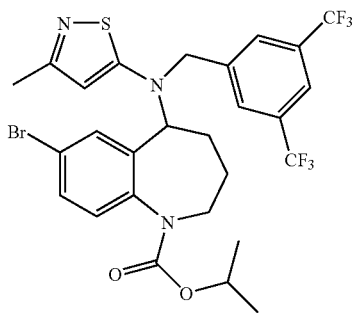

Step 1. Preparation of (+/−)-Isopropyl 7-bromo-5-(3-methylisothiazol-5-ylamino)-2,3,4,5-tetrahydrobenzo[b]azepine-1-carboxylate

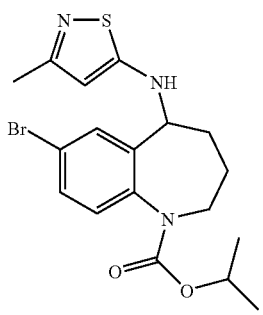

Add titanium isopropoxide to a stirring solution of 5-amino-3-methylisothiazole hydrochloride and isopropyl 7-bromo-5-oxo-2,3,4,5-tetrahydro benzo[b]azepine-1-carboxylate (Example 1, Step 3) in anhydrous tetrahydrofuran at room temperature under nitrogen. After the appropriate stirring time, dilute the solution with methanol and slowly add sodium borohydride, and stir at room temperature. After an appropriate stirring time, dilute the reaction with addition of 2 N NaOH and water and stir for 30 min. Remove the solids by vacuum filtration and wash the solids with ethyl acetate/ethanol (4:1). Separate the filtrate and wash the organic layer with 2 N NaOH, 2 N hydrochloric acid, and brine. Dry the organic layer over anhydrous sodium sulfate and remove the solvent under reduced pressure to afford the title compound.

Step 2. Preparation of (+/−)-Isopropyl 5-[(3,5-bistrifluoromethylbenzyl)-(3-methylisothiazol-5-yl)amino]-7-bromo-2,3,4,5-tetrahydrobenzo[b]azepine-1-carboxylate

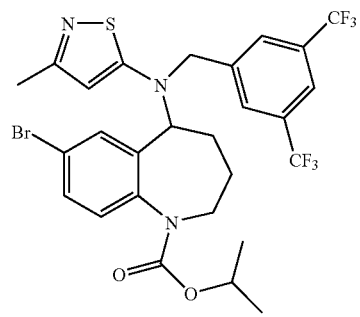

Add sodium hydride to a stirring solution of isopropyl 7-bromo-5-(3-methylisothiazol-5-ylamino)-2,3,4,5-tetrahydrobenzo[b]azepine-1-carboxylate in anhydrous tetrahydrofuran at room temperature under nitrogen. After the appropriate stirring time, treat the mixture with 3,5-bis(trifluoromethyl)benzyl bromide and continue stirring for an appropriate time. Dilute the mixture with ethyl acetate, wash with water and brine and dry over sodium sulfate. Remove the solvents under reduced pressure and purify the residue by flash column chromatography on silica gel to provide the title compound.

Example 3

Synthesis of (S)-(3,5-Bistrifluoromethylbenzyl)-(1-cyclopentylmethyl-7-methyl-8-trifluoromethyl-2,3,4,5-tetrahydro-1H-benzo[b]azepin-5-yl)-(2-methyl-2H-tetrazol-5-yl)amine

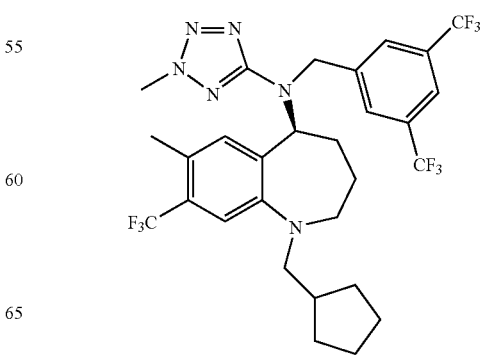

Step 1. Preparation of Methyl 2-nitro-4-trifluoromethylbenzoate

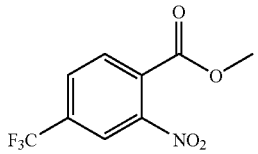

Add concentrated sulfuric acid (120 mL) dropwise to a solution of 2-nitro-4-trifluoromethylbenzoic acid (200 g, 850 mmol) in methanol (2 L) at room temperature under nitrogen and heat the mixture at reflux for 48 h. Cool the solution to room temperature and remove most of the solvent by evaporation at 45° C. under reduced pressure. Pour the turbid residue onto ice/water (2 L) and extract with ethyl acetate (2×1 L). Wash the combined organic extracts with brine (1 L), dry over anhydrous magnesium sulfate, filter and remove the solvent under reduced pressure to provide the title compound as a yellow oil (212.2 g, >99%). $^1$H NMR (300 MHz, CDCl$_3$) δ 8.21 (s, 1H), 7.95 (d, J=1.13 Hz, 1H), 7.90 (s, 1H), 3.97 (s, 3H).

Step 2. Preparation of Methyl 2-amino-4-trifluoromethylbenzoate

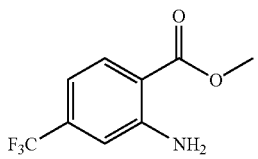

Add a solution of methyl 2-nitro-4-trifluoromethylbenzoate (106 g, 425 mmol) in ethyl acetate (2.2 L) to a slurry of 10% palladium on carbon (11.0 g) in ethyl acetate (200 mL) and stir the suspension at room temperature under an atmosphere of hydrogen at 60 psi for 3 h. Filter the suspension through a pad of Celite® and wash the pad with additional ethyl acetate. Remove the solvents under reduced pressure and purify the residue by column chromatography on silica gel, eluting with isohexane/ethyl acetate (9:1), to provide the title compound as a white crystalline solid (84 g, 95%). $^1$H NMR (300 MHz, CD$_3$OD) δ 7.93 (d, J=8.48 Hz, 1H), 7.06 (s, 1H), 6.78 (s, 1H), 4.86 (s, 3H), 3.89 (s, 3H).

Step 3. Preparation of methyl 2-amino-5-iodo-4-trifluoromethylbenzoate

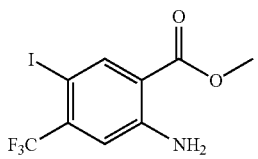

Add a solution of methyl 2-amino-4-trifluoromethylbenzoate (178 g, 812 mmol) in ethanol (3.3 L) to a suspension of iodine (206.1 g, 812 mmol) and silver (II) sulfate (253 g, 812 mmol) in ethanol (5 L) at room temperature under an atmosphere of nitrogen and stir for 2 h. Filter the suspension through a pad of a Celite®, wash the pad with additional ethanol (2 L) and remove the solvents from the combined filtrates under reduced pressure at 40° C. Dissolve the residue in ethyl acetate (7.5 L) and wash with saturated sodium bicarbonate solution (3×1.5 L), water (3×1.5 L) and brine (2 L). Dry the organic phase over anhydrous magnesium sulfate, filter and remove the solvent under reduced pressure to give the title compound as a pale brown crystalline solid (276.0 g, 99%). $^1$H NMR (300 MHz, CDCl$_3$) δ 8.39 (1H, s), 6.99 (1H, s), 5.93 (2H, s), 3.90 (3 H, s).

Step 4. Preparation of Methyl 2-amino-5-methyl-4-trifluoromethylbenzoate

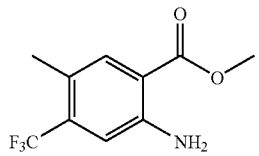

Add cesium fluoride (184.3 g, 1.21 mol), methyl boronic acid (63.7 g, 1.05 mol, 3 mol equiv.) and bis(diphenylphosphinoferrocene)palladium(II) chloride (27.83 g, 35.1 mmol) to a solution of methyl 2-amino-5-iodo-4-trifluoromethylbenzoate (121 g, 351 mmol) in anhydrous 1,4-dioxane (2.5 L) at room temperature under an atmosphere of nitrogen and heat the mixture at 80° C. for 3 h. Allow the mixture to cool to room temperature then partition between ethyl acetate (2.5 L) and water (2.5 L) and filter through a pad of Celite® to remove the fine black suspension. Extract the aqueous phase with ethyl acetate (2×100 mL) and wash the combined organic extracts with brine (1 L). Dry over anhydrous magnesium sulfate, filter and remove the solvent under reduced pressure at 45° C. to give a red oil. Purify the residue by column chromatography on silica gel, eluting with isohexane/ethyl acetate (9:1), to give the title compound as a pale yellow crystalline solid (75.25 g, 92%). $^1$H NMR (300 MHz, CDCl$_3$) δ 7.73 (s, 1H), 6.93 (s, 1H), 5.70 (s, 2H), 3.90 (s, 3H), 2.33 (s, 3H).

Step 5. Preparation of methyl 2-(N-Isopropoxycarbonyl)amino-5-methyl-4-trifluoromethylbenzoate

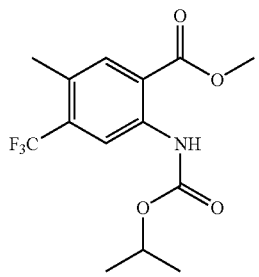

Add isopropyl chloroformate (900 mL, 900 mmol, 1M in toluene) dropwise to a solution of methyl 2-amino-5-methyl-4-trifluoromethylbenzoate (200 g, 858 mmol) and pyridine (170 mL, 2.14 mol) in anhydrous dichloromethane (2 L) at 0-5° C. under an atmosphere of nitrogen, keeping the internal reaction temperature below 5° C. during the addition. Allow the solution/suspension to warm to room temperature and stir for 2 h. Add 1M HCl (2 L) and stir the mixture for 10 min. Collect the organic phase and wash with brine (1 L), dry over anhydrous magnesium sulfate, filter and remove the solvents under reduced pressure at 45° C. to give the title compound as a yellow crystalline solid (283 g, >99%). $^1$H NMR (300 MHz, CDCl$_3$) δ 10.25 (s, 1H), 8.80 (s, 1H), 7.88 (s, 1H), 4.97-5.09 (m, 1H), 3.95 (s, 3H), 2.43 (d, J=1.32 Hz, 3H), 1.27-1.35 (m, 6H).

Step 6. Preparation of Methyl 2-{N-isopropoxycarbonyl-N-(3-methoxycarbonylpropyl)}amino-5-methyl-4-trifluoromethylbenzoate

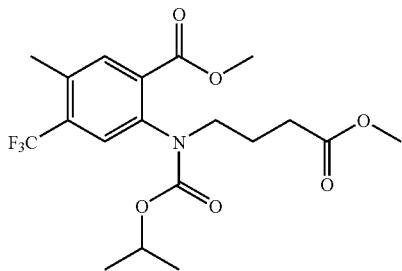

Add cesium carbonate (504 g, 1.55 mol, 2.5 mol equiv.) and methyl 4-bromobutyrate (100 mL, 800 mmol) to a solution of methyl 2-(N-isopropoxycarbonyl)amino-5-methyl-4-trifluoromethylbenzoate (204 g, 618 mmol) in anhydrous N,N-dimethylformamide (2.4 L) at room temperature under an atmosphere of nitrogen and heat the suspension at 55° C. for 2.5 h. Pour the cooled mixture into ice/water (7.5 L) and stir for 1 h. Filter the suspension and wash the filter pad with water (3×1 L) and pull dry. Dry at 40° C. under vacuum to provide the title compound as a cream solid (261.3 g, 96%). $^1$H NMR (300 MHz, dimethyl sulfoxide-d$_6$) at 80° C. δ 7.84 (s, 1H), 7.57 (s, 1H), 3.76-3.84 (m, 3H), 3.52-3.65 (m, 5H), 2.33 (t, J=7.25 Hz, 2H), 1.72-1.83 (m, 2H), 1.09 (d, J=4.71 Hz, 6H).

Step 7. Preparation of (+/−)-1-Isopropyl 4-methyl-7-methyl-5-oxo-8-trifluoromethyl-2,3,4,5-tetrahydrobenzo[b]azepine-1,4-dicarboxylate

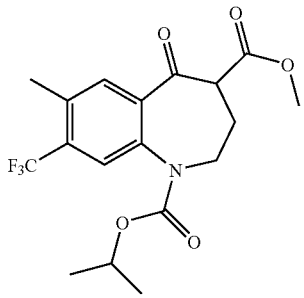

Add a solution of methyl 2-{N-isopropoxycarbonyl-N-(3-methoxycarbonylpropyl)}amino-5-methyl-4-trifluoromethylbenzoate (130 g, 310 mmol) in tetrahydrofuran (3.7 L) to a solution of potassium tert-butoxide (618 mL, 618 mmol, 1M in tetrahydrofuran) in tetrahydrofuran (3.7 L) at room temperature under an atmosphere of nitrogen over a period of 2 h. Stir for 1 h and acidify the mixture to neutral pH with 1M HCl (600 mL). Extract with dichloromethane (2×4 L) and wash the combined organic extracts with brine (3×1 L). Dry over anhydrous magnesium sulfate, filter and remove the solvents under reduced pressure. Purify the residue by column chromatography on silica gel, eluting with isohexane/ethyl acetate (9:1), to give the title compound as a pale yellow solid (99.7 g, 83%). LC MS m/z 410 (M+Na)$^+$.

Step 8. Preparation of Isopropyl 7-methyl-5-oxo-8-trifluoromethyl-2,3,4,5-tetrahydrobenzo[b]azepine-1-carboxylate

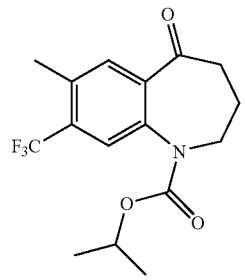

Add 5 M HCl (2.115 L) to a solution of (+/−)-1-isopropyl-4-methyl-7-methyl-5-oxo-8-trifluoromethyl-2,3,4,5-tetrahydrobenzo[b]azepine-1,4-dicarboxylate (197.2 g, 509 mmol) in glacial acetic acid (500 mL) at room temperature under an atmosphere of nitrogen and heat the stirred mixture at 87-88° C. for 24 h. Allow the mixture to cool to room temperature with stirring and filter the suspension. Wash the collected solids with water and pull dry. Dry under vacuum at 45° C. to give the title compound as a cream solid (145.4 g, 87%). $^1$H NMR (400 MHz, CDCl$_3$) δ 7.74 (s, 2H), 5.03-5.09 (m, 1H), 3.79 (t, J=6.24 Hz, 2H), 2.77 (t, J=6.72 Hz, 2H), 2.49 (d, J=1.47 Hz, 3H), 2.10-2.20 (m, J=6.72, 6.72, 6.72, 6.72 Hz, 2H), 1.27 (d, J=3.91 Hz, 6H).

Step 9. Preparation of 7-Methyl-8-trifluoromethyl-1,2,3,4-tetrahydrobenzo[b]azepin-5-one

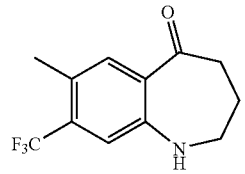

Heat a degassed mixture of isopropyl 7-methyl-5-oxo-8-trifluoromethyl-2,3,4,5-tetrahydrobenzo[b]azepine-1-carboxylate (6.68 g, 20.28 mmol) and sodium chloride (37.5 g) in water (7 mL) and dimethyl sulfoxide (180 mL) at reflux under nitrogen for 5 h. Dilute the cooled mixture with water (500 mL) and extract with ethyl acetate (2×300 mL). Wash the combined organic extracts with brine (200 mL), dry over anhydrous sodium sulfate and filter. Remove the solvents under reduced pressure and purify the residue by column chromatography on silica gel, eluting with ethyl acetate/hexanes (1:4), to afford the title compound as a yellow solid (3.94 g, 80%). ESI MS m/z 242 (M−H)$^−$.

Step 10. Preparation of tert-Butyl 7-methyl-5-oxo-8-trifluoromethyl-2,3,4,5-tetrahydrobenzo[b]azepine-1-carboxylate

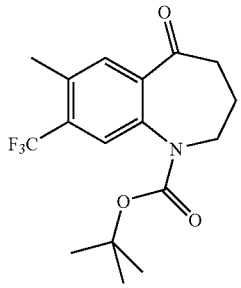

Add di-tert-butyl dicarbonate (6.67 g, 30.58 mmol), diisopropylethylamine (5.32 mL, 30.58 mmol) and 4-DMAP (374 mg, 3.1 mmol) to a solution of 7-methyl-8-trifluoromethyl-1,2,3,4-tetrahydrobenzo[b]azepin-5-one (2.48 g, 10.19 mmol) in dichloromethane (50 mL) under nitrogen at 0° C. and warm the mixture to room temperature. Stir the mixture for 24 h and dilute with dichloromethane (50 mL). Wash the mixture with 2 N HCl (2×20 mL) and brine (20 mL) and dry over anhydrous sodium sulfate and filter. Remove the solvents under reduced pressure and purify the residue by column chromatography on silica gel, eluting with ethyl acetate/hexanes (1:3), to provide the title compound as an off-white solid (2.20 g, 63%). ESI MS m/z (243 (M–Boc)⁻.

Step 11. Preparation of (R)-tert-Butyl 5-hydroxy-7-methyl-8-trifluoromethyl-2,3,4,5-tetrahydrobenzo[b]azepine-1-carboxylate

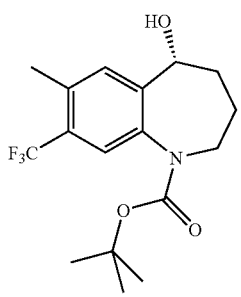

Add a solution of borane dimethylsulfide complex (3.8 mL, 7.58 mmol, 2 M in tetrahydrofuran) dropwise to a solution of (S)-2-methyl-CBS-oxazaborolidine (9.5 mL, 9.48 mmol, 1M in toluene) in dichloromethane (20 mL) at −30° C. under nitrogen. Stir the mixture for 30 min and add a solution of tert-butyl 7-methyl-5-oxo-8-trifluoromethyl-2,3,4,5-tetrahydrobenzo[b]azepine-1-carboxylate (2.17 g, 6.32 mmol) in dichloromethane (20 mL) dropwise and warm the mixture slowly to 0° C. Pour the mixture into methanol (200 mL) at −20° C. and slowly warm the stirring mixture to room temperature over 1 h. Remove the solvents under reduced pressure and purify the residue by column chromatography on silica gel, eluting with ethyl acetate/hexanes (1:2), to provide the title compound as a colorless oil (1.65 g, 76%). APCI MS m/z 345 (M+H)⁺.

Step 12. Preparation of (S)-tert-Butyl 5-azido-7-methyl-8-trifluoromethyl-2,3,4,5-tetrahydrobenzo[b]azepine-1-carboxylate

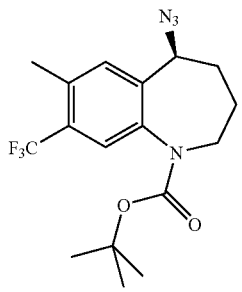

Heat a mixture of (R)-tert-butyl 5-hydroxy-7-methyl-8-trifluoromethyl-2,3,4,5-tetrahydrobenzo[b]azepine-1-carboxylate (1.60 g, 4.65 mmol), diphenylphosphoryl azide (DPPA, 1.4 mL, 6.50 mmol) and DBU (1.0 mL, 6.50 mmol) in toluene (20 mL) at 65° C. under nitrogen for 12 h. Add silica gel to the cooled mixture and remove the solvents under reduced pressure. Purify the residue by column chromatography, eluting with ethyl acetate/hexanes (1:2), to provide the title compound as a colorless oil (1.45 g, 85%). APCI MS m/z 356 (M−N₂)⁻.

Step 13. Preparation of (S)-tert-Butyl 5-amino-7-methyl-8-trifluoromethyl-2,3,4,5-tetrahydrobenzo[b]azepine-1-carboxylate

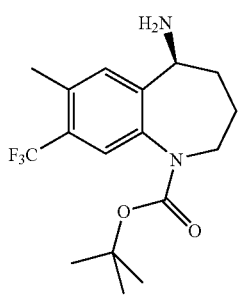

Shake a mixture of (S)-tert-butyl 5-azido-7-methyl-8-trifluoromethyl-2,3,4,5-tetrahydrobenzo[b]azepine-1-carboxylate (1.44 g, 3.89 mmol) and 5% palladium on charcoal (0.15 g, 50% wet) in methanol (50 mL) under 20 psi of hydrogen in a Parr bottle at room temperature for 12 h. Filter the mixture through Celite® and remove the solvents under reduced pressure to provide the title compound as a colorless oil (1.30 g, >99%), which is used in the next step without further purification. APCI MS m/z 344 (M+H)⁺.

Step 14. Preparation of (S)-tert-butyl 5-(3,5-bistrifluoromethylbenzylamino)-7-methyl-8-trifluoromethyl-2,3,4,5-tetrahydrobenzo[b]azepine-1-carboxylate

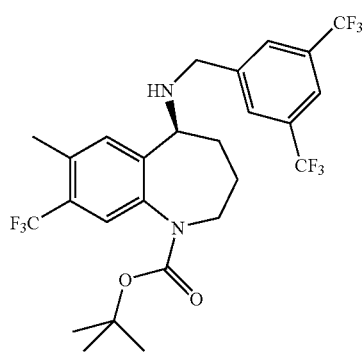

Add 3,5-bistrifluoromethylbenzaldehyde (909 mg, 3.75 mmol) to a solution of (S)-tert-butyl 5-amino-7-methyl-8-trifluoromethyl-2,3,4,5-tetrahydrobenzo[b]azepine-1-carboxylate (1.29 g, 3.75 mmol) in methanol (20 mL) at room temperature under nitrogen and stir for 2 h. Add sodium borohydride (283 mg, 7.5 mmol) and stir the mixture for 2 h. Remove the solvents under reduced pressure and dilute the residue with dichloromethane (50 mL) and water (50 mL). Collect the organic layer and extract the aqueous layer with dichloromethane (3×30 mL). Wash the combined organic extracts with water (20 mL) and brine (20 mL) and dry over anhydrous sodium sulfate. Filter and remove the solvents under reduced pressure to provide the title compound as an amber oil (2.09 g, 98%), which is used in the next step without purification. APCI MS m/z 570 (M+H)$^+$.

Step 15. Preparation of (S)-tert-butyl 5-[(3,5-bistrifluoromethylbenzyl)cyanoamino]-7-methyl-8-trifluoromethyl-2,3,4,5-tetrahydrobenzo[b]azepine-1-carboxylate

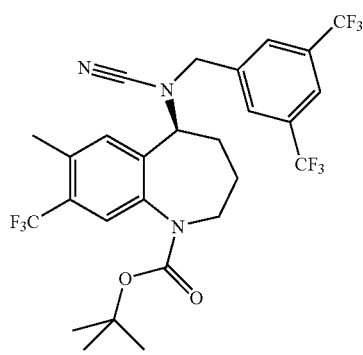

Add cyanogen bromide (1.21 mL, 6.04 mmol, 5 M solution in acetonitrile) to a solution of (S)-tert-butyl 5-(3,5-bistrifluoromethylbenzylamino)-7-methyl-8-trifluoromethyl-2,3,4,5-tetrahydrobenzo[b]azepine-1-carboxylate (2.30 g, 4.03 mmol) and diisopropylethylamine (1.05 mL, 6.04 mmol) in tetrahydrofuran (50 mL) at room temperature under nitrogen and heat the mixture at 50° C. for 12 h. Add silica gel to the cooled mixture and remove the solvents under reduced pressure. Purify the residue by column chromatography on silica gel, eluting with ethyl acetate/hexanes (2:3), to provide the title compound as a colorless oil (2.10 g, >99%), which is used in the next step without further purification: APCI MS m/z 496 (M+H−Boc)$^+$.

Step 16. Preparation of (S)-tert-Butyl 5-[(3,5-bistrifluoromethylbenzyl)-(2H-tetrazol-5-yl)amino]-7-methyl-8-trifluoromethyl-2,3,4,5-tetrahydrobenzo[b]azepine-1-carboxylate

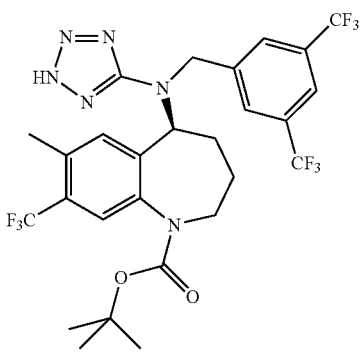

Heat a mixture of (S)-tert-butyl 5-[(3,5-bistrifluoromethylbenzyl)cyanoamino]-7-methyl-8-trifluoromethyl-2,3,4,5-tetrahydrobenzo[b]azepine-1-carboxylate (2.0 g, 3.36 mmol), triethylamine hydrochloride (694 mg, 5.04 mmol) and sodium azide (328 mg, 5.04 mmol) in anhydrous toluene (20 mL) at reflux under nitrogen for 12 h. Dilute the cooled mixture with ethyl acetate (100 mL) and wash with 2 N HCl (2×50 mL), water (50 mL) and brine (50 mL) and dry over anhydrous sodium sulfate. Filter and remove the solvent under reduced pressure to provide the title compound as an off-white foam (2.12 g, >99%), which is used in the next step without purification. ESI MS m/z 637 (M−H)$^−$.

Step 17. Preparation of (S)-tert-Butyl 5-[(3,5-bistrifluoromethylbenzyl)-(2-methyl-2H-tetrazol-5-yl)amino]-7-methyl-8-trifluoromethyl-2,3,4,5-tetrahydrobenzo[b]azepine-1-carboxylate

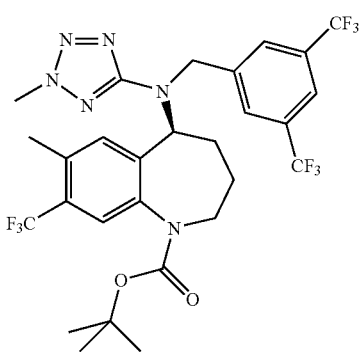

Add diisopropyl azodicarboxylate (0.56 mL, 3.94 mmol) to a solution of (S)-tert-butyl 5-[(3,5-bistrifluoromethylbenzyl)-(2H-tetrazol-5-yl)amino]-7-methyl-8-trifluoromethyl-2,3,4,5-tetrahydrobenzo[b]azepine-1-carboxylate (2.10 g, 3.29 mmol) and triphenylphosphine (1.03 g, 3.94 mmol) in methanol (0.20 mL, 4.94 mmol) and toluene (30 mL) at 0° C. under nitrogen. Warm the mixture to room temperature and stir for 12 h. Add silica gel, remove the solvents under reduced pressure and purify the residue by column chromatography on silica gel, eluting with ethyl acetate/hexanes (1:3), to provide the title compound as a colorless oil (2.04 g, 95%). APCI MS m/z 653 (M+H)⁺.

Step 18. Preparation of (S)-(3,5-bistrifluoromethyl-benzyl)-(2-methyl-2H-tetrazol-5-yl)-(7-methyl-8-trifluoromethyl-2,3,4,5-tetrahydro-1H-benzo[b]azepin-5-yl)amine

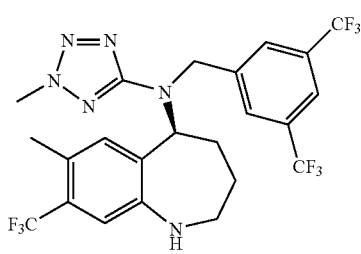

Add trifluoroacetic acid (10 mL) to a solution of (S)-tert-butyl 5-[(3,5-bistrifluoromethylbenzyl)-(2-methyl-2H-tetrazol-5-yl)amino]-7-methyl-8-trifluoromethyl-2,3,4,5-tetrahydrobenzo[b]azepine-1-carboxylate (2.04 g, 3.13 mmol) in methylene chloride (50 mL) at 0° C. under nitrogen. Warm the mixture to room temperature, stir for 8 h and pour the mixture into saturated aqueous sodium bicarbonate solution (200 mL). Extract the mixture with methylene chloride (200 mL) and wash the combined organic extracts with brine (50 mL), dry over anhydrous sodium sulfate and filter. Remove the solvent under reduced pressure to provide the title compound as a colorless oil (1.73 g, >99%), which is used in the next step without purification. APCI MS m/z 553 (M+H)⁺.

Step 19. Preparation of (S)-(3,5-Bistrifluoromethyl-benzyl)-(1-cyclopentylmethyl-7-methyl-8-trifluoromethyl-2,3,4,5-tetrahydro-1H-benzo[b]azepin-5-yl)-(2-methyl-2H-tetrazol-5-yl)amine

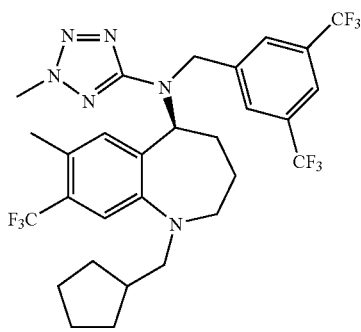

Add cyclopentanecarboxaldehyde (462 mg, 4.71 mmol) to a solution of (S)-(3,5-bistrifluoromethylbenzyl)-(2-methyl-2H-tetrazol-5-yl)-(7-methyl-8-trifluoromethyl-2,3,4,5-tetrahydro-1H-benzo[b]azepin-5-yl)amine (520 mg, 0.941 mmol) in acetic acid (1 mL) and 1,2-dichloroethane (10 mL) at room temperature under nitrogen and stir for 1 h. Add sodium triacetoxy borohydride (998 mg, 4.71 mmol) and stir for 5 min. Dilute the mixture with methylene chloride (30 mL) and wash with saturated aqueous sodium bicarbonate solution (2×10 mL). Extract the combined aqueous washes with methylene chloride (20 mL) and wash the combined organic extracts with brined (20 mL) and dry over anhydrous sodium sulfate. Remove the solvents under reduced pressure and purify the residue by column chromatography on silica gel, eluting with ethyl acetate/hexanes (1:2), to provide the title compound as a colorless oil (420 mg, 70%). APCI MS m/z 635 (M+H)⁺.

Alternative preparation of methyl 2-(N-isopropoxycarbonyl)amino-5-methyl-4-trifluoromethylbenzoate.

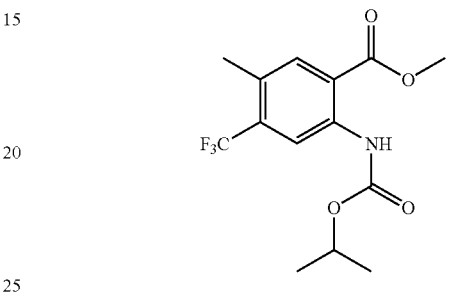

Step 1. Preparation of 2-Iodo-4-methyl-5-trifluoromethylphenylamine

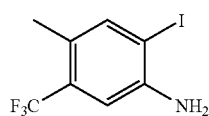

Add a solution of iodine monochloride (27.8 g, 171 mmol) in dichloromethane (180 mL) to a solution of 4-methyl-3-trifluoromethylaniline (25.0 g, 143 mmol) and sodium bicarbonate (14.4 g, 171 mmol) in methanol (180 mL) and dichloromethane (730 mL) at room temperature under nitrogen. Stir the mixture for 3 h and dilute the cooled mixture with aqueous sodium metabisulfite (500 mL). Collect the organic phase, and extract the aqueous phase with methylene chloride (200 mL). Wash the combined organic extracts with brine (250 mL), dry over anhydrous sodium sulfate and filter. Remove the solvent under reduced pressure to provide a brown oil, which crystallizes upon standing to afford the title compound as brown needles (44.4 g, >99%), which is used in the next step without purification. APCI MS m/z 302 (M+H)⁺.

Step 2. Preparation of isopropyl (2-iodo-4-methyl-5-trifluoromethylphenyl)carbamate

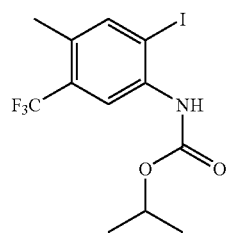

Add a solution of isopropyl chloroformate (99.6 mL, 99.6 mmol, 1M in toluene) dropwise to a solution of 2-iodo-4-methyl-5-trifluoromethylphenylamine (27.26 g, 90.55 mmol) and pyridine (14.6 mL, 181.1 mmol) in dichloromethane (350 mL) at 5° C. under an atmosphere of nitrogen and warm the mixture to room temperature. Stir for 3 h and wash the mixture with 2 N HCl (100 mL) and brine (100 mL). Dry over anhydrous sodium sulfate, filter and remove the solvent under reduced pressure to afford the title compound as a tan solid (33.59 g, 96%), which is used in the next step without purification. APCI MS m/z 388 (M+H)+.

Step 3. Preparation of methyl 2-(N-isopropoxycarbonyl)amino-5-methyl-4-trifluoromethylbenzoate

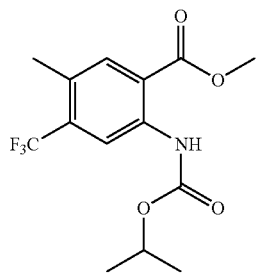

Add tetrakis(triphenylphosphine)palladium(0) (8.53 g, 7.4 mmol) to a solution of isopropyl (2-iodo-4-methyl-5-trifluoromethylphenyl)carbamate (28.59 g, 73.8 mmol) and triethylamine (10.3 mL, 73.8 mmol) in methanol (75 mL) and acetonitrile (150 mL) at room temperature under nitrogen in a stirred Parr high pressure reaction vessel and charge the unit to 20 psi of carbon monoxide. Heat the mixture to 60° C. and stir the mixture for 18 h, periodically recharging the vessel to 20-30 psi of carbon monoxide. Add silica gel to the cooled mixture and remove the solvents under reduced pressure. Purify the residue using column chromatography on silica gel, eluting with ethyl acetate/hexanes (1:9), to provide the title compound as an orange solid (19.80 g, 84%): APCI MS m/z 320 (M+H)+.

Example 4

Synthesis of 5-[(3,5-Bis-trifluoromethyl-benzyl)-(1H-tetrazol-5-yl)-amino]-7-methyl-8-trifluoromethyl-2,3,4,5-tetrahydro-benzo[b]azepine-1-carboxylic acid ethyl ester

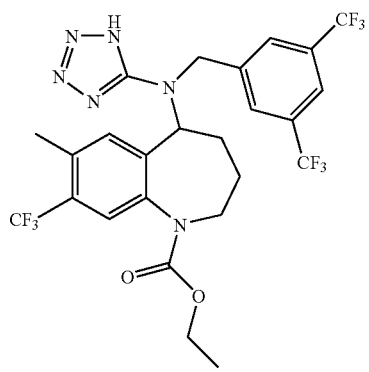

Step 1. Preparation of 5-[(3,5-Bis-trifluoromethyl-benzyl)-(1H-tetrazol-5-yl)-amino]-7-methyl-8-trifluoromethyl-2,3,4,5-tetrahydro-benzo[b]azepine-1-carboxylic acid tert-butyl ester

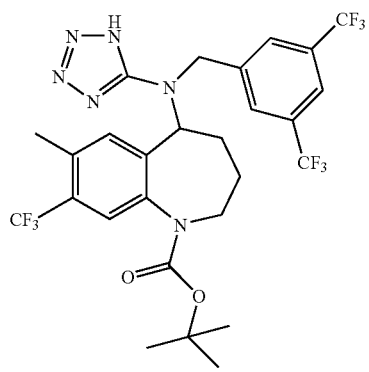

The titled compound was prepared using procedures analogous to those used in Example 1, Steps 4 to 6 and substituting tert-butyl 7-methyl-5-oxo-8-trifluoromethyl-2,3,4,5-tetrahydrobenzo[b]azepine-1-carboxylate (Example 3, step 10) for isopropyl 7-bromo-5-oxo-2,3,4,5-tetrahydro benzo[b]azepine-1-carboxylate in Example 1, Step 4. MS (ES+): 637 (M−H).

Step 2. Preparation of (3,5-Bis-trifluoromethyl-benzyl)-(7-methyl-8-trifluoromethyl-2,3,4,5-tetrahydro-1H-benzo[b]azepin-5-yl)-(1H-tetrazol-5-yl)-amine

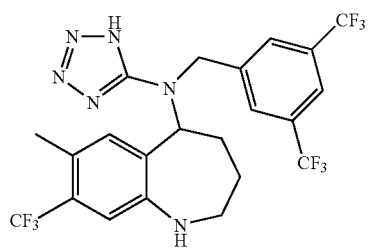

Add dichloromethane (5 mL) and trifluoroacetic acid (5 mL) to 5-[(3,5-bis-trifluoromethyl-benzyl)-(1H-tetrazol-5-yl)-amino]-7-methyl-8-trifluoromethyl-2,3,4,5-tetrahydro-benzo[b]azepine-1-carboxylic acid tert-butyl ester (0.18 g, 0.24 mmol). After stirring for 1-2 h, neutralize the reaction with sodium carbonate. Wash the organic phase with water (5 mL) and brine (5 mL). Dry the organics over sodium sulfate and filter. Chromatograph the crude material, eluting with ethyl acetate/hexane (20-60%) to provide the title compound (0.13 g, 85%) as an oil. MS (ES+): 539 (M+H).

Step 3. Preparation of 5-[(3,5-Bis-trifluoromethyl-benzyl)-(1H-tetrazol-5-yl)-amino]-7-methyl-8-trifluoromethyl-2,3,4,5-tetrahydro-benzo[b]azepine-1-carboxylic acid ethyl ester

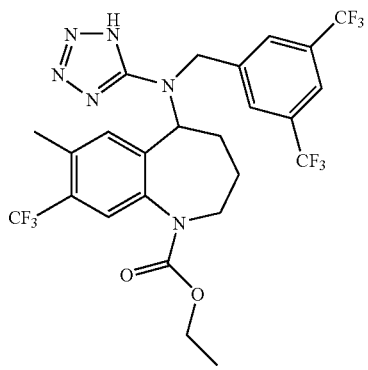

Add ethyl chloroformate (0.24 mmol) and pyridine (0.24 mmol) to a dichloromethane (5 mL) solution of (3,5-bis-trifluoromethyl-benzyl)-(7-methyl-8-trifluoromethyl-2,3,4,5-tetrahydro-1H-benzo[b]azepin-5-yl)-(1H-tetrazol-5-yl)-amine (0.045 g, 0.08 mmol). After stirring 14 h, wash the reaction with 5% HCl (3 mL), water (3 mL) and brine (3 mL). Dry the organic portion over sodium sulfate and filter. Chromatograph the crude product, eluting with ethyl acetate/hexane (20-60%), to provide the title compound (0.01 g, 20%) as an oil: MS (ES+): 611 (M+H).

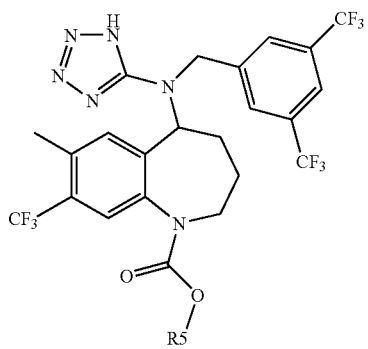

Additional compounds could be prepared following procedures described in Example 4 by replacing ethyl chloroformate with the appropriate reagent.

| Example # | Reagent | R5 |
|---|---|---|
| 5 | Isopropyl chloroformate | Isopropyl |
| 6 | 1,1,1-trifluoro-2-propyl chloroformate | 1,1,1-trifluoro-2-propyl |
| 7 | 2-butyl chloroformate | 2-butyl |
| 8 | Cyclobutyl chloroformate | cyclobutyl |
| 9 | Cyclopentyl chloroformate | cyclopentyl |
| 10 | Cyclohexyl chloroformate | cyclohexyl |

-continued

| Example # | Reagent | R5 |
|---|---|---|
| 11 | 3-pentyl chloroformate | 3-pentyl |
| 12 | 3-methyl-2-butyl chloroformate | 3-methyl-2-butyl |
| 13 | (S)-(+)-tetrahydrofuran-3-yl chloroformate | (S)-(+)-tetrahydrofuran-3-yl |
| 14 | (R)-(−)-tetrahydrofuran-3-yl chloroformate | (R)-(−)-tetrahydrofuran-3-yl |

Example 15

Synthesis of (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid ethyl ester

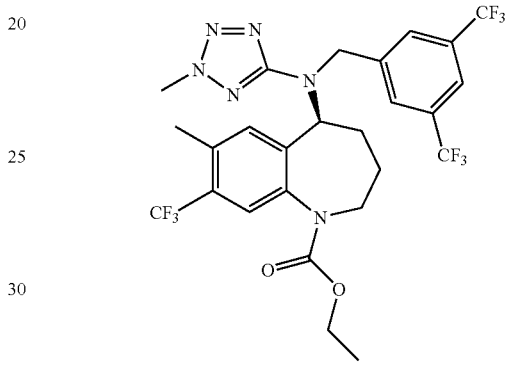

Add ethyl chloroformate (0.0223 mL, 0.233 mmol) dropwise to a solution of (S)-(3,5-bistrifluoromethylbenzyl)-(2-methyl-2H-tetrazol-5-yl)-(7-methyl-8-trifluoromethyl-2,3,4,5-tetrahydro-1H-benzo[b]azepin-5-yl)amine (0.0430 g, 0.0778 mmol) (Example 3, Step 18) and pyridine (0.0190 mL, 0.233 mmol) in dichloromethane (1 mL) at room temperature under an atmosphere of nitrogen and stir for 2 h. Dilute the reaction mixture with ethyl acetate (10 mL) and wash with 1.0 N hydrochloric acid (10 mL) and water (3×10 mL). Dry the organic layer over anhydrous sodium sulfate, filter, and remove the solvent under reduced pressure. Purify the residue using column chromatography on silica gel, eluting with ethyl acetate/hexanes (0-20%), to provide the title compound (0.0320 g, 65%). MS (ES+): 625 (M+H).

Example 16

Synthesis of (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid isopropyl ester

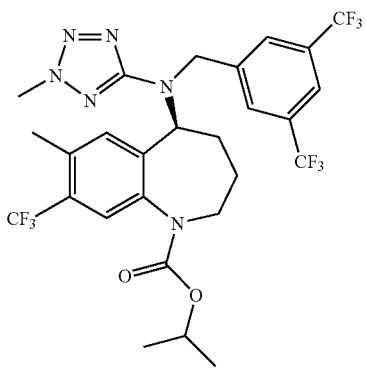

Prepare the titled compound by essentially following the procedures described in Example 15, by substituting ethyl chloroformate with isopropyl chloroformate MS (ES+): 639 (M+H).

Example 17

Synthesis of (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid tert-butyl ester

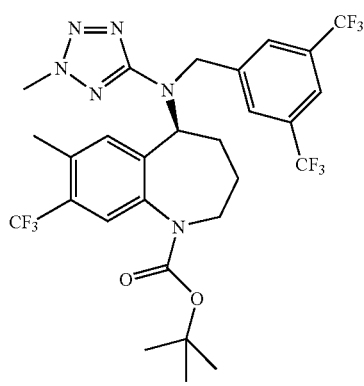

Prepare the titled compound by essentially following the procedures described in Example 3, Step 17. MS (ES+): 675 (M+Na)

Example 18

Synthesis of (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid 1-ethyl-propyl ester

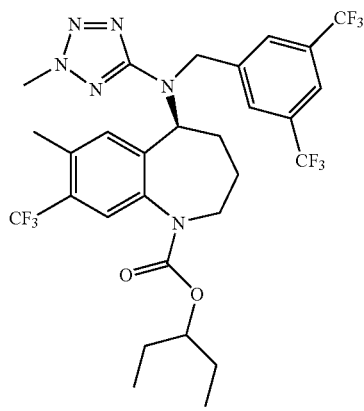

To a mixture of pentan-3-ol (0.117 ml, 1.08 mmol) diisopropyl ethyl amine (0.189 ml, 1.08 mmol) in dichloromethane at 0° C. with 20% phosgene in toluene (0.480 ml, 0.905 mmol). Stir the mixture at 0° C. for 10 minutes, and then warm up to room temperature for an hour. Add a solution of (S)-(3,5-bis-trifluoromethyl-benzyl)-(2-methyl-2H-tetrazol-5-yl)-(7-methyl-8-trifluoromethyl-2,3,4,5-tetrahydro-1H-benzo[b]azepin-5-yl)-amine (0.100 mg, 0.181 mmol) (Example 3, Step 18)) in dichloromethane (1.00 ml) followed by pyridine (0.0730 ml, 0.905 mmol). Continue the reaction at room temperature overnight. Dilute the mixture with dichloromethane (5.05 ml), wash with 1N hydrochloric acid (5.00 ml) and water (3×5.00 ml), dry over $Na_2SO_4$ and concentrated. Purify by silica gel chromatography (gradient eluent, 0-25% ethyl acetate in hexane) to provide the titled compound (0.0710 g, 59%). MS (ES+): 667 (M+H).

Example 19

Synthesis of (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid cyclopentyl ester

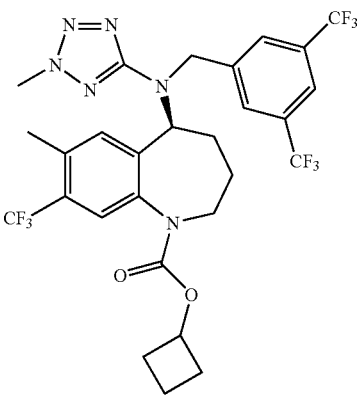

The title compound can be prepared following the procedures described in Example 18 by replacing pentan-3-ol with cyclobutanol.

Example 20

Synthesis of (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid cyclopentyl ester

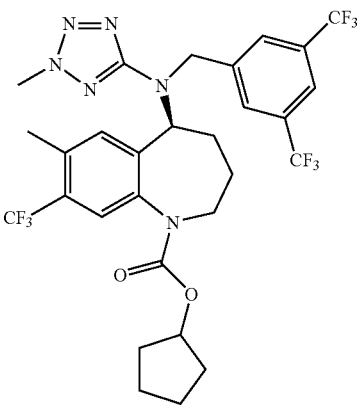

Prepare the title compound by following the procedures described in Example 18 by replacing pentan-3-ol with cyclopentanol. MS (ES+): 665 (M+H).

Example 21

Synthesis of (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid cyclopentyl ester

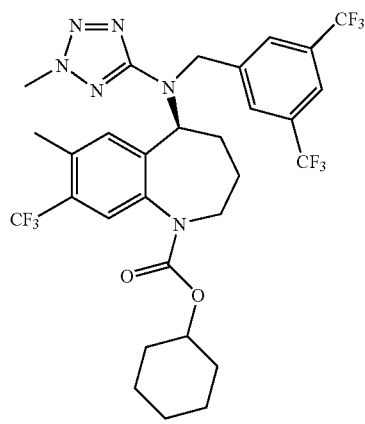

The title compound can be prepared following the procedures described in Example 18 by replacing pentan-3-ol with cyclohexanol.

Example 22

Synthesis of (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid 2,2,2-trifluoro-1-methyl-ethyl ester

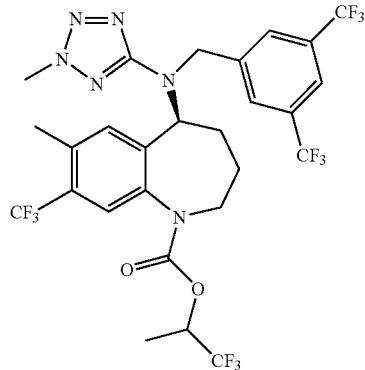

The title compound can be prepared following the procedures described in Example 18 by replacing pentan-3-ol with 1,1,1-trifluoro-propan-2-ol.

Example 23

Synthesis of (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid sec-butyl ester

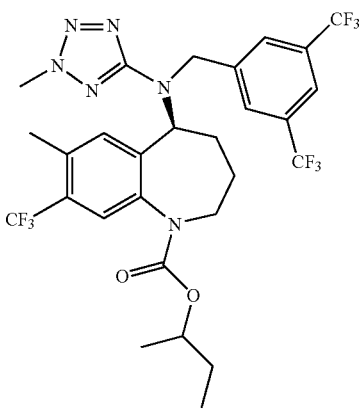

The title compound can be prepared following the procedures described in Example 18 by replacing pentan-3-ol with butan-2-ol.

Example 24

Synthesis of (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid 1,2-dimethyl-propyl ester

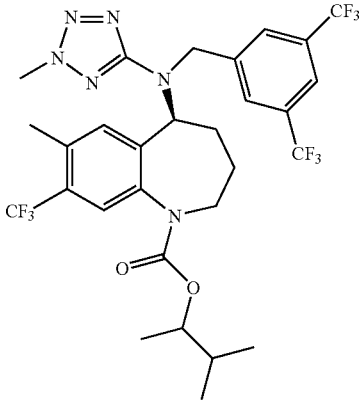

The title compound may be prepared by following the procedures described in Example 18 by replacing pentan-3-ol with 3-methyl-butan-2-ol.

Example 25

Synthesis of (+/−)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid 1-ethyl-2-methyl-propyl ester

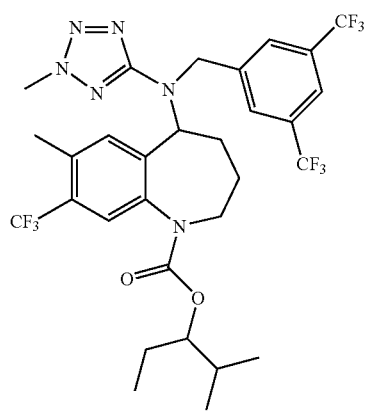

Prepare the title compound by essentially following the procedures described in Example 18 by replacing pentan-3-ol with 2-methyl-pentan-3-ol. MS (ES+): 681 (M+H).

Example 26

Synthesis of (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid tetrahydro-pyran-4-yl ester

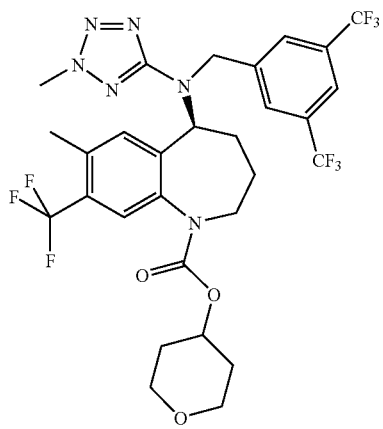

Prepare the title compound by essentially following the procedures described in Example 18 by replacing pentan-3-ol with tetrahydro-4H-pyran-4-ol. MS (ES+): 681 (M+H).

Example 27

Synthesis of (S)-2-{5-[(3,5-Bis-trifluoromethyl-benzyl)-(1-cyclopentylmethyl-7-methyl-8-trifluoromethyl-2,3,4,5-tetrahydro-1H-benzo[b]azepin-5-yl)-amino]-tetrazol-2-yl}-ethanol

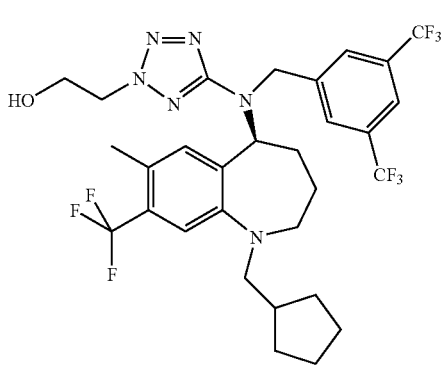

Step 1. Preparation of (S)-5-{(3,5-Bis-trifluoromethyl-benzyl)-[2-(2-hydroxy-ethyl)-2H-tetrazol-5-yl]-amino}-7-methyl-8-trifluoromethyl-2,3,4,5-tetrahydro-benzo[b]azepine-1-carboxylic acid tert-butyl ester

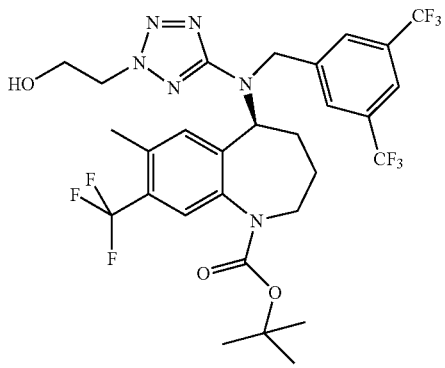

Dissolve (S)-tert-Butyl 5-[(3,5-bistrifluoromethylbenzyl)-(2H-tetrazol-5-yl)amino]-7-methyl-8-trifluoromethyl-2,3,4,5-tetrahydrobenzo[b]azepine-1-carboxylate (Example 3, Step 16) (0.252 g, 0.395 mmole) in DMF (4 mL), add potassium carbonate (0.0929 g, 0.672 mmole) in one portion. Inject 2-bromoethanol (0.0420 mL, 0.593 mmole) dropwise. Stir at room temperature overnight. Partition the reaction mixture between ethyl acetate (50 mL) and water (50 mL). Extract aqueous back with more ethyl acetate (20 mL). Combine organic layers, Dry over sodium sulfate, filter and concentrate the solution. Chromatograph the residue over silica gel, eluting with ethyl acetate/hexanes (0-100%), to provide the title compound as a colorless oil (0.0700 g, 26%). MS (ES+): 705 (M+Na).

Step 2. Preparation of (S)-2-{5-[(3,5-Bis-trifluoromethyl-benzyl)-(7-methyl-8-trifluoromethyl-2,3,4,5-tetrahydro-1H-benzo[b]azepin-5-yl)-amino]-tetrazol-2-yl}-ethanol

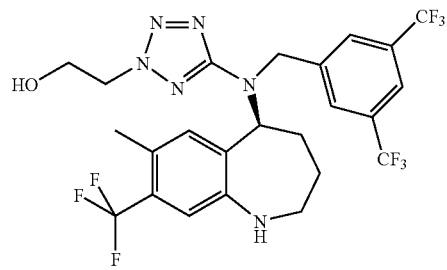

Add trifluoroacetic acid (2 mL) to a solution of (S)-5-{(3,5-Bis-trifluoromethyl-benzyl)-[2-(2-hydroxy-ethyl)-2H-tetrazol-5-yl]-amino}-7-methyl-8-trifluoromethyl-2,3,4,5-tetrahydro-benzo[b]azepine-1-carboxylic acid tert-butyl ester (0.0650 g, 0.0952 mmol) in methylene chloride (2 mL) at room temperature, stir for 1 h. Evaporate solvents and partition the residue between saturated aqueous sodium bicarbonate solution (10 mL). Extract the mixture with methylene chloride (10 mL). Separate two layers and dry over anhydrous sodium sulfate and filter. Remove the solvent under reduced pressure. Chromatograph the residue over silica gel, eluting with ethyl acetate/hexanes (0-100%), to provide the title compound as a colorless oil (0.0340 g, 62%). MS (ES+): 583 (M+H).

Step 3. Preparation of (S)-2-{5-[(3,5-Bis-trifluoromethyl-benzyl)-(1-cyclopentylmethyl-7-methyl-8-trifluoromethyl-2,3,4,5-tetrahydro-1H-benzo[b]azepin-5-yl)-amino]-tetrazol-2-yl}-ethanol

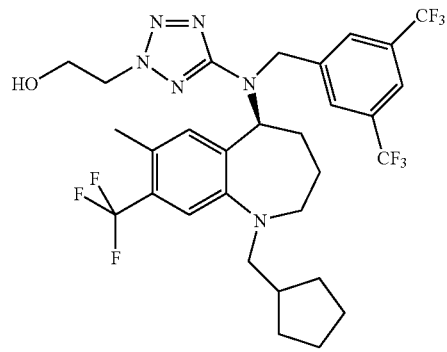

Prepare the title compound by essentially following the procedures described in Example 3, Step 19 by replacing (S)-(3,5-bistrifluoromethylbenzyl)-(2-methyl-2H-tetrazol-5-yl)-(7-methyl-8-trifluoromethyl-2,3,4,5-tetrahydro-1H-benzo[b]azepin-5-yl)amine with (S)-2-{5-[(3,5-Bis-trifluoromethyl-benzyl)-(7-methyl-8-trifluoromethyl-2,3,4,5-tetrahydro-1H-benzo[b]azepin-5-yl)-amino]-tetrazol-2-yl}-ethanol. MS (ES+): 665 (M+H).

Examples 28-29 can be prepared following the procedures as essentially described in Example 3, Step 19, using (S)-(3,5-bis-trifluoromethyl-benzyl)-(2-methyl-2H-tetrazol-5-yl)-(7-methyl-8-trifluoromethyl-2,3,4,5-tetrahydro-1H-benzo[b]azepin-5-yl)-amine (Example 3, Step 18) and the corresponding aldehyde as starting materials.

Example 28

Synthesis of (S)-(3,5-Bis-trifluoromethyl-benzyl)-(1-cyclobutylmethyl-7-methyl-8-trifluoromethyl-2,3,4,5-tetrahydro-1H-benzo[b]azepin-5-yl)-(2-methyl-2H-tetrazol-5-yl)-amine

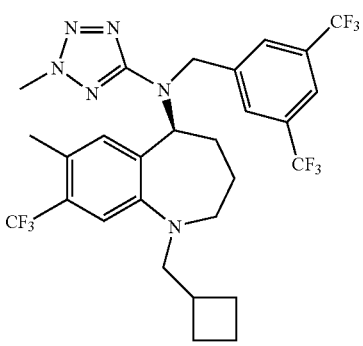

Example 29

Synthesis of (S)-(3,5-Bis-trifluoromethyl-benzyl)-(1-cyclohexylmethyl-7-methyl-8-trifluoromethyl-2,3,4,5-tetrahydro-1H-benzo[b]azepin-5-yl)-(2-methyl-2H-tetrazol-5-yl)-amine

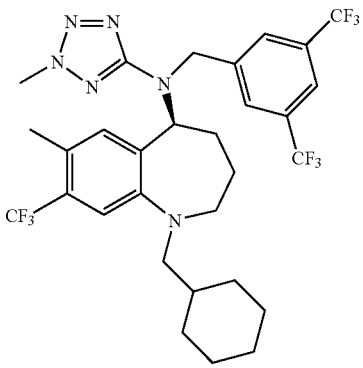

Example 30

Synthesis of (S)-(3,5-Bis-trifluoromethyl-benzyl)-(1-ethyl-7-methyl-8-trifluoromethyl-2,3,4,5-tetrahydro-1H-benzo[b]azepin-5-yl)-(2-methyl-2H-tetrazol-5-yl)-amine

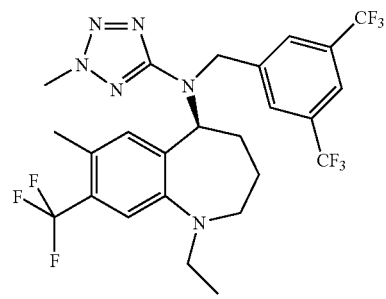

Prepare the title compound by essentially following the procedures described in Example 3, Step 19 using (S)-(3,5-bis-trifluoromethyl-benzyl)-(2-methyl-2H-tetrazol-5-yl)-(7-methyl-8-trifluoromethyl-2,3,4,5-tetrahydro-1H-benzo[b]azepin-5-yl)-amine (Example 3, Step 18) and replacing cyclopentanecarboxaldehyde with acetaldehyde. MS (ES+): 681 (M+H).

Example 31

Synthesis of (4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-cyclohexyl)-acetic acid

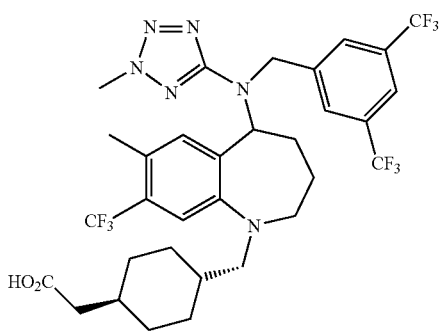

Step 1. Preparation of (4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-cyclohexyl)-acetic acid benzyl ester

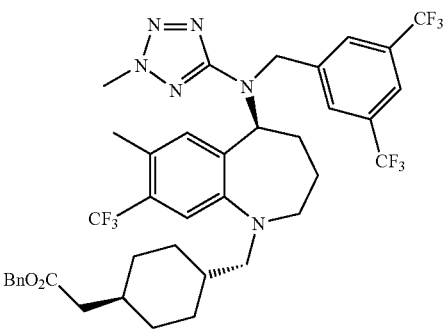

Prepare the title compound by essentially following the procedures described in Example 3, Step 19 by replacing cyclopentanecarboxaldehyde with (4-formyl-cyclohexyl)-acetic acid benzyl ester. MS (ES+): 797 (M+H).

Step 2. Preparation of (4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-cyclohexyl)-acetic acid

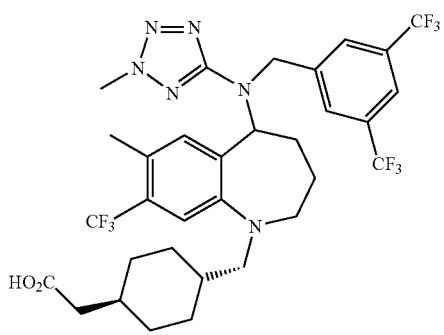

Heat the mixture of (4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-cyclohexyl)-acetic acid benzyl ester (0.0340 g, 0.0427 mmol) in 5.0 N NaOH (1 mL) and methanol (1 mL) at 60° C. for 2 h. Evaporate the solvents and re-dissolve in water (10 mL). Adjust to pH=2 by adding 5.0 N HCl. Extract with ethyl acetate (2×10 mL). Combine organic layers, dry over anhydrous sodium sulfate and filter. Remove the solvent under reduced pressure. Chromatograph the residue over silica gel, eluting with ethyl acetate/hexanes (0-50%), to provide the title compound as a colorless oil (0.0200 g, 67%). MS (ES+): MS (ES+): 707 (M+H).

Example 32

Synthesis of (S)-5-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-3,3-dimethyl-pentanoic acid

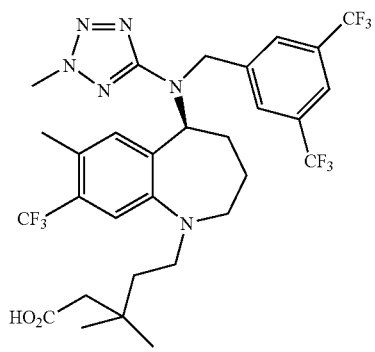

Step 1. Preparation of (S)-5-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-3,3-dimethyl-pentanoic acid methyl ester

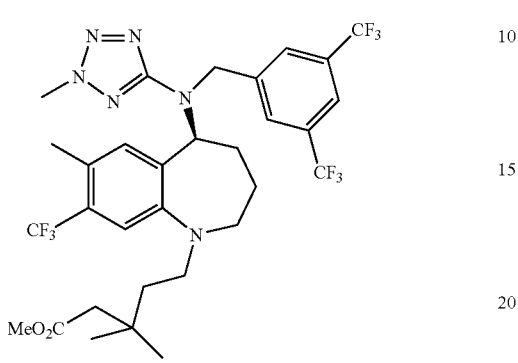

Prepare the title compound by essentially following the procedures described in Example 3, Step 19 by replacing cyclopentanecarboxaldehyde with 3,3-dimethyl-5-oxo-pentanoic acid methyl ester (Example 74, Step 2). MS (ES+): 695 (M+H).

Step 2. Preparation of (S)-5-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-3,3-dimethyl-pentanoic acid

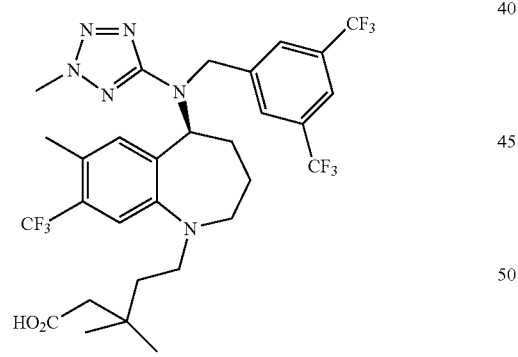

Heat the mixture of (0.0400 g, 0.0576 mmol) in 2.0 N NaOH (0.350 mL) and methanol (1 mL) at 50° C. for 2 h. Evaporate the solvents and re-dissolve in water (10 mL). Adjust to pH=2 by adding 5.0 N HCl. Extract with ethyl acetate (2×10 mL). Combine organic layers, dry over anhydrous sodium sulfate and filter. Remove the solvent under reduced pressure. Chromatograph the residue over silica gel, eluting with ethyl acetate/hexanes (0-50%), to provide the title compound as a colorless oil (0.0310 g, 79%). MS (ES+): 681 (M+H).

Example 33
Synthesis of (S)-2-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-ethanol

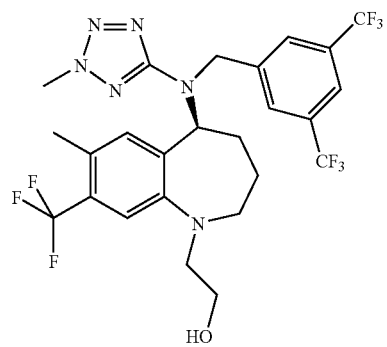

Step 1. Preparation of (S)-[1-(2-Benzyloxy-ethyl)-7-methyl-8-trifluoromethyl-2,3,4,5-tetrahydro-1H-benzo[b]azepin-5-yl]-(3,5-bis-trifluoromethyl-benzyl)-(2-methyl-2H-tetrazol-5-yl)-amine

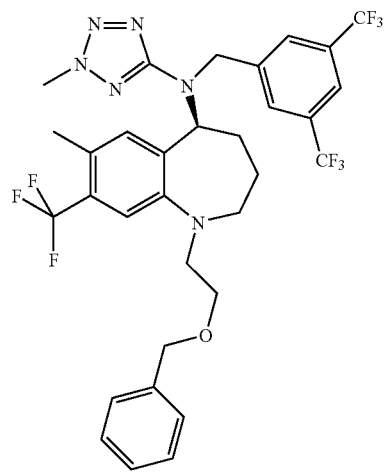

Prepare the title compound by essentially following the procedures described in Example 3, Step 19 by replacing cyclopentanecarboxaldehyde with benzyloxy-acetaldehyde. MS (ES+): 687 (M+H).

Step 2. Preparation of (S)-2-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-ethanol

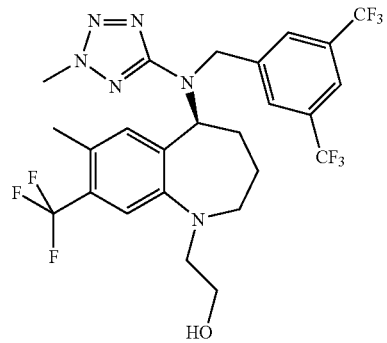

Stir a mixture of (S)-[1-(2-Benzyloxy-ethyl)-7-methyl-8-trifluoromethyl-2,3,4,5-tetrahydro-1H-benzo[b]azepin-5-yl]-(3,5-bis-trifluoromethyl-benzyl)-(2-methyl-2H-tetrazol-5-yl)-amine (0.420 g, 0.612 mmol) and 10% palladium on charcoal (0.210 g) in ethanol (50 mL) under a hydrogen balloon at room temperature for 3 h. Filter the mixture through Celite® and remove the solvents under reduced pressure to provide the title compound as a colorless foam (0.350 g, 97%). MS (ES+): 597 (M+H).

Example 34

Synthesis of (S)-5-[(3,5-Bis-trifluoromethyl-benzyl)-(2-methyl-2H-tetrazol-5-yl)-amino]-7-ethyl-8-trifluoromethyl-2,3,4,5-tetrahydro-benzo[b]azepine-1-carboxylic acid tert-butyl ester

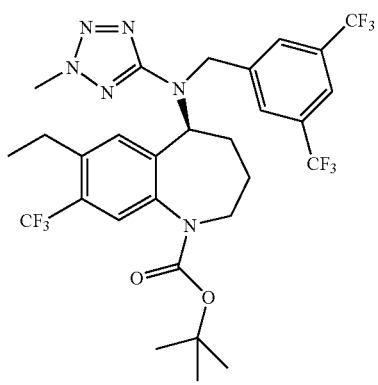

Step 1. Preparation of 2-Amino-4-trifluoromethyl-5-vinyl-benzoic acid methyl ester

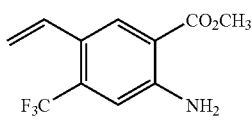

Add tetrakis palladium(triphenylphosphine)(0) (5.00 g, 4.33 mmol) to a mixture of 2-amino-5-iodo-4-trifluoromethyl-benzoic acid methyl ester (Example 3, Step 3) (17.25 g, 49.99 mmol) and tributyl(vinyl)tin (16.10 mL, 55.14 mmol) in toluene (500 mL) and heat at reflux for 14 h. Allow the reaction to cool to room temperature dilute the mixture with ethyl acetate (1 L). Wash the mixture with saturated aqueous potassium fluoride solution (3×300 mL), then water (300 mL), followed by brine (500 mL). Dry the organic layer over anhydrous sodium sulfate, filter, and remove the solvents under reduced pressure. Purify the residue by column chromatography on silica gel, eluting with ethyl acetate/hexanes (0 to 15%), to provide the title compound as a pale yellow solid (8.73 g, 71%): TLC $R_f$ 0.52 (3:1 hexanes/ethyl acetate); $^1$H NMR (CDCl$_3$, 300 MHz) δ 3.89 (s, 3H), 5.21-5.30 (m, 1H), 5.60-5.71 (m, 1H), 5.98 (bs, 2H), 6.83-7.02 (m, 2H), 8.19 (s, 1H).

Step 2. Preparation of 2-Isopropoxycarbonylamino-4-trifluoromethyl-5-vinyl-benzoic acid methyl ester

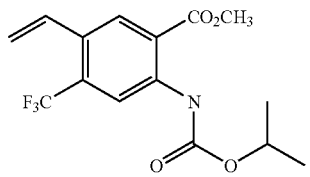

Add a 1.0 M solution of isopropyl chloroformate in toluene (183.0 mL, 183.0 mmol) to a 0° C. cooled solution of 2-amino-4-trifluoromethyl-5-vinyl-benzoic acid methyl ester (34.47 g, 140.58 mmol) and pyridine (35.0 mL, 429.20 mmol) in methylene chloride (500 mL). Allow the mixture to stir for 2 h at 0° C. then 16 h at room temperature under an atmosphere of N$_2$. Wash the mixture with saturated aqueous sodium bicarbonate solution (2×200 mL) followed by aqueous 2 N HCl solution (2×200 mL). Wash the combined organic extracts with brine (20 mL) and dry over anhydrous sodium sulfate. Remove the solvents under reduced pressure and purify the residue by column chromatography on silica gel, eluting with ethyl acetate/hexanes (0 to 15%), to provide the title compound as an off-white solid (40.50 g, 87%): TLC $R_f$ 0.62 (3:1 hexanes/ethyl acetate); $^1$H NMR (CDCl$_3$, 300 MHz) δ 1.32-1.33 (m, 6H), 3.89 (s, 3H), 5.21-5.27 (m, 1H), 5.41-5.44 (m, 1H), 5.63-5.70 (m, 1H), 7.03-7.11 (m, 1H), 8.23 (s, 1H), 8.89 (s, 1H), 10.32 (bs, 1H).

Step 3. Preparation of 5-Ethyl-2-isopropoxycarbonylamino-4-trifluoromethyl-benzoic acid methyl ester

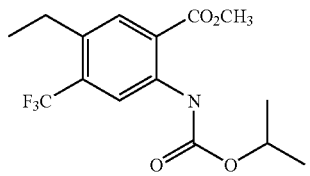

Add 10% palladium on carbon (4.06 g, 12.22 mmol) to a solution of 2-isopropoxycarbonylamino-4-trifluoromethyl-5-vinyl-benzoic acid methyl ester (40.48 g, 122.19 mmol) in methanol (350 mL) in a Parr bottle. Subject the mixture to a hydrogen atmosphere at a pressure of 30 psi at room temperature with shaking on a Parr shaker apparatus for 2 h. Filter the mixture through Celite and remove the solvent under reduced pressure to provide the title compound as a white solid (39.07 g, 96%): TLC $R_f$ 0.62 (3:1 hexanes/ethyl acetate); $^1$H NMR (CDCl$_3$, 300 MHz) δ 1.13-1.42 (m, 9H), 2.71-2.80 (m, 2H), 3.89 (s, 3H), 5.21-5.27 (m, 1H), 7.98 (s, 1H), 8.81 (s, 1H), 10.23 (bs, 1H).

Step 4. Preparation of 5-Ethyl-2-[isopropoxycarbonyl-(3-methoxycarbonyl-propyl)-amino]-4-trifluoromethyl-benzoic acid methyl ester

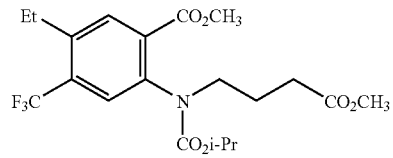

Add 4-bromo-butyric acid methyl ester (74.30 g, 410.46 mmol) to a mixture of 5-ethyl-2-isopropoxycarbonylamino-4-trifluoromethyl-benzoic acid methyl ester (39.05 g, 117.16 mmol) and cesium carbonate (114.65 g, 351.88 mmol) in N,N-dimethylformamide (800 mL). Heat the mixture at 90° C. for 4 h and the allow it to cool to room temperature. Filter the mixture through Celite then dilute the mixture with water (2 L) and ethyl acetate (2 L). Wash the organic layer with water (500 mL) and brine (500 mL). Dry the organic layer over anhydrous sodium sulfate and filter. Remove the solvents under reduced pressure and purify the resulting residue by column chromatography on silica gel, eluting with ethyl acetate/hexanes (0 to 15%), to provide the title compound as a white solid (39.75 g, 78%): TLC $R_f$ 0.42 (3:1 hexanes/ethyl acetate); $^1$H NMR (CDCl$_3$, 300 MHz) δ 1.0-1.10 (m, 3H), 1.22-1.32 (m, 6H), 1.78-1.89 (m, 2H), 2.37-2.40 (m, 2H), 2.82-2.89 (m, 2H), 3.41-3.80 (m, 5H), 3.89 (s, 3H), 4.78-5.02 (m, 1H), 7.43 (s, 1H), 7.91 (s, 1H).

Step 5. Preparation of 7-Ethyl-5-oxo-8-trifluoromethyl-2,3,4,5-tetrahydro-benzo[b]azepine-1,4-dicarboxylic acid 1-isopropyl ester 4-methyl ester

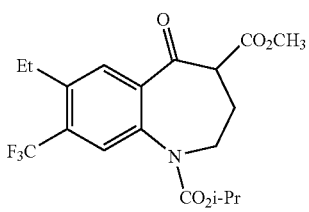

To a 0° C. cooled solution of 5-ethyl-2-[isopropoxycarbonyl-(3-methoxycarbonyl-propyl)-amino]-4-trifluoromethyl-benzoic acid methyl ester (39.72 g, 91.64 mmol) in toluene add potassium tert-butoxide (24.68 g, 219.92 mmol). Stir the mixture at room temperature for 30 min under an atmosphere of N$_2$. Quench the mixture with 2 N HCl (150 mL) and dilute with ethyl acetate (1.5 L). Wash with water (2×400 mL) and brine (500 mL). Dry the organic layer over anhydrous sodium sulfate and filter through Celite to provide the title compound as a yellow viscous oil (31.25 g, 85%): TLC $R_f$ 0.63 (3:1 hexanes/ethyl acetate); $^1$H NMR (CDCl$_3$, 300 MHz) δ 1.0-1.40 (m, 9H), 2.31-2.55 (m, 2H), 2.88-2.94 (m, 1H), 3.75 (s, 3H), 3.89 (s, 3H), 4.89-4.93 (m, 1H), 5.11-5.12 (m, 1H), 7.43 (s, 1H), 7.91 (s, 1H).

Step 6. Preparation of 7-Ethyl-8-trifluoromethyl-1,2,3,4-tetrahydro-benzo[b]azepin-5-one

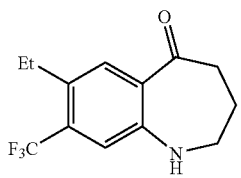

Heat a mixture of 7-ethyl-5-oxo-8-trifluoromethyl-2,3,4,5-tetrahydro-benzo[b]azepine-1,4-dicarboxylic acid 1-isopropyl ester 4-methyl ester (23.55 g, 58.61 mmol), sodium chloride (52.50 g), and water (10.0 mL) in dimethylsulfoxide (500 mL) at reflux for 46 h. Allow the mixture to cool to room temperature and dilute it with water (200 mL) and ethyl acetate (200 mL). Wash the organic layer with water (350 mL). Dry the organic layer over anhydrous sodium sulfate and filter. Remove the solvents under reduced pressure and purify the resulting residue by column chromatography on silica gel, eluting with ethyl acetate/hexanes (0 to 15%), to provide the title compound as a yellow solid (9.17 g, 61%) TLC $R_f$ 0.32 (3:1 hexanes/ethyl acetate); $^1$H NMR (CDCl$_3$, 300 MHz) δ 1.10-1.23 (m, 3H), 2.13-2.21 (m, 2H), 2.63-2.71 (m, 2H), 2.83-2.92 (m, 2H), 3.22-3.31 (m, 2H), 4.74 (bs, 1H), 7.03 (s, 1H), 7.68 (s, 1H).

Step 7. Preparation of 7-Ethyl-5-oxo-8-trifluoromethyl-2,3,4,5-tetrahydro-benzo[b]azepine-1-carboxylic acid tert-butyl ester

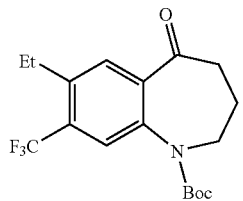

Add di-tert-butyl dicarbonate (21.12 g, mmol) to a mixture of ethyl-8-trifluoromethyl-1,2,3,4-tetrahydro-benzo[b]azepin-5-one (8.30 g, 32.26 mmol), di-isopropylethylamine (20.0 mL, 114.18 mmol), and dimethylaminopyridine (0.395 g) in tetrahydrofuran (300 mL) at room temperature. Stir the mixture for 16 h under an atmosphere of N$_2$. Dilute the mixture with aqueous saturated sodium bicarbonate solution (100 mL) and ethyl acetate (1 L). Wash the organic layer with brine (500 mL) and dry it over anhydrous sodium sulfate and filter. Remove the solvents under reduced pressure and purify the resulting residue by column chromatography on silica gel, eluting with ethyl acetate/hexanes (0 to 15%), to provide the title compound as a white gum (8.66 g, 75%): TLC $R_f$ 0.69 (3:1 hexanes/ethyl acetate); $^1$H NMR (CDCl$_3$, 300 MHz) δ 1.19-1.25 (m, 3H), 1.45 (s, 11H), 2.19-2.22 (m, 2H), 2.74-2.83 (m, 2H), 3.43-3.55 (m, 2H), 7.62-7.65 (bs, 1H), 7.80 (s, 1H).

Step 8. Preparation of (R)-7-Ethyl-5-hydroxy-8-trifluoromethyl-2,3,4,5-tetrahydro-benzo[b]azepine-1-carboxylic acid tert-butyl ester

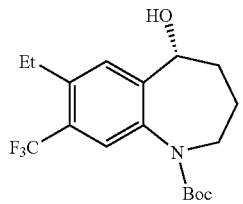

Add a solution of borane dimethylsulfide complex (16.0 mL, 16.0 mmol, 1M in tetrahydrofuran) dropwise to a solution of (S)-2-methyl-CBS-oxazaborolidine (7.50 mL, 7.50 mmol, 1M in toluene) in dichloromethane (100 mL) at −30° C. under nitrogen. Stir the mixture for 30 min and add a solution of tert-butyl 7-ethyl-5-oxo-8-trifluoromethyl-2,3,4, 5-tetrahydrobenzo[b]azepine-1-carboxylate (8.60 g, 24.0 mmol) in dichloromethane (50 mL) dropwise and warm the mixture slowly to 0° C. over a period of 6 h. Pour the mixture into methanol (200 mL) at −20° C. and slowly warm the stirring mixture to room temperature over 1 h. Remove the solvents under reduced pressure and purify the residue by column chromatography on silica gel, eluting with ethyl acetate/hexanes (0 to 15%), to provide the title compound as a colorless oil (7.62 g, 88%): TLC $R_f$ 0.49 (3:1 hexanes/ethyl acetate); $^1$H NMR (CDCl$_3$, 300 MHz) δ 1.21-2.30 (m, 19H), 2.83-2.89 (m, 2H), 4.78-4.80 (m, 1H), 7.31-7.45 (m, 2H); Chiral HPLC (OD Column) 91.6% ee; APCI MS m/z 360 (M+H)$^+$.

Step 9. Preparation of (S)-5-Azido-7-ethyl-8-trifluoromethyl-2,3,4,5-tetrahydro-benzo[b]azepine-1-carboxylic acid tert-butyl ester

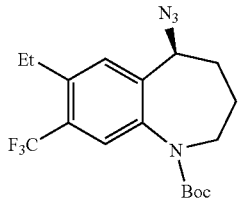

Heat a mixture of (R)-7-ethyl-5-hydroxy-8-trifluoromethyl-2,3,4,5-tetrahydro-benzo[b]azepine-1-carboxylic acid tert-butyl ester (7.59 g, 21.12 mmol), diphenylphosphoryl azide (DPPA, 5.50 mL, 25.64 mmol) and DBU (3.95 mL, 26.41 mmol) in toluene (200 mL) at 65° C. under nitrogen for 12 h. Add silica gel to the cooled mixture and remove the solvents under reduced pressure. Purify the residue by column chromatography, eluting with ethyl acetate/hexanes (1:2), to provide the title compound as a colorless oil (5.79 g, 71%): $^1$H NMR (CDCl$_3$, 300 MHz) δ 1.21-2.30 (m, 18H), 2.83-2.89 (m, 2H), 4.78-4.80 (m, 1H), 7.31-7.45 (m, 2H); APCI MS m/z 356 (M−N2)−.

Step 10. Preparation of (S)-5-Amino-7-ethyl-8-trifluoromethyl-2,3,4,5-tetrahydro-benzo[b]azepine-1-carboxylic acid tert-butyl ester

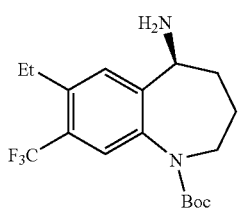

Shake a mixture of (S)-5-amino-7-ethyl-8-trifluoromethyl-2,3,4,5-tetrahydro-benzo[b]azepine-1-carboxylic acid tert-butyl ester (5.75 g, 14.96 mmol) and 5% palladium on charcoal (0.630 g, 50% wet) in ethanol (200 mL) under 25 psi of hydrogen in a Parr bottle at room temperature for 2 h. Filter the mixture through Celite® and remove the solvents under reduced pressure to provide the title compound as a colorless oil (4.93 g, >99%), which is used in the next step without further purification. $^1$H NMR (CDCl$_3$, 300 MHz) δ 1.21-2.30 (m, 19H), 2.83-2.89 (m, 3H), 4.78-4.80 (m, 1H), 7.31-7.45 (m, 2H); APCI MS m/z 359 (M+H)$^+$.

Step 11. Preparation of (S)-5-(3,5-Bis-trifluoromethyl-benzylamino)-7-ethyl-8-trifluoromethyl-2,3,4,5-tetrahydro-benzo[b]azepine-1-carboxylic acid tert-butyl ester

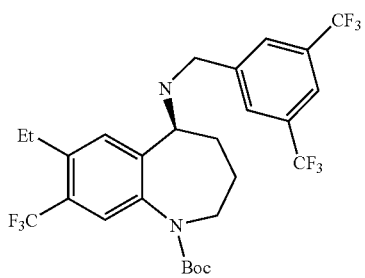

Add 3,5-bistrifluoromethylbenzaldehyde (4.30 g, 24.22 mmol) to a solution of (S)-5-amino-7-ethyl-8-trifluoromethyl-2,3,4,5-tetrahydro-benzo[b]azepine-1-carboxylic acid tert-butyl ester (4.91 g, 13.70 mmol) in dichloromethane (100 mL) and glacial acetic acid (6 mL) at room temperature under nitrogen and stir for 2 h. Add sodium triacetoxyborohydride (6.01 g, 28.35 mmol) and stir the mixture for 2 h. Remove the solvents under reduced pressure and dilute the residue with dichloromethane (50 mL) and water (50 mL). Collect the organic layer and extract the aqueous layer with dichloromethane (3×30 mL). Wash the combined organic extracts with water (20 mL) and brine (20 mL) and dry over anhydrous sodium sulfate. Filter and remove the solvents under reduced pressure to provide the title compound as an amber oil (6.58 g, 75%), which is used in the next step without purification. $^1$H NMR (CDCl$_3$, 300 MHz) δ 1.21-2.30 (m, 19H), 2.83-2.89 (m, 2H), 4.78-4.80 (m, 3H), 6.89-7.60 (m, 3H), 7.70-7.91 (m, 2H); APCI MS m/z 585 (M+H)+.

Step 12. Preparation of (S)-5-[(3,5-bistrifluoromethylbenzyl)cyanoamino]-7-ethyl-8-trifluoromethyl-2,3,4,5-tetrahydrobenzo[b]azepine-1-carboxylic acid tert-butyl ester

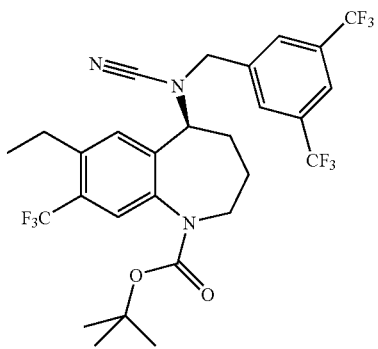

Add cyanogen bromide (0.352 g, 3.33 mmol) to a solution of (S)-5-(3,5-Bis-trifluoromethyl-benzylamino)-7-ethyl-8-trifluoromethyl-2,3,4,5-tetrahydro-benzo[b]azepine-1-carboxylic acid tert-butyl ester (0.647 g, 1.11 mmol) and diisopropylethylamine (0.679 mL, 3.89 mmol) in tetrahydrofuran (3 mL) at room temperature under nitrogen and heat the mixture at 65-70° C. for 16 hours and then for another 90° C.

16 h. Partition the cooled mixture between dichloromethane (40 mL) and brine (40 mL), separated layers. Extract aqueous with more dichloromethane (40 mL). Combine organic layers, dry over anhydrous sodium sulfate, filter and concentrated under reduced pressure. Purify the residue by column chromatography on silica gel, eluting with ethyl acetate/hexanes (0-20%), to provide the title compound (0.517 g, 76%), MS (ES+): 627 (M+NH$_4$), 632 (M+Na).

Step 13. Preparation of (S)-5-[(3,5-bistrifluoromethylbenzyl)-(2H-tetrazol-5-yl)amino]-7-ethyl-8-trifluoromethyl-2,3,4,5-tetrahydrobenzo[b]azepine-1-carboxylic acid tert-butyl ester

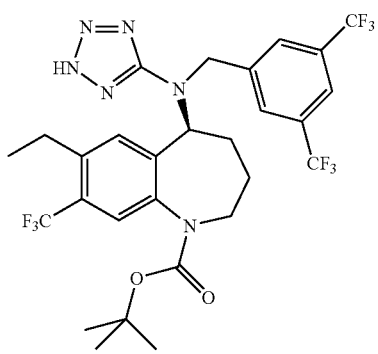

Heat a mixture of (S)-5-[(3,5-bistrifluoromethylbenzyl)cyanoamino]-7-ethyl-8-trifluoromethyl-2,3,4,5-tetrahydrobenzo[b]azepine-1-carboxylic acid tert-butyl ester (0.510 g, 0.837 mmol), azidotributyltin (0.344 mL, 1.26 mmol) in anhydrous toluene (20 mL) at 100° C. under nitrogen for 16 h. Dilute the cooled mixture with ethyl acetate (50 mL) and wash with aqueous NaF (50 mL) and brine (50 mL). Dry over anhydrous sodium sulfate. Filter and remove the solvent under reduced pressure. Purify the residue by column chromatography on silica gel, eluting with ethyl acetate/hexanes (0-60%), to provide the title compound (0.432 g, 79%), MS (ES+): 653 (M+H).

Step 14. Preparation of (S)-5-[(3,5-bistrifluoromethylbenzyl)-(2-methyl-2H-tetrazol-5-yl)amino]-7-ethyl-8-trifluoromethyl-2,3,4,5-tetrahydrobenzo[b]azepine-1-carboxylic acid tert-butyl ester

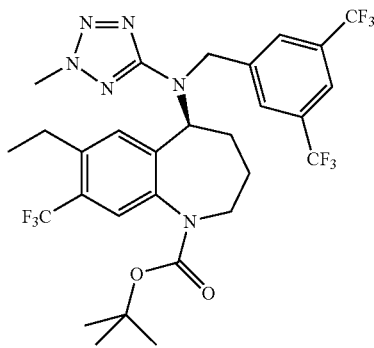

Add diethyl azodicarboxylate (0.0.240 mL, 1.32 mmol) to a solution of (S)-5-[(3,5-bistrifluoromethylbenzyl)cyanoamino]-7-ethyl-8-trifluoromethyl-2,3,4,5-tetrahydrobenzo[b]azepine-1-carboxylic acid tert-butyl ester (0.430 g, 0.659 mmol), triphenylphosphine (0.262 g, 0.989 mmol) and methanol (0.133 mL, 3.30 mmol) in dichloromethane (6 mL) at room temperature under nitrogen. Stir for 2 h. Evaporate the solvent on a rota-vapor. Purify the residue by column chromatography on silica gel, eluting with ethyl acetate/hexanes (0-30%), to provide the title compound (0.386 g, 88%). MS (ES+): 689 (M+Na).

Example 35

Synthesis of (S)-5-[(3,5-Bis-trifluoromethyl-benzyl)-(2-methyl-2H-tetrazol-5-yl)-amino]-7-ethyl-8-trifluoromethyl-2,3,4,5-tetrahydro-benzo[b]azepine-1-carboxylic acid isopropyl ester

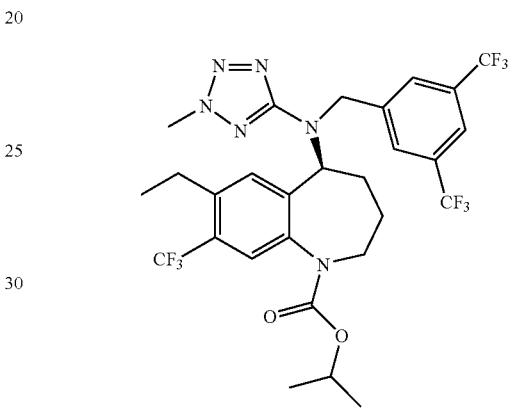

Step 1. Preparation of (S)-(3,5-bistrifluoromethyl-benzyl)-(2-methyl-2H-tetrazol-5-yl)-(7-ethyl-8-trifluoromethyl-2,3,4,5-tetrahydro-1H-benzo[b]azepin-5-yl)amine

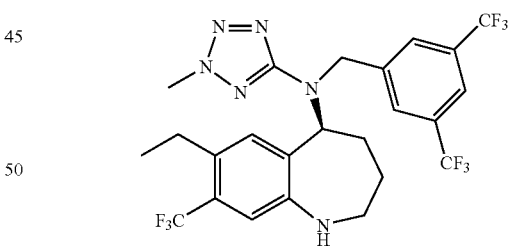

Add trifluoroacetic acid (1 mL) to a solution of (S)-5-[(3,5-bistrifluoromethylbenzyl)-(2-methyl-2H-tetrazol-5-yl)amino]-7-ethyl-8-trifluoromethyl-2,3,4,5-tetrahydrobenzo[b]azepine-1-carboxylic acid tert-butyl ester (2.04 g, 3.13 mmol) in dichloromethane (1 mL). Stir for 30 minutes at room temperature. Dilute the mixture with dichloromethane (40 mL) and wash with saturated aqueous sodium bicarbonate solution (40 mL). Dry organic layer over anhydrous sodium sulfate and filter. Remove the solvent under reduced pressure. Purify the residue by column chromatography on silica gel, eluting with ethyl acetate/hexanes (0-30%), to provide the title compound (0.318 g, 98%). MS (ES+): 567 (M+H).

Step 2. Preparation of (S)-5-[(3,5-Bis-trifluoromethyl-benzyl)-(2-methyl-2H-tetrazol-5-yl)-amino]-7-ethyl-8-trifluoromethyl-2,3,4,5-tetrahydro-benzo[b]azepine-1-carboxylic acid isopropyl ester

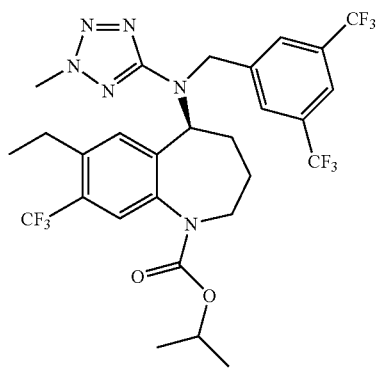

The title compound can be prepared using procedures analogous to those used in Example 15 by replacing (S)-(3,5-bistrifluoromethylbenzyl)-(2-methyl-2H-tetrazol-5-yl)-(7-methyl-8-trifluoromethyl-2,3,4,5-tetrahydro-1H-benzo[b]azepin-5-yl)amine with (S)-(3,5-bistrifluoromethylbenzyl)-(2-methyl-2H-tetrazol-5-yl)-(7-ethyl-8-trifluoromethyl-2,3,4,5-tetrahydro-1H-benzo[b]azepin-5-yl)amine and ethyl chloroformate with isopropyl chloroformate The following Examples 36-43 can be prepared using the same procedures as generally described in Examples 18-25 by replacing (S)-(3,5-bistrifluoromethylbenzyl)-(2-methyl-2H-tetrazol-5-yl)-(7-methyl-8-trifluoromethyl-2,3,4,5-tetrahydro-1H-benzo[b]azepin-5-yl)amine (Example 3, Step 18) with (S)-(3,5-bistrifluoromethylbenzyl)-(2-methyl-2H-tetrazol-5-yl)-(7-ethyl-8-trifluoromethyl-2,3,4,5-tetrahydro-1H-benzo[b]azepin-5-yl)amine (Example 35, Step 1).

Example 36

Synthesis of (S)-5-[(3,5-Bis-trifluoromethyl-benzyl)-(2-methyl-2H-tetrazol-5-yl)-amino]-7-ethyl-8-trifluoromethyl-2,3,4,5-tetrahydro-benzo[b]azepine-1-carboxylic acid 1-ethyl-propyl ester

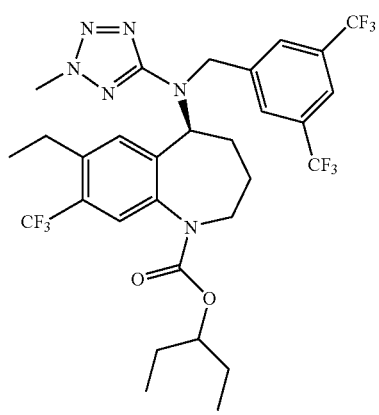

Example 37

Synthesis of (S)-5-[(3,5-Bis-trifluoromethyl-benzyl)-(2-methyl-2H-tetrazol-5-yl)-amino]-7-ethyl-8-trifluoromethyl-2,3,4,5-tetrahydro-benzo[b]azepine-1-carboxylic acid cyclopentyl ester

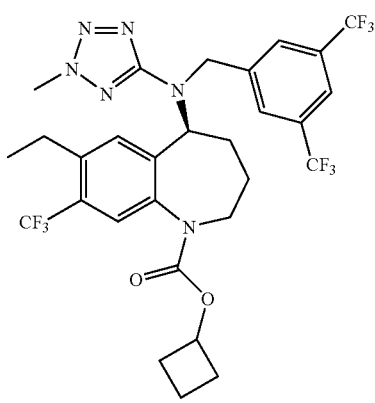

Example 38

Synthesis of (S)-5-[(3,5-Bis-trifluoromethyl-benzyl)-(2-methyl-2H-tetrazol-5-yl)-amino]-7-ethyl-8-trifluoromethyl-2,3,4,5-tetrahydro-benzo[b]azepine-1-carboxylic acid cyclopentyl ester

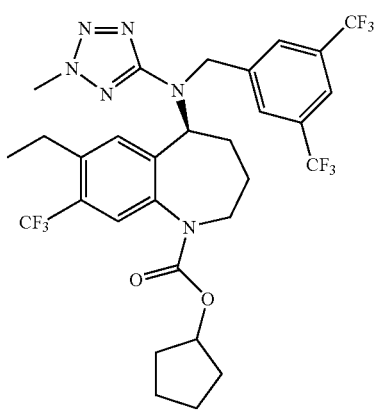

Example 39

Synthesis of (S)-5-[(3,5-Bis-trifluoromethyl-benzyl)-(2-methyl-2H-tetrazol-5-yl)-amino]-7-ethyl-8-trifluoromethyl-2,3,4,5-tetrahydro-benzo[b]azepine-1-carboxylic acid cyclopentyl ester

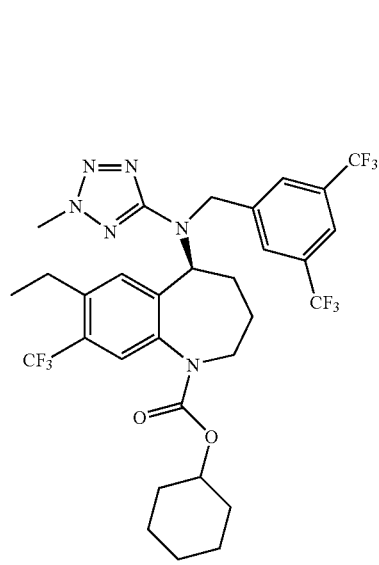

Example 40

Synthesis of (S)-5-[(3,5-Bis-trifluoromethyl-benzyl)-(2-methyl-2H-tetrazol-5-yl)-amino]-7-ethyl-8-trifluoromethyl-2,3,4,5-tetrahydro-benzo[b]azepine-1-carboxylic acid 2,2,2-trifluoro-1-methyl-ethyl ester

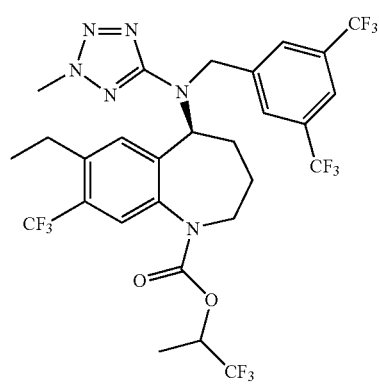

Example 41

Synthesis of (S)-5-[(3,5-Bis-trifluoromethyl-benzyl)-(2-methyl-2H-tetrazol-5-yl)-amino]-7-ethyl-8-trifluoromethyl-2,3,4,5-tetrahydro-benzo[b]azepine-1-carboxylic acid sec-butyl ester

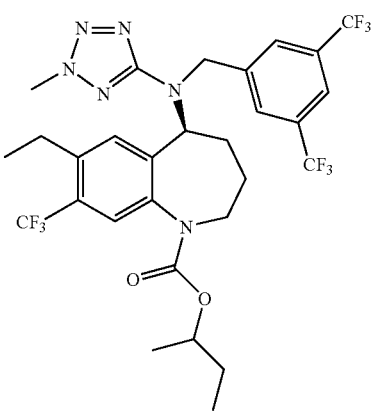

Example 42

Synthesis of (S)-5-[(3,5-Bis-trifluoromethyl-benzyl)-(2-methyl-2H-tetrazol-5-yl)-amino]-7-ethyl-8-trifluoromethyl-2,3,4,5-tetrahydro-benzo[b]azepine-1-carboxylic acid 1,2-dimethyl-propyl ester

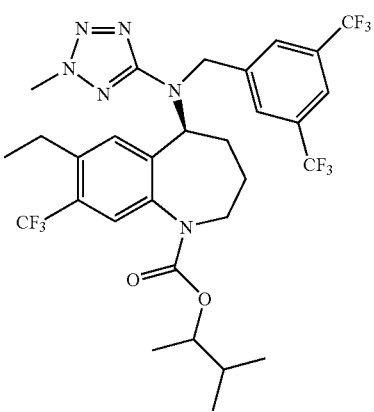

Example 43

Synthesis of (S)-5-[(3,5-Bis-trifluoromethyl-benzyl)-(2-methyl-2H-tetrazol-5-yl)-amino]-7-ethyl-8-trifluoromethyl-2,3,4,5-tetrahydro-benzo[b]azepine-1-carboxylic acid 1-ethyl-2-methyl-propyl ester

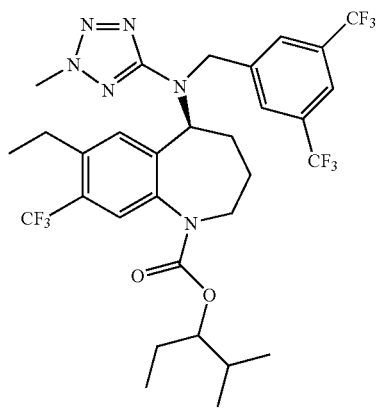

Example 44

Synthesis of (+/−)-9-[(3,5-Bis-trifluoromethyl-benzyl)-(2H-tetrazol-5-yl)-amino]-2,2-difluoro-6,7,8,9-tetrahydro-1,3-dioxa-5-aza-cyclohepta[f]indene-5-carboxylic acid isopropyl ester

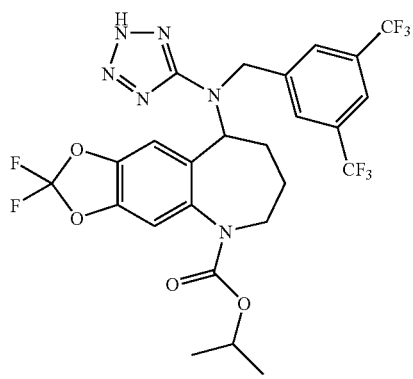

Step 1. Preparation of 2,2-Difluoro-9-oxo-6,7,8,9-tetrahydro-1,3-dioxa-5-aza-cyclohepta[f]indene-5-carboxylic acid isopropyl ester

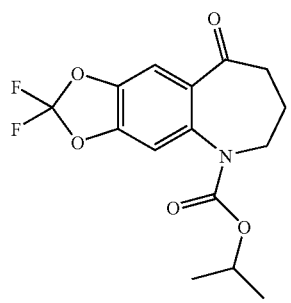

The title compound can be prepared using procedures analogous to those used in Example 3, Steps 1-3 (alternative preparation of methyl-2-(N-isopropoxycarbonyl)amino-5-methyl-4-trifluoromethylbenzoate) starting with 2,2-difluoro-benzo[1,3]dioxol-5-ylamine and then proceeding with Example 3, Steps 6-8.

Step 2. Preparation of (+/−)-9-[(3,5-Bis-trifluoromethyl-benzyl)-(2H-tetrazol-5-yl)-amino]-2,2-difluoro-6,7,8,9-tetrahydro-1,3-dioxa-5-aza-cyclohepta[f]indene-5-carboxylic acid isopropyl ester

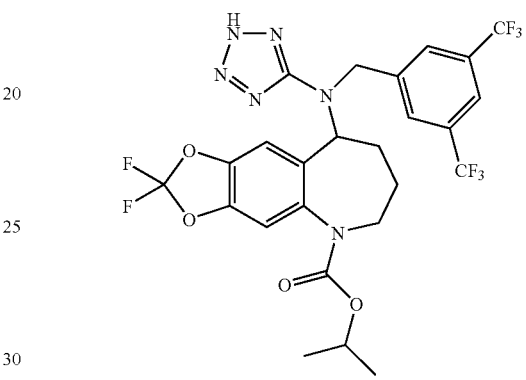

The title compound can be prepared using procedures analogous to those used in Example 1, Steps 4-6, starting with 2,2-difluoro-9-oxo-6,7,8,9-tetrahydro-1,3-dioxa-5-aza-cyclohepta[f]indene-5-carboxylic acid isopropyl ester.

Example 45

Synthesis of (+/−)-9-[(3,5-Bis-trifluoromethyl-benzyl)-(2-methyl-2H-tetrazol-5-yl)-amino]-2,2-difluoro-6,7,8,9-tetrahydro-1,3-dioxa-5-aza-cyclohepta[f]indene-5-carboxylic acid isopropyl ester

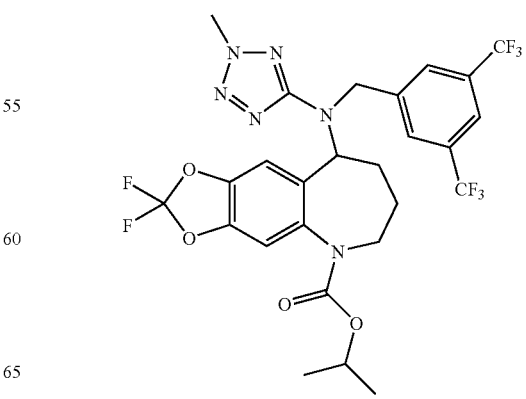

The title compound can be prepared using procedures analogous to those used in Example 1, Step 7, starting with 9-[(3,5-bis-trifluoromethyl-benzyl)-(2H-tetrazol-5-yl)-amino]-2,2-difluoro-6,7,8,9-tetrahydro-1,3-dioxa-5-aza-cyclohepta[f]indene-5-carboxylic acid isopropyl ester.

Example 46

Synthesis of (+/−)-Isopropyl 5-[(3,5-bistrifluoromethyl-benzyl)-(1H-tetrazol-5-yl)-amino]-8-chloro-2,3,4,5-tetrahydrobenzo[b]azepine-1-carboxylate

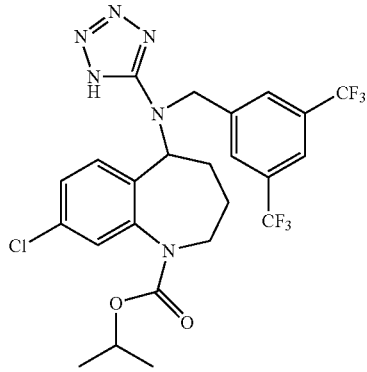

Step 1. Preparation of (+/−) Isopropyl 5-(3,5-bistrifluoromethyl-benzylamino)-8-chloro-2,3,4,5-tetrahydrobenzo[b]azepine-1-carboxylate

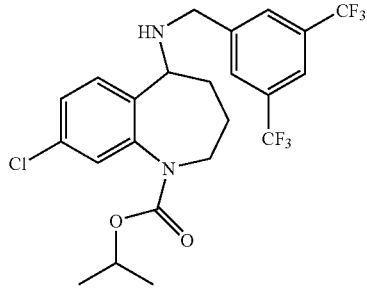

Prepare the titled compound by following the procedures as essentially described in Example 1, Step 1-4, by replacing methyl 2-amino-5-bromobenzoate with methyl-2-amino-4-chlorobenzoate in Example 1, Step 1.

Step 2. Preparation of (+/−)-Isopropyl 5-[(3,5-bistrifluoromethyl-benzyl)-cyano-amino]-8-chloro-2,3,4,5-tetrahydrobenzo[b]azepine-1-carboxylate

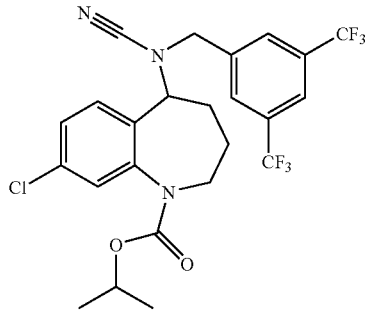

Add a solution of cyanogen bromide (68 mg, 0.63 mmol) in ether (2.6 mL) to a solution of isopropyl 5-(3,5-bistrifluoromethyl-benzylamino)-8-chloro-2,3,4,5-tetrahydrobenzo[b]azepine-1-carboxylate (512 mg, 1.0 mmol) in ether (2.6 mL). Stir the mixture overnight at room temperature. Filter off the resulting solid and wash with ether. Wash the filtrate with water, dry over anhydrous sodium sulfate, filter and remove the solvent under reduced pressure. Purify the residue by flash chromatography, eluting with hexanes/ethyl acetate, to afford the title compound (204 mg, 38%): MS (ES+): 534 (M+H).

Step 3. Preparation of (+/−)-isopropyl 5-[(3,5-bistrifluoromethyl-benzyl)-(1H-tetrazol-5-yl)-amino]-8-chloro-2,3,4,5-tetrahydrobenzo[b]azepine-1-carboxylate

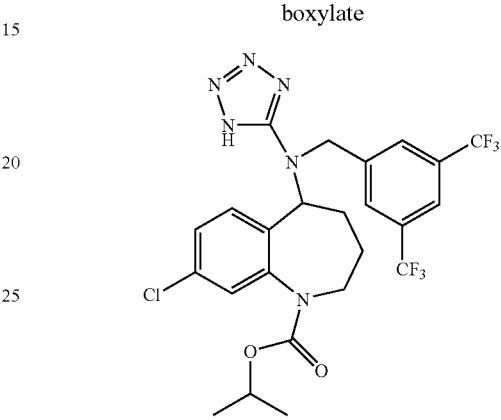

Add azidotributyltin (0.19 mL, 0.68 mmol) to a solution of (+/−)-isopropyl 5-[(3,5-bistrifluoromethyl-benzyl)-cyano-amino]-8-chloro-2,3,4,5-tetrahydrobenzo[b]azepine-1-carboxylate (180 mg, 0.34 mmol) in toluene (3.6 mL). Stir the mixture at 80° C. overnight. Cool down the mixture to room temperature; add ethyl acetate and 1N HCl (8.2 mL) and stir at room temperature for 1 h. Separate the layers, wash the organic phase with saturated KF, then with brine, dry over anhydrous sodium sulfate, filter and remove the solvent under reduced pressure. Purify the residue by flash chromatography, eluting with dichloromethane/methanol, and then by reverse phase purification to provide 198 mg (quantitative) of the title compound. MS (ES−): 575 (M−H).

Example 47

Synthesis of (+/−)-isopropyl 5-[(3,5-bistrifluoromethyl-benzyl)-(2-methyl-2H-tetrazol-5-yl)-amino]-8-chloro-2,3,4,5-tetrahydrobenzo[b]azepine-1-carboxylate

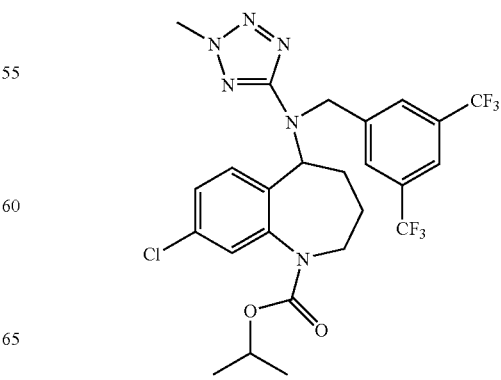

Add sodium carbonate (36 mg, 0.34 mmol) and methyl iodide (0.021 mL, 0.34 mmol) to a solution of (+/−)-isopropyl 5-[(3,5-bistrifluoromethyl-benzyl)-(1H-tetrazol-5-yl)-amino]-8-chloro-2,3,4,5-tetrahydrobenzo[b]azepine-1-carboxylate (98 mg, 0.17 mmol) in dimethylformamide/acetone (1:1) (1 mL). Stir the reaction mixture at room temperature overnight. Then add water and dichloromethane. Separate the layers and wash the organic phase with brine. Dry the organic layer over anhydrous sodium sulfate, filter and remove the solvent under reduced pressure. Purify the residue by flash chromatography, eluting with hexanes/ethyl acetate, to afford the title compound (70 mg, 70%). MS (ES+): 591 (M+H).

Example 48

Synthesis of (+/−) isopropyl-6-[(3,5-bistrifluoromethyl-benzyl)-(1H-tetrazol-5-yl)-amino]-2,3,6,7,8,9-hexahydro-1H-10-aza-cyclohepta[e]indene-10-carboxylate

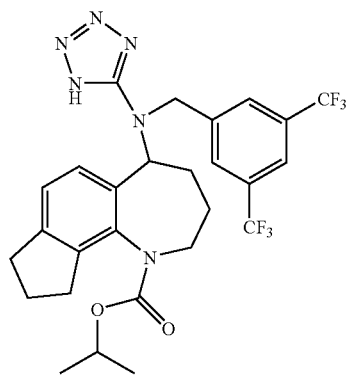

Step 1. Preparation of 2-Hydroxyimino-N-indan-4-yl-acetamide

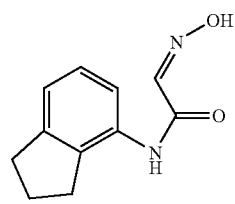

To a solution of chloral hydrate (5.46 g, 33 mmol) and anhydrous sodium sulfate (25.6 g, 180 mmol) in water (92 mL) add a mixture of hydroxylamine sulfate (25.6 g, 156 mmol), 4-aminoindane (4 g, 30 mmol), concentrated hydrochloric acid (3.1 mL) in water (30.8 mL). Heat the mixture up to 45° C. for 90 min, to 52° C. over 45 min and to 75° C. for 60 min. Cool the mixture to room temperature and filter the solid. Wash the solid with water and hexane. Dry the solid under vacuum to yield the title compound (5.54 g, 90%). MS (ES−): 203 (M−H).

Step 2. Preparation of 1,6,7,8-Tetrahydro-1-aza-as-indacene-2,3-dione

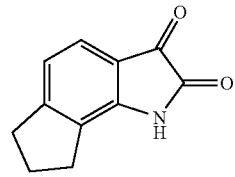

Add 2-Hydroxyimino-N-indan-4-yl-acetamide (5.54 g, 27.1 mmol) in small portions at 80° C. to methanesulfonic acid (21 mL). Stir the mixture at this temperature for 25 min. Cool to room temperature, pour into ice water and filter the precipitate. Dissolve the solid in warmed 1N NaOH, and neutralize with acetic acid. Filter the resulting solid and acidify the filtrate with concentrated HCl. Filter the precipitate and wash with water. Dry the solid to yield the title compound (3.80 g, 72%). MS (ES−): 186 (M−H).

Step 3. Preparation of 4-Amino-indan-5-carboxylic acid methyl ester

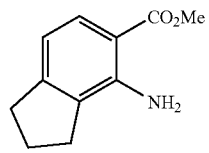

Add 30% aqueous hydrogen peroxide solution (5 mL) in water (44 mL) to a solution of 1,6,7,8-Tetrahydro-1-aza-as-indacene-2,3-dione (3.80 mg, 20.3 mmol) and NaOH (5.03 g, 126 mmol) in water (97 mL) over a period of 30 minutes, stir the mixture at room temperature for 1 h. Acidulate with 1N hydrochloric acid, filter the solid, wash with water and dry to afford 4-amino-indan-5-carboxylic acid (3.13 g, 87%). Dissolve 4-amino-indan-5-carboxylic acid (3.07 g, 17.3 mmol) in ethyl acetate (87 mL) and ethanol (87 mL) and add (trimethylsilyl) diazomethane (17.3 mL, 34.6 mmol, 2 M in hexanes) at room temperature and stir the solution for 1 h. Remove the solvent under reduced pressure. Purify the residue by flash chromatography, eluting with hexanes/ethyl acetate, to afford the title compound (2.50 g, 76%). $^1$H NMR (MeOD, 300 MHz) δ 2.12 (quintuplet, J=7.6 Hz, 2H), 2.75 (t, J=7.5 Hz, 2H), 2.89 (t, J=7.5 Hz, 2H), 3.83 (s, 3H), 6.53 (d, J=8.1 Hz, 1H), 7.66 (d, J=8.1 Hz, 1H). MS (ES+): 192 (M+H).

Step 4. Preparation of 4-Isopropoxycarbonylamino-indan-5-carboxylic acid methyl ester

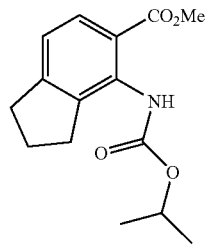

Add isopropyl chloroformate (2.22 mL, 2.22 mmol, 1.0 M in toluene) dropwise to a solution of 4-amino-indan-5-carboxylic acid methyl ester (425 mg, 2.22 mmol) and pyridine (0.44 mL, 5.5 mmol) in dichloromethane (4.4 mL) at 0° C. under an atmosphere of nitrogen and stir at room temperature for 24 h. Add 1M HCl and separate the layers. Extract the aqueous layer with dichloromethane. Dry the organic layers over anhydrous sodium sulfate, filter, and remove the solvent under reduced pressure, to afford the title compound (576 mg, 93%). ¹H NMR (MeOD) δ 1.37 (d, J=6.5 Hz, 6H), 2.16 (quintuplet, J=7.7 Hz, 2H), 2.97 (t, J=7.3 Hz, 2H), 3.05 (t, J=7.3 Hz, 2H), 3.94 (s, 3H), 4.97 (m, 1H), 7.22 (d, J=8.1 Hz, 1H), 7.80 (d, J=8.1 Hz, 1H). MS (ES+): 278 (M+H).

Step 5. Preparation of 4-[(3-Ethoxycarbonyl-propyl)-isopropoxycarbonyl-amino]-indan-5-carboxylic acid methyl ester

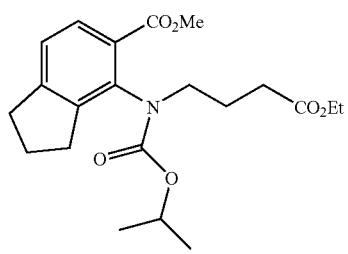

Add a solution of 4-isopropoxycarbonylamino-indan-5-carboxylic acid methyl ester (570 mg, 2.1 mmol) in dimethylformamide (8.2 mL) to a suspension of sodium hydride 60% dispersion mineral oil (82 mg, 2.1 mmol) in dimethylformamide (8.2 mL) at 0° C. under an atmosphere of nitrogen and allow to reach room temperature over 1 h. Add ethyl 4-bromobutyrate (0.44 mL, 3.09 mmol) and stir at room temperature for 14 h, then heat at 65° C. for 2 h. Cool the mixture to room temperature, dilute with ethyl acetate, wash with 1M HCl, water, and brine. Dry the organic layer over anhydrous sodium sulfate, filter and remove the solvent under reduced pressure. Purify the residue by flash chromatography, eluting with hexanes/ethyl acetate, to provide the title compound (651 mg, 81%). ¹H NMR (MeOD, 300 MHz) δ 1.03-1.34 (m, 9H), 1.85 (m, 2H), 2.10 (m, 2H), 2.30 (m, 2H), 2.82-3.01 (m, 4H), 3.32 (m, 1H), 3.68 (m, 1H), 3.86 (s, 3H), 4.08 (m, 2H), 4.91 (m, 1H), 7.19 (d, J=7.7 Hz, 1H), 7.77 (d, J=7.7 Hz, 1H). MS (ES+): 392 (M+H).

Step 6. Preparation of 6-Oxo-2,3,6,7,8,9-hexahydro-1H-10-aza-cyclohepta[e]indene-10-carboxylic acid isopropyl ester

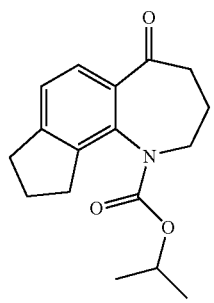

Add a solution of 4-[(3-ethoxycarbonyl-propyl)-isopropoxycarbonyl-amino]-indan-5-carboxylic acid methyl ester (510 mg, 1.30 mmol) in tetrahydrofuran (20.4 mL) to a solution of potassium tert-butoxide (2.60 mL, 2.60 mmol, 1M in tetrahydrofuran) in tetrahydrofuran (18 mL) at room temperature under an atmosphere of nitrogen. After 30 min, pour the mixture into ice/water. Treat the aqueous phase with 1M HCl to pH neutral and extract with dichloromethane. Dry the organic layer over anhydrous sodium sulfate, filter, and remove the solvent under reduced pressure. Dissolve the former crude in dimethyl sulfoxide (11 mL) and add water (2 drops) followed by addition of lithium chloride (134 mg, 3.2 mmol) and heat the resulting solution at 160° C. for 30 minutes. Cool the mixture to room temperature and pour into brine. Extract the mixture with ethyl acetate. Dry the organic layers over anhydrous sodium sulfate, filter and remove the solvent under reduced pressure. Purify the residue by flash chromatography, eluting with hexanes/ethyl acetate, to afford the title compound (302 mg, 81% over two steps). MS (ES+): 288 (M+H).

Step 7. Preparation of (+/−) isopropyl-6-[(3,5-bistrifluoromethyl-benzyl)-(1H-tetrazol-5-yl)-amino]-2,3,6,7,8,9-hexahydro-1H-10-aza-cyclohepta[e]indene-10-carboxylate

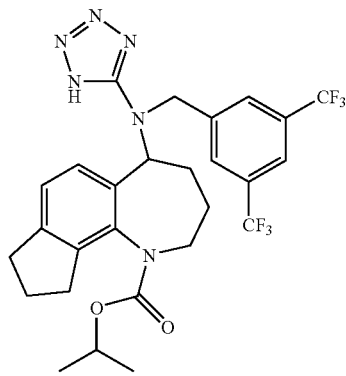

Add 3,5-bis(trifluoromethyl)benzylamine (349 mg, 1.15 mmol) followed by titanium isopropoxide (414 mg, 1.46 mmol) to 6-oxo-2,3,6,7,8,9-hexahydro-1H-10-aza-cyclohepta[e]indene-10-carboxylic acid isopropyl ester (300 mg, 1.04 mmol) at room temperature under an atmosphere of nitrogen and stir the solution for 14 h. Add methanol (4.3 mL) and sodium borohydride (59 mg, 1.56 mmol) and stir the mixture under nitrogen at room temperature for 45 min. Add 0.1M NaOH and stir for 30 min. Filter through Celite® and wash the residue with ethyl acetate. Separate the organic layer and extract the aqueous with ethyl acetate. Wash the organic layer with brine and dry the organic layers over anhydrous sodium sulfate. Filter and remove the solvent under reduced pressure. Purify the residue by flash chromatography, eluting with hexanes/ethyl acetate, to afford (+/−)isopropyl-6-(3,5-bis-trifluoromethyl-benzylamino)-2,3,6,7,8,9-hexahydro-1H-10-aza-cyclohepta[e]indene-10-carboxylate (443 mg, 83%).

The titled compound was prepared in a manner analogous to the procedure for the preparation of (+/−)-isopropyl 5-[(3,5-bistrifluoromethyl-benzyl)-(1H-tetrazol-5-yl)-amino]-8-chloro-2,3,4,5-tetrahydrobenzo[b]azepine-1-carboxylate (Example 46, from Step 2 to Step 3) by replacing (+/−)-isopropyl 5-(3,5-bistrifluoromethyl-benzylamino)-8-chloro-2,3,4,5-tetrahydrobenzo[b]azepine-1-carboxylate with (+/−)-isopropyl 6-(3,5-bis-trifluoromethyl-benzylamino]-2,3,6,7,8,9-hexahydro-1H-10-aza-cyclohepta[e]indene-10-carboxylate (prepared above) in Example 46 Step 2. MS (ES−): 581 (M−H).

Example 49

Synthesis of (+/−)-9-[(3,5-Bis-trifluoromethyl-benzyl)-(2H-tetrazol-5-yl)-amino]-2,3,6,7,8,9-hexahydro-1H-5-aza-cyclohepta[f]indene-5-carboxylic acid isopropyl ester

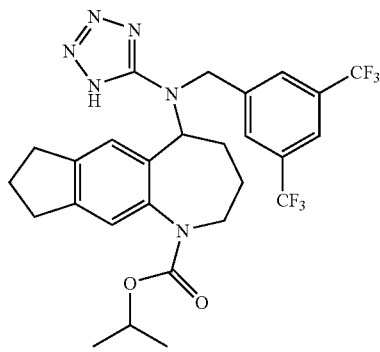

Step 1. Preparation of 2-Hydroxyimino-N-indan-5-yl-acetamide

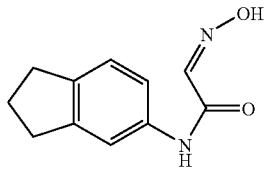

To a solution of chloral hydrate (5.56 g, 33.63 mmol) and anhydrous sodium sulfate (28.58 g, 201.20 mmol) in water (90 mL) add a mixture of hydroxylamine sulfate (25.63 g, 156.16 mmol), 5-aminoindane (4 g, 30.03 mmol), concentrated hydrochloric acid (3.14 mL) in water (30 mL). Heat the mixture at 45° C. for 1 h and at 75° C. for 2 h. Cool the mixture to room temperature and filter the solid. Wash the solid with water and ethyl ether. Dry the solid under vacuum to yield the title compound (4.98 g, 81%). $^1$H NMR (dimethyl sulfoxide-$d_6$, 300 MHz) δ 1.90 (quintuplet, J=7.8 Hz, 2H), 2.72 (q, J=7.8 Hz, 4H), 7.06 (d, J=8.2 Hz, 1H), 7.28 (dd, J=1.5, 8.2 Hz, 1H), 7.49 (bs, 1H), 9.94 (s, 1H), 12.02 (s, 1H). MS (ES−): 203 (M−H).

Step 2. Preparation of 1,5,6,7-Tetrahydro-1-aza-s-indacene-2,3-dione

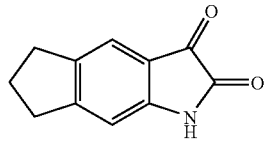

Add 2-hydroxyimino-N-indan-5-yl-acetamide (4.66 g, 22.84 mmol) in small portions at 65° C. to concentrated sulfuric acid (22 mL) and heat the mixture at 80° C. for 15 minutes. Cool to room temperature, pour into ice water (200 mL) and filter the precipitate. Dissolve the solid in warmed ethanol and leave to cool overnight. Filter the precipitate and wash with ethyl ether. Dry the solid to yield the title compound (3.3 g, 77%). $^1$H NMR (dimethyl sulfoxide-$d_6$, 300 MHz) δ 1.98 (quintuplet, J=7.7 Hz, 2H), 2.76 (t, J=7.7 Hz, 2H), 2.85 (t, J=7.7 Hz, 2H), 6.74 (s, 1H), 7.28 (s, 1H). MS (ES−): 186 (M−H).

Step 3. Preparation of 6-Amino-indan-5-carboxylic acid methyl ester

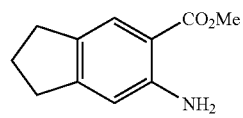

Add 30% aqueous hydrogen peroxide solution (3 mL) to a solution of 1,5,6,7-tetrahydro-1-aza-s-indacene-2,3-dione (2.18 g, 11.66 mmol) in 2 N NaOH (23 mL) over a period of 5 minutes, stir the mixture at room temperature for 3 h. Add 1N hydrochloric acid to pH=5 and extract with ethyl acetate (3×20 mL). Wash with brine, dry the organic layer over anhydrous sodium sulfate, filter and remove the solvent under reduced pressure to afford 6-amino-indan-5-carboxylic acid (1.7 g, 86%). Dissolve in ethyl acetate (2 mL) and ethanol (2 mL) and add (trimethylsilyl) diazomethane (9.6 mL, 19.2 mmol, 2 M in hexane) at room temperature and stir the solution for 16 h. Remove the solvent under reduced pressure. Chromatograph the residue over silica gel, eluting with hexanes/ethyl acetate (9:1), to afford the title compound (1.19 g, 66%). $^1$H NMR (CDCl$_3$, 300 MHz) δ 2.05 (quintuplet, J=7.3 Hz, 2H), 2.80 (q, J=7.7 Hz, 4H), 6.59 (s, 1H), 7.69 (s, 1H). MS (ES+): 192 (M+H).

Step 4. Preparation of 9-Oxo-2,3,6,7,8,9-hexahydro-1H-5-aza-cyclohepta[f]indene-5-carboxylic acid isopropyl ester

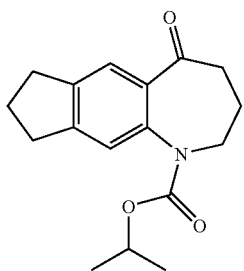

Prepare the titled compound by following the procedure as essentially described for the preparation of methyl-5-bromo-2-[isopropoxycarbonyl-(3-methoxycarbonylpropyl)amino]benzoate (Example 1, Steps 1 and 2) and followed by the procedure described for the preparation of 6-Oxo-2,3,6,7,8,9-hexahydro-1H-10-aza-cyclohepta[e]indene-10-carboxylic acid isopropyl ester (Example 48, Step 6) by replacing methyl 2-amino-5-bromobenzoate with 6-amino-indan-5-carboxylic acid methyl ester in Example 1, Step 1. MS (ES+): 288 (M+H).

Step 5. Preparation of (+/−)-9-[(3,5-Bis-trifluoromethyl-benzyl)-(2H-tetrazol-5-yl)-amino]-2,3,6,7,8,9-hexahydro-1H-5-aza-cyclohepta[f]indene-5-carboxylic acid isopropyl Ester

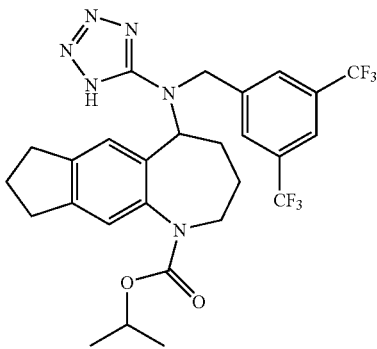

Add 3,5-bis(trifluoromethyl)benzylamine (187 mg, 0.77 mmol) followed by titanium isopropoxide (835 mg, 2.94 mmol) to 9-oxo-2,3,6,7,8,9-hexahydro-1H-5-aza-cyclohepta[f]indene-5-carboxylic acid isopropyl ester (200 mg, 0.7 mmol) at room temperature under an atmosphere of nitrogen and stir the solution for 3 days. Add methanol (3 mL) and sodium borohydride (40 mg, 1.05 mmol) and stir the mixture under nitrogen at room temperature for 16 h. Add sodium bicarbonate saturated solution, filter through Celite® and wash the residue with ethyl acetate. Separate organic layer, extract aqueous with ethyl acetate. Wash organic layer with brine and dry the organic layers over anhydrous sodium sulfate. Filter and remove the solvent under reduced pressure. Purify the residue by silica cartridge, eluting with hexanes/ethyl acetate 9:1, to afford (+/−)-isopropyl-9-(3,5-bis-trifluoromethyl-benzylamino)-2,3,6,7,8,9-hexahydro-1H-5-aza-cyclohepta[f]indene-5-carboxylate (220 mg).

The titled compound was prepared in a manner analogous to the procedure for the preparation of (+/−)-isopropyl 5-[(3,5-bistrifluoromethyl-benzyl)-(1H-tetrazol-5-yl)-amino]-8-chloro-2,3,4,5-tetrahydrobenzo[b]azepine-1-carboxylate (Example 46, from Step 2 to Step 3) by replacing isopropyl 5-(3,5-bistrifluoromethyl-benzylamino)-8-chloro-2,3,4,5-tetrahydrobenzo[b]azepine-1-carboxylate with (+/−)-isopropyl-9-(3,5-bis-trifluoromethyl-benzylamino)-2,3,6,7,8,9-hexahydro-1H-5-aza-cyclohepta[f]indene-5-carboxylate (prepared above) in Example 46 Step 2. MS (ES−): 581 (M−H).

Example 50

Synthesis of (+/−)-9-[(3,5-Bis-trifluoromethyl-benzyl)-(2-methyl-2H-tetrazol-5-yl)-amino]-2,3,6,7,8,9-hexahydro-1H-5-aza-cyclohepta[f]indene-5-carboxylic acid isopropyl ester

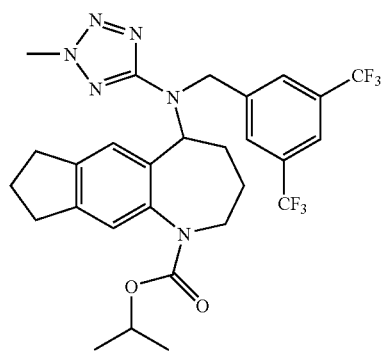

To a solution of (+/−)-isopropyl 9-[(3,5-bis-trifluoromethyl-benzyl)-(2H-tetrazol-5-yl)-amino]-2,3,6,7,8,9-hexahydro-1H-5-aza-cyclohepta[f]indene-5-carboxylate (Example 49) (48 mg, 0.082 mmol) and methanol (0.015 mL, 0.36 mmol) in dichloromethane (1 mL) at room temperature, under nitrogen atmosphere, add triphenyl phosphine (22 mg, 0.082 mmol) in one portion. Add diethyl azodicarboxylate (0.015 mL, 0.082 mmol). The reaction mixture was allowed to stir at room temperature overnight. Add methanol (0.015 mL, 0.36 mmol), triphenyl phosphine (22 mg, 0.082 mmol) and diethyl azodicarboxylate (0.015 mL, 0.082 mmol). After stirring for 6 h, remove the solvents under reduced pressure. Purify the residue by flash chromatography, eluting with hexanes/ethyl acetate, to afford the title compound (25 mg, 51%). MS (ES+): 597 (M+H).

Example 51

Synthesis of (+/−)-isopropyl 5-[(3,5-bistrifluoromethyl-benzyl)-(5-methyl-1H-pyrazol-3-yl)-amino]-8-chloro-2,3,4,5-tetrahydrobenzo[b]azepine-1-carboxylate

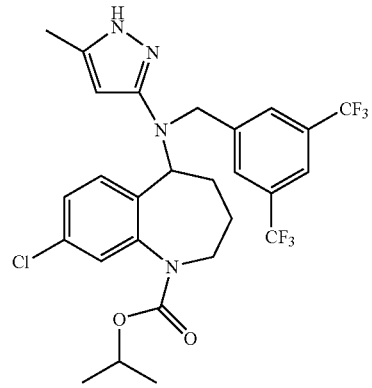

Step 1. Preparation of (+/−)-isopropyl 5-[(3,5-bistrifluoromethyl-benzyl)-(3-oxo-butyryl)-amino]-8-chloro-2,3,4,5-tetrahydrobenzo[b]azepine-1-carboxylate

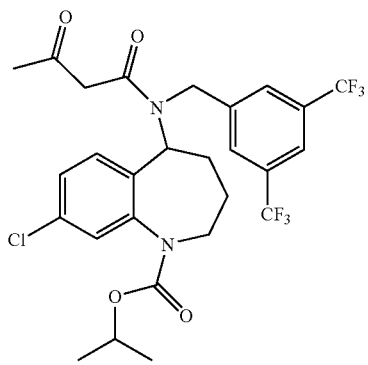

To a solution of isopropyl 5-(3,5-bistrifluoromethyl-benzylamino)-8-chloro-2,3,4,5-tetrahydrobenzo[b]azepine-1-carboxylate (Example 46, Step 1) (200 mg, 0.39 mmol) and 4-dimethylaminopyridine (6 mg, 0.049 mmol) in dry tetrahydrofuran (1.4 mL) at 0° C. under a nitrogen atmosphere, add a solution of diketene (0.033 mL, 0.43 mmol) in dry tetrahydrofuran (0.4 mL). After stirring 1.5 h at 0° C., remove the solvent under reduced pressure. Purify the by flash chromatography, eluting with hexanes/ethyl acetate, to afford the title compound (169 mg, 73%). MS (ES+): 593 (M+H).

Step 2. Preparation of (+/−)-isopropyl 5-[(3,5-bistrifluoromethyl-benzyl)-(5-methyl-1H-pyrazol-3-yl)-amino]-8-chloro-2,3,4,5-tetrahydrobenzo[b]azepine-1-carboxylate

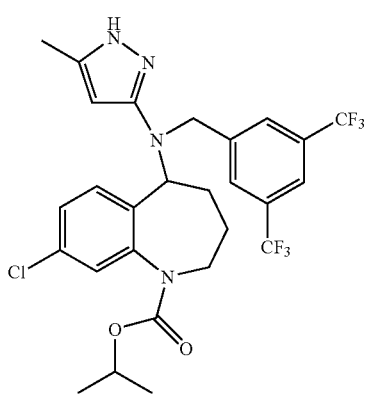

Add cold (ice bath) absolute EtOH (1 mL) slowly to a cooled 0° C. stirred mixture of (+/−)-5-[(3,5-bistrifluoromethyl-benzyl)-(3-oxo-butyryl)-amino]-8-chloro-2,3,4,5-tetrahydrobenzo[b]azepine-1-carboxylic acid isopropyl ester (118 mg, 0.20 mmol) and phosphorus pentoxide (511 mg, 3.6 mmol). Then, add hydrazine hydrate (0.062 mL, 2.0 mmol) dropwise while keeping the mixture cooled at 0° C. Heat at 100° C. overnight in a sealed tube. Cool down the mixture and remove the solvents under reduce pressure. Partition the residue between water and dichloromethane. Separate the layers, and dry organic phase over anhydrous magnesium sulfate, filter and concentrate in vacuo. Purify the residue by flash chromatography, eluting with hexanes/ethyl acetate, and then by a SCX cartridge to afford the title compound (25 mg, 21%). MS (ES+): 589 (M+H).

Example 52

Synthesis of (+/−)-isopropyl 5-[(3,5-bistrifluoromethyl-benzyl)-(5-methyl-isoxazol-5-yl)-amino]-8-chloro-2,3,4,5-tetrahydrobenzo[b]azepine-1-carboxylate

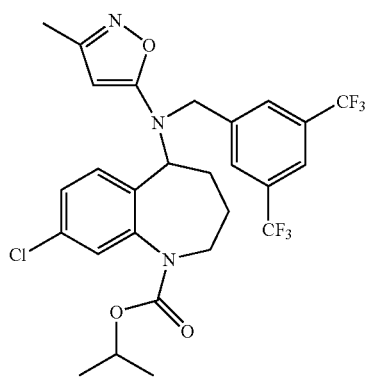

Add hydroxylamine hydrochloride (39 mg, 0.55 mmol) and sodium acetate (1.5 mg, 0.018 mmol). to a solution of compound (+/−)-5-[(3,5-bistrifluoromethyl-benzyl)-(3-oxo-butyryl)-amino]-8-chloro-2,3,4,5-tetrahydrobenzo[b]azepine-1-carboxylic acid isopropyl ester (Example 51, Step 1) (218 mg, 0.37 mmol) in methanol (1.8 mL) at 0° C., Heat the reaction mixture under reflux overnight. Cool and remove the solvents under reduce pressure. Dilute the residue with ethyl acetate and brine. Separate the layers and dry the organic phase over magnesium sulfate, filter and concentrate in vacuo. Purify the residue by flash chromatography, eluting with hexanes/ethyl acetate to afford the title compound (85 mg, 39%). MS (ES+): 590 (M+H).

Example 53

Synthesis of (+/−)-isopropyl 5-[(3,5-bistrifluoromethyl-benzyl)-(2-methyl-2H-tetrazol-5-yl)-amino]-9-methyl-8-trifluormethyl-2,3,4,5-tetrahydrobenzo[b]azepine-1-carboxylate

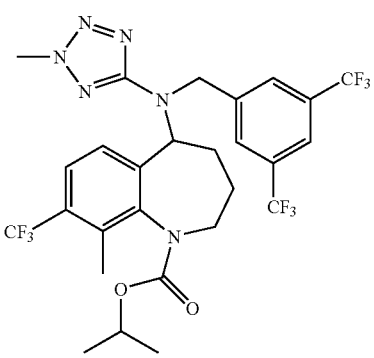

Step 1. Preparation of 7-methyl-6-trifluoromethyl-1H-indole,2,3-dione

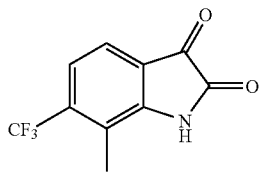

To a solution of chloral hydrate (6.08 g, 36.74 mmol) and anhydrous sodium sulfate (28.5 g, 200.4 mmol) in water (102 mL) add a mixture of hydroxylamine sulfate (28.5 g, 173.68 mmol), 2-methyl-3-trifluoromethyl-phenylamine (5.85 g, 33.4 mmol), concentrated hydrochloric acid (3.5 mL) in water (34 mL). Heat the mixture at 35° C. for 1 h, then heat up to 52° C. for 90 min and at 75° C. for 1 h. Cool the mixture to room temperature and filter the solid. Wash the solid with water and hexane. Dry the solid under vacuum to afford 2-hydroxyimino-N-(2-methyl-3-trifluoromethyl-phenyl)-acetamide: MS (ES+): 245 (M–H). Add the former crude in small portions at 60° C. to concentrated sulfuric acid (44 mL) and heat the mixture at 80° C. for 1 h. Cool to room temperature, pour into ice water (100 mL) and filter the precipitate. Wash the solid with cool water twice. Dry the solid to afford the title compound (3.54 g, 46% two steps). MS (ES–): 228 (M–H).

Step 2. Preparation of 2-Amino-3-methyl-4-trifluoromethyl-benzoic acid

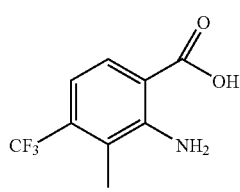

Add 30% aqueous hydrogen peroxide solution (3.8 mL) in water (33 mL) to solution of 7-methyl-6-trifluoromethyl-1H-indole,2,3-dione (3.54 g, 15.46 mmol) and NaOH (3.83 g, 95.84 mmol) in water (74 mL) slowly. Then stir the mixture at room temperature for 1 h. Add 1N hydrochloric acid to acidulate the mixture. Filter the resulting solid and wash with water. Dry the solid to afford the title compound (1.7 g, 50%). MS (ES+): 218 (M–H).

Step 3. Preparation of (+/–)-isopropyl 5-[(3,5-bistrifluoromethyl-benzyl)-cyano-amino]-9-methyl-8-trifluormethyl-2,3,4,5-tetrahydrobenzo[b]azepine-1-carboxylate

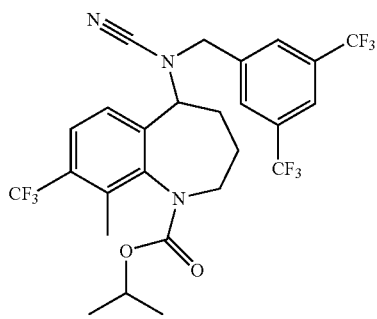

Prepare isopropyl 5-(3,5-bistrifluoromethyl-benzylamino)-9-methyl-8-trifluormethyl-2,3,4,5-tetrahydrobenzo[b]azepine-1-carboxylate following procedures as generally described for Example 48, Step 3 to 7, using 2-amino-3-methyl-4-trifluoromethyl-benzoic acid.

To a suspension of sodium hydride 60% in mineral oil (32 mg, 0.81 mmol) in dry dimethyl sulfoxide (3 mL), add isopropyl 5-(3,5-bistrifluoromethyl-benzylamino)-9-methyl-8-trifluormethyl-2,3,4,5-tetrahydrobenzo[b]azepine-1-carboxylate (300 mg, 0.54 mmol) and dry dimethylformamide (2 mL). Add cyanogen bromide (176 mg, 1.62 mmol) and stir the reaction mixture at room temperature overnight. Add sodium hydride 60% in mineral oil (32 mg, 0.81 mmol) and cyanogen bromide (176 mg, 1.62 mmol) and stir at room temperature for one hour. Add additional sodium hydride 60% in mineral oil (32 mg, 0.81 mmol) and cyanogen bromide (176 mg, 1.62 mmol) and stir one hour. Add water and ethyl acetate. Separate the layers and dry the organic phase over anhydrous magnesium sulfate, filter and remove the solvent under reduced pressure. Purify the residue by flash chromatography, eluting with hexanes/ethyl acetate, to afford the titled compound (124 mg, 40%). MS (ES+): 582 (M+H).

Step 4. Preparation of (+/–)-isopropyl 5-[(3,5-bistrifluoromethyl-benzyl)-(1H-tetrazol-5-yl)-amino]-9-methyl-8-trifluormethyl-2,3,4,5-tetrahydrobenzo[b]azepine-1-carboxylate

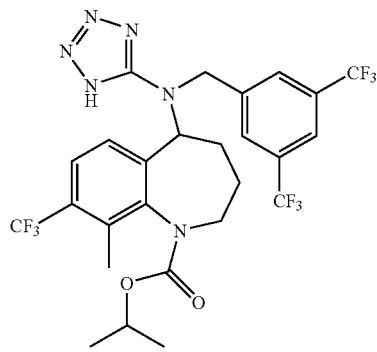

Add sodium azide (42 mg, 0.64 mmol) and triethylamine hydrochloride (88 mg, 0.64 mmol) to a solution of (+/–)-isopropyl 5-[(3,5-bistrifluoromethyl-benzyl)-cyano-amino]-9-methyl-8-trifluormethyl-2,3,4,5-tetrahydrobenzo[b]azepine-1-carboxylate (124 mg, 0.21 mmol) in toluene (2 mL). Stir the mixture at 110° C. overnight. Cool down the mixture to room temperature, add 1N HCl (5 mL) and dichloromethane. Separate the layers, dry the organic phase over anhydrous magnesium sulfate, filter and remove the solvent under reduced pressure to provide 117 mg (89%) of the title compound. MS (ES–): 623 (M–H).

Step 5. Preparation of (+/−)-isopropyl 5-[(3,5-bistrif-luoromethyl-benzyl)-(2-methyl-2H-tetrazol-5-yl)-amino]-9-methyl-8-trifluormethyl-2,3,4,5-tetrahydrobenzo[b]azepine-1-carboxylate

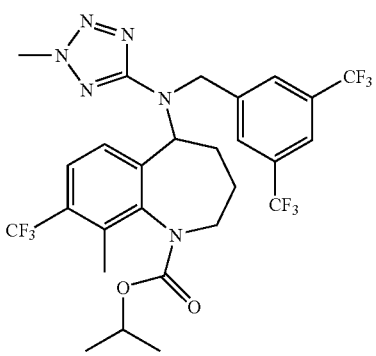

To a solution of (+/−)-isopropyl 5-[(3,5-bistrifluoromethyl-benzyl)-(1H-tetrazol-5-yl)-amino]-9-methyl-8-trifluormethyl-2,3,4,5-tetrahydrobenzo[b]azepine-1-carboxylate (87 mg, 0.139 mmol), methanol (0.564 mL, 13.9 mmol), triphenyl phosphine (73 mg, 0.278 mmol) in dry dichloromethane (3.4 mL) at 0° C., under nitrogen, add diethyl azodicarboxylate (0.128 mL, 0.278 mmol). Stir the reaction mixture at room temperature for 3 h. Remove the solvents under reduced pressure and purify the residue by flash chromatography, eluting with hexanes/ethyl acetate to afford the title compound (47 mg, 53%). MS (ES+): 639 (M+H).

Example 54

Synthesis of (+/−)-isopropyl 5-[(3,5-bistrifluoromethyl-benzyl)-(2-methyl-2H-tetrazol-5-yl)-amino]-7,9-methyl-8-trifluormethyl-2,3,4,5-tetrahydrobenzo[b]azepine-1-carboxylate

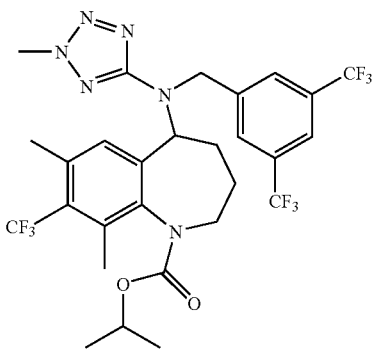

To a solution of (S)-(3,5-Bis-trifluoromethyl-benzyl)-(7,9-dimethyl-8-trifluoromethyl-2,3,4,5-tetrahydro-1H-benzo[b]azepin-5-yl)-(2-methyl-2H-tetrazol-5-yl)-amine (Example 148, Step 2) (0.12 mmol) in dichloromethane (5 mL) add pyridine (0.37 mmol) followed by isopropyl chloroformate (0.37 mmol) as a 1.0 M solution in toluene. After stirring at room temperature for 14 h dilute the reaction with dichloromethane (10 mL) and water (10 mL). Acidify the aqueous by dropwise addition of 5M HCl. Separate the organics and wash the aqueous with dichloromethane (2×5 mL). Dry the combined organics over sodium sulfate, filtered, and remove solvent. Chromatograph the mixture over silica gel using ethyl acetate/hexane (5-30%). This affords the title compound as a colorless foam. MS (ES+): 653 (M+H).

Example 55

Synthesis of (S)-6-[(3,5-Bis-trifluoromethyl-benzyl)-(2-methyl-2H-tetrazol-5-yl)-amino]-4-methyl-2,3,6,7,8,9-hexahydro-1H-10-aza-cyclohepta[e]indene-10-carboxylic acid isopropyl ester

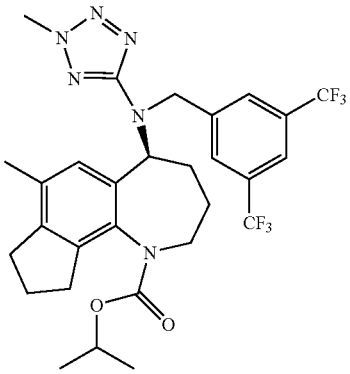

Step 1. Preparation of 4-Amino-7-bromo-indan-5-carboxylic acid methyl ester

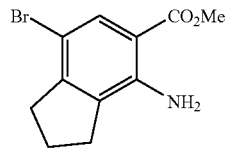

Add N-bromosuccinimide (1.99 g, 11.2 mmol) to 4-amino-indan-5-carboxylic acid methyl ester (2.15 g, 11.2 mmol) (Example 48, Step 3) in acetic acid (13 mL). Stir the mixture at room temperature for 48 h. Pour the mixture into ice water and add ethyl acetate. Separate the layers and wash the organic phase with saturated NaHCO$_3$ and brine and dry over sodium sulfate. Remove the solvent under reduced pressure to afford the title compound (3.10 g, quantitative). MS (ES+): 271 (M+H).

Step 2. Preparation of 4-Bromo-6-oxo-2,3,6,7,8,9-hexahydro-1H-10-aza-cyclohepta[e]indene-10-carboxylic acid isopropyl ester

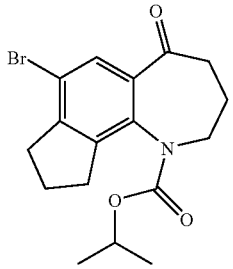

Prepare the title compound by essentially following the procedure described in Example 3, Steps 5-8 by replacing methyl 2-amino-5-methyl-4-trifluoromethylbenzoate with 4-amino-7-bromo-indan-5-carboxylic acid methyl ester in Example 3, Step 5. MS (ES+): 366, 368 (M+H).

Step 3. Preparation of (S)-6-(3,5-Bis-trifluoromethyl-benzylamino)-4-bromo-2,3,6,7,8,9-hexahydro-1H-10-aza-cyclohepta[e]indene-10-carboxylic acid isopropyl ester

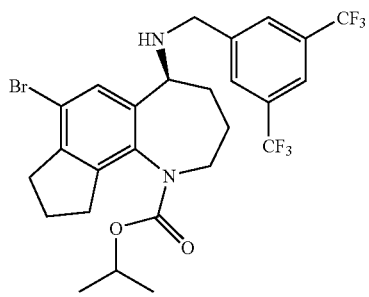

Prepare the title compound by essentially following the procedure described in Example 3, Steps 11-14 by replacing tert-butyl-7-methyl-5-oxo-8-trifluoromethyl-2,3-4,5-tetrahydrobenzo[b]azepine-1-carboxylate with 4-Bromo-6-oxo-2,3,6,7,8,9-hexahydro-1H-10-aza-cyclohepta[e]indene-10-carboxylic acid isopropyl ester in Example 3, Step 11. MS (ES+): 593, 595 (M+H).

Step 4. Preparation of (S)-6-(3,5-Bis-trifluoromethyl-benzylamino)-4-methyl-2,3,6,7,8,9-hexahydro-1H-10-aza-cyclohepta[e]indene-10-carboxylic acid isopropyl ester

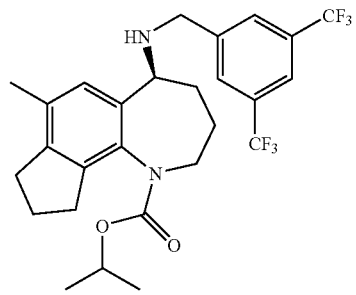

Add cesium carbonate (383 mg, 2.52 mmol), methyl boronic acid (76 mg, 1.26 mmol) and [1,1'-bis(diphenylphosphino)-ferrocene]dichloropalladium (II) complex with dichloromethane (1:1) (69 mg, 0.084 mmol) to a solution of (S)-6-(3,5-bis-trifluoromethyl-benzylamino)-4-bromo-2,3,6,7,8,9-hexahydro-1H-10-aza-cyclohepta[e]indene-10-carboxylic acid isopropyl ester (500 mg, 0.84 mmol) in dioxane (7 mL). Stir the mixture under nitrogen at 110° C. for 2 h. Cool down the mixture to room temperature and filter over Celite® washing with dichloromethane. Evaporate the solvent and purify the crude by chromatography, eluting with hexane/ethyl acetate (90/10) to afford the title compound (355 mg, 0.67 mmol, 80%). MS (ES+): 529 (M+H).

Step 5. Preparation of (S)-6-[(3,5-Bis-trifluoromethyl-benzyl)-(2H-tetrazol-5-yl)-amino]-4-methyl-2,3,6,7,8,9-hexahydro-1H-10-aza-cyclohepta[e]indene-10-carboxylic acid isopropyl ester

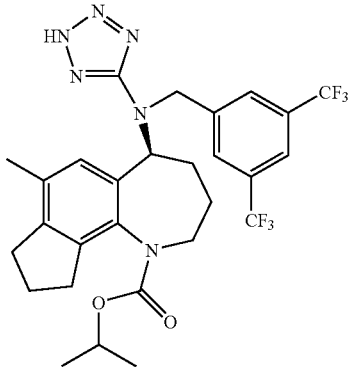

Prepare the title compound by essentially following the procedure described in Example 3, Steps 15-16 by replacing (S)-tert-butyl 5-(3,5-bistrifluoromethylbenzylamino)-7methyl-8-trifluoromethyl-2,3,4,5-tetrahydrobenzo[b]azepine-1-carboxylate with (S)-6-(3,5-Bis-trifluoromethyl-benzylamino)-4-methyl-2,3,6,7,8,9-hexahydro-1H-10-aza-cyclohepta[e]indene-10-carboxylic acid isopropyl ester in Example 3, Step 15. MS (ES+): 597 (M+H).

Step 6. Preparation of (S)-6-[(3,5-Bis-trifluoromethyl-benzyl)-(2-methyl-2H-tetrazol-5-yl)-amino]-4-methyl-2,3,6,7,8,9-hexahydro-1H-10-aza-cyclohepta[e]indene-10-carboxylic acid isopropyl ester

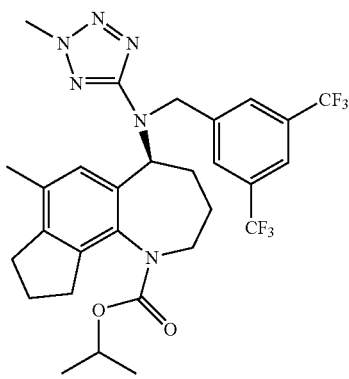

Prepare the title compound by essentially following the procedure described in Example 3, Step 17 by replacing (S)-tert-butyl 5-[(3,5-bistrifluoromethylbenzyl)-(2H-tetrazol-5-yl)amino]-7-methyl-8-trifluoromethyl-2,3,4,5-tetrahydrobenzo[b]azepine-1-carboxilate with (S)-6-[(3,5-Bis-trifluoromethyl-benzyl)-(2H-tetrazol-5-yl)-amino]-4-methyl-2,3,6,7,8,9-hexahydro-1H-10-aza-cyclohepta[e]indene-10-carboxylic acid isopropyl ester in Example 3, Step 17. MS (ES+): 611 (M+H).

Example 56

Synthesis of (S)-isopropyl 5-[(3,5-bistrifluoromethyl-benzyl)-(2-methyl-2H-tetrazol-5-yl)-amino]-8,9-dimethyl-2,3,4,5-tetrahydrobenzo[b]azepine-1-carboxylate

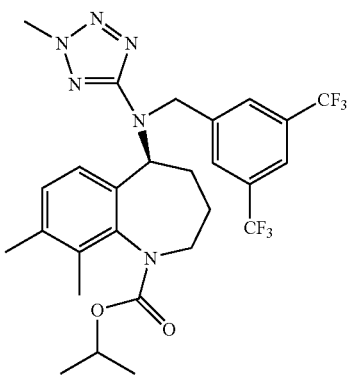

Step 1. Preparation of 2-Amino-4-bromo-3-methyl-benzoic acid

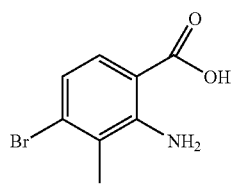

Prepare the titled compound by following the procedure as essentially described for the preparation of 2-Amino-3-methyl-4-trifluoromethyl-benzoic acid (Example 53, from Step 1 to Step 2) by replacing 2-methyl-3-trifluoromethyl-phenylamine with 3-bromo-2-methyl-phenylamine in Step 1. MS (ES−): 229 (M−H).

Step 2. Preparation of methyl 2-amino-4-bromo-3-methylbenzoate

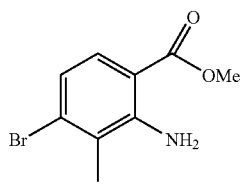

Add (trimethylsilyl)diazomethane (16.5 mL, 33 mmol, 2 M in hexane) to a solution of 2-amino-4-bromo-3-methyl-benzoic acid (3.8 g, 16.5 mmol) in ethyl acetate (50 mL) and ethanol (50 mL) at room temperature and stir the solution for 16 h. Remove the solvent under reduced pressure. Chromatograph the residue over silica gel, eluting with hexanes/ethyl acetate, to afford the title compound (3.54 g, 88%). MS (ES+): 245 (M+H).

Step 3. Preparation of 8-bromo-9-methyl-5-oxo-2,3,4,5-tetrahydro-benzo[b]azepine-1-carboxylic acid isopropyl ester

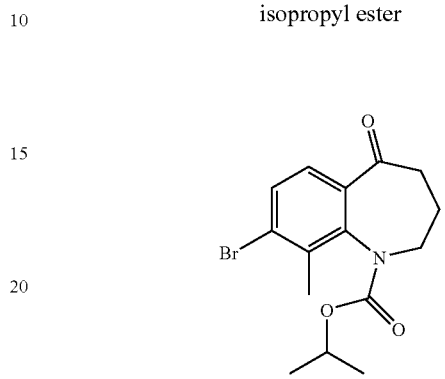

Prepare the titled compound by following the procedure as essentially described for the preparation of isopropyl 7-methyl-5-oxo-8-trifluoromethyl-2,3,4,5-tetrahydrobenzo[b]azepine-1-carboxylate (Example 3, Steps 5 to 8) by replacing methyl 2-amino-5-methyl-4-trifluoromethylbenzoate with methyl 2-amino-4-bromo-3-methylbenzoate in Step 5. MS (ES+): 341 (M+H).

Step 4. Preparation of 8,9-dimethyl-5-oxo-2,3,4,5-tetrahydro-benzo[b]azepine-1-carboxylic acid isopropyl ester

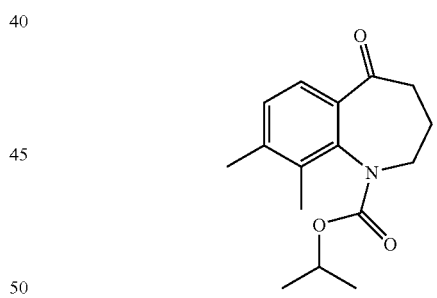

Add cesium carbonate (456 mg, 3.0 mmol), methyl boronic acid (90 mg, 1.5 mmol) and [1,1′-bis(diphenylphosphino)-ferrocene]dichloropalladium (II) complex with dichloromethane (1:1) (82 mg, 0.1 mmol) to a solution of 8-bromo-9-methyl-5-oxo-2,3,4,5-tetrahydro-benzo[b]azepine-1-carboxylic acid isopropyl ester (341 mg, 1.0 mmol) in dioxane (8 mL). Stir the mixture under nitrogen at 110° C. for 1 h and 30 min. Cool down the mixture to room temperature and filter over Celite® washing with ethyl acetate. Evaporate the solvent and purify the crude by chromatography, eluting with hexane/ethyl acetate to afford the title compound (239 mg, 87%). MS (ES+): 276 (M+H).

Step 5. Preparation of (S) isopropyl 5-[(3,5-bistrifluoromethyl-benzyl)-(1H-tetrazol-5-yl)-amino]-8,9-dimethyl-2,3,4,5-tetrahydrobenzo[b]azepine-1-carboxylate

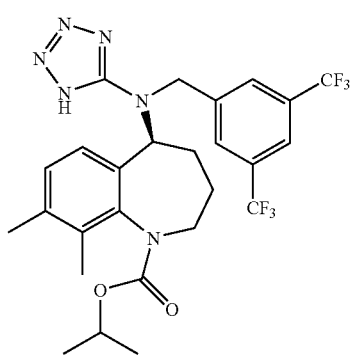

Prepare the titled compound by following the procedure as essentially described for the preparation of (S)-tert-Butyl 5-[(3,5-bistrifluoromethylbenzyl)-(2H-tetrazol-5-yl)amino]-7-methyl-8-trifluoromethyl-2,3,4,5-tetrahydrobenzo[b]azepine-1-carboxylate (Example 3, Steps 11-16) by replacing tert-butyl 7-methyl-5-oxo-8-trifluoromethyl-2,3,4,5-tetrahydrobenzo[b]azepine-1-carboxylate with 8,9-dimethyl-5-oxo-2,3,4,5-tetrahydro-benzo[b]azepine-1-carboxylic acid isopropyl ester in Step 11. MS (ES−): 569 (M−H).

Step 6. Preparation of (S) isopropyl 5-[(3,5-bistrifluoromethyl-benzyl)-(2-methyl-2H-tetrazol-5-yl)-amino]-8,9-dimethyl-2,3,4,5-tetrahydrobenzo[b]azepine-1-carboxylate

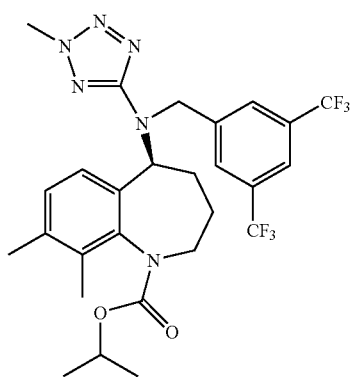

Prepare the titled compound by following the procedure as essentially described for the preparation of (+/−)-isopropyl 5-[(3,5-bistrifluoromethyl-benzyl)-(2-methyl-2H-tetrazol-5-yl)-amino]-9-methyl-8-trifluormethyl-2,3,4,5-tetrahydrobenzo[b]azepine-1-carboxylate (Example 53, Step 5) by replacing (+/−)-isopropyl 5-[(3,5-bistrifluoromethyl-benzyl)-(1H-tetrazol-5-yl)-amino]-9-methyl-8-trifluormethyl-2,3,4,5-tetrahydrobenzo[b]azepine-1-carboxylate with (S) isopropyl 5-[(3,5-bistrifluoromethyl-benzyl)-(1H-tetrazol-5-yl)-amino]-8,9-dimethyl-2,3,4,5-tetrahydrobenzo[b]azepine-1-carboxylate MS (ES+): 585 (M+H).

Example 57

Synthesis of (S)-isopropyl 5-{(3,5-Bis-trifluoromethyl-benzyl)-[2-(2-hydroxy-ethyl)-2H-tetrazol-5-yl]-amino}-8,9-dimethyl-2,3,4,5-tetrahydrobenzo[b]azepine-1-carboxylate

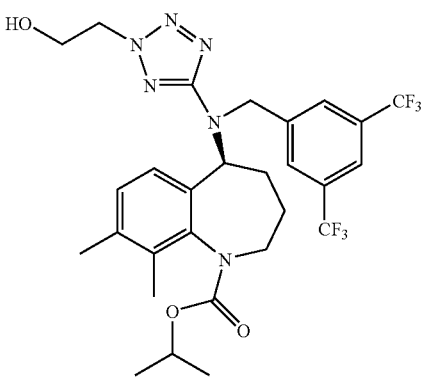

Add potassium carbonate (58 mg, 0.42 mmol) and 2-bromoethanol (0.038 mL, 0.53 mmol) to a solution of (S)-isopropyl 5-[(3,5-bistrifluoromethyl-benzyl)-(1H-tetrazol-5-yl)-amino]-8,9-dimethyl-2,3,4,5-tetrahydrobenzo[b]azepine-1-carboxylate (Example 56, Step 5) (120 mg, 0.21 mmol) in DMF (0.4 mL) at room temperature in a tube. Seal the tube and stir the mixture at 50° C. for 3 h. Cool the mixture at room temperature and add water and ethyl acetate. Separate the layers, dry the organic phase over anhydrous Na₂SO₄, filter and remove the solvent under reduced pressure. Purify the residue by flash chromatography, eluting with hexane/ethyl acetate, to provide 58 mg (45%) of the title compound. MS (ES+): 615 (M+H).

Example 58

Synthesis of (+/−)-9-[(3,5-Bis-trifluoromethyl-benzyl)-(2H-tetrazol-5-yl)-amino]-4-methyl-2,3,6,7,8,9-hexahydro-1H-5-aza-cyclohepta[f]indene-5-carboxylic acid isopropyl ester

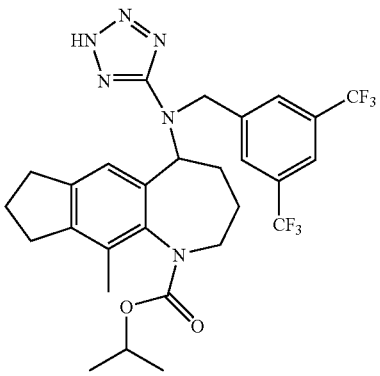

113

Step 1. Preparation of methyl 6-amino-1-methyl-indan-5-carboxylate

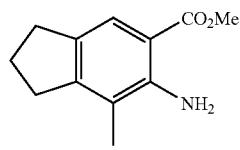

Add N-bromosuccinimide (1.87 g, 10.5 mmol) to methyl 6-amino-indan-5-carboxylate (1.82 g, 9.53 mmol) (Example 49, Step 3) in acetic acid (9.3 mL). Stir the mixture at room temperature for 1 h. Pour the mixture into ice water and add ethyl acetate. Separate the layers and wash the organic phase with saturated NaHCO3 and brine and dry over sodium sulfate. Remove the solvent under reduced pressure. Purify with silica gel cartridge, eluting with hexanes/ethyl acetate to afford methyl 5-amino-1-bromo-indan carboxylate (2.45 g, 95%): MS (ES+): 271, 272 (M+H). Add methyl boronic acid (1.6 g, 26.7 mmol), cesium fluoride (4.6 g, 30.22 mmol) and 1-bis(diphenylphosphinoferrocene) palladium chloride (727 mg, 0.89 mmol) to methyl 5-amino-1-bromo-indan carboxylate (2.40 g, 8.89 mmol) in dioxane (60 ml), and stir at 90° C. for 12 h. Partition between water and ethyl acetate. Extract with more ethyl acetate and then combine the organic phases. Dry over sodium sulfate and remove the solvent under reduced pressure. Purify with silica gel cartridge, eluting with hexanes/ethyl acetate to afford the titled compound (1.73 g, 95%). MS (ES+): 206 (M+H).

Step 2. Preparation of (+/−)-9-[(3,5-Bis-trifluoromethyl-benzyl)-(2H-tetrazol-5-yl)-amino]-4-methyl-2,3,6,7,8,9-hexahydro-1H-5-aza-cyclohepta[f]indene-5-carboxylic acid isopropyl ester

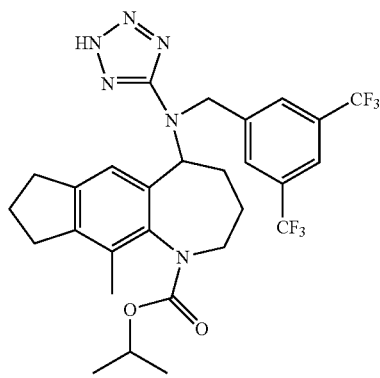

The titled compound can be prepared in a manner analogous to the procedure for the preparation of (+/−)-isopropyl 5-[(3,5-bistrifluoromethyl-benzyl)-(1H-tetrazol-5-yl)-amino]-8-chloro-2,3,4,5-tetrahydrobenzo[b]azepine-1-carboxylate (Example 46, Steps 1 to 3) by replacing methyl-2-amino-4-chlorobenzoate with methyl 6-amino-1-methyl-indan-5-carboxylatein Example 46, Step 1.

114

Example 59

Synthesis of (+/−)-9-[(3,5-Bis-trifluoromethyl-benzyl)-(2-methyl-2H-tetrazol-5-yl)-amino]-4-methyl-2,3,6,7,8,9-hexahydro-1H-5-aza-cyclohepta[f]indene-5-carboxylic acid isopropyl ester

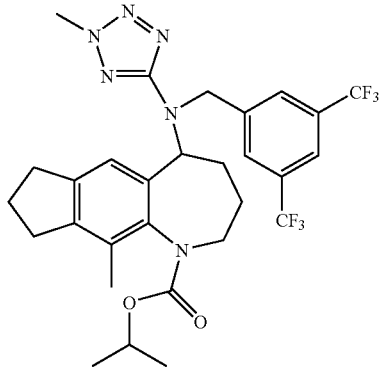

The title compound can be prepared in a manner analogous to the procedure set forth in preparation of (+/−)-9-[(3,5-bis-trifluoromethyl-benzyl)-(2-methyl-2H-tetrazol-5-yl)-amino]-2,3,6,7,8,9-hexahydro-1H-5-aza-cyclohepta[f]indene-5-carboxylic acid isopropyl ester (Example 50) by replacing (+/−)-9-[(3,5-bis-trifluoromethyl-benzyl)-(2H-tetrazol-5-yl)-amino]-2,3,6,7,8,9-hexahydro-1H-5-aza-cyclohepta[f]indene-5-carboxylic acid isopropyl ester with (+/−)-9-[(3,5-bis-trifluoromethyl-benzyl)-(2H-tetrazol-5-yl)-amino]-4-methyl-2,3,6,7,8,9-hexahydro-1H-5-aza-cyclohepta[f]indene-5-carboxylic acid isopropyl ester (Example 58).

Example 60

Synthesis of (S)-9-[(3,5-Bis-trifluoromethyl-benzyl)-(2H-tetrazol-5-yl)-amino]-2,3,6,7,8,9-hexahydro-1H-5-aza-cyclohepta[f]indene-5-carboxylic acid tert-butyl ester

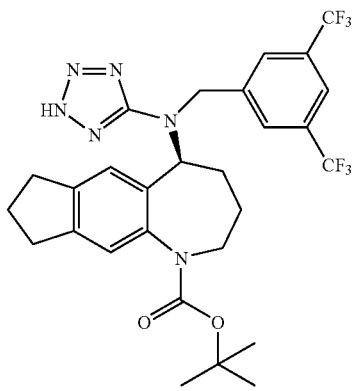

Prepare the title compound by following the procedure as essentially described for the preparation of (S)-tert-Butyl 5-[(3,5-bistrifluoromethylbenzyl)-(2H-tetrazol-5-yl) amino]-7-methyl-8-trifluoromethyl-2,3,4,5-tetrahydrobenzo[b]azepine-1-carboxylate (Example 3, steps 5 to 16) by replacing Methyl 2-amino-5-methyl-4-trifluoromethylbenzoate (Example 3, step 4) with 6-Amino-indan-5-carboxylic acid methyl ester (Example 49, step 3) in Example 3, step 5. MS (ES−): 595 (M−H).

Examples 61 to 63 can be prepared following the procedures described in Example 4 by replacing 5-[(3,5-bis-trifluoromethyl-benzyl)-(1H-tetrazol-5-yl)-amino]-7-methyl-8-trifluoromethyl-2,3,4,5-tetrahydro-benzo[b]azepine-1-carboxylic acid tert-butyl ester with (S)-9-[(3,5-bis-trifluoromethyl-benzyl)-(2H-tetrazol-5-yl)-amino]-2,3,6,7,8,9-hexahydro-1H-5-aza-cyclohepta[f]indene-5-carboxylic acid tert-butyl ester (Example 60) in Example 4, Step 2, and ethyl chloroformate by the appropriate chloroformate in Example 4, Step 3.

Example 61

Synthesis of (S)-9-[(3,5-Bis-trifluoromethyl-benzyl)-(2H-tetrazol-5-yl)-amino]-2,3,6,7,8,9-hexahydro-1H-5-aza-cyclohepta[f]indene-5-carboxylic acid 1-ethyl-propyl ester

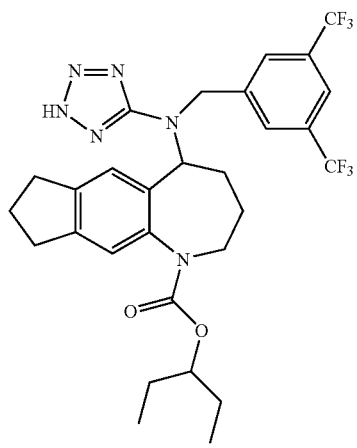

Example 62

Synthesis of (S)-9-[(3,5-Bis-trifluoromethyl-benzyl)-(2H-tetrazol-5-yl)-amino]-2,3,6,7,8,9-hexahydro-1H-5-aza-cyclohepta[f]indene-5-carboxylic acid cyclopentyl ester

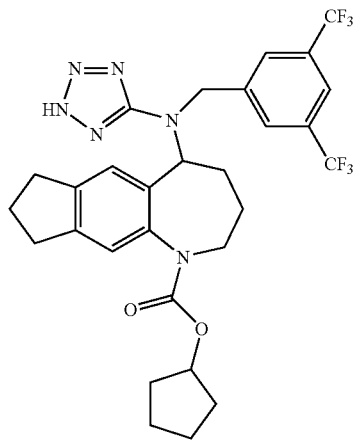

Example 63

Synthesis of (S)-9-[(3,5-Bis-trifluoromethyl-benzyl)-(2H-tetrazol-5-yl)-amino]-2,3,6,7,8,9-hexahydro-1H-5-aza-cyclohepta[f]indene-5-carboxylic acid 1-ethyl-2-methyl-propyl ester

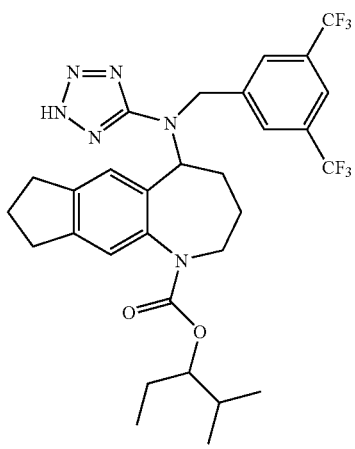

Example 64

Synthesis of (S)-(3,5-Bis-trifluoromethyl-benzyl)-(5-cyclopentylmethyl-1,2,3,5,6,7,8,9-octahydro-5-aza-cyclohepta[f]inden-9-yl)-(2H-tetrazol-5-yl)-amine

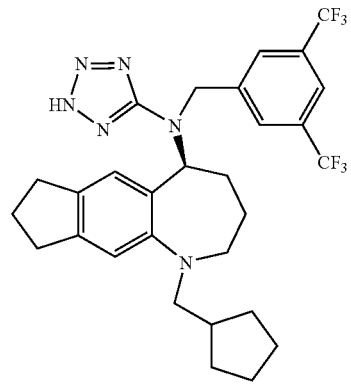

The title compound can be prepared by removing the tBOC of (S)-9-[(3,5-bis-trifluoromethyl-benzyl)-(2H-tetrazol-5-yl)-amino]-2,3,6,7,8,9-hexahydro-1H-5-aza-cyclohepta[f]indene-5-carboxylic acid tert-butyl ester (Example 60) as essentially described in Example 4, Step 2, and then stirring (S)-(3,5-bis-trifluoromethyl-benzyl)-(1,2,3,5,6,7,8,9-octahydro-5-aza-cyclohepta[f]inden-9-yl)-(1H-tetrazol-5-yl)-amine with cyclopentane carboxaldehyde (1-5 eq) in the presence of acetic acid (1-5 eq) and sodium triacetoxyborohydride (1-5 eq) or sodium borohydride (1-5 eq).

Example 65

(S)-9-[(3,5-Bis-trifluoromethyl-benzyl)-(2-methyl-2H-tetrazol-5-yl)-amino]-2,3,6,7,8,9-hexahydro-1H-5-aza-cyclohepta[f]indene-5-carboxylic acid tert-butyl ester

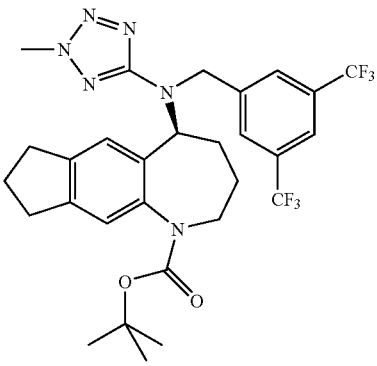

Prepare the title compound by essentially following the procedure described in Example 3, Steps 5-17 for the preparation of (S)-tert-Butyl 5-[(3,5-bistrifluoromethylbenzyl)-(2-methyl-2H-tetrazol-5-yl)amino]-7-methyl-8-trifluoromethyl-2,3,4,5-tetrahydrobenzo[b]azepine-1-carboxylate by replacing methyl 2-amino-5-methyl-4-trifluoromethylbenzoate (Example 3, step 4) with 6-amino-indan-5-caboxylic acid methyl ester (Example 49, Step 3) in Example 3, Step 5. MS (ES+): 611 (M+H)

Example 66

Synthesis of (S)-9-[(3,5-Bis-trifluoromethyl-benzyl)-(2-methyl-2H-tetrazol-5-yl)-amino]-2,3,6,7,8,9-hexahydro-1H-5-aza-cyclohepta[f]indene-5-carboxylic acid 1-ethyl-propyl ester

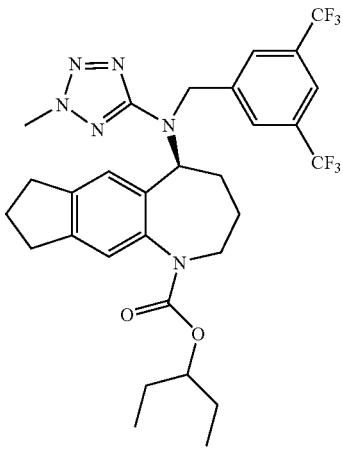

The titled compound can be prepared in a manner analogous to the procedure set forth in preparation of Example 50 (+/−)-9-[(3,5-bis-trifluoromethyl-benzyl)-(2-methyl-2H-tetrazol-5-yl)-amino]-2,3,6,7,8,9-hexahydro-1H-5-aza-cyclohepta[f]indene-5-carboxylic acid isopropyl ester by replacing isopropyl (+/−)-9-[(3,5-bis-trifluoromethyl-benzyl)-(2H-tetrazol-5-yl)-amino]-2,3,6,7,8,9-hexahydro-1H-5-aza-cyclohepta[f]indene-5-carboxylate with (S)-9-[(3,5-bis-trifluoromethyl-benzyl)-(2H-tetrazol-5-yl)-amino]-4-methyl-2,3,6,7,8,9-hexahydro-1H-5-aza-cyclohepta[f]indene-5-carboxylic acid 1-ethyl-propyl ester (Example 61).

Example 67

Synthesis of (S)-9-[(3,5-Bis-trifluoromethyl-benzyl)-(2-methyl-2H-tetrazol-5-yl)-amino]-2,3,6,7,8,9-hexahydro-1H-5-aza-cyclohepta[f]indene-5-carboxylic acid cyclopentyl ester

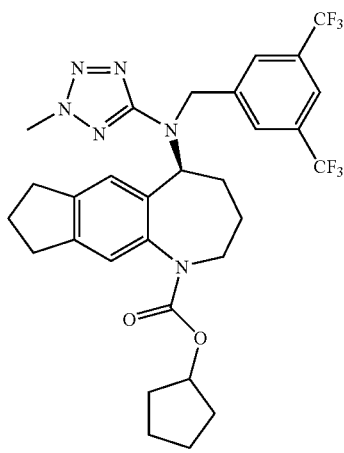

The titled compound can be prepared in a manner analogous to the procedure set forth in preparation of Example 50 (+/−)-9-[(3,5-bis-trifluoromethyl-benzyl)-(2-methyl-2H-tetrazol-5-yl)-amino]-2,3,6,7,8,9-hexahydro-1H-5-aza-cyclohepta[f]indene-5-carboxylic acid isopropyl ester by replacing isopropyl (+/−)-9-[(3,5-bis-trifluoromethyl-benzyl)-(2H-tetrazol-5-yl)-amino]-2,3,6,7,8,9-hexahydro-1H-5-aza-cyclohepta[f]indene-5-carboxylate with (S)-9-[(3,5-bis-trifluoromethyl-benzyl)-(2H-tetrazol-5-yl)-amino]-4-methyl-2,3,6,7,8,9-hexahydro-1H-5-aza-cyclohepta[f]indene-5-carboxylic acid cyclopentyl ester (Example 62).

Example 68

Synthesis of (S)-9-[(3,5-Bis-trifluoromethyl-benzyl)-(2-methyl-2H-tetrazol-5-yl)-amino]-2,3,6,7,8,9-hexahydro-1H-5-aza-cyclohepta[f]indene-5-carboxylic acid 1-ethyl-2-methyl-propyl ester

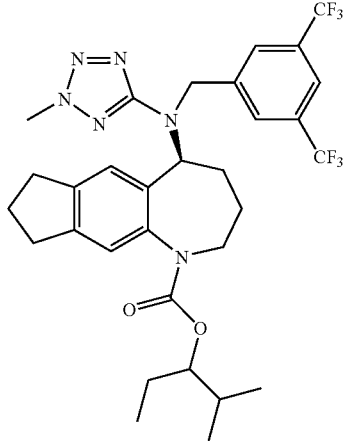

The titled compound can be prepared in a manner analogous to the procedure set forth in preparation of Example 50 (+/−)-9-[(3,5-bis-trifluoromethyl-benzyl)-(2-methyl-2H-tetrazol-5-yl)-amino]-2,3,6,7,8,9-hexahydro-1H-5-aza-cyclohepta[f]indene-5-carboxylic acid isopropyl ester by replacing isopropyl (+/−)-9-[(3,5-bis-trifluoromethyl-benzyl)-(2H-tetrazol-5-yl)-amino]-2,3,6,7,8,9-hexahydro-1H-5-aza-cyclohepta[f]indene-5-carboxylate with (S)-9-[(3,5-bis-trifluoromethyl-benzyl)-(2H-tetrazol-5-yl)-amino]-4-methyl-2,3,6,7,8,9-hexahydro-1H-5-aza-cyclohepta[f]indene-5-carboxylic acid 1-ethyl-2-methyl-propyl ester (Example 63).

Examples 69 to 70 can be prepared following the procedures described in Example 3, Steps 18-19 by replacing (S)-tert-butyl 5[(3,5-bistrifluoromethylbenzyl)-(2-methyl-2H-tetrazol-5-yl)amino]-7-methyl-8-trifluoromethyl-2,3,4,5-tetrahydrobenzo[b]azepine-1-carboxylate with (S)-9-[(3,5-Bis-trifluoromethyl-benzyl)-(2-methyl-2H-tetrazol-5-yl)-amino]-2,3,6,7,8,9-hexahydro-1H-5-aza-cyclohepta[f]indene-5-carboxylic acid tert-butyl ester (Example 65) in Example 3, Step 18, and using the corresponding aldehyde in Example 3, Step 19.

Example 69

Synthesis (S)-4-{9-[(3,5-Bis-trifluoromethyl-benzyl)-(2-methyl-2H-tetrazol-5-yl)-amino]-2,3,6,7,8,9-hexahydro-1H-5-aza-cyclohepta[f]inden-5-ylmethyl}-cyclohexanecarboxylic acid

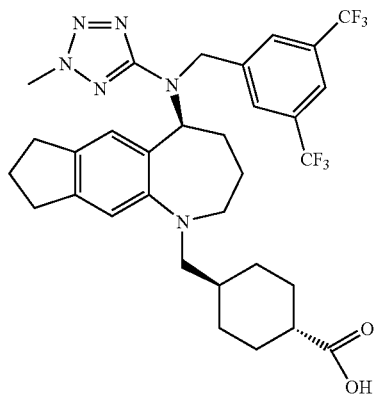

Example 70

Synthesis of (S)-5-{9-[(3,5-Bis-trifluoromethyl-benzyl)-(2-methyl-2H-tetrazol-5-yl)-amino]-2,3,6,7,8,9-hexahydro-1H-5-aza-cyclohepta[f]inden-5-yl}-3,3-dimethyl-pentanoic acid

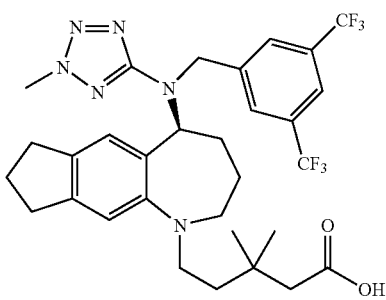

Example 71

Synthesis of (S)-(3,5-Bis-trifluoromethyl-benzyl)-(5-cyclopentylmethyl-1,2,3,5,6,7,8,9-octahydro-5-aza-cyclohepta[f]inden-9-yl)-(2-methyl-2H-tetrazol-5-yl)-amine

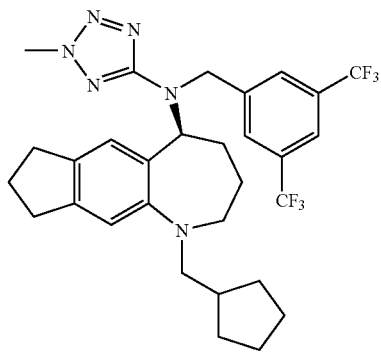

Prepare the title compound by essentially following the procedure described in Example 3, Steps 18-19 by replacing (S)-tert-butyl 5[(3,5-bistrifluoromethylbenzyl)-(2-methyl-2H-tetrazol-5-yl)amino]-7-methyl-8-trifluoromethyl-2,3,4,5-tetrahydrobenzo[b]azepine 1-carboxylate with (S)-9-[(3,5-Bis-trifluoromethyl-benzyl)-(2-methyl-2H-tetrazol-5-yl)-amino]-2,3,6,7,8,9-hexahydro-1H-5-aza-cyclohepta[f]indene-5-carboxylic acid tert-butyl ester (Example 65) in Example 3, Step 18. MS (ES+): 593 (M+H).

Example 72

Synthesis of 9-[(3,5-Bis-trifluoromethyl-benzyl)-(2-ethyl-2H-tetrazol-5-yl)-amino]-2,3,6,7,8,9-hexahydro-1H-5-aza-cyclohepta[f]indene-5-carboxylic acid isopropyl ester

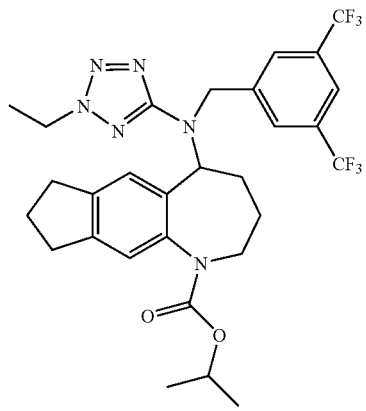

The titled compound can be prepared in a manner analogous to the procedure set forth in preparation of Example 50, (+/−)-9-[(3,5-bis-trifluoromethyl-benzyl)-(2-methyl-2H-tetrazol-5-yl)-amino]-2,3,6,7,8,9-hexahydro-1H-5-aza-cyclohepta[f]indene-5-carboxylic acid isopropyl ester by replacing methanol with ethanol.

Example 73

Synthesis of (S)-(3,5-Bis-trifluoromethyl-benzyl)-(5-cyclopentylmethyl-3,5,6,7,8,9-hexahydro-1H-2-oxa-5-aza-cyclohepta[f]inden-9-yl)-(2-methyl-2H-tetrazol-5-yl)-amine

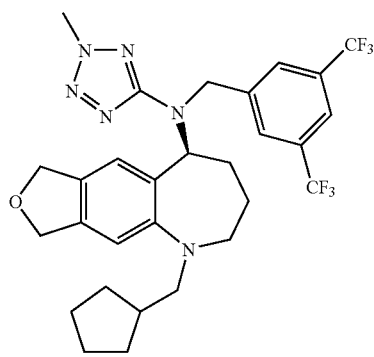

Step 1. Preparation of 1,3-Dihydro-isobenzofuran-5-ylamine

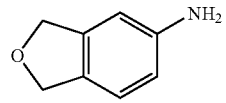

To a solution of 1,3-dihydro-isobenzofuran (83.2 mmol) in sulfuric acid (75 mL), cooled in an ice bath, add a solution of potassium nitrate (83.2 mmol) in sulfuric acid (25 mL) dropwise. After stirring for 30 min, pour the reaction mixture over ice and collect the resulting precipitate on a glass frit. Wash the precipitate with water (200 mL) and dry under vacuum. Dissolve the precipitate in ethanol (250 mL) and add tin chloride dihydrate (273.6 mmol). After heating at 70° C. for 2 h, dilute with water (200 mL), cool to room temperature, and neutralize the reaction with 5 N NaOH. Extract the mixture with ethyl acetate (3×200 mL) and dry the organic portion over sodium sulfate. Remove the solvent in vacuo to afford the title compound as a tan solid. $^1$H NMR (CDCl$_3$, 400 MHz) δ 3.50 (bs, 2H), 5.02 (s, 4H), 6.56 (d, J=2.4 Hz, 1H), 6.60 (dd, J=2.4, 8.0 Hz, 1 H), 7.01 (d, J=8.0 Hz, 1H).

Step 2. Preparation of 6-Iodo-1,3-dihydro-isobenzofuran-5-ylamine

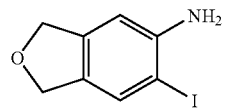

Dropwise, add a 1.0 M solution of iodine monochloride (64 mmol) to a solution of 1,3-dihydro-isobenzofuran-5-ylamine (64 mmol) in dichloromethane (200 mL), methanol (50 mL) and sodium bicarbonate (96 mmol). After stirring for 1 h, quench the reaction with aqueous sodium metabisulfite (100 mL). Separate the organic phase and wash the aqueous with dichloromethane (2×100 mL). Combine the organics and dry over sodium sulfate. Filter the reaction and remove solvent under vacuum. Chromatograph (0-20% ethyl acetate/hexane) the crude mixture over silica gel to give the title compound as a tan solid. $^1$H NMR (CDCl$_3$, 400 MHz): δ 4.10 (bs, 2H), 4.97 (s, 4H), 6.63 (s, 1H), 7.49 (s, 1H).

Step 3. Preparation of 6-Amino-1,3-dihydro-isobenzofuran-5-carboxylic acid methyl ester

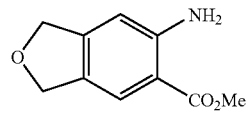

Add palladium (II) acetate (2.8 mmol), 1,1-bis(diphenylphosphino)ferrocene (2.8 mmol), potassium carbonate (86.1 mmol), and triethyl amine (28.7 mmol) to a solution of 6-iodo-1,3-dihydro-isobenzofuran-5-ylamine (28.7 mmol) in acetonitrile (150 mL) and methanol (75 mL). Using a balloon of carbon monoxide, vacuum purge the reaction mixture several times, then heat to 70° C. After heating under a balloon of carbon monoxide for 1.5 h, cool the reaction to room temperature. Dilute the reaction with ethyl acetate (500 mL), wash with water (3×100 mL), followed by brine. Dry the organic phase over sodium sulfate, filter, and remove the solvent under vacuum. Chromatograph the product over silica gel, eluting with ethyl acetate/hexane (5-35%) to provide the title compound as an off white solid. $^1$H NMR (CDCl$_3$, 400 MHz) δ 3.85 (s, 3H), 4.97 (s, 4H), 6.54 (s, 1H), 7.71 (s, 1H).

Step 4. Preparation of (S)-9-(3,5-Bis-trifluoromethyl-benzylamino)-1,3,6,7,8,9-hexahydro-2-oxa-5-aza-cyclohepta[f]indene-5-carboxylic acid tert-butyl ester

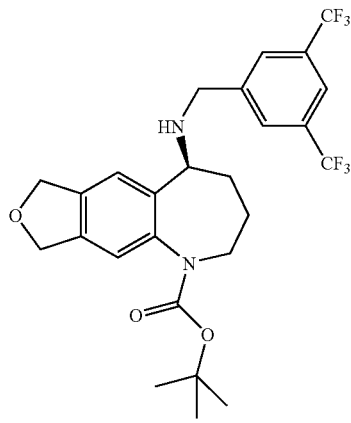

Prepare the titled compound by following the procedure as essentially described in the synthesis of (S) tert-butyl 5-(3,5-Bistrifluoromethylbenzylamino)-(7-methyl-8-trifluoromethyl-2,3,4,5-tetrahydrobenzo[b]azepine-1-carboxylate Example 3, Steps 5 to 14 and substituting methyl 2-amino-5-methyl-4-trifluoromethylbenzoate with 6-amino-1,3-dihydro-isobenzofuran-5-carboxylic acid methyl ester in Example 3, Step 5. MS (ES+): 531.2 (M+H).

Step 5. Preparation of (S)-9-[(3,5-Bis-trifluoromethyl-benzyl)-cyano-amino]-1,3,6,7,8,9-hexahydro-2-oxa-5-aza-cyclohepta[f]indene-5-carboxylic acid tert-butyl ester

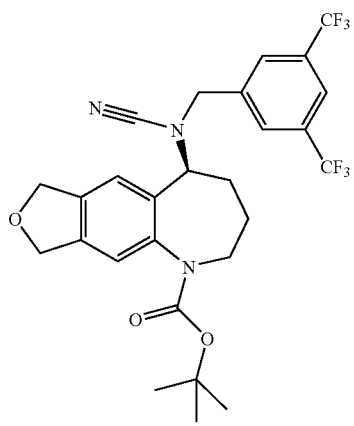

To a solution of (S)-9-(3,5-bis-trifluoromethyl-benzylamino)-1,3,6,7,8,9-hexahydro-2-oxa-5-aza-cyclohepta[f]indene-5-carboxylic acid tert-butyl ester (1.75 mmol) in tetrahydrofuran (7 mL) and diisopropyl ethylamine (5.25 mmol), add cyanogenbromide (5.25 mmol) and heat to 65° C. After stirring overnight, cool to room temperature and dilute with ethyl acetate (10 mL). Wash the organic portion with water (10 mL), followed by brine (10 mL). Dry the organic portion over sodium sulfate, filter, and remove solvent under vacuum. Chromatograph the product over silica gel, eluting with ethyl acetate/hexane (5-35%) to afford the title compound as an oil. MS (ES+): 554.2 (M–H).

Step 6. Preparation of (S)-9-[(3,5-Bis-trifluoromethyl-benzyl)-(2H-tetrazol-5-yl)-amino]-1,3,6,7,8,9-hexahydro-2-oxa-5-aza-cyclohepta[f]indene-5-carboxylic acid tert-butyl ester

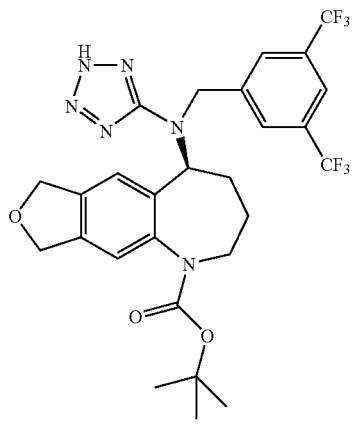

To a solution of (S)-9-[(3,5-bis-trifluoromethyl-benzyl)-cyano-amino]-1,3,6,7,8,9-hexahydro-2-oxa-5-aza-cyclohepta[f]indene-5-carboxylic acid tert-butyl ester (1.61 mmol) in toluene (10 mL), add azidotributyltin (3.22 mmol) and heat to 100° C. After stirring for 12 h, cool the reaction to room temperature and quench with methanol (1 mL). Dilute the reaction mixture with ethyl acetate (100 mL) and wash with aqueous sodium fluoride (50 mL) and brine (50 mL). Dry the organic portion over sodium sulfate, filter, and remove the solvent under vacuum. Chromatograph the product over silica gel, eluting with methanol/dichloromethane (1-5%) to afford the title compound as a colorless foam. MS (ES+): 597.3 (M–H).

Step 7. Preparation of (S)-(3,5-Bis-trifluoromethyl-benzyl)-(3,5,6,7,8,9-hexahydro-1H-2-oxa-5-aza-cyclohepta[f]inden-9-yl)-(2-methyl-2H-tetrazol-5-yl)-amine

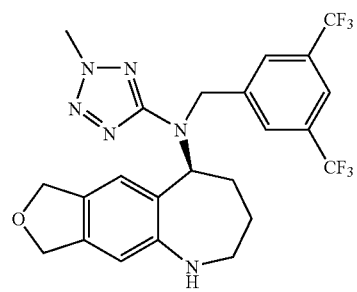

To a solution of (S)-9-[(3,5-bis-trifluoromethyl-benzyl)-(2H-tetrazol-5-yl)-amino]-1,3,6,7,8,9-hexahydro-2-oxa-5-aza-cyclohepta[f]indene-5-carboxylic acid tert-butyl ester (1.17 mmol) in dichloromethane (20 mL), add methanol (5.85 mmol) and triphenylphosphine (3.51 mmol). To this solution, add diethyl azodicarboxylate (3.51 mmol) dropwise at room temperature. After stirring for 12 h, remove the solvent under vacuum and chromatograph the intermediate over silica gel eluting with ethyl acetate/hexane (2-35%) to afford (S)-9-[(3, 5-bis-trifluoromethyl-benzyl)-(2-methyl-2H-tetrazol-5-yl)-amino]-1,3,6,7,8,9-hexahydro-2-oxa-5-aza-cyclohepta[f]indene-5-carboxylic acid tert-butyl ester as a colorless oil. To this intermediate in dichloromethane (5 mL), add TFA (2 mL). After stirring for 2 h, quench the reaction with aqueous sodium carbonate (5 mL) and dilute with dichloromethane (10 mL). Separate the organic portion, dry over sodium sulfate, filter, and remove the solvent under vacuum. This provides the title compound as a crude oil that is further used without purification.

Step 8. Preparation of (S)-(3,5-Bis-trifluoromethyl-benzyl)-(5-cyclopentylmethyl-3,5,6,7,8,9-hexahydro-1H-2-oxa-5-aza-cyclohepta[f]inden-9-yl)-(2-methyl-2H-tetrazol-5-yl)-amine

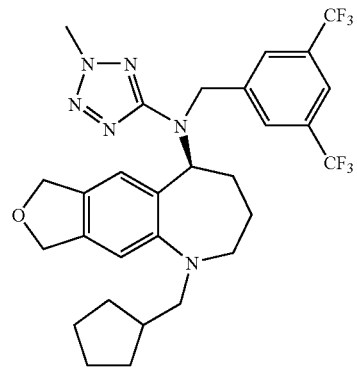

To a solution of (S)-(3,5-bis-trifluoromethyl-benzyl)-(3,5,6,7,8,9-hexahydro-1H-2-oxa-5-aza-cyclohepta[f]inden-9-yl)-(2-methyl-2H-tetrazol-5-yl)-amine (0.195 mmol) dichloroethane (5 mL), add cyclopentanecarbaldehyde (0.780 mmol) along with a catalytic amount of acetic acid. Add sodium triacetoxyborohydride (0.975 mmol) and stir at room temperature overnight. Quench the reaction with aqueous sodium carbonate (5 mL) and dilute with dichloromethane (5 mL). Dry the organic portion, filter, and remove the solvent under vacuum. Chromatograph the product over silica gel eluting with ethyl acetate/hexane (5-35%) to afford the title compound as a colorless foam. MS (ES+): 595.2 (M+H).

Example 74

Synthesis of (S)-5-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-yl}-3,3-dimethyl-pentanoic acid

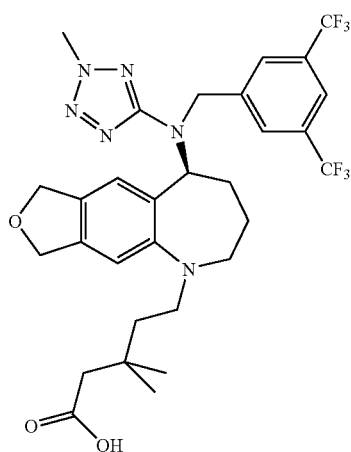

Step 1: Preparation of 3,3-Dimethylpentanedioic acid monomethyl ester

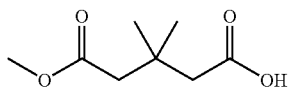

Combine 3,3-dimethylglutaric anhydride (1.00 g, 7.03 mmol) and sodium methoxide (2.5 mL, 14.1 mmol, 30 wt % in methanol) in methanol (20 mL) and heat at reflux for 3 h. Cool the reaction to room temperature and pour into ice water (100 mL). Add diethyl ether (25 mL) and adjust the pH of the mixture to pH=2 with 2 N HCl (10 mL) and separate the layers. Extract the aqueous layer with diethyl ether (25 mL) and combine the organic layers, dry over sodium sulfate, filter and remove the solvent under reduced pressure to afford 3,3-dimethylpentanedioic acid monomethyl ester as a colorless oil (0.827 g, 68%): $^1$H NMR (CDCl$_3$, 300 MHz) δ 1.14 (s, 6H), 2.46 (s, 2H), 2.48 (s, 2H), 3.67 (s, 3H), 10.9 (br s, 1H); APCI MS (Negative mode) m/z 173 [C$_8$H$_{14}$O$_4$–H]$^-$.

Step 2. Preparation of 3,3-Dimethyl-5-oxo-pentanoic acid methyl ester

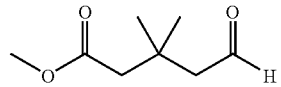

Use the procedure as describe in *Journal of Fluorine Chemistry*, (1992), 56, 373-383, to prepare the titled compound from 3,3-dimethylpentanedioic acid monomethyl ester.

Step 3. Preparation of (S)-5-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-yl}-3,3-dimethyl-pentanoic acid methyl ester

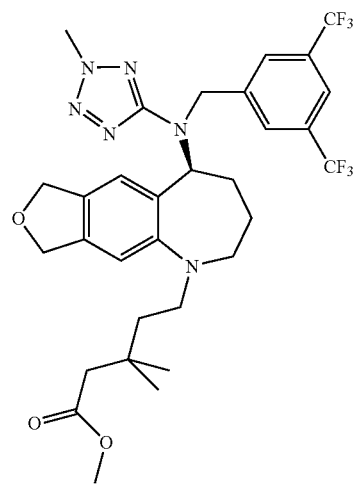

To a solution of (S)-(3,5-bis-trifluoromethyl-benzyl)-(3,5,6,7,8,9-hexahydro-1H-2-oxa-5-aza-cyclohepta[f]inden-9-yl)-(2-methyl-2H-tetrazol-5-yl)-amine (0.195 mmol) in dichloroethane (5 mL), add 3,3-dimethyl-5-oxo-pentanoic acid methyl ester (0.585 mmol) along with a catalytic amount of acetic acid. To this stirred solution add sodium triacetoxyborohydride (0.975 mmol). After stirring for 12 h, quench the reaction with aqueous sodium carbonate (5 mL) and dilute with dichloromethane (5 mL). Dry the organic portion, filter, and remove the solvent under vacuum. Chromatograph the product over silica gel, eluting with ethyl acetate/hexane (2-35%) to afford the title compound as a colorless oil. MS (ES+): 655.2 (M+H).

Step 4. Preparation of (S)-5-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-yl}-3,3-dimethyl-pentanoic acid

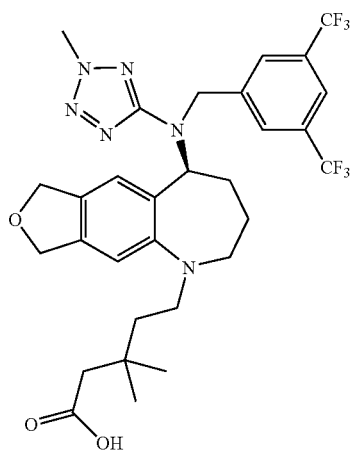

To a solution of (S)-5-{9-[(3,5-bis-trifluoromethyl-benzyl)-(2-methyl-2H-tetrazol-5-yl)-amino]-1,3,6,7,8,9-hexahydro-2-oxa-5-aza-cyclohepta[f]inden-5-yl}-3,3-dimethyl-pentanoic acid methyl ester (0.113 mmol) in methanol (3 mL), add 5 N NaOH (2 mL) and heat to 60° C. After stirring for 6 h, cool the reaction to room temperature, dilute with water (10 mL) and neutralize with 5 M HCl. Extract the organics with ethyl acetate (2×20 mL). Combine the organic portions, dry over sodium sulfate, filter, and remove the solvent under vacuum. Chromatograph the product over silica gel, eluting with ethyl acetate/hexane (20-60%) to afford the title compound as a colorless foam. MS (ES+): 641.3 (M+H).

Example 75

Synthesis of (S)-5-(9-{(3,5-Bis-trifluoromethyl-benzyl)-[2-(2-hydroxy-ethyl)-2H-tetrazol-5-yl]-amino}-1,3,6,7,8,9-hexahydro-2-oxa-5-aza-cyclohepta[f]inden-5-yl)-3,3-dimethyl-pentanoic acid

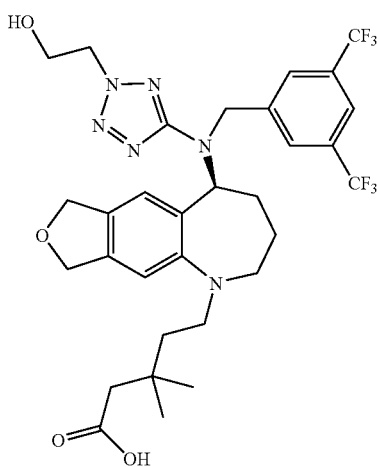

Step 1. Preparation of (S)-9-{(3,5-Bis-trifluoromethyl-benzyl)-[2-(2-tert-butoxy-ethyl)-2H-tetrazol-5-yl]-amino}-1,3,6,7,8,9-hexahydro-2-oxa-5-aza-cyclohepta[f]indene-5-carboxylic acid tert-butyl ester

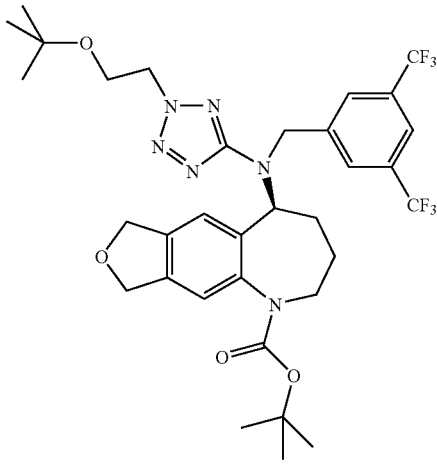

To a solution of (S)-9-[(3,5-bis-trifluoromethyl-benzyl)-(2H-tetrazol-5-yl)-amino]-1,3,6,7,8,9-hexahydro-2-oxa-5-aza-cyclohepta[f]indene-5-carboxylic acid tert-butyl ester (Example 73, Step 6) (0.167 mmol) in dichloromethane (20 mL), add 2-tert-butoxy-ethanol (0.835 mmol) and triphenylphosphine (0.501 mmol). To this solution, add diethyl azodicarboxylate (0.501 mmol) dropwise at room temperature. After stirring for 12 h, remove the solvent under vacuum. Chromatograph the intermediate over silica gel, eluting with ethyl acetate/hexane (2-35%) to afford the title compound as an oil. MS (ES+): 699 (M+H).

Step 2. (S)-2-{5-[(3,5-Bis-trifluoromethyl-benzyl)-(3,5,6,7,8,9-hexahydro-1H-2-oxa-5-aza-cyclohepta[f]inden-9-yl)-amino]-tetrazol-2-yl}-ethanol

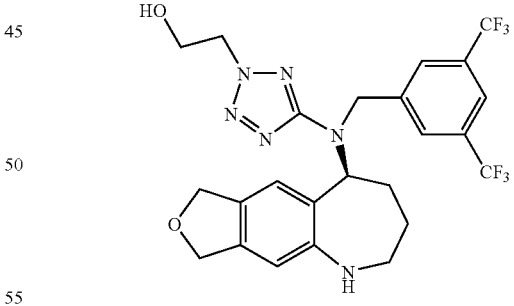

Dissolve (S)-9-{(3,5-bis-trifluoromethyl-benzyl)-[2-(2-tert-butoxy-ethyl)-2H-tetrazol-5-yl]-amino}-1,3,6,7,8,9-hexahydro-2-oxa-5-aza-cyclohepta[f]indene-5-carboxylic acid tert-butyl ester (0.140 mmol) in 4 M hydrochloric acid/dioxane (10 mL). After stirring overnight at room temperature, neutralize the reaction with aqueous sodium carbonate and dilute with ethyl acetate (20 mL). Dry the organic portion over sodium sulfate, filter, and remove the solvent under vacuum. Chromatograph the product over silica gel eluting with ethyl acetate/hexane (10-40%) to provide the title compound as an oil.

Step 3. Preparation of (S)-5-(9-{(3,5-Bis-trifluoromethyl-benzyl)-[2-(2-hydroxy-ethyl)-2H-tetrazol-5-yl]-amino}-1,3,6,7,8,9-hexahydro-2-oxa-5-aza-cyclohepta[f]inden-5-yl)-3,3-dimethyl-pentanoic acid

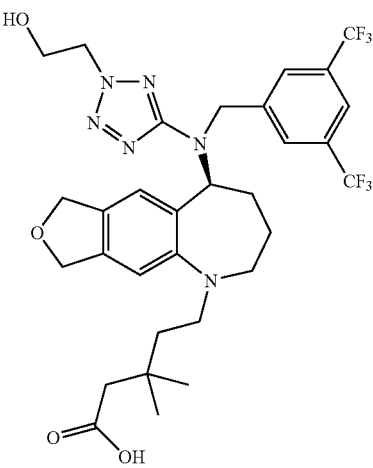

Prepare the title compound by following the procedure as essentially described for the synthesis of (S)-5-{9-[(3,5-bis-trifluoromethyl-benzyl)-(2-methyl-2H-tetrazol-5-yl)-amino]-1,3,6,7,8,9-hexahydro-2-oxa-5-aza-cyclohepta[f]inden-5-yl}-3,3-dimethyl-pentanoic acid (Example 74, Steps 1-4), starting with 2-{5-[(3,5-bis-trifluoromethyl-benzyl)-(3,5,6,7,8,9-hexahydro-1H-2-oxa-5-aza-cyclohepta[f]inden-9-yl)-amino]-tetrazol-2-yl}-ethanol. MS (ES+): 671.3 (M+H).

Example 76

Synthesis of (S)-9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]indene-5-carboxylic acid isopropyl ester

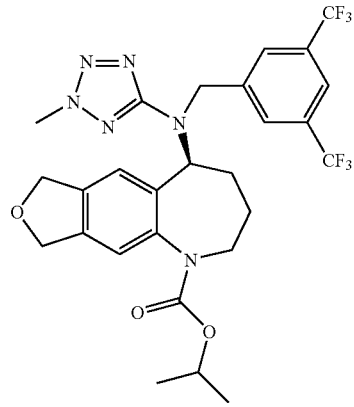

Prepare the title compound by following the procedure as essentially described in the synthesis of (+/−)-isopropyl 5-[(3,5-bistrifluoromethylbenzyl)-(2-methyl-2H-tetrazol-5-yl)amino]-7-bromo-2,3,4,5-tetrahydrobenzo[b]azepine-1-carboxylate (Example 1), starting with 6-amino-1,3-dihydro-isobenzofuran-5-carboxylic acid methyl ester (Example 73, Step 3). MS (ES+): 599 (M+H)

Example 77

Synthesis of (3,5-Bis-trifluoromethyl-benzyl)-(1-cyclopentylmethyl-2,3,4,5,7,8,9,10-octahydro-1H-naphtho[2,3-b]azepin-5-yl)-(2-methyl-2H-tetrazol-5-yl)-amine

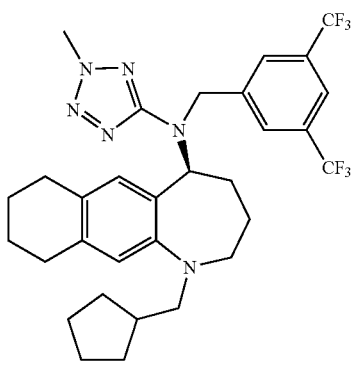

Step 1. Preparation of 5,6,7,8-Tetrahydro-naphthalen-2-ylamine

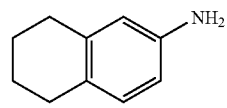

To a stirred solution of tetralin (0.30 mol), cooled in an ice bath, add a mixture of sulfuric acid (25 mL) and nitric acid (0.60 mol) dropwise over 30 minutes. After stirring an additional 30 minutes at 0° C., pour the mixture over ice and extract the organics with dichloromethane (3×200 mL). Wash the combined organic portions with sodium carbonate (200 mL) and dry over sodium sulfate. Filter, remove the solvent under vacuum, and chromatograph the product over silica gel, eluting with ethyl acetate/hexane (0-20%). This provides the nitro intermediate as an oil. Dissolve this intermediate in ethanol (200 mL) and add RaNi (catalytic). Vacuum purge the mixture several times with hydrogen. After stirring 48 h at room temperature under a balloon of hydrogen, filter the mixture through Celite®. Remove the solvent under vacuum and chromatograph the product over silica gel eluting with ethyl acetate/hexane (0-25%), to afford the title compound as an oil. $^1$H NMR (CDCl$_3$, 400 MHz) δ1.80 (m, 4H), 2.68 (m, 4H), 3.39 (bs, 2H), 6.44 (m, 1H), 6.49 (m, 1H), 6.87 (d, J=8.0 Hz, 1H).

Step 2. Preparation of (S)-5-[(3,5-Bis-trifluoromethyl-benzyl)-(2-methyl-2H-tetrazol-5-yl)-amino]-2,3,4,5,7,8,9,10-octahydro-naphtho[2,3-b]azepine-1-carboxylic acid tert-butyl ester

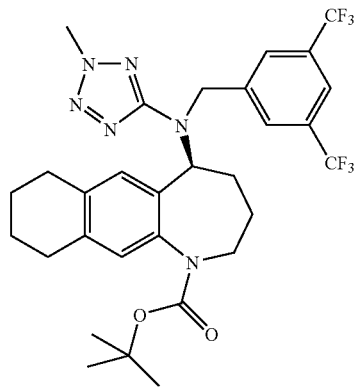

Prepare the title compound by following the procedure as essentially described for the synthesis of (S)-(3,5-bis-trifluoromethyl-benzyl)-(5-cyclopentylmethyl-3,5,6,7,8,9-hexahydro-1H-2-oxa-5-aza-cyclohepta[f]inden-9-yl)-(2-methyl-2H-tetrazol-5-yl)-amine starting with 5,6,7,8-tetrahydro-naphthalen-2-ylamine.

Step 3. Preparation of (S)-(3,5-Bis-trifluoromethyl-benzyl)-(2-methyl-2H-tetrazol-5-yl)-(2,3,4,5,7,8,9,10-octahydro-1H-naphtho[2,3-b]azepin-5-yl)-amine

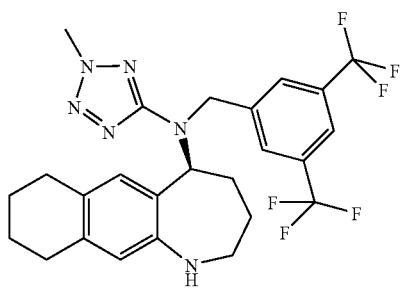

To a solution of (S)-5-[(3,5-Bis-trifluoromethyl-benzyl)-(2-methyl-2H-tetrazol-5-yl)-amino]-2,3,4,5,7,8,9,10-octahydro-naphtho[2,3-b]azepine-1-carboxylic acid tert-butyl ester (0.67 mmol) in dichloromethane (18 mL) add trifluoroacetic acid (2 mL). After stirring at room temperature for 1 h, quench with concentrated sodium carbonate (10 mL) and dilute with dichloromethane (20 mL) and water (20 mL). Separate the organic phase and wash the aqueous with dichloromethane (2×10 mL). Dry the combined organics over sodium sulfate, filter, and remove solvent under vacuum. Chromatograph the product over silica gel eluting with ethyl acetate/hexane (5-30%) to afford the title compound as a colorless foam. MS (ES+): 525 (M+H).

Step 4. Preparation of (S)-(3,5-Bis-trifluoromethyl-benzyl)-(1-cyclopentylmethyl-2,3,4,5,7,8,9,10-octahydro-1H-naphtho[2,3-b]azepin-5-yl)-(2-methyl-2H-tetrazol-5-yl)-amine

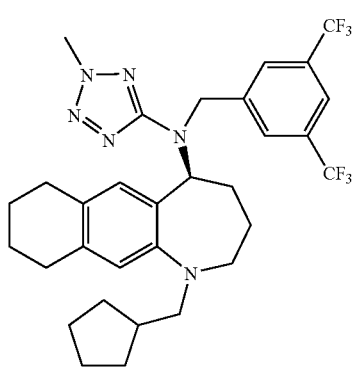

Prepare the title compound by following the procedure as essentially described for the synthesis of (S)-(3,5-bis-trifluoromethyl-benzyl)-(5-cyclopentylmethyl-3,5,6,7,8,9-hexahydro-1H-2-oxa-5-aza-cyclohepta[f]inden-9-yl)-(2-methyl-2H-tetrazol-5-yl)-amine in starting with (S)-(3,5-Bis-trifluoromethyl-benzyl)-(2-methyl-2H-tetrazol-5-yl)-(2,3,4,5,7,8,9,10-octahydro-1H-naphtho[2,3-b]azepin-5-yl)-amine. MS (ES+): 607.2 (M+H).

Example 78

Synthesis of 5-[(3,5-Bis-trifluoromethyl-benzyl)-(2-methyl-2H-tetrazol-5-yl)-amino]-2,3,4,5,7,8,9,10-octahydro-naphtho[2,3-b]azepine-1-carboxylic acid isopropyl ester

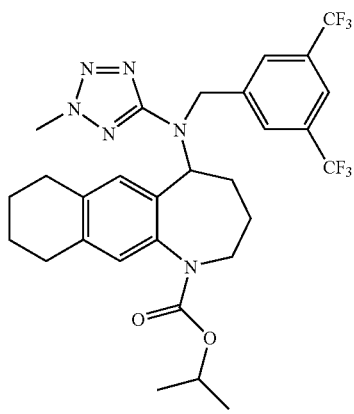

The title compound can be prepared using procedures analogous to those used in the synthesis of (+/−)-isopropyl 5-[(3,5-bistrifluoromethylbenzyl)-(2-methyl-2H-tetrazol-5-yl)amino]-7-bromo-2,3,4,5-tetrahydrobenzo[b]azepine-1-carboxylate (Example 1), starting with 3-amino-5,6,7,8-tetrahydro-naphthalene-2-carboxylic acid methyl ester.

3-amino-5,6,7,8-tetrahydro-naphthalene-2-carboxylic acid methyl ester could be prepared using procedures as described in Example 73, Steps 2 and 3 starting with 5,6,7,8-tetrahydro-naphthalen-2-ylamine.

Example 79

Synthesis of (S)-9-{(3,5-Bis-trifluoromethyl-benzyl)-[2-(2-hydroxy-ethyl)-2H-tetrazol-5-yl]-amino}-2,3,6,7,8,9-hexahydro-1H-5-aza-cyclohepta[f]indene-5-carboxylic acid isopropyl ester

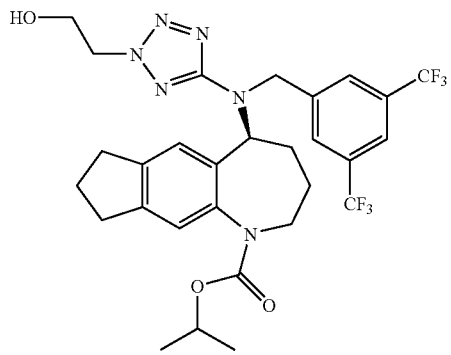

Step 1. Preparation of (S)-9-[(3,5-Bis-trifluoromethyl-benzyl)-(2H-tetrazol-5-yl)-amino]-2,3,6,7,8,9-hexahydro-1H-5-aza-cyclohepta[f]indene-5-carboxylic acid isopropyl ester

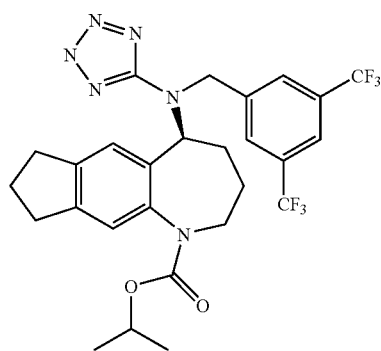

Prepare the title compound by essentially following the procedure described in Example 3, Step 11-16, by replacing tert-butyl-7-methyl-5-oxo-8-trifluoromethyl-2,3-4,5-tetrahydrobenzo[b]azepine-1-carboxylate with 9-oxo-2,3,6,7,8,9-hexahydro-1H-5-aza-cyclohepta[f]indene-5-carboxylic acid isopropyl ester (Example 49, Step 4) in Example 3, Step 11. MS (ES−): 581 (M−H).

Step 2. Preparation of (S)-9-{(3,5-Bis-trifluoromethyl-benzyl)-[2-(2-hydroxy-ethyl)-2H-tetrazol-5-yl]-amino}-2,3,6,7,8,9-hexahydro-1H-5-aza-cyclohepta[f]indene-5-carboxylic acid isopropyl ester

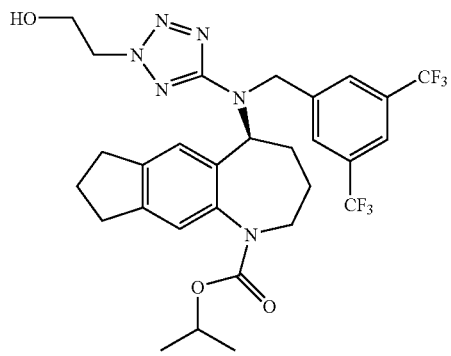

Add potassium carbonate (40 mg, 0.29 mmol) and bromoethanol (0.018 mL, 0.26 mmol) to a solution of (S)-9-[(3,5-Bis-trifluoromethyl-benzyl)-(2H-tetrazol-5-yl)-amino]-2,3,6,7,8,9-hexahydro-1H-5-aza-cyclohepta[f]indene-5-carboxylic acid isopropyl ester (50 mg, 0.086 mmol) in dimethylformamide (0.3 mL). Stir at room temperature for 18 hrs in a sealed tube. Then add bromoethanol (0.018 mL, 0.26 mmol) and stir for 2 hrs. Add a 1N solution of hydrochloric acid and extract with dichloromethane. Dry the organic phase over anhydrous sodium sulfate, filter and concentrate in vacuo. Purify the residue using silica gel cartridge, eluting with ethyl acetate/hexanes to afford the title compound (26 mg, 49%). MS (ES+): 627 (M+H).

Example 80

Synthesis of (R)-9-[(3,5-Bis-trifluoromethyl-benzyl)-(2-methyl-2H-tetrazol-5-yl)-amino]-2,3,6,7,8,9-hexahydro-1H-5-aza-cyclohepta[f]indene-5-carboxylic acid isopropyl ester

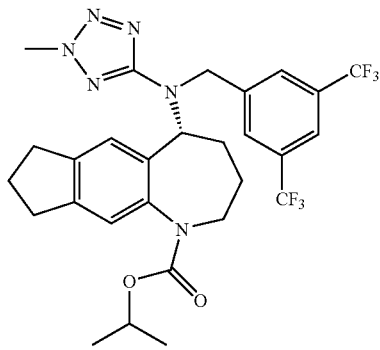

The title compound is obtained by chiral resolution of Example 50 on a Chiralpak AD (20×250 mm), flow rate 10-12 mL/min (15 min). Gradient: 10-30% propan-2-ol in hexane 0.05% TFA, R$_f$=5.2 min, wavelength: 215.16, e.e.>98%. MS (ES+): 597 (M+H).

Example 81

Synthesis of (S)-9-[(3,5-Bis-trifluoromethyl-benzyl)-(2-methyl-2H-tetrazol-5-yl)-amino]-2,3,6,7,8,9-hexahydro-1H-5-aza-cyclohepta[f]indene-5-carboxylic acid isopropyl ester

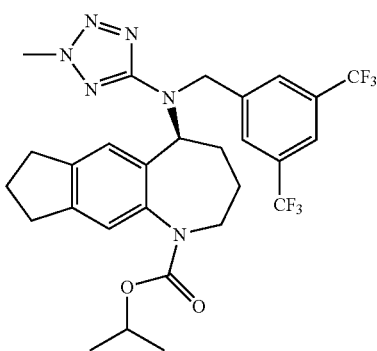

The title compound is obtained by chiral resolution of Example 50 on a Chiralpak AD (20×250 mm), flow rate 10-12 mL/min (15 min). Gradient: 10-30% propan-2-ol in hexane 0.05% TFA, R$_f$=11.2 min, wavelength: 215.16, e.e.>98%. MS (ES+): 597 (M+H).

Example 82

Synthesis of (S)-6-{(3,5-Bis-trifluoromethyl-benzyl)-[2-(2-hydroxy-ethyl)-2H-tetrazol-5-yl]-amino}-2,3,6,7,8,9-hexahydro-1H-10-aza-cyclohepta[e]indene-10-carboxylic acid isopropyl ester

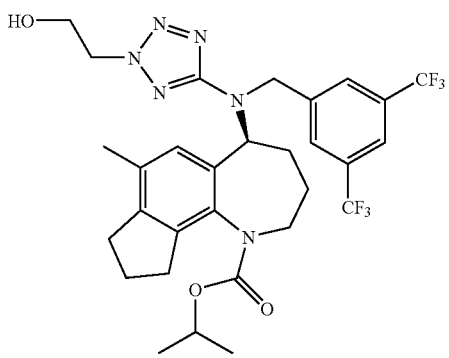

Prepare the title compound by essentially following the procedure described in Example 79, Step 2 by replacing (S)-9-[(3,5-Bis-trifluoromethyl-benzyl)-(2H-tetrazol-5-yl)-amino]-2,3,6,7,8,9-hexahydro-1H-5-aza-cyclohepta[f]indene-5-carboxylic acid isopropyl ester with (S)-6-[(3,5-Bis-trifluoromethyl-benzyl)-(2H-tetrazol-5-yl)-amino]-4-methyl-2,3,6,7,8,9-hexahydro-1H-10-aza-cyclohepta[e]indene-10-carboxylic acid isopropyl ester (Example 55, Step 5) in Example 79, Step 2. MS (ES+): 641 (M+H).

Example 83

Synthesis of (S)-6-{(3,5-Bis-trifluoromethyl-benzyl)-[2-(2-hydroxy-ethyl)-2H-tetrazol-5-yl]-amino}-4-methyl-2,3,6,7,8,9-hexahydro-1H-10-aza-cyclohepta[e]indene-10-carboxylic acid isopropyl ester

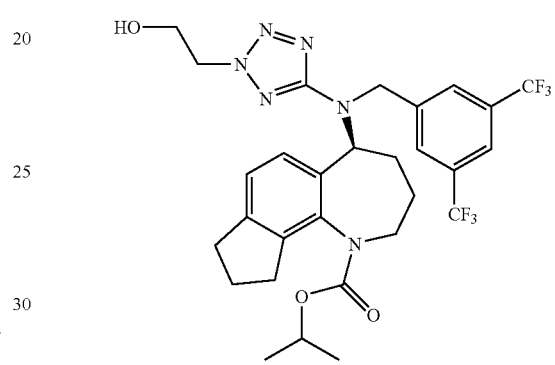

Step 1. Preparation of (S)-6-[(3,5-Bis-trifluoromethyl-benzyl)-(2H-tetrazol-5-yl)-amino]-2,3,6,7,8,9-hexahydro-1H-10-aza-cyclohepta[e]indene-10-carboxylic acid isopropyl ester

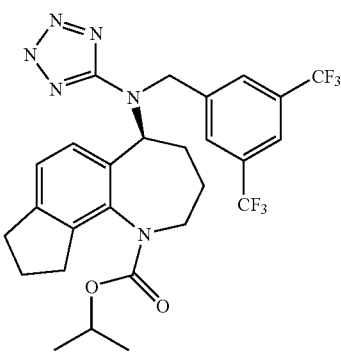

Prepare the title compound by essentially following the procedure described in Example 3, Step 11-16, by replacing tert-butyl-7-methyl-5-oxo-8-trifluoromethyl-2,3,4,5-tetrahydrobenzo[b]azepine-1-carboxylate with 6-Oxo-2,3,6,7,8,9-hexahydro-1H-10-aza-cyclohepta[e]indene-10-carboxylic acid isopropyl ester (Example 48, Step 6) in Example 3, Step 11. MS (ES+): 581 (M−H).

Step 2. Preparation of (S)-6-{(3,5-Bis-trifluoromethyl-benzyl)-[2-(2-hydroxy-ethyl)-2H-tetrazol-5-yl]-amino}-4-methyl-2,3,6,7,8,9-hexahydro-1H-10-aza-cyclohepta[e]indene-10-carboxylic acid isopropyl ester

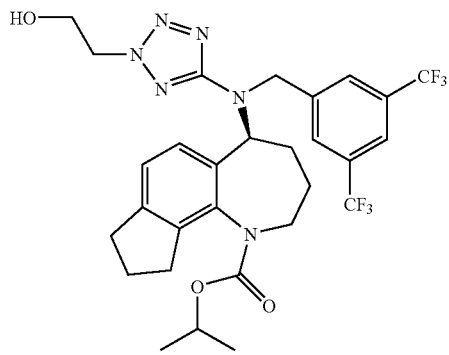

Prepare the title compound by essentially following the procedure described in Example 79, Step 2 by replacing (S)-9-[(3,5-Bis-trifluoromethyl-benzyl)-(2H-tetrazol-5-yl)-amino]-2,3,6,7,8,9-hexahydro-1H-5-aza-cyclohepta[f]indene-5-carboxylic acid isopropyl ester with (S)-6-[(3,5-Bis-trifluoromethyl-benzyl)-(2H-tetrazol-5-yl)-amino]-2,3,6,7,8,9-hexahydro-1H-10-aza-cyclohepta[e]indene-10-carboxylic acid isopropyl ester in Example 79, Step 2. MS (ES+): 627 (M+H).

Example 84

Synthesis of (S)-9-[(3,5-Bis-trifluoromethyl-benzyl)-(2-methyl-2H-tetrazol-5-yl)-amino]-2,3,6,7,8,9-hexahydro-1H-5-aza-cyclohepta[f]indene-5-carboxylic acid 2-methoxycarbonyl-2-methyl-propyl ester

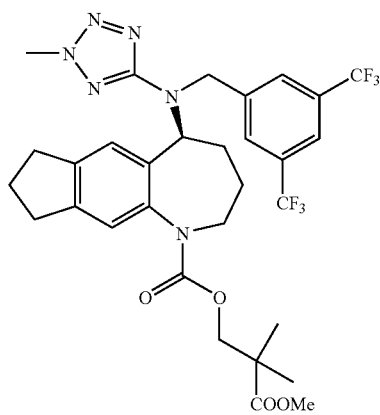

Step 1. Preparation of (S)-(3,5-Bis-trifluoromethyl-benzyl)-(2-methyl-2H-tetrazol-5-yl)-(1,2,3,5,6,7,8,9-octahydro-5-aza-cyclohepta[f]inden-9-yl)-amine

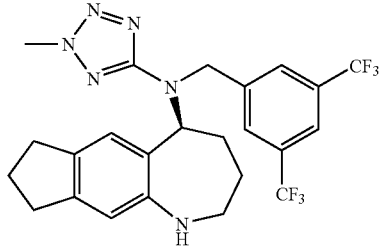

Prepare the title compound by essentially following the procedure described in Example 3, Step 18, by replacing (S)-tert-Butyl 5-[(3,5-bistrifluoromethylbenzyl)-(2-methyl-2H-tetrazol-5-yl)amino]-7-methyl-8-trifluoromethyl-2,3,4,5-tetrahydrobenzo[b]azepine-1-carboxylate with (S)-9-[(3,5-Bis-trifluoromethyl-benzyl)-(2-methyl-2H-tetrazol-5-yl)-amino]-2,3,6,7,8,9-hexahydro-1H-5-aza-cyclohepta[f]indene-5-carboxylic acid tert-butyl ester (Example 65) in Example 3, Step 18. MS (ES+): 511 (M+H).

Step 2. Preparation of (S)-9-[(3,5-Bis-trifluoromethyl-benzyl)-(2-methyl-2H-tetrazol-5-yl)-amino]-2,3,6,7,8,9-hexahydro-1H-5-aza-cyclohepta[f]indene-5-carboxylic acid 2-methoxycarbonyl-2-methyl-propyl ester

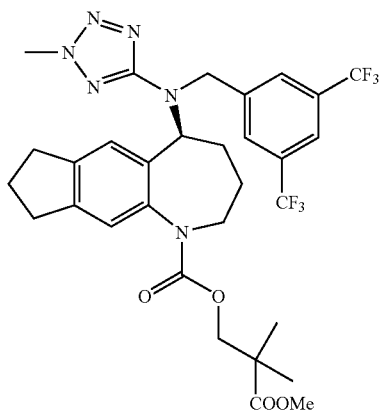

Add a 20% solution of phosgene in toluene (0.43 mL, 0.78 mmol) to a mixture of 3-hydroxy-2,2-dimethyl-propionic acid methyl ester (0.12 mL, 0.96 mmol) and diisopropylethylamine (0.16 mL, 0.96 mmol) in dichloromethane (1.8 mL) at 0° C. under nitrogen. Stir the mixture at 0° C. for 10 minutes, then at room temperature for 1 h. To the former solution add a solution of (S)-(3,5-Bis-trifluoromethyl-benzyl)-(2-methyl-2H-tetrazol-5-yl)-(1,2,3,5,6,7,8,9-octahydro-5-aza-cyclohepta[f]inden-9-yl)-amine (80 mg, 0.16 mmol) in dichloromethane (1.8 mL) followed by pyridine (0.064 mL, 0.78 mmol). Stir the mixture at room temperature for 1 h. Dilute with dichloromethane. Wash with HCl 1M and water. Dry organic layers over anhydrous sodium sulphate and evaporate the solvent. Purify the residue by chromatography (elution with hexane/ethyl acetate) to afford the title compound (78 mg, 73%). MS (ES+): 669 (M+H).

Example 85

Synthesis of (S)-9-[(3,5-Bis-trifluoromethyl-benzyl)-(2-methyl-2H-tetrazol-5-yl)-amino]-2,3,6,7,8,9-hexahydro-1H-5-aza-cyclohepta[f]indene-5-carboxylic acid 2-carboxy-2-methyl-propyl ester

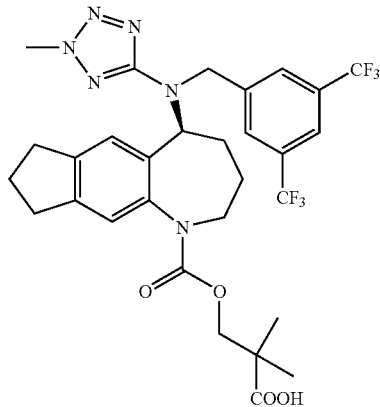

Add aqueous 5 M NaOH (2.4 mL, 12 mmol) to a solution of (S)-9-[(3,5-Bis-trifluoromethyl-benzyl)-(2-methyl-2H-tetrazol-5-yl)-amino]-2,3,6,7,8,9-hexahydro-1H-5-aza-cyclohepta[f]indene-5-carboxylic acid 2-methoxycarbonyl-2-methyl-propyl ester (86 mg, 0.13 mmol) in methanol (3.4 mL). Heat the mixture at 60° C. for 1 h. Cool down to room temperature. Dilute with water and neutralize with 2 M HCl. Extract aqueous phase with ethyl acetate. Dry organic layers with anhydrous sodium sulphate and evaporate the solvent. Purify the residue by chromatography (elution with dichloromethane/methanol) to afford the title compound (62 mg, 73%). MS (ES+): 655 (M+H).

Example 86

Synthesis of (S)-1-{5-[(3,5-Bis-trifluoromethyl-benzyl)-2-methyl-2H-tetrazol-5-yl)-amino]-7-methyl-8-trifluoromethyl-2,3,4,5-tetrahydro-benzo[b]azepin-1-yl}-3-furan-2-ylmethoxy)-propan-2-one

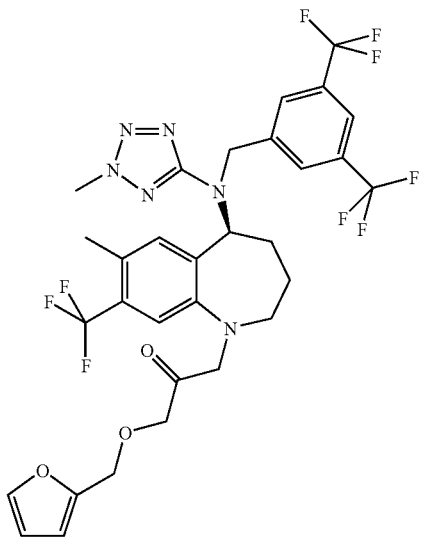

Step 1. Preparation of (S)-1-{5-[(3,5-Bis-trifluoromethyl-benzyl)-2-methyl-2H-tetrazol-5-yl)-amino]-7-methyl-8-trifluoromethyl-2,3,4,5-tetrahydro-benzo[b]azepin-1-yl}-3-furan-2-ylmethoxy)-propan-2-ol

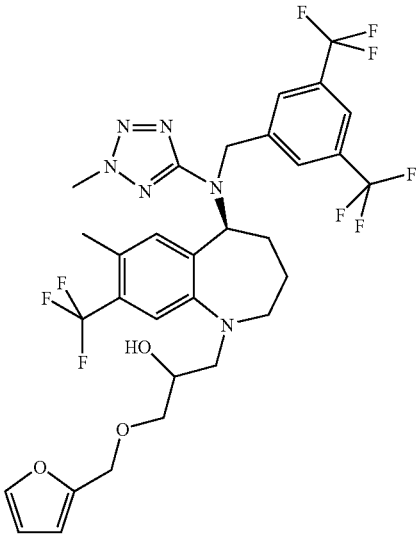

Add furfuryl glycidyl ether (0.068 mL, 0.50 mmol) followed by Ytterbium (III) trifluoromethanesulfonate hydrate (0.012 g, 0.02 mmol) to a solution of (S)-(3,5-bistrifluoromethylbenzyl)-(2-methyl-2H-tetrazol-5-yl)-(7-methyl-8-trifluoromethyl-2,3,4,5-tetrahydro-1H-benzo[b]azepin-5-yl) amine (Example 3, Step 18) (0.055 g, 0.10 mmol) in acetonitrile (1 mL). After, stirring at room temperature for 3 days remove the solvent under vacuum. Dilute with ethyl acetate (20 mL), wash with water, brine, dry and concentrate under reduced pressure. Purify by silica gel column (gradient eluent, 0-50% ethyl acetate in hexane) to obtain the title compound (0.043 g, 61%). mass spectrum: MS (ES+): 707 (M+H).

Step 2. Preparation of (S)-1-{5-[(3,5-Bis-trifluoromethyl-benzyl)-2-methyl-2H-tetrazol-5-yl)-amino]-7-methyl-8-trifluoromethyl-2,3,4,5-tetrahydro-benzo[b]azepin-1-yl}-3-furan-2-ylmethoxy)-propan-2-one

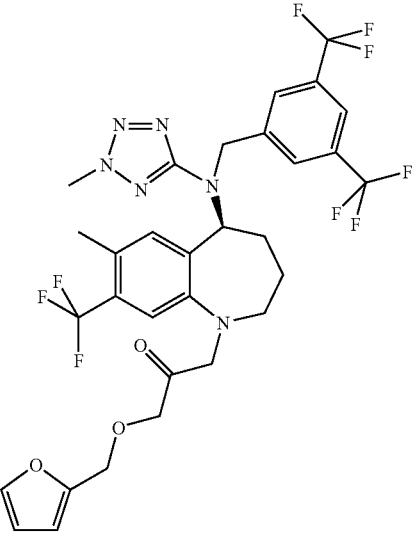

To a mixture of pyridinium chlorochromate (0.037 g, 0.17 mmol), sodium acetate (0.014 g, 0.17 mmol) and 4 A0 molecular sieves (0.10 g) in dichloromethane (1 mL) at room temperature, was added (S)-1-{5-[(3,5-bis-trifluoromethyl-benzyl)-2-methyl-2H-tetrazol-5-yl)-amino]-7-methyl-8-trifluoromethyl-2,3,4,5-tetrahydro-benzo[b]azepin-1-yl}-3-furan-2-ylmethoxy)-propan-2-ol (0.041 g, 0.058 mmol) in dicholormethane (1 mL). Allow the reaction mixture to stir at room temperature for 60 min and dilute with ether. Filter and remove the solvent under reduced pressure. Purify the residue by flash chromatography, eluting with hexanes/ethyl acetate (gradient eluent, 0-30% ethyl acetate in hexane), to provide the title compound (0.026 g, 65%). MS (ES+): 705 (M+H).

Example 87

Synthesis of 2-{5-[(3,5-Bis-trifluoromethyl-benzyl)-2-methyl-2H-tetrazol-5-yl)-amino]-7-methyl-8-trifluoromethyl-2,3,4,5-tetrahydro-benzo[b]azepin-1-yl}-1-phenyl-ethanol and 2-{5-[(3,5-Bis-trifluoromethyl-benzyl)-2-methyl-2H-tetrazol-5-yl)-amino]-7-methyl-8-trifluoromethyl-2,3,4,5-tetrahydro-benzo[b]azepin-1-yl}-2-phenyl-ethanol

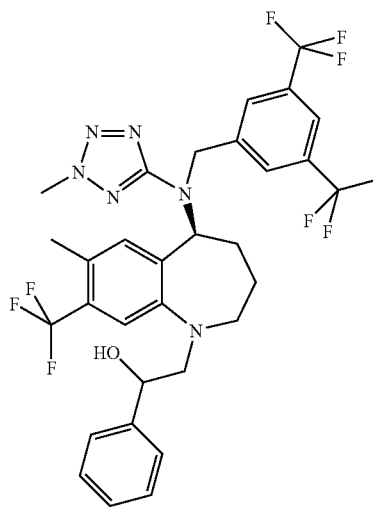

Prepare the title compound by essentially following the procedure described in Example 86, Step 1, using, (S)-(3,5-bistrifluoromethylbenzyl)-(2-methyl-2H-tetrazol-5-yl)-(7-methyl-8-trifluoromethyl-2,3,4,5-tetrahydro-1H-benzo[b]azepin-5-yl)amine (Example 3, Step 18) (0.055 g, 0.10 mmol), styrene oxide (0.057 mL, 0.50 mmol) and Ytterbium (III) trifluoromethanesulfonate hydrate (0.012 g, 0.02 mmol) to give the mixture of two separable regioisomers by column. Purify by silica gel column (gradient eluent, 0-40% ethyl acetate in hexane) to provide isomer-1:2-{5-[(3,5-Bis-trifluoromethyl-benzyl)-2-methyl-2H-tetrazol-5-yl)-amino]-7-methyl-8-trifluoromethyl-2,3,4,5-tetrahydro-benzo[b]azepin-1-yl}-1-phenyl-ethanol (0.015 g, 22%). MS (ES+): 673 (M+H), and isomer-2:2-{5-[(3,5-Bis-trifluoromethyl-benzyl)-2-methyl-2H-tetrazol-5-yl)-amino]-7-methyl-8-trifluoromethyl-2,3,4,5-tetrahydro-benzo[b]azepin-1-yl}-2-phenyl-ethanol (0.012 g, 18%). MS (ES+): 673 (M+H).

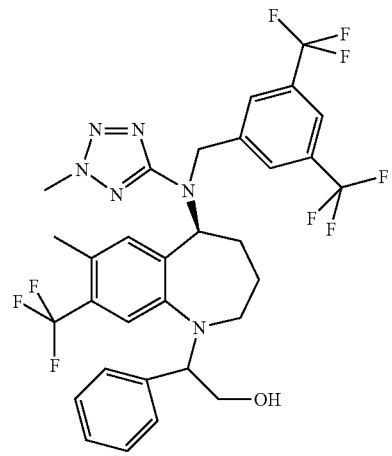

Example 88

Synthesis of (S)-4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-benzoic acid methyl ester

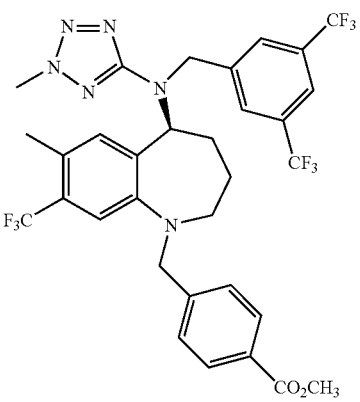

Add 4-formylbenzoic acid methyl ester (133 mg, 0.815 mmol) to a solution of (S)-(3,5-bis-trifluoromethylbenzyl)-(2-methyl-2H-tetrazol-5-yl)-(7-methyl-8-trifluoromethyl-2,3,4,5-tetrahydro-1H-benzo[b]azepin-5-yl)amine (Example 3, Step 18) (150 mg, 0.272 mmol) in acetic acid (1 mL) and 1,2-dichloroethane (10 mL) at room temperature under nitrogen and stir for 2 h. Add sodium triacetoxy borohydride (231 mg, 1.08 mmol) and stir for 3 h. Dilute the mixture with methylene chloride (30 mL) and wash with saturated aqueous sodium bicarbonate solution (2×10 mL). Extract the combined aqueous washes with methylene chloride (20 mL) and wash the combined organic extracts with brined (20 mL) and dry over anhydrous sodium sulfate. Remove the solvents under reduced pressure and purify the residue by column chromatography on silica gel, eluting with ethyl acetate/hexanes (1:2), to provide the title compound as a white solid (100 mg, 52%): mp 71-74° C. dec; $^1$H NMR (CDCl3, 300 MHz) δ 1.61-1.65 (m, 2H), 2.02-2.22 (m, 2H), 2.29 (s, 3H), 2.71-2.80 (m, 1H), 3.02-3.11 (m, 1H), 3.89 (s, 3H), 4.18 (s, 3H), 4.22-4.40 (m, 2H), 4.89-5.10 (m, 2H), 5.55-5.60 (m, 1H), 6.90 (s, 1H), 7.21 (s, 1 H), 7.45-7.49 (m, 2H), 7.65-7.70 (m, 2H), 7.75-7.80 (m, 1H), 7.97-7.81 (m, 2H); ESI MS m/z 701 [C32H29F9N6O2+H]+; HPLC 98.3%, tR 19.6 min.

Example 89

Synthesis of (S)-4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-benzoic acid

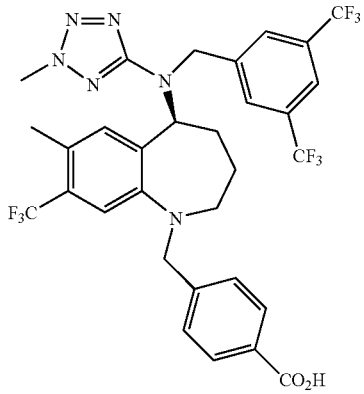

Add 5 N sodium hydroxide solution (0.5 mL) to a solution of (S)-4-{5-[(3,5-bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-benzoic acid methyl ester (70 mg, 0.100 mmol) in methanol (1 mL) and heat at 60° C. for 4 h. After the reaction cools to room temperature, acidify to pH 4 with 2 N hydrochloric acid solution and extract the aqueous mixture with ethyl acetate (3×10 mL). Wash the organic layer with water and brine (10 mL each). Dry the organic layer over anhydrous sodium sulfate, filter and remove the solvent under reduced pressure to provide the title compound as a white solid (62 mg, 90%). mp 95-98° C.; $^1$H NMR (CDCl3, 300 MHz) δ 1.63-1.71 (m, 2H), 1.99-2.05 (m, 2H), 2.29 (s, 3H), 2.75-2.84 (m, 1H), 2.98-3.10 (m, 1H), 4.15 (s, 3H), 4.31-4.50 (m, 2H), 4.82-5.12 (m, 2H), 5.51-5.60 (m, 1H), 6.95 (s, 1H), 7.31-7.37 (m, 1H), 7.51-7.60 (m, 2H), 7.65-7.70 (m, 2H), 7.78-7.82 (m, 1H), 8.10-8.17 (m, 2H); ESI MS m/z 687 [C31H27F9N6O2+H]+; HPLC 98.1%, tR 17.0 min.

Example 90

Synthesis of (S)-3-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-benzoic acid methyl ester

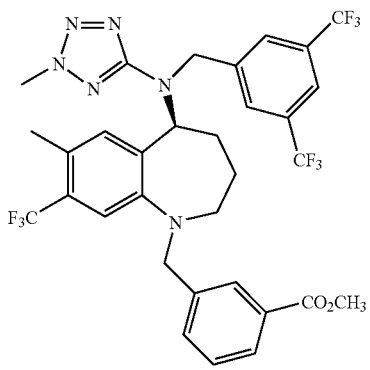

Add 3-formylbenzoic acid methyl ester (133 mg, 0.815 mmol) to a solution of (S)-(3,5-bis-trifluoromethylbenzyl)-(2-methyl-2H-tetrazol-5-yl)-(7-methyl-8-trifluoromethyl-2,3,4,5-tetrahydro-1H-benzo[b]azepin-5-yl)amine (Example 3, Step 18) (150 mg, 0.272 mmol) in acetic acid (1 mL) and 1,2-dichloroethane (10 mL) at room temperature under nitrogen and stir for 2 h. Add sodium triacetoxy borohydride (231 mg, 1.08 mmol) and stir for 3 h. Dilute the mixture with methylene chloride (30 mL) and wash with saturated aqueous sodium bicarbonate solution (2×10 mL). Extract the combined aqueous washes with methylene chloride (20 mL) and wash the combined organic extracts with brined (20 mL) and dry over anhydrous sodium sulfate. Remove the solvents under reduced pressure and purify the residue by column chromatography on silica gel, eluting with ethyl acetate/hexanes (1:2), to provide the title compound as a white solid (101 mg, 53%): mp 62-65° C. dec; $^1$H NMR (CDCl3, 300 MHz) δ 1.50-1.70 (m, 2H), 2.07-2.25 (m, 2H), 2.29 (s, 3H), 2.73-2.85 (m, 1H), 2.95-3.09 (m, 1H), 3.89 (s, 3H), 4.18 (s, 3H), 4.31-4.40 (m, 2H), 4.81-5.02 (m, 2H), 6.93 (s, 1H), 7.31-7.42 (m, 2H), 7.55-7.63 (m, 4H), 7.79-7.82 (m, 1H), 7.89-7.92 (m, 1H), 8.10 (s, 1H); ESI MS m/z 701 [C32H29F9N6O2+H]+; HPLC 97.6%, tR 19.7 min.

Example 91

Synthesis of (S)-3-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-benzoic acid

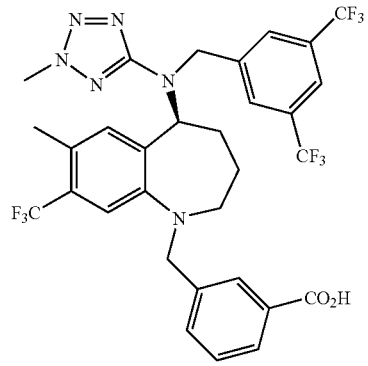

Add 5 N sodium hydroxide solution (0.5 mL) to a solution of (S)-3-{5-[(3,5-bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-benzoic acid methyl ester (70 mg, 0.100 mmol) in methanol (1 mL) and heat at 60° C. for 4 h. After the reaction cools to room temperature, acidify to pH 4 with 2 N hydrochloric acid solution and extract the aqueous mixture with ethyl acetate (3×10 mL). Wash the organic layer with water and brine (10 mL each). Dry the organic layer over anhydrous sodium sulfate, filter and remove the solvent under reduced pressure to provide the title compound as a white solid (67 mg, >99%): mp 83-86° C.; $^1$H NMR (CDCl3, 300 MHz) δ 1.51-1.71 (m, 2H), 2.00-2.12 (m, 2H), 2.29 (s, 3H), 2.78-2.85 (m, 1H), 3.02-3.09 (m, 1H), 4.17 (s, 3H), 4.31-4.43 (m, 2H), 4.86-5.16 (m, 2H), 5.51-5.60 (m, 1H), 6.98 (s, 1H), 7.25 (s, 1H), 7.43-7.49 (m, 1H), 7.60-7.82 (m, 4H), 7.99-8.03 (m, 1H), 8.15 (s, 1H); ESI MS m/z 687 [C31H27F9N6O2+H]+; HPLC 97.6%, tR 17.0 min.

Example 92

Synthesis of (S)-4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-benzoic acid

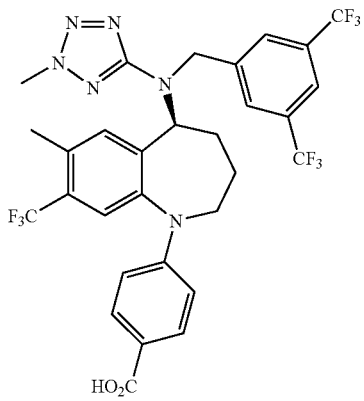

Step 1. Preparation of (S)-4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-benzoic acid methyl ester

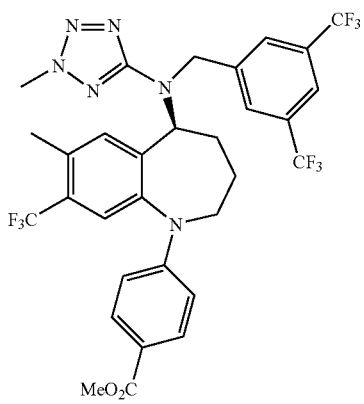

Combine tris(dibenzylideneacetone)dipalladium (0) (16 mg, 0.018 mmol), 2-dicyclohexylphosphino-2'-(N,N-dimethylamino)biphenyl (14 mg, 0.036 mmol) and sodium t-butoxide (43 mg, 0.452 mmol) in toluene (5 mL) and purge this suspension with nitrogen at room temperature for 5 min. Add (S)-(3,5-bistrifluoromethylbenzyl)-(2-methyl-2H-tetrazol-5-yl)-(7-methyl-8-trifluoromethyl-2,3,4,5-tetrahydro-1H-benzo[b]azepin-5-yl)amine (Example 3, Step 18) (100 mg, 0.181 mmol) followed by methyl-4-iodobenzoate (47 mg, 0.181 mmol) and heat this mixture at 100° C. under nitrogen for 2 h. Cool the mixture to room temperature, dilute with dichloromethane, filter through Celite®, and concentrate under reduced pressure. Chromatograph the residue over silica gel, eluting with hexanes/ethyl acetate (20:1 to 1:2), to provide the title compound as an off-white solid (50 mg, 40%). mp 101-105° C.; TLC Rf 0.50 (3:1 hexanes/ethyl acetate); 1H NMR (CDCl3, 300 MHz) δ 1.72-1.89 (m, 1H), 2.00-2.32 (m, 3H), 2.29 (s, 3H), 3.33-3.40 (m, 1H), 3.89 (s, 3H), 3.99-4.09 (m, 1H), 4.19 (s, 3H), 4.69-5.33 (m, 3H), 6.68-6.73 (m, 2H), 7.15 (s, 1H), 7.45 (s, 1H), 7.62-7.72 (m, 2H), 7.79 (s, 1H), 7.96-8.05 (m, 2H); ESI MS m/z 687 [C31H27F9N6O2+H]+.

Step 2. Preparation of (S)-4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-benzoic acid

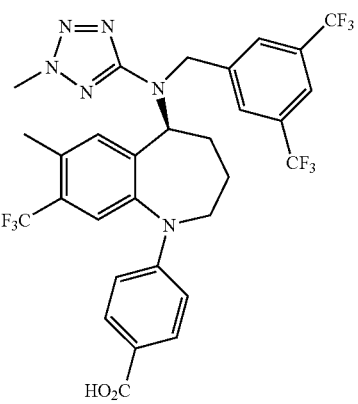

Add 5 N sodium hydroxide solution (0.5 mL) to a solution of (S)-4-{5-[(3,5-bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-benzoic acid methyl ester (40 mg, 0.058 mmol) in methanol (1 mL) and heat at 60° C. for 4 h. After the reaction cools to room temperature, acidify to pH 4 with 2 N hydrochloric acid solution and extract the aqueous mixture with ethyl acetate (3×10 mL). Wash the organic layer with water and brine (10 mL each). Dry the organic layer over anhydrous sodium sulfate, filter and remove the solvent under reduced pressure to provide the title compound as an off-white solid (20 mg, 51%). mp 101-105° C.; 1H NMR (CDCl3, 300 MHz) δ 1.75-1.91 (m, 1H), 2.05-2.36 (m, 3H), 2.29 (s, 3H), 3.35-3.43 (m, 1H) 3.99-4.09 (m, 1H), 4.19 (s, 3H), 4.70-5.35 (m, 3H), 6.70-6.75 (m, 2H), 7.20 (s, 1H), 7.47 (s, 1H), 7.63-7.72 (m, 2H), 7.80 (s, 1H), 7.96-8.10 (m, 2H); ESI MS m/z 673 [C30H25F9N6O2+H]+.

Example 93

Synthesis of (4-{5-[(3,5-Bis-trifluoromethyl-benzyl)-(3-methyl-isoxazol-5-yl)-amino]-7-methyl-8-trifluoromethyl-2,3,4,5-tetrahydro-benzo[b]azepin-1-ylmethyl}-cyclohexyl)-acetic acid methyl ester

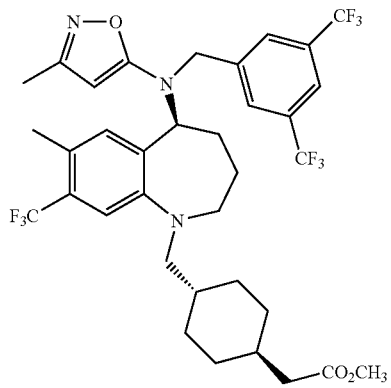

Step 1. Preparation of (S)-5-[(3,5-Bis-trifluoromethyl-benzyl)-(3-oxo-butyryl)-amino]-7-methyl-8-trifluoromethyl-2,3,4,5-tetrahydro-benzo[b]azepine-1-carboxylic acid tert-butyl ester

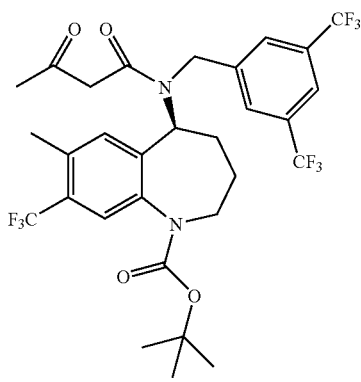

To a solution of (S)-5-(3,5-bis-trifluoromethyl-benzylamino)-7-methyl-8-trifluoromethyl-2,3,4,5-tetrahydro-benzo[b]azepine-1-carboxylic acid tert-butyl ester (Example 3, Step 14) (1.0 g, 1.75 mmol) and 4-dimethylaminopyridine (25 mg, 0.21 mmol) in dry tetrahydrofuran (10 mL) at 0° C. under a nitrogen atmosphere, add diketene (0.147 mL, 1.93 mmol). After stirring 1.5 h at 0° C., remove the solvent under reduced pressure. Purify the by flash chromatography, eluting with hexanes/ethyl acetate (20:1 to 1:2), to provide the title compound as an off-white solid (1.12 g, 97%). TLC Rf 0.40 (3:1 hexanes/ethyl acetate); $^1$H NMR (CDCl3, 300 MHz) δ 1.10-2.10 (m, 13H), 2.29 (s, 3H), 2.52 (s, 3H), 3.41-3.53 (m, 1H), 4.14-4.54 (m, 4H), 4.89-5.12 (m, 1H), 5.57-5.69 (m, 1H), 6.89 (s, 1H), 7.24-7.92 (m, 4H).

Step 2. Preparation of (S)-5-[(3,5-Bis-trifluoromethyl-benzyl)-(3-methyl-isoxazol-5-yl)-amino]-7-methyl-8-trifluoromethyl-2,3,4,5-tetrahydro-benzo[b]azepine-1-carboxylic acid tert-butyl ester

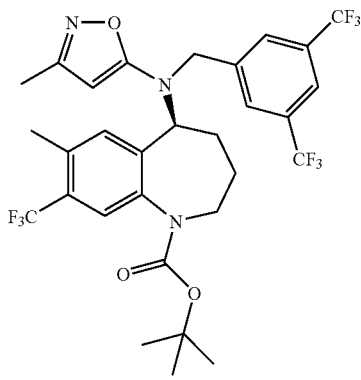

To a solution of compound (S)-5-[(3,5-bis-trifluoromethyl-benzyl)-(3-oxo-butyryl)-amino]-7-methyl-8-trifluoromethyl-2,3,4,5-tetrahydro-benzo[b]azepine-1-carboxylic acid tert-butyl ester (600 mg, 0.916 mmol) in methanol (5 mL) at 0° C., add hydroxylamine hydrochloride (96 mg, 1.37 mmol) and sodium acetate (3 mg, 0.046 mmol). Heat the reaction mixture under reflux for 4 h. Cool and remove the solvents under reduced pressure. Dilute the residue with ethyl acetate and brine. Separate the layers and dry the organic phase over sodium sulfate, filter and concentrate under reduced pressure. Purify the residue by flash chromatography, eluting with hexanes/ethyl acetate (20:1 to 3:1) to afford the title compound as an off-white solid (100 mg, 17%). $^1$H NMR (CDCl3, 300 MHz) δ 1.10-2.10 (m, 16H), 2.21 (s, 3H), 2.54 (s, 3H), 4.22-4.83 (m, 3H), 6.89-6.92 (m, 1H), 7.36-7.89 (m, 4H); ESI MS m/z 652 [C30H30F9N3O3+H]+.

Step 3. Preparation of (S)-(3,5-Bis-trifluoromethyl-benzyl)-(3-methyl-isoxazol-5-yl)-(7-methyl-8-trifluoromethyl-2,3,4,5-tetrahydro-1H-benzo[b]azepin-5-yl)-amine

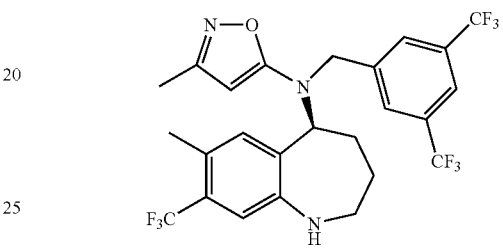

Add trifluoroacetic acid (10 mL) to a solution of (S)-5-[(3,5-bis-trifluoromethyl-benzyl)-(3-methyl-isoxazol-5-yl)-amino]-7-methyl-8-trifluoromethyl-2,3,4,5-tetrahydro-benzo[b]azepine-1-carboxylic acid tert-butyl ester (140 mg, 0.458 mmol) in methylene chloride (5 mL) at 0° C. under nitrogen. Warm the mixture to room temperature, stir for 4 h and pour the mixture into saturated aqueous sodium bicarbonate solution (20 mL). Extract the mixture with methylene chloride (20 mL) and wash the combined organic extracts with brine (10 mL), dry over anhydrous sodium sulfate and filter. Remove the solvent under reduced pressure to provide the title compound as a colorless oil (90 mg, 76%), which is used in the next step without purification: ESI MS m/z 552 [C25H22F9N3O+H]+.

Step 4. Preparation of 4-{5-[(3,5-Bis-trifluoromethyl-benzyl)-(3-methyl-isoxazol-5-yl)-amino]-7-methyl-8-trifluoromethyl-2,3,4,5-tetrahydro-benzo[b]azepin-1-ylmethyl}-cyclohexyl)-acetic acid methyl ester

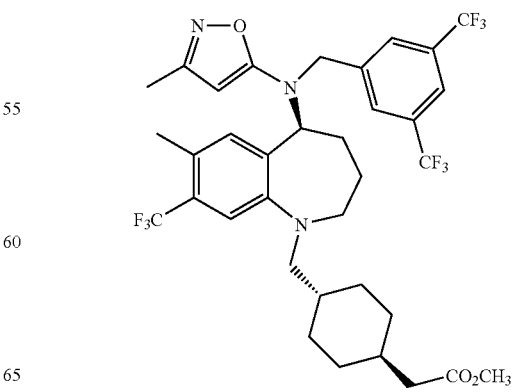

Add (4-formyl-cyclohexyl)-acetic acid methyl ester (68 mg, 0.368 mmol) to a solution of (S)-(3,5-bis-trifluoromethyl-benzyl)-(3-methyl-isoxazol-5-yl)-(7-methyl-8-trifluoromethyl-2,3,4,5-tetrahydro-1H-benzo[b]azepin-5-yl)-amine (80 mg, 0.122 mmol) in acetic acid (0.5 mL) and 1,2-dichloroethane (5 mL) at room temperature under nitrogen and stir for 2 h. Add sodium triacetoxy borohydride (103 mg, 0.488 mmol) and stir for 3 h. Dilute the mixture with methylene chloride (30 mL) and wash with saturated aqueous sodium bicarbonate solution (2×10 mL). Extract the combined aqueous washes with methylene chloride (20 mL) and wash the combined organic extracts with brined (20 mL) and dry over anhydrous sodium sulfate. Remove the solvents under reduced pressure and purify the residue by column chromatography on silica gel, eluting with ethyl acetate/hexanes (1:2), to provide the title compound as a colorless semisolid (73 mg, 85%). $^1$H NMR (CDCl3, 300 MHz) δ 0.72-2.34 (m, 21H), 2.60-2.65 (m, 1H), 2.82-2.90 (m, 1H), 3.00-3.10 (m, 2H), 3.89 (s, 3H), 4.60-4.89 (m, 3H), 5.12-5.18 (m, 1H), 6.89 (s, 1H), 7.15 (s, 1H), 7.68-7.71 (m, 3H), 7.82 (s, 1H); ESI MS m/z 720 [C35H38F9N3O3+H]+; HPLC 96.1%, tR 22.1 min.

Example 94

Synthesis of (4-{5-[(3,5-Bis-trifluoromethyl-benzyl)-(3-methyl-isoxazol-5-yl)-amino]-7-methyl-8-trifluoromethyl-2,3,4,5-tetrahydro-benzo[b]azepin-1-ylmethyl}-cyclohexyl)-acetic acid

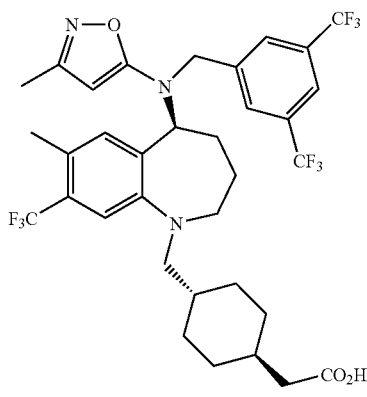

Add 5 N sodium hydroxide solution (2 mL) to a solution of (4-{5-[(3,5-bis-trifluoromethyl-benzyl)-(3-methyl-isoxazol-5-yl)-amino]-7-methyl-8-trifluoromethyl-2,3,4,5-tetrahydro-benzo[b]azepin-1-ylmethyl}-cyclohexyl)-acetic acid methyl ester (63 mg, 0.088 mmol) in methanol (5 mL) and heat at 60° C. for 4 h. After the reaction cools to room temperature, acidify to pH 4 with 2 N hydrochloric acid solution and extract the aqueous mixture with ethyl acetate (3×10 mL). Wash the organic layer with water and brine (10 mL each). Dry the organic layer over anhydrous sodium sulfate, filter and remove the solvent under reduced pressure to provide the title compound as an off-white solid (58 mg, 95%). $^1$H NMR (CDCl3, 300 MHz) δ 0.78-2.45 (m, 22H), 2.63-3.10 (m, 4H), 4.61-4.82 (m, 3H), 5.12-5.19 (m, 1H), 6.89 (s, 1H), 7.12-7.33 (m, 2H), 7.62-7.81 (m, 3H); ESI MS m/z 706 [C34H36F9N3O3+H]+; HPLC 96.3%, tR 18.9 min.

Example 95

Synthesis of (S)-(3,5-Bis-trifluoromethyl-benzyl)-(7-methyl-1-pyridin-4-ylmethyl-8-trifluoromethyl-2,3,4,5-tetrahydro-1H-benzo[b]azepin-5-yl)-(2-methyl-2H-tetrazol-5-yl)-amine

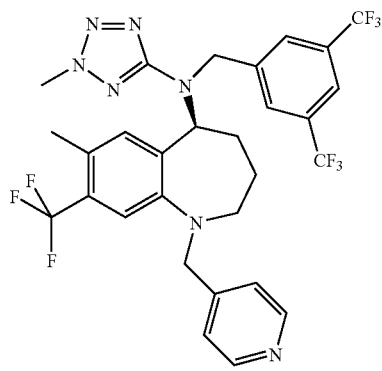

Prepare the title compound by essentially following the procedure described in Example 3, Step 19, using (S)-(3,5-bis-trifluoromethyl-benzyl)-(2-methyl-2H-tetrazol-5-yl)-(7-methyl-8-trifluoromethyl-2,3,4,5-tetrahydro-1H-benzo[b]azepin-5-yl)-amine (Example 3, Step 18) and replacing cyclopentanecarboxaldehyde with 4-pyridine-carboxaldehyde. MS (ES+): 644 (M+H).

Example 96

Synthesis of (S)-(3,5-Bis-trifluoromethyl-benzyl)-(7-methyl-1-pyridin-4-ylmethyl-8-trifluoromethyl-2,3,4,5-tetrahydro-1H-benzo[b]azepin-5-yl)-(2-methyl-2H-tetrazol-5-yl)-amine hydrochloride

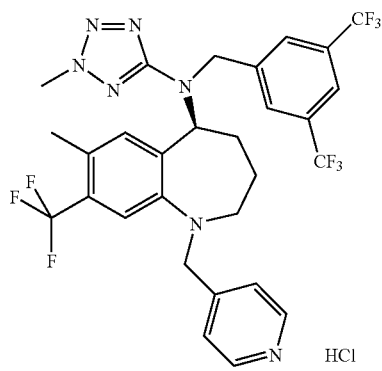

Add 1.0 N HCl in ethyl ether (0.0500 mL) to a solution of (S)-(3,5-Bis-trifluoromethyl-benzyl)-(7-methyl-1-pyridin-4-ylmethyl-8-trifluoromethyl-2,3,4,5-tetrahydro-1H-benzo[b]azepin-5-yl)-(2-methyl-2H-tetrazol-5-yl)-amine (0.0230 mg, 0.0357 mmole) in ethyl ether (0.500 mL), stir for 10 minutes. Evaporate the solvent to provide the title compound. MS (ES+): 644 (M+H).

Example 97

Synthesis of (S)-(3,5-Bis-trifluoromethyl-benzyl)-(7-methyl-1-pyridin-3-ylmethyl-8-trifluoromethyl-2,3,4,5-tetrahydro-1H-benzo[b]azepin-5-yl)-(2-methyl-2H-tetrazol-5-yl)-amine

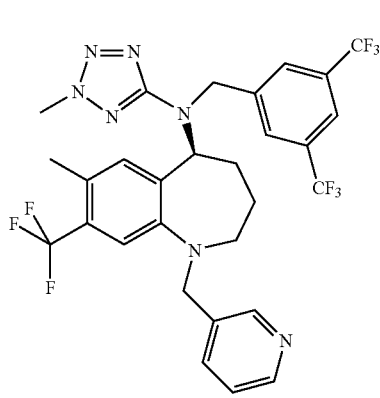

Prepare the title compound by essentially following the procedure described in Example 3, Step 19, using (S)-(3,5-bis-trifluoromethyl-benzyl)-(2-methyl-2H-tetrazol-5-yl)-(7-methyl-8-trifluoromethyl-2,3,4,5-tetrahydro-1H-benzo[b]azepin-5-yl)-amine (Example 3, Step 18) and replacing cyclopentanecarboxaldehyde with 3-pyridine-carboxaldehyde. MS (ES+): 644 (M+H).

Example 98

Synthesis of (S)-(3,5-Bis-trifluoromethyl-benzyl)-(1-cyclopropylmethyl-7-methyl-8-trifluoromethyl-2,3,4,5-tetrahydro-1H-benzo[b]azepin-5-yl)-(2-methyl-2H-tetrazol-5-yl)-amine

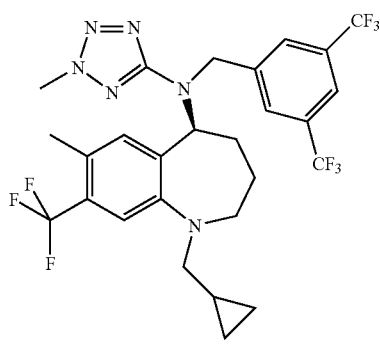

Prepare the title compound by essentially following the procedure described in Example 3, Step 19, using (S)-(3,5-bis-trifluoromethyl-benzyl)-(2-methyl-2H-tetrazol-5-yl)-(7-methyl-8-trifluoromethyl-2,3,4,5-tetrahydro-1H-benzo[b]azepin-5-yl)-amine (Example 3, Step 18) and replacing cyclopentanecarboxaldehyde with cyclopropanecarboxaldehyde. MS (ES+): 607 (M+H).

Example 99

Synthesis of (S)-2-{5-[(3,5-Bis-trifluoromethyl-benzyl)-(2-methyl-2H-tetrazol-5-yl)-amino]-7-ethyl-8-trifluoromethyl-2,3,4,5-tetrahydro-benzo[b]azepin-1-yl}-ethanol

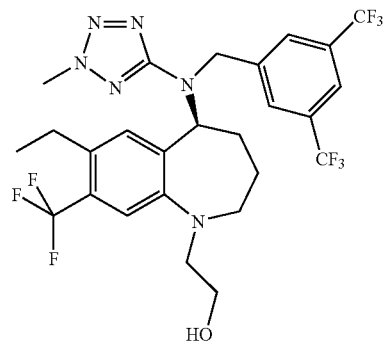

Prepare the title compound by essentially following the procedure described in Example 33 by replacing (S)-(3,5-bis-trifluoromethyl-benzyl)-(2-methyl-2H-tetrazol-5-yl)-(7-methyl-8-trifluoromethyl-2,3,4,5-tetrahydro-1H-benzo[b]azepin-5-yl)-amine (Example 3, Step 18) with (S)-(3,5-bis-trifluoromethyl-benzyl)-(2-methyl-2H-tetrazol-5-yl)-(7-ethyl-8-trifluoromethyl-2,3,4,5-tetrahydro-1H-benzo[b]azepin-5-yl)-amine (Example 35, Step 1). MS (ES+): 611 (M+H).

Example 100

Synthesis of (S)-(2-{5-[(3,5-Bis-trifluoromethyl-benzyl)-(2-methyl-2H-tetrazol-5-yl)-amino]-7-ethyl-8-trifluoromethyl-2,3,4,5-tetrahydro-benzo[b]azepin-1-yl}-ethyl)-carbamic acid tert-butyl ester

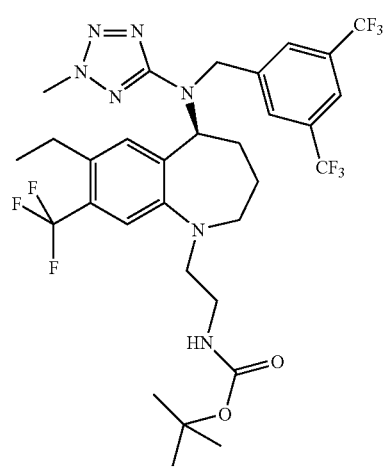

Prepare the title compound by essentially following the procedures described in Example 3, Step 19, by replacing (S)-(3,5-bis-trifluoromethyl-benzyl)-(2-methyl-2H-tetrazol-5-yl)-(7-methyl-8-trifluoromethyl-2,3,4,5-tetrahydro-1H-benzo[b]azepin-5-yl)-amine (Example 3, Step 18) with (S)-(3,5-bis-trifluoromethyl-benzyl)-(2-methyl-2H-tetrazol-5-yl)-(7-ethyl-8-trifluoromethyl-2,3,4,5-tetrahydro-1H-benzo[b]azepin-5-yl)-amine (Example 35, Step 1), and replacing cyclopentanecarboxaldehyde with (2-oxo-ethyl)-carbamic acid tert-butyl ester. MS (ES+): 710 (M+H).

Example 101

Synthesis of (S)-4-{5-[(3,5-Bis-trifluoromethyl-benzyl)-(2-methyl-2H-tetrazol-5-yl)-amino]-7-ethyl-8-trifluoromethyl-2,3,4,5-tetrahydro-benzo[b]azepin-1-ylmethyl}-benzoic acid

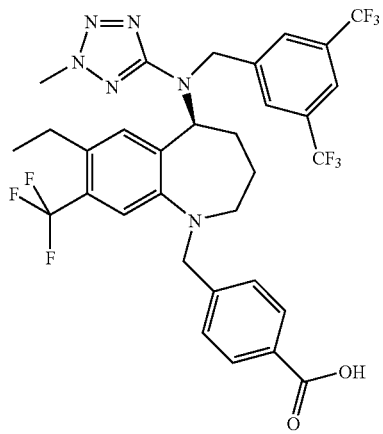

Prepare the title compound by essentially following the procedures described in Example 3, Step 19 by replacing (S)-(3,5-bis-trifluoromethyl-benzyl)-(2-methyl-2H-tetrazol-5-yl)-(7-methyl-8-trifluoromethyl-2,3,4,5-tetrahydro-1H-benzo[b]azepin-5-yl)-amine (Example 3, Step 18) with (S)-(3,5-bis-trifluoromethyl-benzyl)-(2-methyl-2H-tetrazol-5-yl)-(7-ethyl-8-trifluoromethyl-2,3,4,5-tetrahydro-1H-benzo[b]azepin-5-yl)-amine (Example 35, Step 1), and replacing cyclopentanecarboxaldehyde with 4-carboxybenzaldehyde. MS (ES+): 701 (M+H).

Example 102

Synthesis of (S)5-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-ylmethyl}-thiophene-2-carboxylic acid

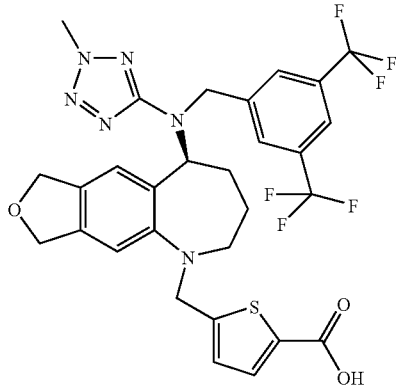

To a solution of (S)-(3,5-Bis-trifluoromethyl-benzyl)-(3,5,6,7,8,9-hexahydro-1H-2-oxa-5-aza-cyclohepta[f]inden-9-yl)-(2-methyl-2H-tetrazol-5-yl)-amine (Example 73, Step 7) (0.16 mmol) in dichloroethane (5 mL), add 5-formyl-thiophene-2-carboxylic acid (0.63 mmol) followed by acetic acid (cat.). Add NaB(OAc)$_3$H (0.78 mmol) and stir the mixture at room temperature for 14 h. Dilute the reaction with dichloromethane (10 mL) and quench with water (5 mL). Separate the organics and wash the aqueous with dichloromethane (2×10 mL). Dry the combined organics over Na$_2$SO$_4$, filter, and remove the solvent under vacuum. Chromatograph the product over silica gel eluting with MeOH/DCM (1-5%) to provide the title compound as a colorless foam. MS (ES+): 651 (M–H).

Example 103

Synthesis of (S)-(3,5-Bis-trifluoromethyl-benzyl)-(2-methyl-2H-tetrazol-5-yl)-(5-pyridin-4-ylmethyl-3,5,6,7,8,9-hexahydro-1H-2-oxa-5-aza-cyclohepta[f]inden-9-yl)-amine

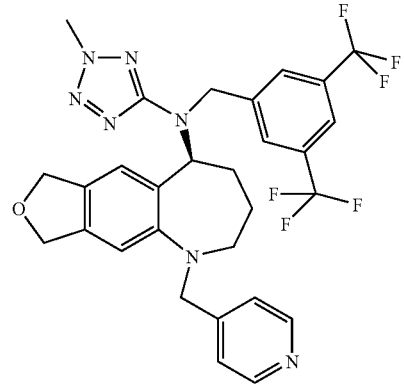

Prepare the title compound by essentially following the procedures described in the synthesis of (S)-5-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-ylmethyl}-thiophene-2-carboxylic acid (Example 102), starting with (S)-(3,5-Bis-trifluoromethyl-benzyl)-(3,5,6,7,8,9-hexahydro-1H-2-oxa-5-aza-cyclohepta[f]inden-9-yl)-(2-methyl-2H-tetrazol-5-yl)-amine (Example 73, Step 7) and 4-pyridine carboxaldehyde. MS (ES+): 604 (M+H).

Example 104

Synthesis of (S)-(4-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-ylmethyl}-cyclohexyl)-acetic acid

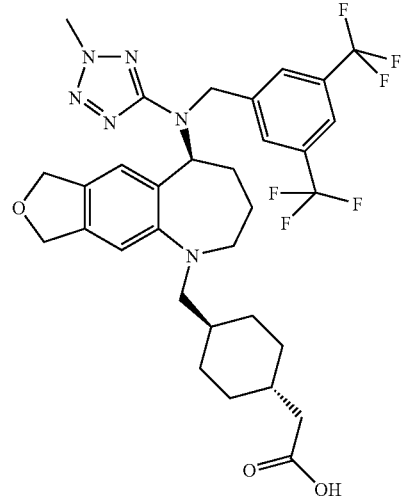

Step 1. Preparation of (S)-(4-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-ylmethyl}-cyclohexyl)-acetic acid benzyl ester

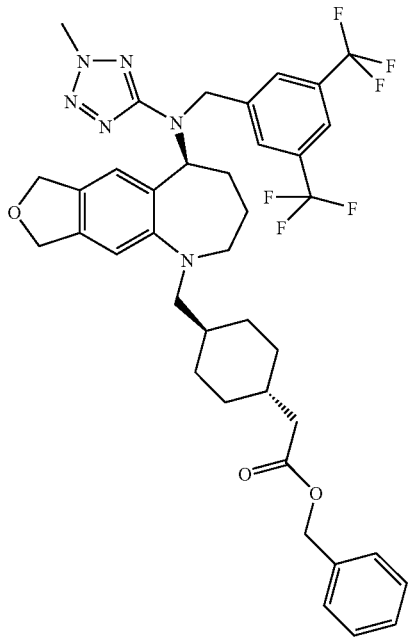

Prepare the title compound by essentially following the procedures described in the synthesis of (S)5-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-ylmethyl}-thiophene-2-carboxylic acid (Example 102), starting with (S)-(3,5-Bis-trifluoromethyl-benzyl)-(3,5,6,7,8,9-hexahydro-1H-2-oxa-5-aza-cyclohepta[f]inden-9-yl)-(2-methyl-2H-tetrazol-5-yl)-amine (Example 73, Step 7) and (4-Formyl-cyclohexyl)-acetic acid benzyl ester. MS: 757 (M+H).

Step 2. Preparation of (S)-(4-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-ylmethyl}-cyclohexyl)-acetic acid

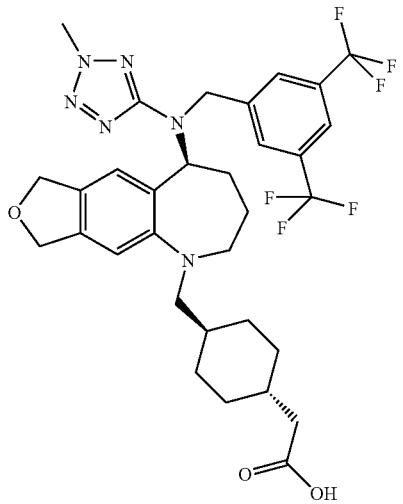

To a solution of (S)-(4-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-ylmethyl}-cyclohexyl)-acetic acid benzyl ester (0.07 mmol) in methanol (5 mL), add NaOH (3 mL of 5N) and heat to 60° C. for 2 h. After cooling to room temperature, dilute with water (20 mL) and neutralize using 5 M HCl. Extract the organic phase using ethyl acetate (3×10 mL). Dry the combined organics over sodium sulfate, filter, and remove solvent under vacuum, to provide the title compound as a colorless foam. MS (ES+): 667 (M+H).

Example 105

Synthesis of (S)-2-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-yl}-ethanol

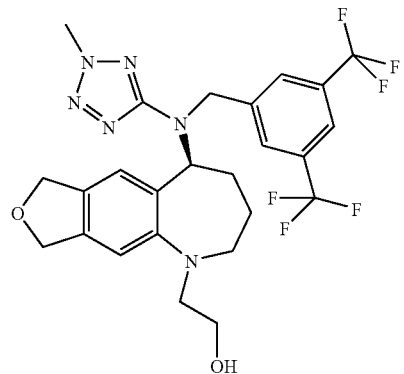

Step 1. Preparation of (S)-[5-(2-Benzyloxy-ethyl)-3,5,6,7,8,9-hexahydro-1H-2-oxa-5-aza-cyclohepta[f]inden-9-yl]-(3,5-bis-trifluoromethyl-benzyl)-(2-methyl-2H-tetrazol-5-yl)-amine

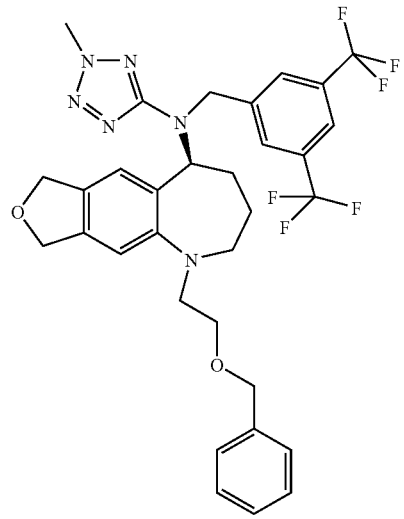

Prepare the title compound by essentially following the procedures described in the synthesis of (S)-5-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-ylmethyl}-thiophene-2-carboxylic acid (Example 102), starting with (S)-(3,5-Bis-trifluoromethyl-benzyl)-(3,5,6,7,8,9-hexahydro-1H-2-oxa-5-aza-cyclohepta[f]inden-9-yl)-(2-methyl-2H-tetrazol-5-yl)-amine (Example 73, Step 7) and benzyloxy-acetaldehyde.

Step 2. Preparation of (S)-2-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-yl}-ethanol

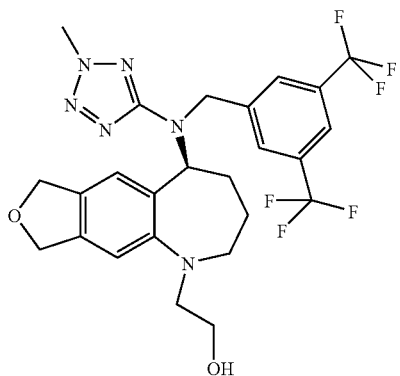

Purge a solution of (S)-[5-(2-Benzyloxy-ethyl)-3,5,6,7,8,9-hexahydro-1H-2-oxa-5-aza-cyclohepta[f]inden-9-yl]-(3,5-bis-trifluoromethyl-benzyl)-(2-methyl-2H-tetrazol-5-yl)-amine (0.14 mmol) in methanol (20 mL) with nitrogen and add a catalytic amount of Pd/C. Purge the resulting mixture with hydrogen and stir at room temperature for 5 h. Purge the reaction with nitrogen, filter through Celite®, and wash with methanol (50 mL). Remove solvent under vacuum. Chromatograph the crude product over silica gel, eluting with ethyl acetate/hexane (5-100%) to provide the title compound as a colorless foam. MS (ES+): 557 (M+H).

Example 106

Synthesis of (S)-9-[[2-(2-Amino-ethyl)-2H-tetrazol-5-yl]-(3,5-bis-trifluoromethyl-benzyl)-amino]-1,3,6,7,8,9-hexahydro-2-oxa-5-aza-cyclohepta[f]indene-5-carboxylic acid tert-butyl ester

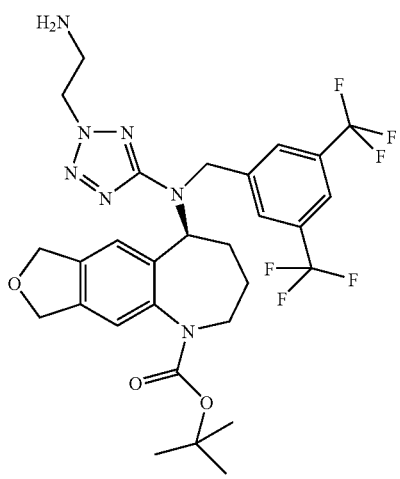

Step 1. Preparation of (S)-9-((3,5-Bis-trifluoromethyl-benzyl)-{2-[2-(1,3-dioxo-1,3-dihydro-isoindol-2-yl)-ethyl]-2H-tetrazol-5-yl}-amino)-1,3,6,7,8,9-hexahydro-2-oxa-5-aza-cyclohepta[f]indene-5-carboxylic acid tert-butyl ester

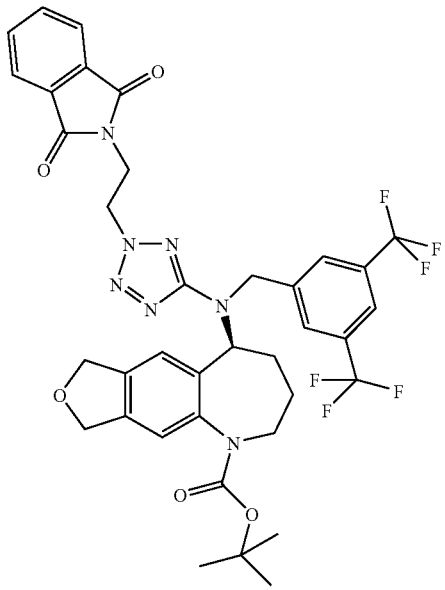

To a solution of (S)-9-[(3,5-bis-trifluoromethyl-benzyl)-(2H-tetrazol-5-yl)-amino]-1,3,6,7,8,9-hexahydro-2-oxa-5-aza-cyclohepta[f]indene-5-carboxylic acid tert-butyl ester (Example 72, Step 6) (0.84 mmol) and N-(2-Hydroxyethyl) phthalimide (2.51 mmol) in dichloromethane (10 mL), add triphenylphosphine (2.51 mmol) followed by dropwise addition of diethylazodicarboxylate (2.51 mmol). After stirring at room temperature for 14 h, remove the solvent under vacuum. Chromatograph over silica gel eluting with ethyl acetate/hexane (5-50%) to provide the title compound as a colorless foam. MS (ES+): 772 (M+H).

Step 2. Preparation of (S)-9-[[2-(2-Amino-ethyl)-2H-tetrazol-5-yl]-(3,5-bis-trifluoromethyl-benzyl)-amino]-1,3,6,7,8,9-hexahydro-2-oxa-5-aza-cyclohepta[f]indene-5-carboxylic acid tert-butyl ester

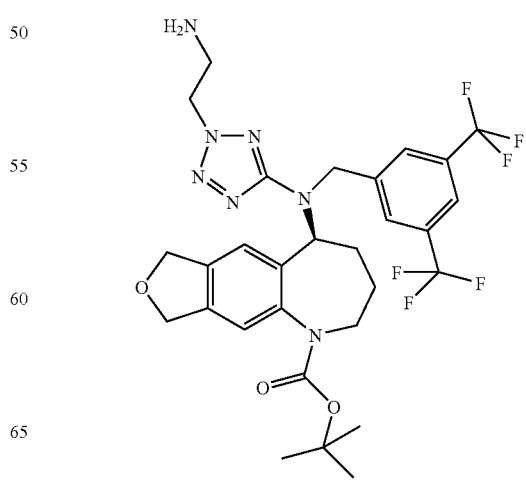

Add hydrazine monohydrate (1.94 mmol) to a solution of (S)-9-((3,5-Bis-trifluoromethyl-benzyl)-{2-[2-(1,3-dioxo-1,3-dihydro-isoindol-2-yl)-ethyl]-2H-tetrazol-5-yl}-amino)-1,3,6,7,8,9-hexahydro-2-oxa-5-aza-cyclohepta[f]indene-5-carboxylic acid tert-butyl ester (0.13 mmol) in methanol (5 mL). After heating the mixture at 60° C. for 4 h cool to room temperature and stir for 14 h. Remove solvent under vacuum. Chromatograph over silica gel eluting with methanol/dichloromethane (0-5%) to provide the title compound as a colorless foam. MS (ES+): 642 (M+H).

Example 107

Synthesis of (S)-[2-(2-Amino-ethyl)-2H-tetrazol-5-yl]-(5-benzyl-3,5,6,7,8,9-hexahydro-1H-2-oxa-5-aza-cyclohepta[f]inden-9-yl)-(3,5-bis-trifluoromethyl-benzyl)-amine

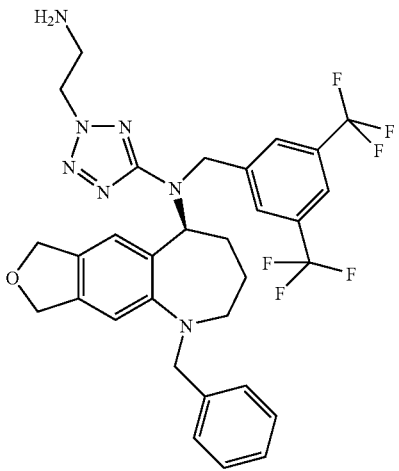

Step 1. Preparation of (S)-2-(2-{5-[(3,5-Bis-trifluoromethyl-benzyl)-(3,5,6,7,8,9-hexahydro-1H-2-oxa-5-aza-cyclohepta[f]inden-9-yl)-amino]-tetrazol-2-yl}-ethyl)-isoindole-1,3-dione

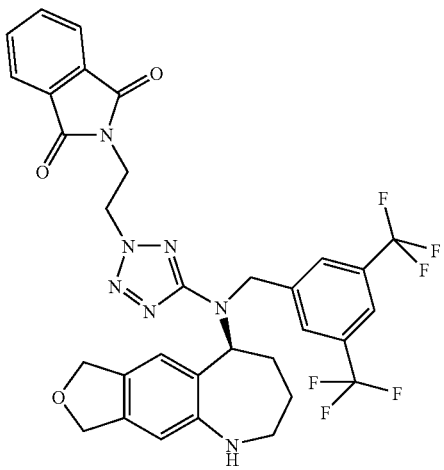

To a solution of (S)-9-((3,5-Bis-trifluoromethyl-benzyl)-{2-[2-(1,3-dioxo-1,3-dihydro-isoindol-2-yl)-ethyl]-2H-tetrazol-5-yl}-amino)-1,3,6,7,8,9-hexahydro-2-oxa-5-aza-cyclohepta[f]indene-5-carboxylic acid tert-butyl ester (Example 106, Step 1) (0.39 mmol) in dichloromethane (5 mL), add trifluoroacetic acid (2 mL). After stirring at room temperature for 3 h, quench the reaction with concentrated sodium carbonate, dilute with dichloromethane (20 mL), and water (20 mL). Separate the organic phase and wash the aqueous with dichloromethane (2×10 mL). Dry the combined organics over sodium sulfate, filter, and remove solvent under vacuum. Chromatograph the product over silica gel eluting with ethyl acetate/hexane (10-50%) to provide the title intermediate as a colorless foam. MS (ES+): 730 (M+59).

Step 2. Preparation of (S)-2-(2-{5-[(5-Benzyl-3,5,6,7,8,9-hexahydro-1H-2-oxa-5-aza-cyclohepta[f]inden-9-yl)-(3,5-bis-trifluoromethyl-benzyl)-amino]-tetrazol-2-yl}-ethyl)-isoindole-1,3-dione

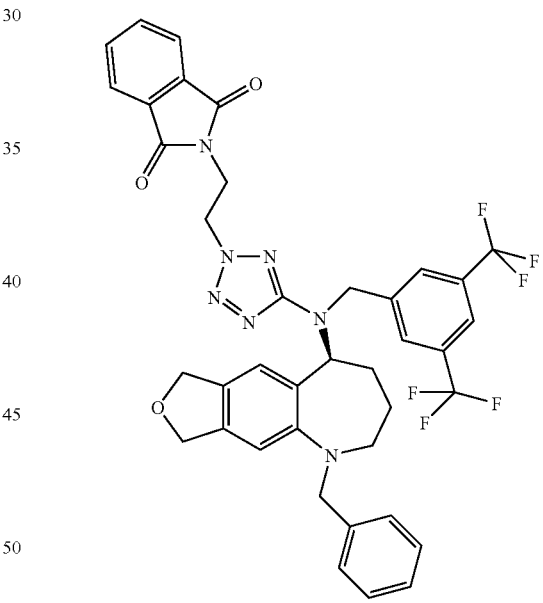

Prepare the title compound by essentially following the procedures described in the synthesis of (S)-5-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-ylmethyl}-thiophene-2-carboxylic acid (Example 102), starting with (S)-2-(2-{5-[(3,5-Bis-trifluoromethyl-benzyl)-(3,5,6,7,8,9-hexahydro-1H-2-oxa-5-aza-cyclohepta[f]inden-9-yl)-amino]-tetrazol-2-yl}-ethyl)-isoindole-1,3-dione and benzaldehyde. MS (ES+): 762 (M+H).

Step 3. Preparation of (S)-[2-(2-Amino-ethyl)-2H-tetrazol-5-yl]-(5-benzyl-3,5,6,7,8,9-hexahydro-1H-2-oxa-5-aza-cyclohepta[f]inden-9-yl)-(3,5-bis-trifluoromethyl-benzyl)-amine

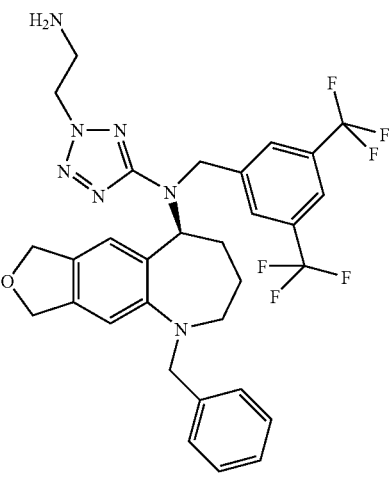

Prepare the title compound by essentially following the procedures described in the synthesis of (S)-9-[[2-(2-Amino-ethyl)-2H-tetrazol-5-yl]-(3,5-bis-trifluoromethyl-benzyl)-amino]-1,3,6,7,8,9-hexahydro-2-oxa-5-aza-cyclohepta[f]indene-5-carboxylic acid tert-butyl ester (Example 106, Step 2) starting with (S)-2-(2-{5-[(5-Benzyl-3,5,6,7,8,9-hexahydro-1H-2-oxa-5-aza-cyclohepta[f]inden-9-yl)-(3,5-bis-trifluoromethyl-benzyl)-amino]-tetrazol-2-yl}-ethyl)-isoindole-1,3-dione. MS (ES+): 632 (M+H).

Example 108

Synthesis of (S)-[2-(2-Amino-ethyl)-2H-tetrazol-5-yl]-(3,5-bis-trifluoromethyl-benzyl)-[5-(3,3,3-trifluoro-propyl)-3,5,6,7,8,9-hexahydro-1H-2-oxa-5-aza-cyclohepta[f]inden-9-yl]-amine

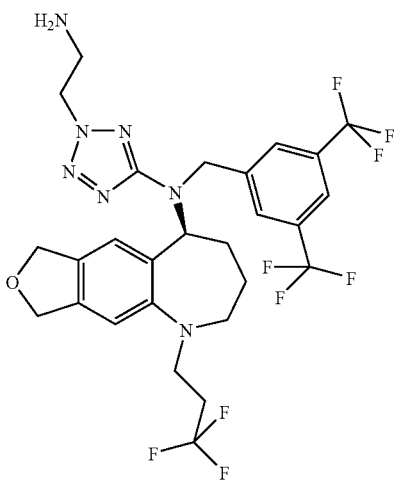

Prepare the title compound by essentially following the procedures described in the synthesis of (S)-[2-(2-Amino-ethyl)-2H-tetrazol-5-yl]-(5-benzyl-3,5,6,7,8,9-hexahydro-1H-2-oxa-5-aza-cyclohepta[f]inden-9-yl)-(3,5-bis-trifluoromethyl-benzyl)-amine (Example 107) starting with (S)-2-(2-{5-[(3,5-Bis-trifluoromethyl-benzyl)-(3,5,6,7,8,9-hexahydro-1H-2-oxa-5-aza-cyclohepta[f]inden-9-yl)-amino]-tetrazol-2-yl}-ethyl)-isoindole-1,3-dione and 3,3,3-Trifluoro-propionaldehyde in Example 107, Step 2. MS (ES+): 638 (M+H).

Example 109

Synthesis of (S)-5-{5-[(3,5-Bis-trifluoromethyl-benzyl)-(2-methyl-2H-tetrazol-5-yl)-amino]-2,3,4,5,7,8,9,10-octahydro-naphtho[2,3-b]azepin-1-yl}-3,3-dimethyl-pentanoic acid

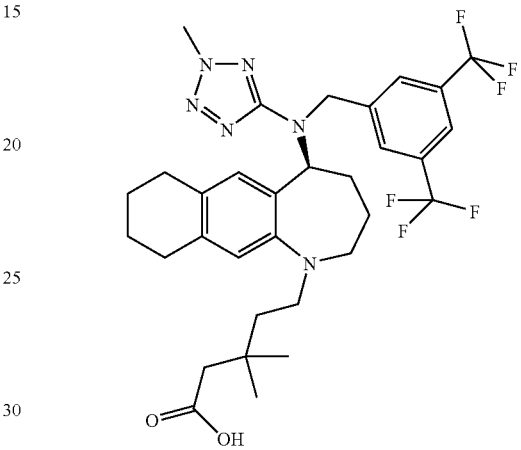

Prepare the title compound by essentially following the procedures described in the synthesis of (S)-5-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-yl}-3,3-dimethyl-pentanoic acid (Example 74) by replacing (S)-(3,5-bis-trifluoromethyl-benzyl)-(3,5,6,7,8,9-hexahydro-1H-2-oxa-5-aza-cyclohepta[f]inden-9-yl)-(2-methyl-2H-tetrazol-5-yl)-amine with (S)-(3,5-Bis-trifluoromethyl-benzyl)-(2-methyl-2H-tetrazol-5-yl)-(2,3,4,5,7,8,9,10-octahydro-1H-naphtho[2,3-b]azepin-5-yl)-amine (Example 77, Step 3) in Example 74, Step 3. MS (ES+): 653 (M+H).

Example 110

Synthesis of (S)-(3,5-Bis-trifluoromethyl-benzyl)-(1-cyclopentylmethyl-11-methyl-2,3,4,5,7,8,9,10-octahydro-1H-naphtho[2,3-b]azepin-5-yl)-(2-methyl-2H-tetrazol-5-yl)-amine

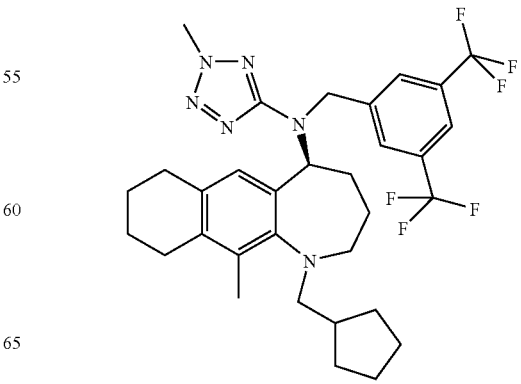

Step 1. Preparation of (S)-(3,5-Bis-trifluoromethyl-benzyl)-(11-methyl-2,3,4,5,7,8,9,10-octahydro-1H-naphtho[2,3-b]azepin-5-yl)-(2-methyl-2H-tetrazol-5-yl)-amine

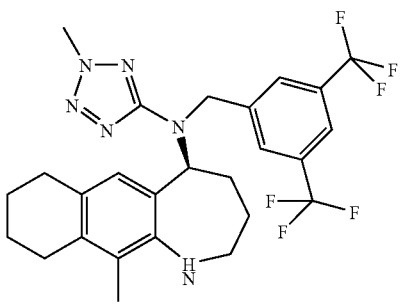

To a solution of (S)-(3,5-Bis-trifluoromethyl-benzyl)-(2-methyl-2H-tetrazol-5-yl)-(2,3,4,5,7,8,9,10-octahydro-1H-naphtho[2,3-b]azepin-5-yl)-amine (Example 77, Step 3) (0.19 mmol) in dichloromethane (5 mL), add sodium bicarbonate (0.28 mmol) and methanol (2 mL). Add a 1.0 M solution of iodine monochloride (0.28 mmol) in dichloromethane dropwise. After stirring for 1 h at room temperature, quench the reaction with concentrated aqueous sodium metabisulfite. Dilute with dichloromethane (20 mL) and water (20 mL). Separate the organic phase and wash the aqueous with dichloromethane (2×10 mL). Dry the combined organics over sodium sulfate, filter, and remove solvent under vacuum. Dissolve the crude intermediate in dioxane (5 mL) and purge with nitrogen. To this solution add palladium acetate (0.04 mmol), diphenylphosphinoferrocene (0.04 mmol), cesium fluoride (0.76 mmol), and methylboronic acid (0.76 mmol). Heat the mixture at 60° C. for 4 h, then cool to room temperature and remove the solvent under vacuum. Chromatograph the product over silica gel eluting with ethyl acetate/hexane (5-25%) to afford the title compound. MS (ES+): 539 (M+H).

Step 2. Preparation of (S)-(3,5-Bis-trifluoromethyl-benzyl)-(1-cyclopentylmethyl-11-methyl-2,3,4,5,7,8,9,10-octahydro-1H-naphtho[2,3-b]azepin-5-yl)-(2-methyl-2H-tetrazol-5-yl)-amine

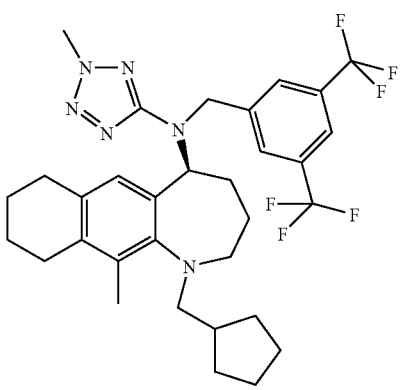

Prepare the title compound by essentially following the procedures described in the synthesis of (S)-5-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-ylmethyl}-thiophene-2-carboxylic acid (Example 102), starting with (S)-(3,5-Bis-trifluoromethyl-benzyl)-(11-methyl-2,3,4,5,7,8,9,10-octahydro-1H-naphtho[2,3-b]azepin-5-yl)-(2-methyl-2H-tetrazol-5-yl)-amine and cyclopentanecarboxaldehyde. MS (ES+): 621 (M+H).

Example 111

Synthesis of (S)-5-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-thiophene-2-carboxylic acid

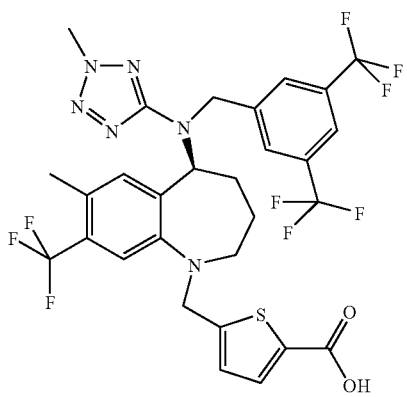

To a solution of (S)-(3,5-bistrifluoromethylbenzyl)-(2-methyl-2H-tetrazol-5-yl)-(7-methyl-8-trifluoromethyl-2,3,4,5-tetrahydro-1H-benzo[b]azepin-5-yl)amine (Example 3, Step 18) (6.10 mmol) in dichloroethane (5 mL), add 5-Formyl-thiophene-2-carboxylic acid (0.4 mmol) followed by acetic acid (cat.). Add NaB(OAc)$_3$H (0.5 mmol) and stir the mixture at room temperature for 14 h. Dilute the reaction with dichloromethane (10 mL) and quench with water (5 mL). Separate the organics and wash the aqueous with dichloromethane (2×10 mL). Dry the combined organics over Na$_2$SO$_4$, filter, and remove the solvent under vacuum. Chromatograph the product over silica gel eluting with MeOH/DCM (1-5%) to provide the title compound as a colorless foam. MS (ES+): 693 (M+H).

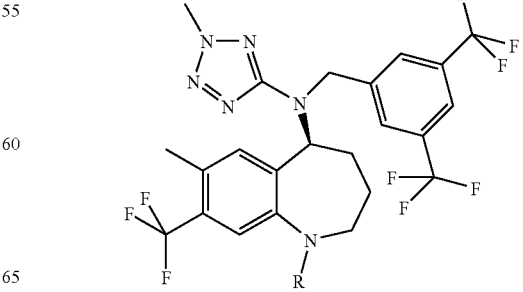

Prepare Examples 112-119 by essentially following the procedures described in the synthesis of (S)-5-{5[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-thiophene-2-carboxylic acid (Example 111) by replacing 5-formyl-thiophene-2-carboxylic acid with the appropriate aldehyde.

| Example # | Reagent | R |
|---|---|---|
| 112 | 2-Methyl-3-oxo-propionic acid ethyl ester | 2-methyl-propionic acid ethyl ester; |
| 113 | formaldehyde | methyl |
| 114 | 2-thiazolecarboxaldehyde | thiazol-2-ylmethyl |
| 115 | 1-Methyl-1H-imidazole-2-carbaldehyde | 1-methyl-1H-imidazol-2-ylmethyl |
| 116 | Benzaldehyde | benzyl |
| 117 | (4-Formyl-phenyl)-acetic acid | 4-phenylacetic acid |
| 118 | 4-Oxo-butyric acid | butyric acid |
| 119 | Oxo-acetic acid ethyl ester | acetic acid ethyl ester |

Example 120

Synthesis of (S)-(3,5-Bis-trifluoromethyl-benzyl)-(7-methyl-1-piperidin-4-ylmethyl-8-trifluoromethyl-2,3,4,5-tetrahydro-1H-benzo[b]azepin-5-yl)-(2-methyl-2H-tetrazol-5-yl)-amine

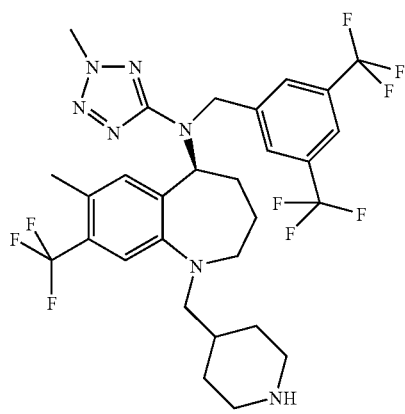

Step 1. Preparation of (S)-4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-piperidine-1-carboxylic acid tert-butyl ester

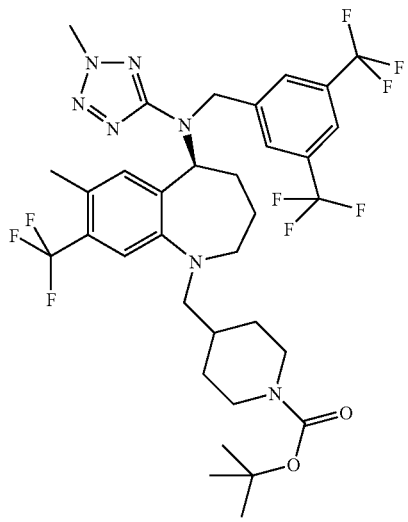

Prepare the title compound by essentially following the procedures described in the synthesis of (S)-5-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-thiophene-2-carboxylic acid. (Example 111) starting with (S)-(3,5-bistrifluoromethylbenzyl)-(2-methyl-2H-tetrazol-5-yl)-(7-methyl-8-trifluoromethyl-2,3,4,5-tetrahydro-1H-benzo[b]azepin-5-yl)amine (Example 3, Step 18) and 4-Formyl-piperidine-1-carboxylic acid tert-butyl ester. MS (ES+): 750 (M+H).

Step 2. Preparation of (S)-(3,5-Bis-trifluoromethyl-benzyl)-(7-methyl-1-piperidin-4-ylmethyl-8-trifluoromethyl-2,3,4,5-tetrahydro-1H-benzo[b]azepin-5-yl)-(2-methyl-2H-tetrazol-5-yl)-amine

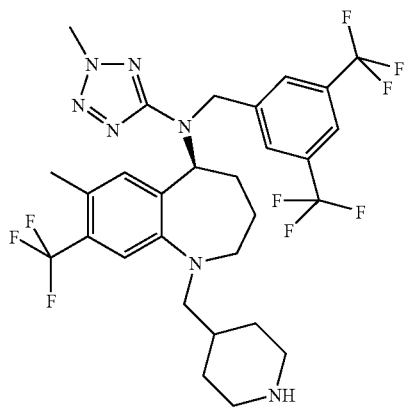

To a solution of (S)-4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-piperidine-1-carboxylic acid tert-butyl ester (0.09) in dichloromethane (10 mL), add trifluoroacetic acid (2 mL).

After stirring for 1 h at room temperature, quench the reaction with concentrated sodium carbonate (10 mL) and dilute with dichloromethane (20 mL) and water (20 mL). Separate the organics and wash the aqueous with dichloromethane (2×10 mL). Dry the combined organics over sodium sulfate, filter, and remove solvent under vacuum. Chromatograph the reaction over silica gel eluting with methanol/dichloromethane (0-5%) to afford the title compound as a colorless foam. MS (ES+): 650 (M+H).

Example 121

Synthesis of (S)-(4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-piperidin-1-yl)-acetic acid ethyl ester

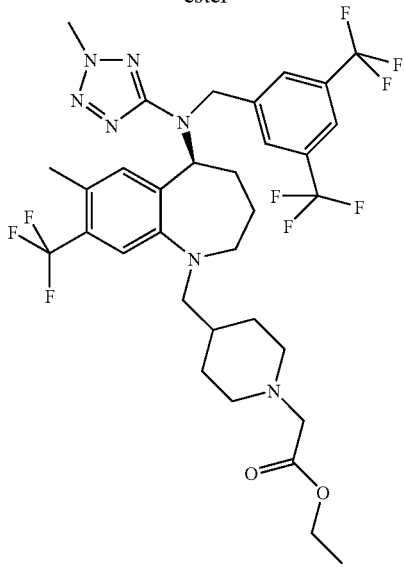

To a solution of (S)-(3,5-Bis-trifluoromethyl-benzyl)-(7-methyl-1-piperidin-4-ylmethyl-8-trifluoromethyl-2,3,4,5-tetrahydro-1H-benzo[b]azepin-5-yl)-(2-methyl-2H-tetrazol-5-yl)-amine (Example 120) (0.18 mmol) in DMF (3 mL), add bromo-acetic acid ethyl ester (0.54 mmol) and cesium carbonate (0.90 mmol). After heating the mixture at 50° C. for 30 minutes, cool to room temperature and dilute the reaction with water (15 mL) and extract with ethyl acetate (3×10 mL). Dry the combined organic phases over sodium sulfate, filter, and remove solvent under vacuum. Chromatograph the product over silica gel, eluting with ethyl acetate/hexane (5-50%), to give the title compound as a colorless foam. MS (ES+): 736 (M+H).

Example 122

Synthesis of (S)-(4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-piperidin-1-yl)-acetic acid

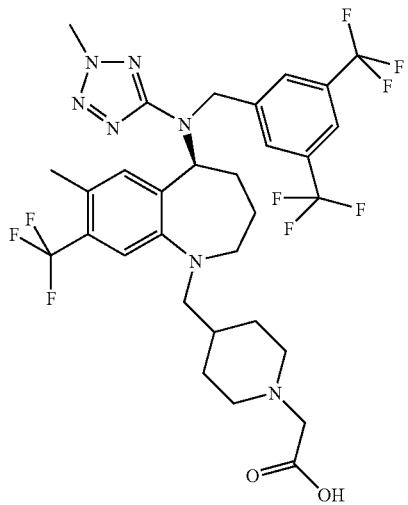

To a solution of (S)-(4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-piperidin-1-yl)-acetic acid ethyl ester (0.11 mmol) in methanol (5 mL), add 5.0 N sodium hydroxide (2 mL). After heating at 60° C. for 6 h cool to room temperature and dilute with water (20 mL). Extract the organics with ethyl acetate (3×10 mL). Dry the combined organic phases over sodium sulfate, filter, and remove solvent under vacuum, to afford the title compound as a colorless foam. MS (ES+): 708 (M+H).

Example 123

Synthesis of (S)-3-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-2-methyl-propionic acid

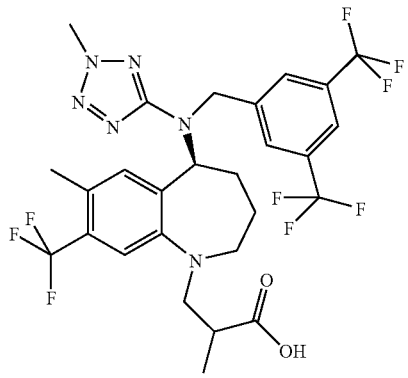

To a solution of (S)-3-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-2-methyl-propionic acid ethyl ester (Example 112) (0.04 mmol) in methanol (5 mL), add 5.0 N sodium hydroxide (2 mL). After heating at 60° C. for 6 h cool to room temperature and dilute with water (20 mL). Extract the organics with ethyl acetate (3×10 mL). Dry the combined organic phases over sodium sulfate, filter, and remove solvent under vacuum, to afford the title compound as a mixture of diastereomers. MS (ES+): 639 (M+H).

Example 124

Synthesis of (S)-(3,5-Bis-trifluoromethyl-benzyl)-(7-methyl-1-pyrrolidin-2-ylmethyl-8-trifluoromethyl-2,3,4,5-tetrahydro-1H-benzo[b]azepin-5-yl)-(2-methyl-2H-tetrazol-5-yl)-amine

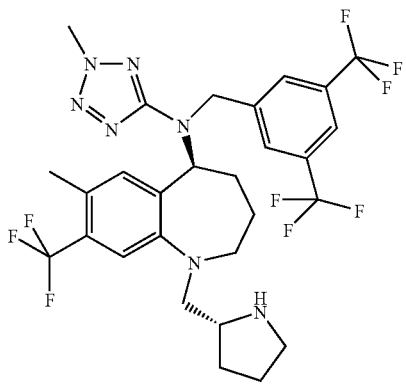

Step 1. Preparation of (S)-2-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-pyrrolidine-1-carboxylic acid tert-butyl ester

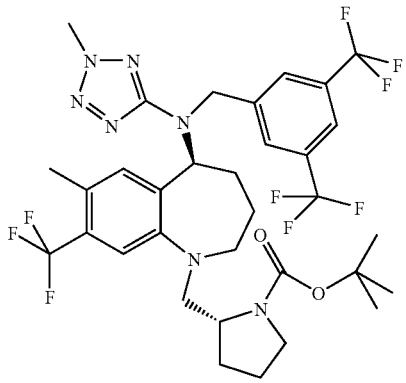

Prepare the title compound by essentially following the procedures described in the synthesis of (S)-5-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-thiophene-2-carboxylic acid (Example 111) starting with (S)-(3,5-bistrifluoromethylbenzyl)-(2-methyl-2H-tetrazol-5-yl)-(7-methyl-8-trifluoromethyl-2,3,4,5-tetrahydro-1H-benzo[b]azepin-5-yl)amine (Example 3, Step 18) and (R)-(−)-2-formyl-pyrrolidine-1-carboxylic acid tert-butyl ester. MS (ES+): 736 (M+H).

Step 2. Preparation of (S)-(3,5-Bis-trifluoromethyl-benzyl)-(7-methyl-1-pyrrolidin-2-ylmethyl-8-trifluoromethyl-2,3,4,5-tetrahydro-1H-benzo[b]azepin-5-yl)-(2-methyl-2H-tetrazol-5-yl)-amine

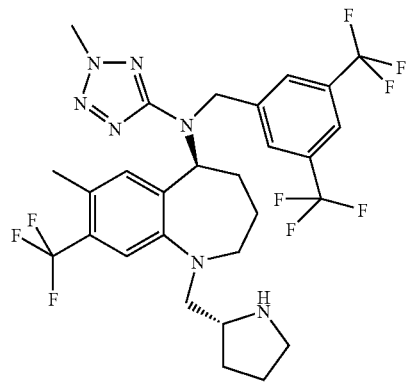

Prepare the title compound by essentially following the procedures described in the synthesis of (S)-(3,5-Bis-trifluoromethyl-benzyl)-(7-methyl-1-piperidin-4-ylmethyl-8-trifluoromethyl-2,3,4,5-tetrahydro-1H-benzo[b]azepin-5-yl)-(2-methyl-2H-tetrazol-5-yl)-amine (Example 120, Step 2) starting with (S)-2-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-pyrrolidine-1-carboxylic acid tert-butyl ester. MS (ES+): 636 (M+H).

Example 125

Synthesis of (S)-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-acetic acid

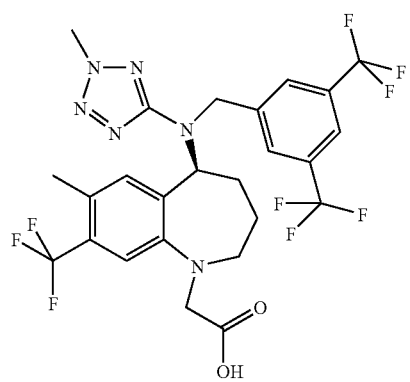

Prepare the title compound by essentially following the procedures described in the synthesis of (S)-3-{5-[(3,5-Bis-trifluoromethyl-benzyl)-(2-methyl-2H-tetrazol-5-yl)-amino]-7-methyl-8-trifluoromethyl-2,3,4,5-tetrahydrobenzo[b]azepin-1-yl}-2-methyl-propionic acid (Example 123) starting with (S)-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-acetic acid ethyl ester (Example 119). MS (ES+): 611 (M+H)

Example 126

Synthesis of (S)-[2-(2-Amino-ethyl)-2H-tetrazol-5-yl]-[1-(2-benzyloxy-ethyl)-7-methyl-8-trifluoromethyl-2,3,4,5-tetrahydro-1H-benzo[b]azepin-5-yl]-(3,5-bis-trifluoromethyl-benzyl)-amine

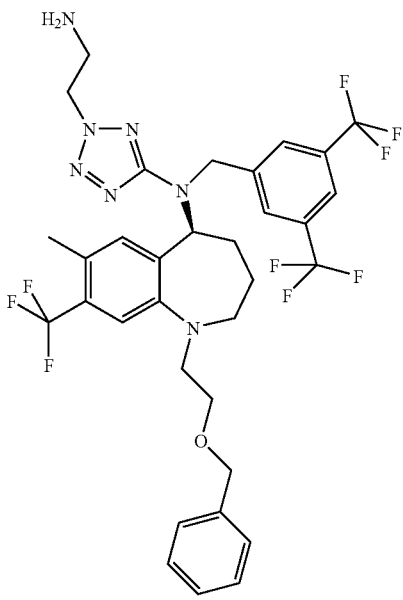

Step 1. Preparation of (S)-5-((3,5-Bis-trifluoromethyl-benzyl)-{2-[2-(1,3-dioxo-1,3-dihydro-isoindol-2-yl)-ethyl]-2H-tetrazol-5-yl}-amino)-7-methyl-8-trifluoromethyl-2,3,4,5-tetrahydro-benzo[b]azepine-1-carboxylic acid tert-butyl ester

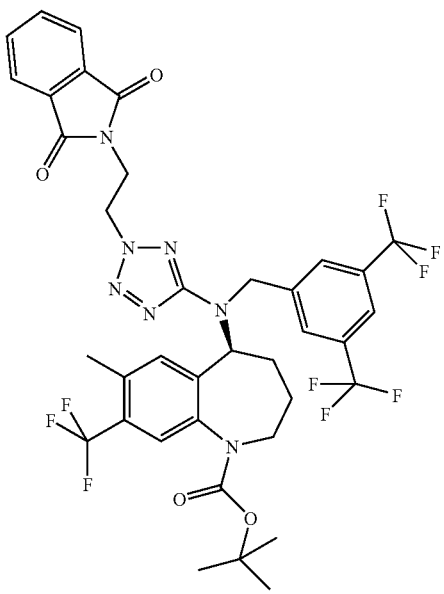

Prepare the title compound by essentially following the procedures described for the synthesis of (S)-9-((3,5-Bis-trifluoromethyl-benzyl)-{2-[2-(1,3-dioxo-1,3-dihydro-isoindol-2-yl)-ethyl]-2H-tetrazol-5-yl}-amino)-1,3,6,7,8,9-hexahydro-2-oxa-5-aza-cyclohepta[f]indene-5-carboxylic acid tert-butyl ester (Example 106, Step 1), starting with (S)-5-[(3,5-Bis-trifluoromethyl-benzyl)-(2H-tetrazol-5-yl)-amino]-7-methyl-8-trifluoromethyl-2,3,4,5-tetrahydro-benzo[b]azepine-1-carboxylic acid tert-butyl ester (Example 3, Step 16). MS (ES+): 812 (M+H).

Step 2. Preparation of (S)-2-(2-{5-[(3,5-Bis-trifluoromethyl-benzyl)-(7-methyl-8-trifluoromethyl-2,3,4,5-tetrahydro-1H-benzo[b]azepin-5-yl)-amino]-tetrazol-2-yl}-ethyl)-isoindole-1,3-dione

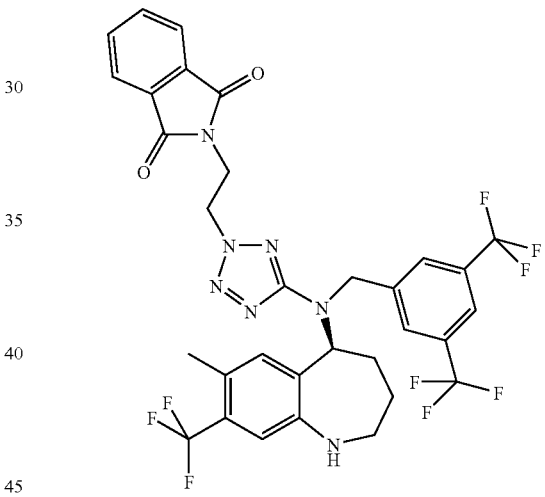

To a solution of (S)-5-((3,5-Bis-trifluoromethyl-benzyl)-{2-[2-(1,3-dioxo-1,3-dihydro-isoindol-2-yl)-ethyl]-2H-tetrazol-5-yl}-amino)-7-methyl-8-trifluoromethyl-2,3,4,5-tetrahydro-benzo[b]azepine-1-carboxylic acid tert-butyl ester (0.12 mmol) in dichloromethane (4 mL), add trifluoroacetic acid (1 mL). After stirring at room temperature for 1 h, quench the reaction with concentrated sodium carbonate (10 mL), and dilute with water (10 mL) and dichloromethane (20 mL). Separate the organic phase and wash the aqueous with dichloromethane (2×10 mL). Dry the combined organics over sodium sulfate, filter, and remove solvent under vacuum, to provide the title compound as a colorless foam. MS (ES+): 712 (M+H).

Step 3. Preparation of (S)-2-(2-{5-[[1-(2-Benzyloxy-ethyl)-7-methyl-8-trifluoromethyl-2,3,4,5-tetrahydro-1H-benzo[b]azepin-5-yl]-(3,5-bis-trifluoromethyl-benzyl)-amino]-tetrazol-2-yl}-ethyl)-isoindole-1,3-dione

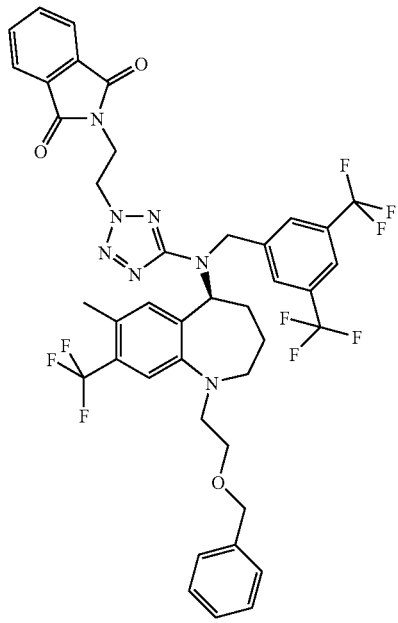

Prepare the title compound by essentially following the procedures described in the synthesis of (S)-5-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-thiophene-2-carboxylic acid (Example 111) starting with (S)-2-(2-{5-[(3,5-Bis-trifluoromethyl-benzyl)-(7-methyl-8-trifluoromethyl-2,3,4,5-tetrahydro-1H-benzo[b]azepin-5-yl)-amino]-tetrazol-2-yl}-ethyl)-isoindole-1,3-dione and benzyloxy-acetaldehyde. MS (ES+): 846 (M+H).

Step 4. Preparation of (S)-[2-(2-Amino-ethyl)-2H-tetrazol-5-yl]-[1-(2-benzyloxy-ethyl)-7-methyl-8-trifluoromethyl-2,3,4,5-tetrahydro-1H-benzo[b]azepin-5-yl]-(3,5-bis-trifluoromethyl-benzyl)-amine

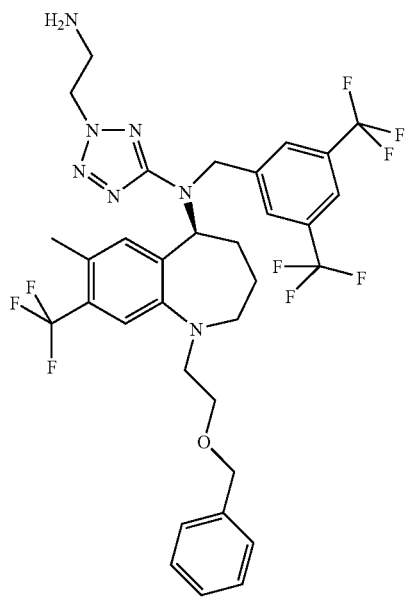

Prepare the title compound by essentially following the procedures described in the synthesis of (S)-9-[[2-(2-Amino-ethyl)-2H-tetrazol-5-yl]-(3,5-bis-trifluoromethyl-benzyl)-amino]-1,3,6,7,8,9-hexahydro-2-oxa-5-aza-cyclohepta[f]indene-5-carboxylic acid tert-butyl ester (Example 106, Step 2) starting with (S)-2-(2-{5-[[1-(2-Benzyloxy-ethyl)-7-methyl-8-trifluoromethyl-2,3,4,5-tetrahydro-1H-benzo[b]azepin-5-yl]-(3,5-bis-trifluoromethyl-benzyl)-amino]-tetrazol-2-yl}-ethyl)-isoindole-1,3-dione. MS (ES+): 716 (M+H).

Example 127

Synthesis of (S)-2-{5-[[2-(2-Amino-ethyl)-2H-tetrazol-5-yl]-(3,5-bis-trifluoromethyl-benzyl)-amino]-7-methyl-8-trifluoromethyl-2,3,4,5-tetrahydro-benzo[b]azepin-1-yl}-ethanol

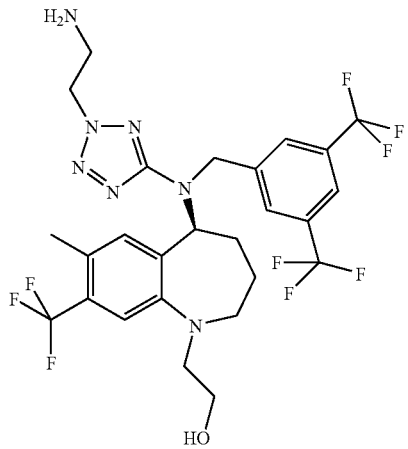

Step 1. Preparation of (S)-2-[2-(5-{(3,5-Bis-trifluoromethyl-benzyl)-[1-(2-hydroxy-ethyl)-7-methyl-8-trifluoromethyl-2,3,4,5-tetrahydro-1H-benzo[b]azepin-5-yl]-amino}-tetrazol-2-yl)-ethyl]-isoindole-1,3-dione

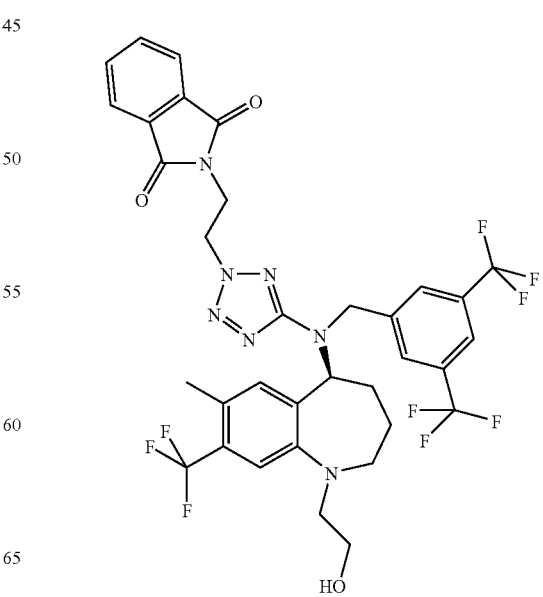

To a solution of (S)-2-(2-{5-[[1-(2-Benzyloxy-ethyl)-7-methyl-8-trifluoromethyl-2,3,4,5-tetrahydro-1H-benzo[b]azepin-5-yl]-(3,5-bis-trifluoromethyl-benzyl)-amino]-tetrazol-2-yl}-ethyl)-isoindole-1,3-dione (Example 126, Step 3) (0.09 mmol) in methanol (20 mL), add a catalytic amount of 10% Pd/C after purging with nitrogen. Purge the reaction with a balloon of hydrogen and stir under a balloon of hydrogen for 14 h. Purge the reaction with nitrogen and filter through Celite®. Collect the filtrate and remove solvent under vacuum. Chromatograph the reaction over silica gel eluting with ethyl acetate/hexane (15-45%) to afford the title compound.

Step 2. Preparation of (S)-2-{5-[[2-(2-Amino-ethyl)-2H-tetrazol-5-yl]-(3,5-bis-trifluoromethyl-benzyl)-amino]-7-methyl-8-trifluoromethyl-2,3,4,5-tetrahydro-benzo[b]azepin-1-yl}-ethanol

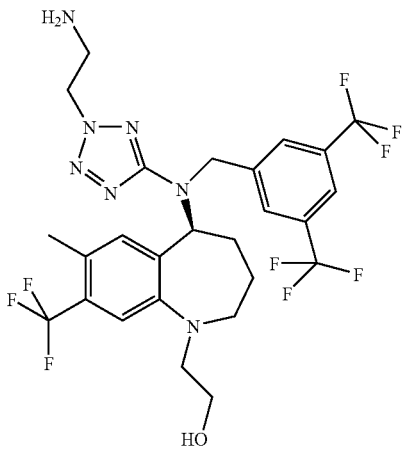

Prepare the title compound by essentially following the procedures described in the synthesis of (S)-9-[[2-(2-Amino-ethyl)-2H-tetrazol-5-yl]-(3,5-bis-trifluoromethyl-benzyl)-amino]-1,3,6,7,8,9-hexahydro-2-oxa-5-aza-cyclohepta[f]indene-5-carboxylic acid tert-butyl ester (Example 106, Step 2) starting with (S)-2-[2-(5-{(3,5-Bis-trifluoromethyl-benzyl)-[1-(2-hydroxy-ethyl)-7-methyl-8-trifluoromethyl-2,3,4,5-tetrahydro-1H-benzo[b]azepin-5-yl]-amino}-tetrazol-2-yl)-ethyl]-isoindole-1,3-dione. MS (ES+): 626 (M+H).

Example 128
Synthesis of (S)-5-[[2-(2-Amino-ethyl)-2H-tetrazol-5-yl]-(3,5-bis-trifluoromethyl-benzyl)-amino]-7-methyl-8-trifluoromethyl-2,3,4,5-tetrahydro-benzo[b]azepine-1-carboxylic acid tert-butyl ester

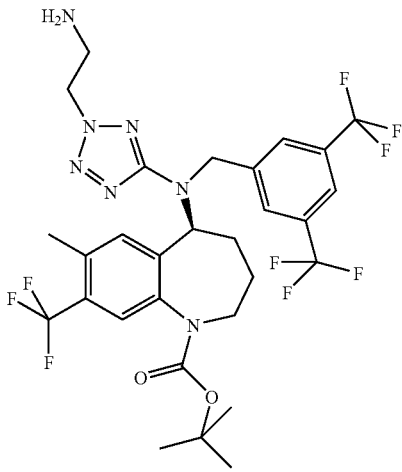

Prepare the title compound uby essentially following the procedures described in the synthesis of (S)-9-[[2-(2-Amino-ethyl)-2H-tetrazol-5-yl]-(3,5-bis-trifluoromethyl-benzyl)-amino]-1,3,6,7,8,9-hexahydro-2-oxa-5-aza-cyclohepta[f]indene-5-carboxylic acid tert-butyl ester (Example 106) starting with (S)-5-[(3,5-Bis-trifluoromethyl-benzyl)-(2H-tetrazol-5-yl)-amino]-7-methyl-8-trifluoromethyl-2,3,4,5-tetrahydro-benzo[b]azepine-1-carboxylic acid tert-butyl ester (Example 3, Step 16). MS (ES+): 682 (M+H).

Example 129
Synthesis of (S)-[2-(2-Amino-ethyl)-2H-tetrazol-5-yl]-(3,5-bis-trifluoromethyl-benzyl)-(7-methyl-1-thiazol-2-ylmethyl-8-trifluoromethyl-2,3,4,5-tetrahydro-1H-benzo[b]azepin-5-yl)-amine

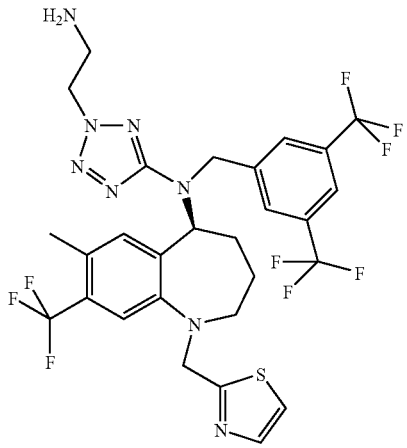

Prepare the title compound by essentially following the procedures described in the synthesis of (S)-[2-(2-Amino-ethyl)-2H-tetrazol-5-yl]-(5-benzyl-3,5,6,7,8,9-hexahydro-1H-2-oxa-5-aza-cyclohepta[f]inden-9-yl)-(3,5-bis-trifluoromethyl-benzyl)-amine (Example 107) starting with (S)-5-[(3,5-Bis-trifluoromethyl-benzyl)-(2H-tetrazol-5-yl)-amino]-7-methyl-8-trifluoromethyl-2,3,4,5-tetrahydro-benzo[b]azepine-1-carboxylic acid tert-butyl ester (Example 3, Step 16) and using thiazole-2-carboxaldehyde in place of benzaldehyde. MS (ES+): 679 (M+H).

Example 130
Synthesis of (S)-(2-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-ethoxy)-acetic acid

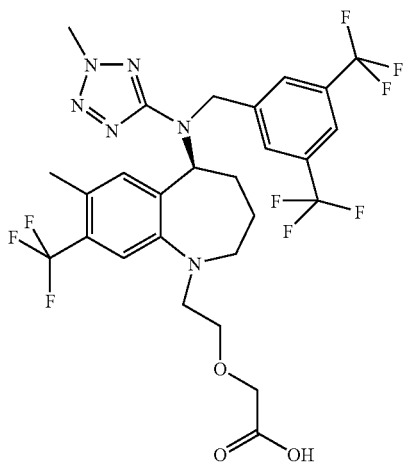

Step 1. Preparation of (S)-[1-(2-Benzyloxy-ethyl)-7-methyl-8-trifluoromethyl-2,3,4,5-tetrahydro-1H-benzo[b]azepin-5-yl]-(3,5-bis-trifluoromethyl-benzyl)-(2-methyl-2H-tetrazol-5-yl)-amine

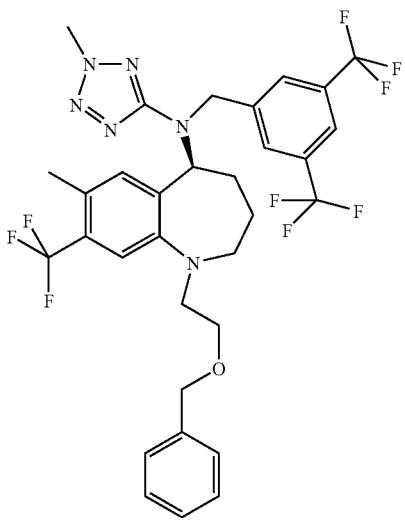

Prepare the title compound by essentially following the procedures described in the synthesis of (S)-5-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-ylmethyl}-thiophene-2-carboxylic acid (Example 102), starting with (S)-(3,5-Bis-trifluoromethyl-benzyl)-(2-methyl-2H-tetrazol-5-yl)-(7-methyl-8-trifluoromethyl-2,3,4,5-tetrahydro-1H-benzo[b]azepin-5-yl)-amine (Example 3, Step 18) and benzyloxy-acetaldehyde. MS (ES+): 687 (M+H).

Step 2. Preparation of (S)-2-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-ethanol

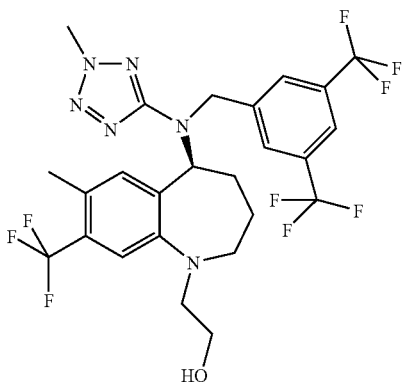

Prepare the title compound by essentially following the procedures described in the synthesis of (S)-2-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-yl}-ethanol. (Example 105, Step 2) starting with (S)-[1-(2-Benzyloxy-ethyl)-7-methyl-8-trifluoromethyl-2,3,4,5-tetrahydro-1H-benzo[b]azepin-5-yl]-(3,5-bis-trifluoromethyl-benzyl)-(2-methyl-2H-tetrazol-5-yl)-amine. MS (ES+): 597 (M+H).

Step 3. Preparation of (S)-(2-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-ethoxy)-acetic acid

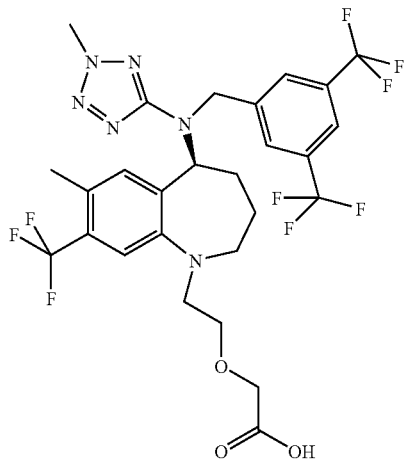

To a solution of (S)-2-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-ethanol (0.17 mmol) in tetrahydrofuran (5 mL), add potassium hydride (0.67 mmol) at room temperature. After stirring for 30 minutes add bromoacetic acid (0.25 mmol) as a solution in tetrahydrofuran (1 mL). After stirring an additional 0.5 h, quench the reaction with wet tetrahydrofuran (2 mL), dilute with water (1 mL), and ethyl acetate (5 mL). Neutralize the reaction with 5M HCl, separate the organic phase, and wash the aqueous with ethyl acetate (2×5 mL). Dry the combined organic phases over sodium sulfate, filter, and remove solvent under vacuum. Chromatograph the product over silica gel, eluting with methanol/dichloromethane (0.5-4%) to afford the title compound as a colorless foam. MS (ES+): 655 (M+H).

Example 131

Synthesis of (S)-Acetic acid 2-{5-[(3,5-bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-ethyl ester

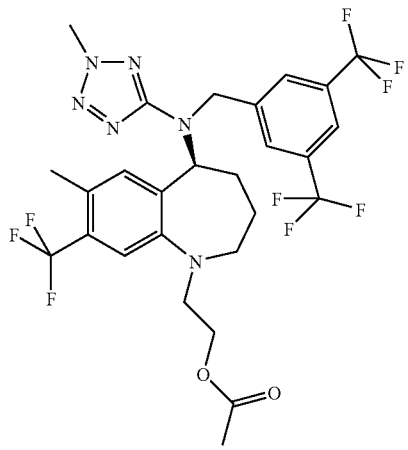

To a solution of (S)-2-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-ethanol (Example 130, Step 2) (0.12 mmol) in dichloromethane (5 mL), add pyridine (0.47 mmol) followed by acetyl chloride (0.47 mmol). After stirring at room temperature for 14 h, quench the reaction with water (5 mL) and dilute with dichloromethane (5 mL). Separate the organic phase and wash the aqueous with dichloromethane (2×5 mL). Dry the combined organics over sodium sulfate, filter, and remove solvent under vacuum. Chromatograph the product over silica gel, eluting with ethyl acetate/hexane (5-40%), to afford the title compound as a colorless foam. MS (ES+): 639 (M+H).

Example 132

Synthesis of (S)-(3,5-Bis-trifluoromethyl-benzyl)-(2-methyl-2H-tetrazol-5-yl)-[7-methyl-1-(2H-tetrazol-5-ylmethyl)-8-trifluoromethyl-2,3,4,5-tetrahydro-1H-benzo[b]azepin-5-yl]-amine

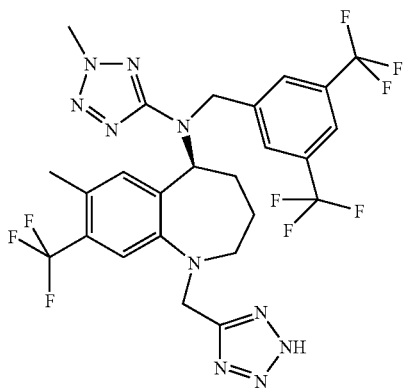

Step 1. Preparation of (S)-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-acetonitrile

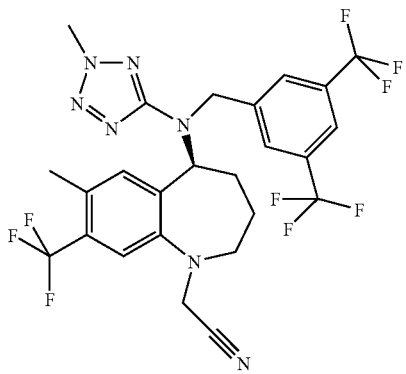

To a solution of (S)-(3,5-Bis-trifluoromethyl-benzyl)-(2-methyl-2H-tetrazol-5-yl)-(7-methyl-8-trifluoromethyl-2,3,4,5-tetrahydro-1H-benzo[b]azepin-5-yl)-amine (Example 3, Step 18) (0.09 mmol) in dimethylformamide (3 mL), add bromoacetonitrile (0.36 mmol) and cesium carbonate (0.36 mmol). After stirring the reaction at 60° C. for 6 h, cool to room temperature and dilute with water (20 mL) and ethyl acetate (30 mL). Separate the organic phase and wash the aqueous with ethyl acetate (2×10 mL). Dry the combined organics over sodium sulfate, filter, and remove solvent under vacuum. Chromatograph the product over silica gel, eluting with ethyl acetate/hexane (5-40%), to afford the title compound as a colorless foam. MS (ES+): 592 (M+H).

Step 2. Preparation of (S)-(3,5-Bis-trifluoromethyl-benzyl)-(2-methyl-2H-tetrazol-5-yl)-[7-methyl-1-(2H-tetrazol-5-ylmethyl)-8-trifluoromethyl-2,3,4,5-tetrahydro-1H-benzo[b]azepin-5-yl]-amine

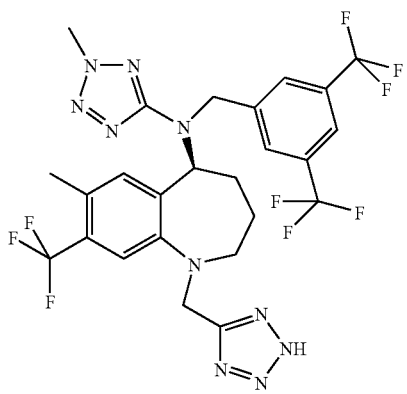

To a solution of (S)-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-acetonitrile (0.1 mmol) in toluene (6 mL), add azidotributyltin (0.1 mmol) and heat at 100° C. After heating for 14 h, cool to room temperature and dilute with ethyl acetate (20 mL). Wash the reaction with concentrated sodium fluoride (2×20 mL), dry the organic phase over sodium sulfate, filter, and remove solvent under vacuum. Chromatograph the product over silica gel, eluting with methanol/dichloromethane (0.5-5%), to afford the title compound as a colorless foam. MS (ES+): 633 (M+H).

Example 133

Synthesis of (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid 2-amino-ethyl ester

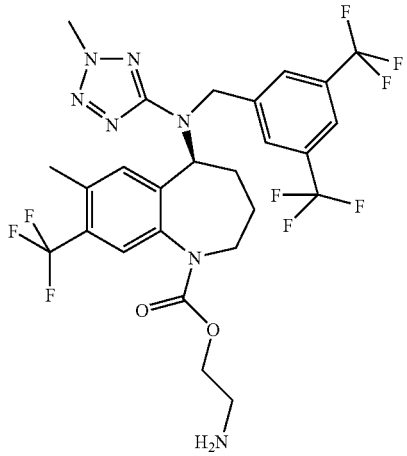

Step 1. Preparation of (S)-5-[(3,5-Bis-trifluorom-
ethyl-benzyl)-(2-methyl-2H-tetrazol-5-yl)-amino]-7-
methyl-8-trifluoromethyl-2,3,4,5-tetrahydro-benzo
[b]azepine-1-carbonyl chloride

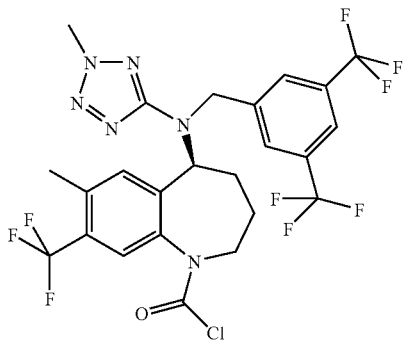

To a solution of (S)-(3,5-Bis-trifluoromethyl-benzyl)-(2-methyl-2H-tetrazol-5-yl)-(7-methyl-8-trifluoromethyl-2,3,4,5-tetrahydro-1H-benzo[b]azepin-5-yl)-amine (Example 3, Step 18) (0.91 mmol) in toluene (5 mL), add phosgene (0.91 mmol) as a 1.93 M solution in toluene. Next, add diisopropylethylamine (0.96 mmol) dropwise at room temperature. After stirring at room temperature for 1 h, dilute the reaction with ethyl acetate (10 mL) and wash with water (5 mL). Dry the organic phase over sodium sulfate, filter, and remove solvent under a stream of nitrogen. Chromatograph the product over silica gel, eluting with ethyl acetate/hexane (5-25%), to afford the title compound as a colorless foam. MS (ES+): 615 (M+H).

Step 2. Preparation of (S)-5-[(3,5-Bis-trifluorom-
ethyl-benzyl)-(2-methyl-2H-tetrazol-5-yl)-amino]-7-
methyl-8-trifluoromethyl-2,3,4,5-tetrahydro-benzo
[b]azepine-1-carboxylic acid 2-amino-ethyl ester

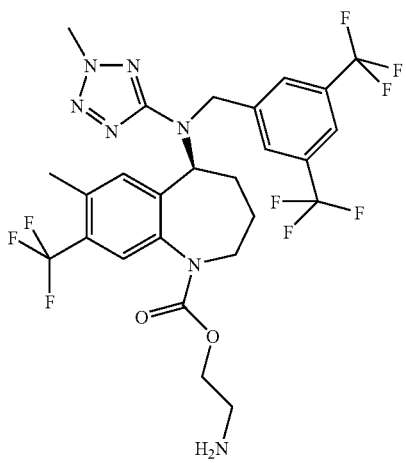

To a solution of (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carbonyl chloride (0.08 mmol) in dimethylformamide (3 mL), add (2-Hydroxy-ethyl)-carbamic acid tert-butyl ester (0.24 mmol) and dimethylaminopyridine (0.08 mmol). Next, add sodium hydride (0.24 mmol) and stir at room temperature for 0.5 h. Quench the reaction with water (15 mL) and dilute with ethyl acetate (10 mL). Separate the organic phase and wash the aqueous with ethyl acetate (2×10 mL). Dry the combined organics over sodium sulfate, filter, and remove solvent under vacuum. Dissolve the crude 5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid 2-tert-butoxycarbonylamino-ethyl ester intermediate in dichloromethane (5 mL) and add trifluoroacetic acid (2 mL). After stirring for 1 h, quench the reaction with concentrated sodium carbonate (5 mL). Dilute the reaction with dichloromethane (10 mL) and water (10 mL). Separate the organic phase and wash the aqueous with dichloromethane (2×10 mL). Dry the combined organics over sodium sulfate, filter, and remove the solvent under vacuum. Chromatograph the product over silica gel, eluting with methanol/dichloromethane (0-5%), to afford the title compound as a colorless foam. MS (ES+): 640 (M+H).

Example 134

Synthesis of (S)-5-[(3,5-Bis-trifluoromethyl-benzyl)-
(2-methyl-2H-tetrazol-5-yl)-amino]-7-methyl-8-
trifluoromethyl-2,3,4,5-tetrahydro-benzo[b]azepine-
1-carboxylic acid 2-carboxy-2-methyl-propyl ester

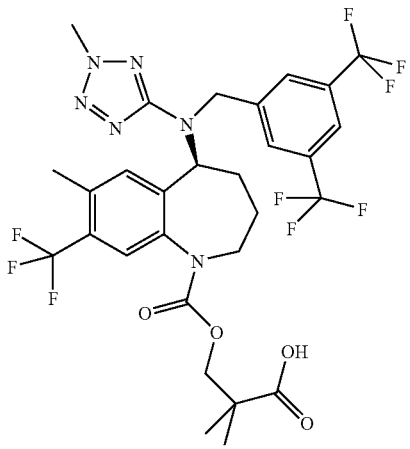

Step 1. Preparation of (S)-5-[(3,5-Bis-trifluorom-
ethyl-benzyl)-(2-methyl-2H-tetrazol-5-yl)-amino]-7-
methyl-8-trifluoromethyl-2,3,4,5-tetrahydro-benzo
[b]azepine-1-carboxylic acid 2-methoxycarbonyl-2-
methyl-propyl ester

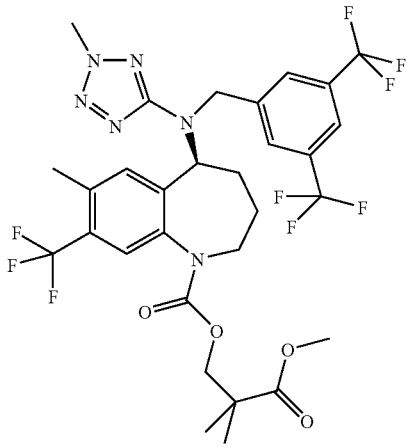

Prepare the title compound by essentially following the procedures described in the synthesis of (S)-5-[(3,5-Bis-trifluoromethyl-benzyl)-(2-methyl-2H-tetrazol-5-yl)-amino]-7-methyl-8-trifluoromethyl-2,3,4,5-tetrahydro-1H-benzo[b]azepine-1-carboxylic acid 2-amino-ethyl ester (Example 133), replacing (2-Hydroxy-ethyl)-carbamic acid tert-butyl ester with 3-Hydroxy-2,2-dimethyl-propionic acid methyl ester in Example 133, Step 2. MS (ES+): 711 (M+H).

Step 2. Preparation of (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid 2-carboxy-2-methyl-propyl ester

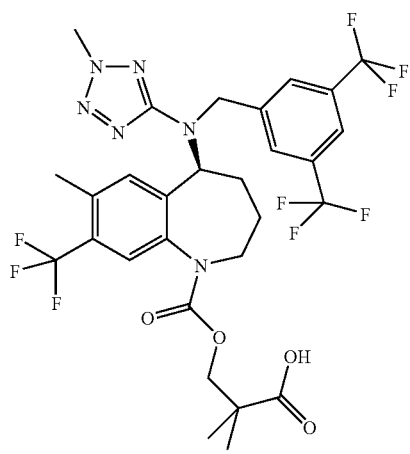

Prepare the title compound by essentially following the procedures described in the synthesis of (S)-3-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-2-methyl-propionic acid (Example 123) starting with (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid 2-methoxycarbonyl-2-methyl-propyl ester. MS (ES+): 697 (M+H).

Example 135

Synthesis of (S)-2-[2-(2-Amino-ethyl)-2H-tetrazol-5-yl]-(3,5-bis-trifluoromethyl-benzyl)-(1-cyclopropylmethyl-7-methyl-8-trifluoromethyl-2,3,4,5-tetrahydro-1H-benzo[b]azepin-5-yl)-amine

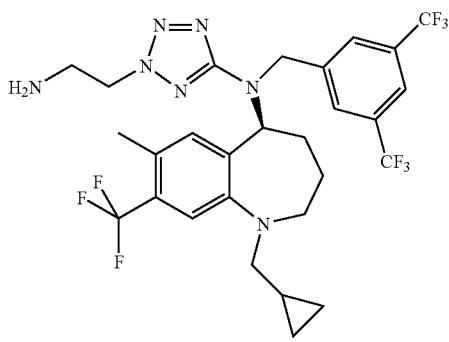

Step 1. Preparation of (S)-2-(2-{5-[(3,5-Bis-trifluoromethyl-benzyl)-(1-cyclopropylmethyl-7-methyl-8-trifluoromethyl-2,3,4,5-tetrahydro-1H-benzo[b]azepin-5-yl)-amino]-tetrazol-2-yl}-ethyl)-isoindole-1,3-dione

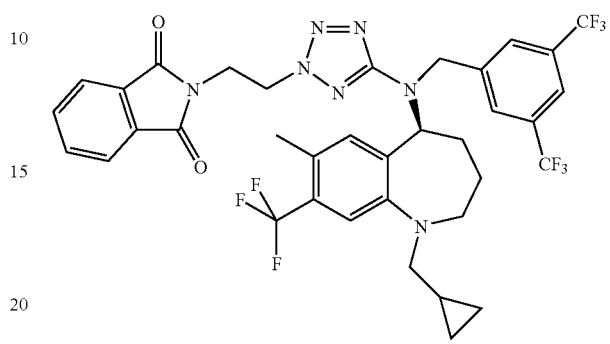

Prepare the title compound by essentially following the procedures described in Example 3, Step 19 by replacing (S)-(3,5-bistrifluoromethylbenzyl)-(2-methyl-2H-tetrazol-5-yl)-(7-methyl-8-trifluoromethyl-2,3,4,5-tetrahydro-1H-benzo[b]azepin-5-yl)amine with (S)-2-(2-{5-[(3,5-Bis-trifluoromethyl-benzyl)-(7-methyl-8-trifluoromethyl-2,3,4,5-tetrahydro-1H-benzo[b]azepin-5-yl)-amino]-tetrazol-2-yl}-ethyl)-isoindole-1,3-dione (Example 126, Step 2), and replacing cyclopentanecarboxaldehyde with cyclopropanecarboxaldehyde. MS (ES+): 766 (M+H).

Step 2. Preparation of (S)-[2-(2-Amino-ethyl)-2H-tetrazol-5-yl]-(3,5-bis-trifluoromethyl-benzyl)-(1-cyclopropylmethyl-7-methyl-8-trifluoromethyl-2,3,4,5-tetrahydro-1H-benzo[b]azepin-5-yl)-amine

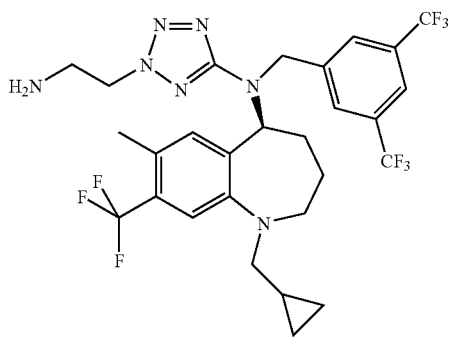

Heat the mixture of (S)-2-(2-{5-[(3,5-Bis-trifluoromethyl-benzyl)-(1-cyclopropylmethyl-7-methyl-8-trifluoromethyl-2,3,4,5-tetrahydro-1H-benzo[b]azepin-5-yl)-amino]-tetrazol-2-yl}-ethyl)-isoindole-1,3-dione (0.140 g, 0.183 mmol) and hydrazine hydrate (0.114 mL, 3.66 mmol) in methanol (2 mL) at 60° C. overnight. Evaporate the solvents.

Chromatograph the residue over silica gel, eluting with ethyl acetate/hexanes (0-100%), to provide the title compound as a colorless oil (0.0700 g, 60%). MS (ES+): 636 (M+H).

Example 136

Synthesis of (S)-[2-(2-Amino-ethyl)-2H-tetrazol-5-yl]-(3,5-bis-trifluoromethyl-benzyl)-(1-cyclopropyl-methyl-7-methyl-8-trifluoromethyl-2,3,4,5-tetrahydro-1H-benzo[b]azepin-5-yl)-amine hydrochloride

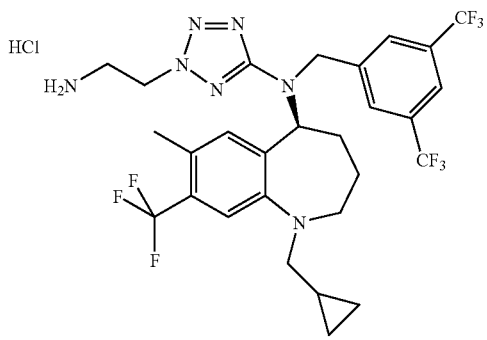

Add 1.0 N HCl in ethyl ether (0.0500 mL) to a solution of (S)-[2-(2-Amino-ethyl)-2H-tetrazol-5-yl]-(3,5-bis-trifluoromethyl-benzyl)-(1-cyclopropylmethyl-7-methyl-8-trifluoromethyl-2,3,4,5-tetrahydro-1H-benzo[b]azepin-5-yl)-amine (0.0300 mg, 0.0472 mmole) in ethyl ether (0.500 mL), stir for 10 minutes. Evaporate the solvent to provide the title compound as white powder. MS (ES+): 636 (M+H).

Example 137

Synthesis of (+/−)-5-[(3,5-Bis-trifluoromethyl-benzyl)-pyridin-3-yl-amino]-7-methyl-8-trifluoromethyl-2,3,4,5-tetrahydro-benzazepine-1-carboxylic acid isopropyl ester

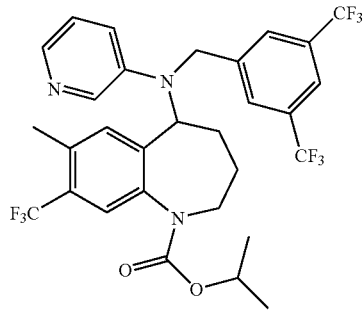

Step 1. Preparation of (+/−)-7-Methyl-5-(pyridin-3-ylamino)-8-trifluoromethyl-2,3,4,5-tetrahydrobenzo[b]azepine-1-carboxylic acid isopropyl ester

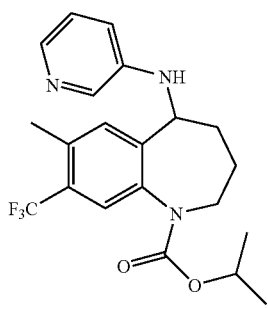

Add isopropyl 7-methyl-5-oxo-8-trifluoromethyl-2,3,4,5-tetrahydrobenzo[b]azepine-1-carboxylate (Example 3, Step 8) (1.16 g, 3.52 mmol), 3-aminopyridine (465 mg, 5.10 mmol), p-toluenesulfonic acid (210 mg, 1.10 mmol) and toluene (8.0 mL) to a sealed tube and stir vigorously for 4 days at 130° C. Evaporate the toluene, dissolve the residue with MeOH (10.0 mL), and add sodium borohydride (146 mg, 3.86 mmol) portionwise. Reflux overnight and evaporate the MeOH. Partition the resulting residue between water (10 mL) and EtOAc (10 mL). Wash the organic layer with 2-mL portions of water and brine, dry (MgSO$_4$), and concentrate. Purify via column chromatography (silica gel; 30% to 70% EtOAc:hexanes to 100% EtOAc gradient) to give 189 mg (13%) of the title compound as a white solid. APCI MS m/z 408 [M+H]$^+$.

Step 2. Preparation of (+/−) 5-[(3,5-Bis-trifluoromethyl-benzoyl)-pyridin-3-yl-amino]-7-methyl-8-trifluoromethyl-2,3,4,5-tetrahydro-benzo[b]azepine-1-carboxylic acid isopropyl ester

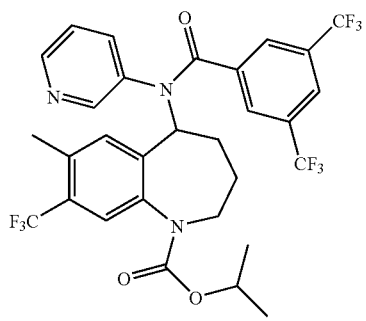

Add 3,5-bis(trifluoromethyl)-benzoyl chloride (0.220 mL, 1.22 mmol) and triethylamine (0.180 mL, 1.29 mmol) over a 24 h period to a solution of 7-methyl-5-(pyridin-3-ylamino)-8-trifluoromethyl-2,3,4,5-tetrahydrobenzo[b]azepine-1-carboxylic acid isopropyl ester (114 mg, 0.280 mmol) in chloroform (1.9 mL) at 70° C. Allow the reaction to cool, dilute with methylene chloride (20 mL) and wash sequentially with 10% HCl, saturated aqueous sodium bicarbonate, water, and then brine. Dry (MgSO$_4$), concentrate, and purify via column chromatography (silica gel; 20% to 40% EtOAc:hexanes) to give 92 mg (51%) of the title compound as a white solid APCI MS m/z 648 [M+H]$^+$.

Step 3. Preparation of (+/−)-5-[(3,5-Bis-trifluoromethyl-benzyl)-pyridin-3-yl-amino]-7-methyl-8-trifluoromethyl-2,3,4,5-tetrahydrobenzo[b]azepine-1-carboxylic acid isopropyl ester

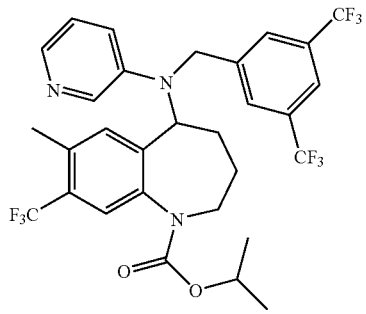

Add a solution of borane-THF complex in THF (1.0 M, 0.2 mL, 0.2 mmol) to 5-[(3,5-Bis-trifluoromethyl-benzoyl)-pyridin-3-yl-amino]-7-methyl-8-trifluoromethyl-2,3,4,5-tetrahydrobenzo[b]azepine-1-carboxylic acid isopropyl ester (90.1 mg, 0.139 mmol) in THF (1.6 mL). Heat in a sealed tube (70° C.) for 14 h. Add saturated aqueous sodium bicarbonate (5 mL) and extract with EtOAc (3×5 mL). Dry (MgSO$_4$), concentrate, and purify via column chromatography (silica gel; 10% to 20% to 25% EtOAc:hexanes) to give 19 mg (22%) of the title compound as a yellow solid. APCI MS m/z 634 [M+H]$^+$.

Example 138

Synthesis of (S)-5-[(3,5-Bis-trifluoromethyl-benzyl)-phenyl-amino]-7-methyl-8-trifluoromethyl-2,3,4,5-tetrahydrobenzo[b]zepine-1-carboxylic acid tert-butyl ester

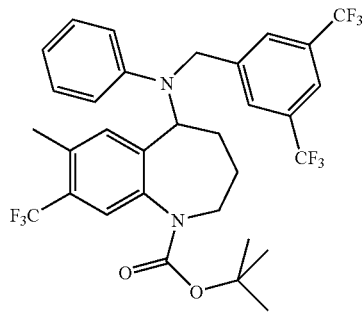

Add (S)-tert-butyl 5-(3,5-bis-trifluoromethylbenzylamino)-7-methyl-8-trifluoromethyl-2,3,4,5-tetrahydrobenzo[b]azepine-1-carboxylate (Example 3, Step 14) (307 mg, 0.538 mmol), sodium t-butoxide (103 mg, 1.07 mmol), bromobenzene (65.0 δL, 0.617 mmol), palladium acetate (2.4 mg, 0.011 mmol), Q-Phos (15.3 mg, 0.022 mmol), and toluene (5.4 mL) to a sealed tube and heat at 130° C. for 24 h. Quench with water (20 mL) and extract with EtOAc (2×20 mL). Dry (MgSO4), concentrate, and purify via column chromatography (silica gel; 5% to 10% to 20% EtOAc:hexanes) to give 180 mg (52%) of the title compound as a white solid. APCI MS m/z 648 [M+H]+.

Example 139

Synthesis of (S)-(3,5-Bis-trifluoromethyl-benzyl)-[7-methyl-1-(tetrahydro-pyran-4-yl)-8-trifluoromethyl-2,3,4,5-tetrahydro-1H-benzo[b]azepin-5-yl]-(2-methyl-2H-tetrazol-5-yl)-amine

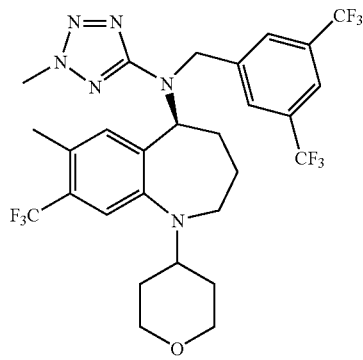

Add sodium triacetoxyborohydride (0.153 g, 0.724 mmol) portionwise to a solution of (S)-(3,5-Bis-trifluoromethyl-benzyl)-(2-methyl-2H-tetrazol-5-yl)-(7-methyl-8-trifluoromethyl-2,3,4,5-tetrahydro-1H-benzo[b]azepin-5-yl)-amine (Example 3, Step 18) (0.100 g, 0.181 mmol), tetrahydro-4-pyranone (0.054 g, 0.543 mmol) and glacial acetic acid (1 mL) in acetonitrile (10 mL) at room temperature under an atmosphere of nitrogen and stir for 24 h. Quench the reaction with saturated sodium bicarbonate (5 mL) and dilute with dichloromethane (15 mL). Separate the layers and wash the organic layer with saturated sodium bicarbonate and brine (20 mL each). Dry the organic layer over sodium sulfate, filter and remove the solvent under reduced pressure. Purify the residue using flash column chromatography on silica gel, eluting with hexanes/ethyl acetate (80:20), to provide the title compound as an off-white solid (0.070 g, 61%). $^1$H NMR (CDCl$_3$, 300 MHz) δ 0.87-0.95 (m, 1H), 1.24-1.34 (m, 1H), 1.61-2.10 (m, 6H), 2.30 (s, 3H), 2.75-2.90 (m, 1H), 3.15-3.22 (m, 1H), 3.41-3.62 (m, 3H), 3.96-4.10 (m, 2H), 4.14 (s, 3H), 4.75-4.95 (m, 2H), 5.37-5.50 (m, 1H), 6.96 (s, 1H), 7.20 (s, 1H), 7.30 (s, 1H), 7.65 (s, 1H), 7.72 (s, 1H); ESI MS m/z 637 [C$_{28}$H$_{29}$F$_9$N$_6$O+H]$^+$.

Example 140

Synthesis of (S)-(3,5-Bis-trifluoromethyl-benzyl)-(1-isopropyl-7-methyl-8-trifluoromethyl-2,3,4,5-tetrahydro-1H-benzo[b]azepin-5-yl)-(2-methyl-2H-tetrazol-5-yl)-amine

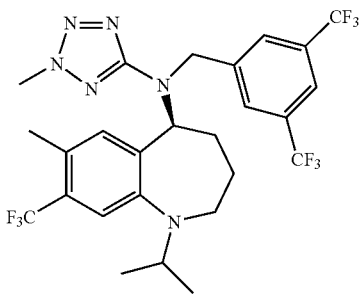

Prepare the title compound by essentially following the procedure described for the preparation of (S)-(3,5-Bis-trifluoromethyl-benzyl)-[7-methyl-1-(tetrahydro-pyran-4-yl)-8-trifluoromethyl-2,3,4,5-tetrahydro-1H-benzo[b]azepin-5-yl]-(2-methyl-2H-tetrazol-5-yl)-amine (Example 139), by substituting tetrahydro-4-pyranone with acetone. $^1$H NMR (CDCl$_3$, 300 MHz) δ 1.10-1.31 (m, 6H), 1.55-1.87 (m, 2H), 1.90-2.15 (m, 1 H), 2.10-2.20 (m, 4H), 2.78-2.90 (m, 1H), 3.00-3.13 (m, 1H), 3.64-3.80 (m, 1H), 4.14. (s, 3H), 4.72-4.93 (m, 2H), 5.32-5.43 (m, 1H), 6.81 (s, 1H), 7.19 (s, 1H), 7.56 (s, 2H), 7.71 (s, 1H); ESI MS m/z 595 [C$_{26}$H$_{27}$F$_9$N$_6$+H]$^+$.

Example 141

Synthesis of (S)-5-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-2-hydroxy-benzoic acid

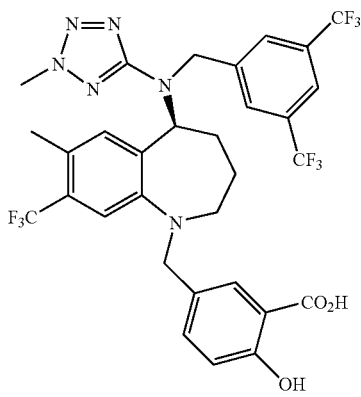

Step 1. Preparation of 5-formyl-2-hydroxy-benzoic acid methyl ester

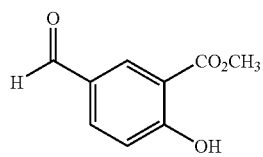

Heat a mixture of 5-formyl-2-hydroxy-benzoic acid (5.0 g, 30.09 mmol) concentrated sulfuric acid (5 mL) in methanol (100 mL) at reflux for 24 h. Cool the mixture to room temperature and concentrate under reduced pressure. Purify the resulting residue by chromatography over silica gel, eluting with hexanes/ethyl acetate (80:20), to provide the title compound as a colorless oil (4.28 g, 79%). $^1$H NMR (CDCl$_3$, 300 MHz) δ 3.88 (s, 3H), 4.52 (bs, 1H), 7.05 (d, J=8.56 Hz, 1H), 7.84 (d, J=8.56 Hz, 1H), 8.40 (s, 1H), 9.85 (s, 1H); TLC Rf=0.34 (3:1 Hexanes/Ethyl Acetate).

Step 2. (S)-5-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-2-hydroxy-benzoic acid methyl ester

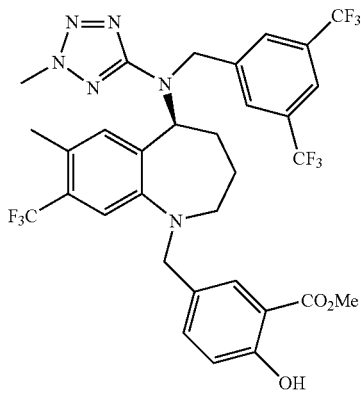

Add sodium triacetoxyborohydride (0.115 g, 0.543 mmol) portionwise to a solution of (S)-(3,5-bis-trifluoromethyl-benzyl)-(2-methyl-2H-tetrazol-5-yl)-(7-methyl-8-trifluoromethyl-2,3,4,5-tetrahydro-1H-benzo[b]azepin-5-yl)-amine (Example 3, Step 18) (0.200 g, 0.362 mmol), 5-formyl-2-hydroxy-benzoic acid methyl ester (0.195 g, 1.08 mmol) and glacial acetic acid (1 mL) in acetonitrile (10 mL) at room temperature under an atmosphere of nitrogen and stir for 24 h. Quench the reaction with saturated sodium bicarbonate (5 mL) and dilute with dichloromethane (15 mL). Separate the layers and wash the organic layer with saturated sodium bicarbonate and brine (20 mL each). Dry the organic layer over sodium sulfate, filter and remove the solvent under reduced pressure. Purify the residue using flash column chromatography on silica gel, eluting with hexanes/ethyl acetate (80:20), to provide the title compound as an off-white foam (0.155 g, 60%). $^1$H NMR (CDCl$_3$, 300 MHz) δ 10.63 (s, 1H), 7.89 (s, 1H), 7.67 (s, 1H), 7.56 (m, 2H), 7.28 (s, 1H), 6.96 (m, 2H), 5.56 (m, 1H), 4.85-4.98 (m, 2H), 4.14 (s, 3H), 3.89 (s, 3H), 2.95-3.00 (m, 1H), 2.73-2.80 (m, 1H), 2.30 (s, 3H), 2.00-2.13 (m, 2H), 1.43-1.72 (m, 2H), 1.21-1.34 (m, 3H); ESI MS m/z 717 [C$_{32}$H$_{29}$F$_9$N$_6$O$_3$+H]$^+$.

Step 3. Preparation of (S)-5-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-2-hydroxy-benzoic acid

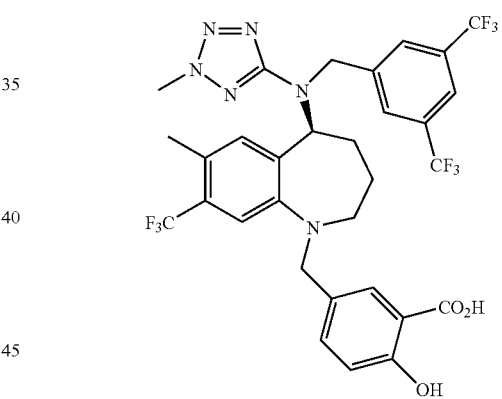

Add 2 N sodium hydroxide solution (2 mL) to a solution of (S)-5-{5-[(3,5-bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-2-hydroxy-benzoic acid methyl ester (0.100 g, 0.139 mmol) in methanol (5 mL) and heat at 60° C. for 4 h. After the reaction cools to room temperature, acidify to pH 4 with 2 N hydrochloric acid solution and extract the aqueous mixture with ethyl acetate (3×10 mL). Wash the organic layer with water and brine (10 mL each). Dry the organic layer over anhydrous sodium sulfate, filter and remove the solvent under reduced pressure to provide the title compound as a white solid (0.076 g, 78%). $^1$H NMR (CDCl$_3$, 300 MHz) δ 1.23-1.32 (m, 2H), 1.51-1.52 (m, 2H), 1.94-2.05 (m, 1H), 2.25 (s, 3H), 2.65-2.71 (m, 1H), 2.95-3.04 (m, 1H), 4.10-4.21 (m, 5H), 4.76-5.03 (m, 2H), 5.50-5.61 (m, 1H), 6.68-6.89 (m, 2H), 7.31-7.40 (m, 2H), 7.49-7.62 (m, 2H), 7.70 (s, 1H), 7.98 (s, 1H), 10.43 (s, 1H); ESI MS m/z 703 [C$_{31}$H$_{27}$F$_9$N$_6$O$_3$+H]$^+$.

Example 142

Synthesis of (S)-5-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-nicotinic acid hydrochloride

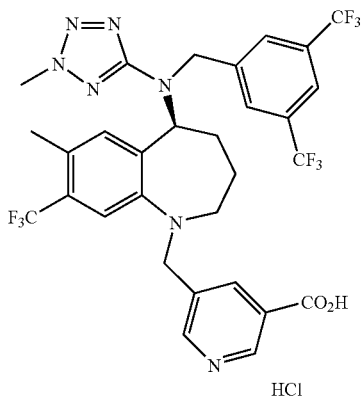

Step 1. Preparation of 5-Formyl-nicotinic acid methyl ester

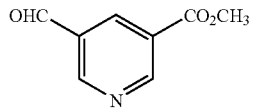

Subject a mixture of methyl-5-bromonicotinate (1.0 g, 4.63 mmol), triethylsilane (0.807 g, 6.94 mmol), tetrakis(triphenylphosphino)palladium (0) (0.531 g, 0.460 mmol), and triethylamine (1.03 g, 10.18 mmol) in acetonitrile (10 mL) to an atmosphere of carbon monoxide gas (20 psi) heated at 60° C. for 5 h. Cool the reaction to room temperature and then absorb directly onto silica gel. Purify the residue by chromatography over silica gel, eluting with hexanes/ethyl acetate (80:20), to provide the title compound as an oil (0.114 g, 15%). $^1$H NMR (CDCl$_3$, 300 MHz) δ 3.90 (s, 3H), 7.35-7.50 (m, 1H), 8.32-8.42 (m, 1H), 8.77-8.90 (m, 1H), 9.23 (s, 1H); TLC Rf=0.37 (4:1 Hexanes/Ethyl Acetate).

Step 2. Preparation of (S)-5-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-nicotinic acid methyl ester

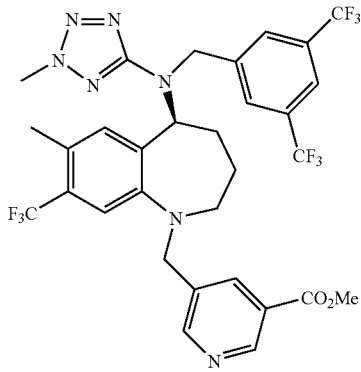

Add sodium triacetoxyborohydride (0.153 g, 0.724 mmol) portionwise to a solution of (S)-(3,5-bis-trifluoromethyl-benzyl)-(2-methyl-2H-tetrazol-5-yl)-(7-methyl-8-trifluoromethyl-2,3,4,5-tetrahydro-1H-benzo[b]azepin-5-yl)-amine (Example 3, Step 18) (0.100 g, 0.181 mmol), 5-formyl-nicotinic acid methyl ester (0.089 g, 0.543 mmol) and glacial acetic acid (1 mL) in acetonitrile (10 mL) at room temperature under an atmosphere of nitrogen and stir for 24 h. Quench the reaction with saturated sodium bicarbonate (5 mL) and dilute with dichloromethane (15 mL). Separate the layers and wash the organic layer with saturated sodium bicarbonate and brine (20 mL each). Dry the organic layer over sodium sulfate, filter and remove the solvent under reduced pressure. Purify the residue using flash column chromatography on silica gel, eluting with hexanes/ethyl acetate (80:20), to provide (the title compound as an off-white foam (0.113 g, 90%). $^1$H NMR (CDCl$_3$, 30 MHz) δ 1.21-1.43 (m, 1H), 1.61-1.71 (m, 1H), 2.04-2.13 (m, 2H), 2.32 (s, 3H), 2.71-2.83 (m, 1H), 3.10-3.18 (m, 1H), 3.89 (s, 3H), 4.14 (s, 3H), 4.32-4.50 (m, 2H), 4.83-5.10 (m, 2H), 5.64-5.0 (m, 1H), 6.89 (s, 1H), 7.21 (s, 1H), 7.65 (s, 2H), 7.72 (s, 1H), 8.35 (s, 1H), 8.83 (s, 1H), 9.12 (s, 1H); ESI MS m/z 702 [C$_{31}$H$_{28}$F$_9$N$_7$O$_2$+H]$^+$

Step 3. Preparation of (S)-5-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-nicotinic acid hydrochloride

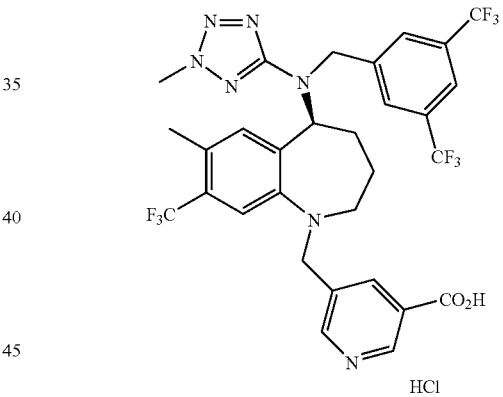

Add 2 N sodium hydroxide solution (2 mL) to a solution of (S)-5-{5-[(3,5-bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-nicotinic acid methyl ester (0.090 g, 0.128 mmol) in methanol (5 mL) and heat at 60° C. for 4 h. After the reaction cools to room temperature, acidify to pH 4 with 2 N hydrochloric acid solution and extract the aqueous mixture with ethyl acetate (3×10 mL). Wash the organic layer with water and brine (10 mL each). Dry the organic layer over anhydrous sodium sulfate, filter and remove the solvent under reduced pressure to provide the title compound as a white solid (0.076 g, 78%). $^1$H NMR (CDCl$_3$, 300 MHz) δ 1.23-2.34 (m, 1H), 1.57-1.64 (m, 2H), 2.03-2.13 (m, 2H), 2.32 (s, 3H), 2.67-2.73 (m, 1H), 3.04-3.14 (m, 1H), 4.14 (s, 3H), 4.32-4.56 (m, 2H), 4.89-5.10 (m, 2H), 5.67-5.70 (m, 1H), 6.89 (s, 1H), 7.23-7.30 (m, 1H), 7.60-7.70 (m, 3H), 8.45 (s, 1H), 8.89 (s, 1H), 9.22 (s, 1H); ESI MS m/z 688 [C$_{30}$H$_{26}$F$_9$N$_7$O$_2$+H]$^+$.

Example 143

Synthesis of (S)-5-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-2-fluoro-benzoic acid

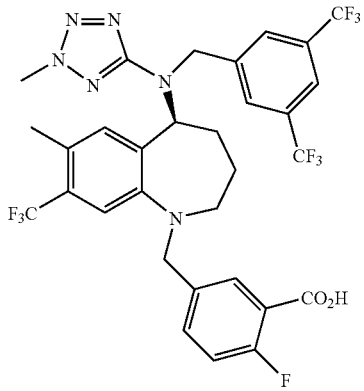

Step 1. Preparation of 2-Fluoro-5-methyl-benzoic acid methyl ester

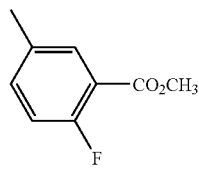

Heat a mixture of 2-fluoro-5-methyl-benzoic acid (1.0 g, 6.48 mmol), iodomethane (1.38 g, 9.73 mmol), and potassium carbonate (2.68 g, 19.44 mmol) in acetone (20 mL) at reflux overnight. Cool the reaction and filter through Celite®. Concentrate the filtrate under reduced pressure to provide the title compound as a colorless gum (0.895 g, 82%). $^1$H NMR (CDCl$_3$, 300 MHz) δ 2.32 (s, 3H), 3.89 (s, 3H), 6.95-7.10 (m, 1H), 7.20-7.30 (m 1H), 7.75-7.80 (m, 1H); TLC Rf=0.45 (2:1 Hexanes/Ethyl Acetate).

Step 2. Preparation of 2-Fluoro-5-formyl-benzoic acid methyl ester

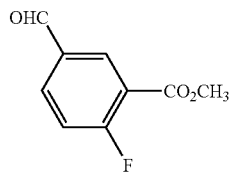

Add N-bromosuccinimide (2.46 g, 13.86 mmol) and benzoyl peroxide (0.152 g, 0.630 mmol) to a solution of 2-fluoro-5-methyl-benzoic acid methyl ester (1.06 g, 6.30 mmol) in carbon tetrachloride (50 mL). Heat the mixture at reflux for 4 h. Cool the mixture to room temperature and wash with saturated aqueous sodium bicarbonate solution (10 mL) and brine (10 mL). Dry the organic layer over anhydrous sodium sulfate, filter, and concentrate under reduced pressure. Dissolve the resulting residue in dimethylsulfoxide (30 mL) and heat at reflux for 16 h. Cool the mixture to room temperature and dilute with water (100 mL) and ethyl acetate (100 mL). Extract the aqueous layer with ethyl acetate (3×100 mL). Wash the combined organic layers with water (3×100 mL), followed by brine (100 mL). Dry the organic layer over anhydrous sodium sulfate, filter and concentrate. Purify the residue by chromatography over silica gel, eluting with hexanes/ethyl acetate (80:20), to provide the title compound as a tan solid (0.228 g, 20%). $^1$H NMR (CDCl$_3$, 300 MHz) δ 3.89 (s, 3H), 7.31-7.44 (m, 1H), 8.05-8.12 (m, 1H), 8.44-8.53 (m, 1H), 10.00 (s, 1H); TLC Rf=0.65 (3:1 Hexanes/Ethyl Acetate).

Step 3. Preparation of (S)-5-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-2-fluoro-benzoic acid methyl ester

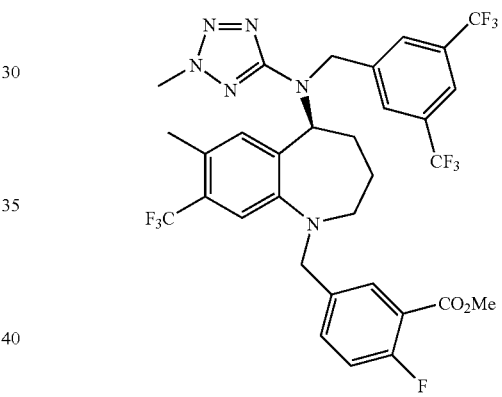

Add sodium triacetoxyborohydride (0.153 g, 0.724 mmol) portionwise to a solution of (S)-(3,5-bis-trifluoromethyl-benzyl)-(2-methyl-2H-tetrazol-5-yl)-(7-methyl-8-trifluoromethyl-2,3,4,5-tetrahydro-1H-benzo[b]azepin-5-yl)-amine (Example 3, Step 18) (0.100 g, 0.181 mmol), 2-fluoro-5-formyl-benzoic acid methyl ester (0.100 g, 0.543 mmol) and glacial acetic acid (1 mL) in acetonitrile (10 mL) at room temperature under an atmosphere of nitrogen and stir for 24 h. Quench the reaction with saturated sodium bicarbonate (5 mL) and dilute with dichloromethane (15 mL). Separate the layers and wash the organic layer with saturated sodium bicarbonate and brine (20 mL each). Dry the organic layer over sodium sulfate, filter and remove the solvent under reduced pressure. Purify the residue using flash column chromatography on silica gel, eluting with hexanes/ethyl acetate (80:20), to provide the title compound as a white foam (0.120 g, 92%), $^1$H NMR (CDCl$_3$, 300 MHz) δ 1.23-1.34 (m, 2H), 1.64-1.72 (m, 2H), 2.10-2.20 (m, 1H), 2.32 (s, 3H), 2.76-2.80 (m, 1H), 2.94-3.02 (m, 1H), 3.89 (s, 3H), 4.14 (s, 3H), 4.23-4.54 (m, 2H), 4.76-5.02 (m, 2H), 5.62-5.70 (m, 1H), 6.90 (s, 1H), 7.10 (m, 1H), 7.35-7.43 (m, 2H), 7.56-7.80 (m, 2H), 7.89-7.92 (m, 1H); ESI MS m/z 719 [C$_{32}$H$_{28}$F$_{10}$N$_6$O$_2$+H]$^+$.

Step 4. Preparation of (S)-5-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-2-fluoro-benzoic acid

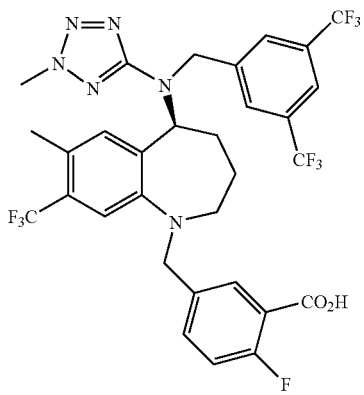

Add 2 N sodium hydroxide solution (2 mL) to a solution of (S)-5-{5-[(3,5-bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-2-fluoro-benzoic acid methyl ester (0.120 g, 0.167 mmol) in methanol (5 mL) and heat at 60° C. for 4 h. After the reaction cools to room temperature, acidify to pH 4 with 2 N hydrochloric acid solution and extract the aqueous mixture with ethyl acetate (3×10 mL). Wash the organic layer with water and brine (10 mL each). Dry the organic layer over anhydrous sodium sulfate, filter and remove the solvent under reduced pressure to provide the title compound as a white solid (0.116 g, 98%). $^1$H NMR (CDCl$_3$, 300 MHz) δ 1.60-1.85 (m, 2H), 2.01-2.10 (m, 2H), 2.32 (s, 3H), 2.75-2.84 (m, 1H), 2.97-3.01 (m, 1H), 4.10-4.11 (m, 1H), 4.14 (s, 3H), 4.20-4.35 (m, 2H), 4.76-5.10 (m, 2H), 5.65-5.70 (m, 1H), 6.89 (s, 1H), 7.10-7.15 (m, 1H), 7.32-7.40 (m, 2H), 7.56-7.60 (m, 2H), 7.67 (s, 1H), 8.10(s, 1H); ESI MS m/z 705 [C$_{31}$H$_{26}$F$_{10}$N$_6$O$_2$+H]$^+$.

Example 144

Synthesis of (S)-1-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-2-ethyl-butan-1-one

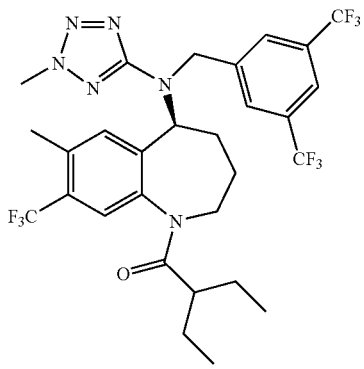

Add 2-ethyl-butyryl chloride (0.014 g, 0.108 mmol) dropwise under an atmosphere of nitrogen to a 0° C. cooled solution of (S)-(3,5-bis-trifluoromethyl-benzyl)-(2-methyl-2H-tetrazol-5-yl)-(7-methyl-8-trifluoromethyl-2,3,4,5-tetrahydro-1H-benzo[b]azepin-5-yl)-amine (Example 3, Step 18) (0.060 g, 0.108 mmol) and pyridine (0.010 g, 0.108 mmol) in methylene chloride (5 mL). After stirring for 1 h, wash the reaction with saturated aqueous sodium bicarbonate solution (10 mL), 2N aqueous hydrogen chloride solution (10 mL), and brine (10 mL). Dry the organic layer over anhydrous sodium sulfate, filter, and concentrate under reduced pressure to afford the title compound as a colorless gum (0.075 g, 98%). $^1$H NMR (CDCl$_3$, 300 MHz) δ 0.71-2.16 (m, 16H), 2.34-2.43 (m, 1H), 2.43 (s, 3H), 2.50-2.41 (m, 1H), 4.14 (s, 3H), 4.25-4.67 (m, 2H), 6.89 (bs, 1H), 7.43 (s, 1H), 7.75 (s, 2H), 7.85 (s, 1H); ESI MS m/z 651 [C$_{29}$H$_{31}$F$_9$N$_6$O+H]$^+$.

Example 145

Synthesis of (S)-1-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-ethanone

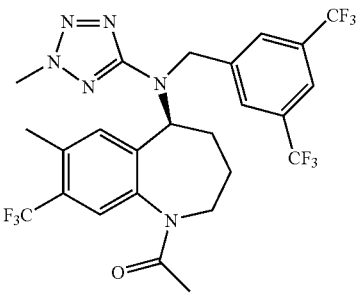

Prepare the title compound by essentially following the procedures described for the preparation of (S)-1-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-2-ethyl-butan-1-one (Example 144), by substituting 2-ethyl-butyryl chloride with acetyl chloride. $^1$H NMR (CDCl3, 300 MHz) δ 0.75-2.123 (m, 8H), 2.43 (s, 3H), 2.50-2.41 (m, 1H), 4.14 (s, 3H), 4.25-4.67 (m, 2H), 5.21-5.50 (m, 1H), 6.89 (bs, 1H), 7.43 (s, 1H), 7.75 (s, 2H), 7.85 (s, 1H); ESI MS m/z 595 [C25H23F9N6O+H]+.

Example 146

Synthesis of (S)-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-cyclohexyl-methanone

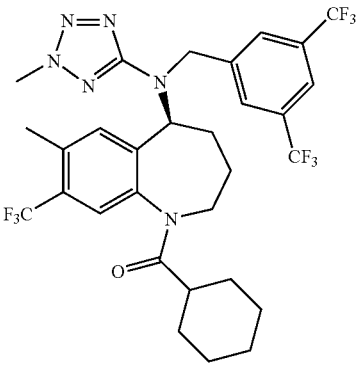

Prepare the title compound by essentially following the procedures described for the preparation of (S)-1-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-2-ethyl-butan-1-one (Example 144), by substituting 2-ethyl-butyryl chloride with cyclohexanecarbonyl chloride. $^1$H NMR (CDCl3, 300 MHz) δ 0.75-2.123 (m, 16H), 2.43 (s, 3H), 2.50-2.41 (m, 1H), 4.14 (s, 3H), 4.25-4.67 (m, 2H), 5.21-5.50 (m, 1H), 6.89 (bs, 1H), 7.43 (s, 1H), 7.75 (s, 2H), 7.85 (s, 1H); ESI MS m/z 663 [C30H31F9N6O+H]+.

Example 147

Synthesis of (S)-(3,5-Bis-trifluoromethyl-benzyl)-(7-methyl-1-piperidin-4-yl-8-trifluoromethyl-2,3,4,5-tetrahydro-1H-benzo[b]azepin-5-yl)-(2-methyl-2H-tetrazol-5-yl)-amine

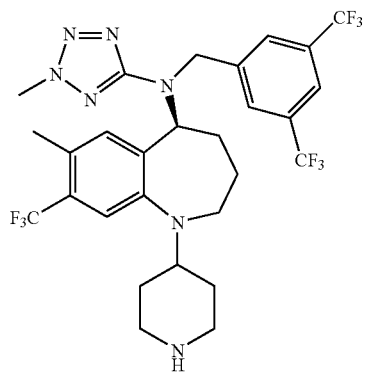

Step 1. Preparation of (S)-[1-(1-Benzyl-piperidin-4-yl)-7-methyl-8-trifluoromethyl-2,3,4,5-tetrahydro-1H-benzo[b]azepin-5-yl]-(3,5-bis-trifluoromethyl-benzyl)-(2-methyl-2H-tetrazol-5-yl)-amine

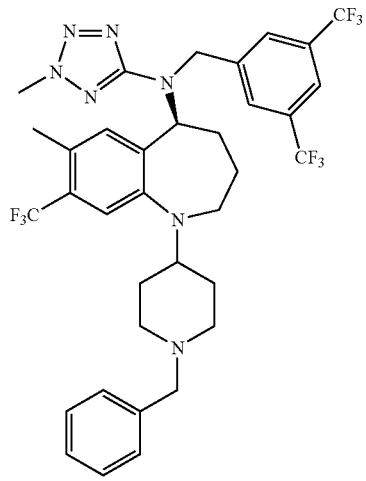

Add sodium triacetoxyborohydride (0.153 g, 0.724 mmol) portionwise to a solution of (S)-(3,5-bis-trifluoromethyl-benzyl)-(2-methyl-2H-tetrazol-5-yl)-(7-methyl-8-trifluoromethyl-2,3,4,5-tetrahydro-1H-benzo[b]azepin-5-yl)-amine (Example 3, Step 18) (0.200 g, 0.362 mmol), 1-benzyl-piperidin-4-one (0.206 g, 1.09 mmol) and glacial acetic acid (1 mL) in acetonitrile (10 mL) at room temperature under an atmosphere of nitrogen and stir for 24 h. Quench the reaction with saturated sodium bicarbonate (5 mL) and dilute with dichloromethane (15 mL). Separate the layers and wash the organic layer with saturated sodium bicarbonate and brine (20 mL each). Dry the organic layer over sodium sulfate, filter and remove the solvent under reduced pressure. Purify the residue using flash column chromatography on silica gel, eluting with hexanes/ethyl acetate (80:20), to provide the title compound as an off-white solid (0.070 g, 61%). $^1$H NMR (CDCl$_3$, 300 MHz) δ 1.63-2.13 (m, 8H), 2.34 (s, 3H), 2.82-3.0 (m, 3H), 3.10-3.22 (m, 1H), 3.33-3.41 (m, 1H), 3.50 (s, 2H), 4.09-4.13 (m, 1H), 4.14 (s, 3H), 4.74-4.97 (m, 2H), 5.34-5.49 (m, 1H), 6.89 (s, 1H), 7.32 (s, 1H), 7.41 (s, 5H), 7.60 (s, 2H), 7.71 (s, 1H); ESI MS m/z 726 [C$_{35}$H$_{36}$F$_9$N$_7$+H]+.

Step 2. Preparation of (S)-(3,5-Bis-trifluoromethyl-benzyl)-(7-methyl-1-piperidin-4-yl-8-trifluoromethyl-2,3,4,5-tetrahydro-1H-benzo[b]azepin-5-yl)-(2-methyl-2H-tetrazol-5-yl)-amine

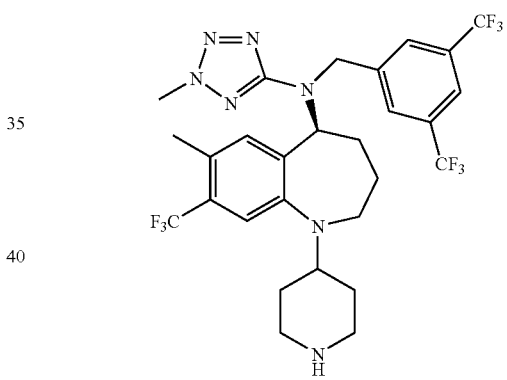

Subject a mixture of (S)-[1-(1-benzyl-piperidin-4-yl)-7-methyl-8-trifluoromethyl-2,3,4,5-tetrahydro-1H-benzo[b]azepin-5-yl]-(3,5-bis-trifluoromethyl-benzyl)-(2-methyl-2H-tetrazol-5-yl)-amine (0.130 g, 0.179 mmol) and palladium on carbon (10% by weight, wet, 0.050 g) in methanol (10 mL) to an atmosphere of hydrogen gas (35 psi) at room temperature on a Parr shaker apparatus. After 5 h, filter the mixture through celite and the concentrate the filtrate under reduced pressure. Purify the resulting residue using flash column chromatography on silica gel, eluting with hexanes/ethyl acetate (80:20), to provide the title compound as white solid (0.055 g, 48%): $^1$H NMR (CDCl$_3$, 300 MHz) δ 1.63-2.13 (m, 10H), 2.34 (s, 3H), 2.82-3.0 (m, 3H), 3.10-3.22 (m, 1H), 3.33-3.41 (m, 1H), 4.09-4.13 (m, 1H), 4.14 (s, 3H), 4.74-4.97 (m, 2H), 5.12 (bs, 1H), 5.34-5.49 (m, 1H), 6.89 (s, 1H), 7.32 (s, 1H), 7.60 (s, 1H), 7.71 (s, 1H); ESI MS m/z 726 [C$_{28}$H$_{30}$F$_9$N$_7$+H]+.

Example 148

Synthesis of (S)-(3,5-Bis-trifluoromethyl-benzyl)-(1-cyclopropylmethyl-7,9-dimethyl-8-trifluoromethyl-2,3,4,5-tetrahydro-1H-benzo[b]azepin-5-yl)-(2-methyl-2H-tetrazol-5-yl)-amine

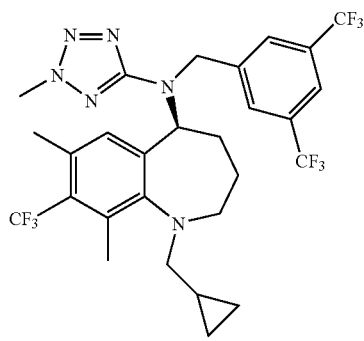

Step 1. Preparation of (S)-(3,5-Bis-trifluoromethyl-benzyl)-(9-bromo-7-methyl-8-trifluoromethyl-2,3,4,5-tetrahydro-1H-benzo[b]azepin-5-yl)-(2-methyl-2H-tetrazol-5-yl)-amine

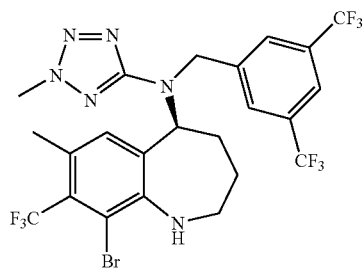

Add N-bromosuccinimide (1.10 g, 6.19 mmol) in one portion to a solution of (S)-(3,5-bistrifluoromethylbenzyl)-(2-methyl-2H-tetrazol-5-yl)-(7-methyl-8-trifluoromethyl-2,3,4,5-tetrahydro-1H-benzo[b]azepin-5-yl)amine (2.85 g, 5.16 mmol) (Example 3, Step 18) in acetic acid (25 mL) at room temperature. Stir for 2 hours. Evaporate the solvent under reduced pressure. Partition the residue between ethyl acetate (250 mL) and aqueous Na$_2$CO$_3$ (250 mL). Separate the layers, dry over Na$_2$SO$_4$, filter and concentrate. Purify the residue by column chromatography on silica gel, eluting with ethyl acetate/hexanes (0-30%), to provide the title compound as an off-white solid (2.99 g, 92%). MS (ES+): 631, 633 (M+H).

Step 2. Preparation of (S)-(3,5-Bis-trifluoromethyl-benzyl)-(7,9-dimethyl-8-trifluoromethyl-2,3,4,5-tetrahydro-1H-benzo[b]azepin-5-yl)-(2-methyl-2H-tetrazol-5-yl)-amine

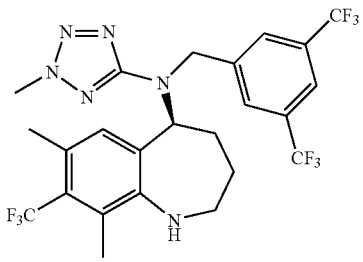

Add cesium fluoride (2.44 g, 16.1 mmol) to a mixture of (S)-(3,5-Bis-trifluoromethyl-benzyl)-(9-bromo-7-methyl-8-trifluoromethyl-2,3,4,5-tetrahydro-1H-benzo[b]azepin-5-yl)-(2-methyl-2H-tetrazol-5-yl)-amine and methyl boronic acid (0.820 g, 13.8 mmol) in dioxane (50.0 mL). Purge the mixture with nitrogen for 15 min. Add 1,1'-bis(diphenylphosphino)ferrocene palladium (II) chloride, complex with dichloromethane (0.290 g, 0.355 mmol) under nitrogen. Heat the reaction mixture for 3 h. Cool down to room temperature and then evaporate the solvent under reduced pressure. Partition the residue between ethyl acetate (100 mL) and water (100 mL). Separate the layers and extract the aqueous with more ethyl acetate (2×50 mL). Combine the organic layers, dry over Na$_2$SO$_4$, filter and concentrate. Purify the residue by column chromatography on silica gel, eluting with ethyl acetate/hexanes (0-35%), to provide the title compound as an off-white solid (2.16 g, 83%). MS (ES+): 567 (M+H).

Step 3. Preparation of (S)-(3,5-Bis-trifluoromethyl-benzyl)-(1-cyclopropylmethyl-7,9-dimethyl-8-trifluoromethyl-2,3,4,5-tetrahydro-1H-benzo[b]azepin-5-yl)-(2-methyl-2H-tetrazol-5-yl)-amine

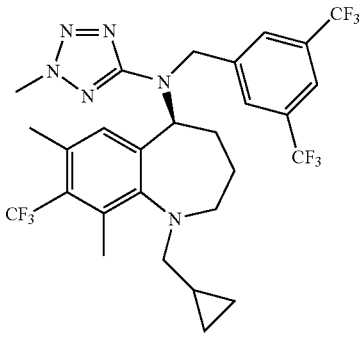

Prepare the title compound by essentially following the procedure described in Example 3, Step 19 by replacing cyclopentanecarboxaldehyde with cyclopropanecarboxaldehyde, and (S)-(3,5-bistrifluoromethylbenzyl)-(2-methyl-2H-tetrazol-5-yl)-(7-methyl-8-trifluoromethyl-2,3,4,5-tetrahydro-1H-benzo[b]azepin-5-yl)amine with (S)-(3,5-Bis-trifluoromethyl-benzyl)-(7,9-dimethyl-8-trifluoromethyl-2, 3,4,5-tetrahydro-1H-benzo[b]azepin-5-yl)-(2-methyl-2H-tetrazol-5-yl)-amine. MS (ES+): 621 (M+H).

Example 149

Synthesis of (S)-(3,5-Bis-trifluoromethyl-benzyl)-(1-cyclopropylmethyl-7,9-dimethyl-8-trifluoromethyl-2,3,4,5-tetrahydro-1H-benzo[b]azepin-5-yl)-(2-methyl-2H-tetrazol-5-yl)-amine hydrochloride

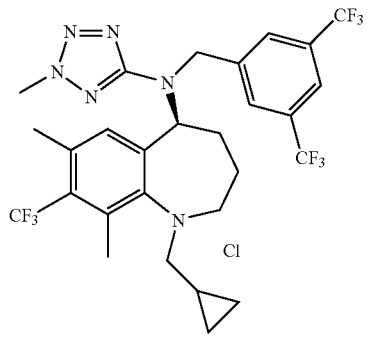

Dissolve (S)-(3,5-Bis-trifluoromethyl-benzyl)-(1-cyclopropylmethyl-7,9-dimethyl-8-trifluoromethyl-2,3,4,5-tetrahydro-1H-benzo[b]azepin-5-yl)-(2-methyl-2H-tetrazol-5-yl)-amine (Example 148) (0.0210 g, 0.0338 mmol) in ethyl ether (0.5 mL). Add HCl in ether (1.0 N, 0.0338 mL). Evaporate the solvent and then triturate the residue with hexane to provide an off-white powder. MS (ES+): 621 (M+H).

Example 150

Synthesis of (S)-(3,5-Bis-trifluoromethyl-benzyl)-(1-cyclopentylmethyl-7,9-dimethyl-8-trifluoromethyl-2,3,4,5-tetrahydro-1H-benzo[b]azepin-5-yl)-(2-methyl-2H-tetrazol-5-yl)-amine

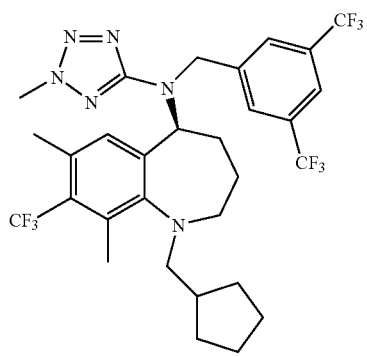

Prepare the title compound by essentially following the procedure described in Example 148, Step 3 by replacing cyclopropanecarboxaldehyde with cyclopentanecarboxaldehyde. MS (ES+): 649 (M+H).

Example 151

Synthesis of (S)-(3,5-Bis-trifluoromethyl-benzyl)-(7,9-dimethyl-1-pyridin-4-ylmethyl-8-trifluoromethyl-2,3,4,5-tetrahydro-1H-benzo[b]azepin-5-yl)-(2-methyl-2H-tetrazol-5-yl)-amine

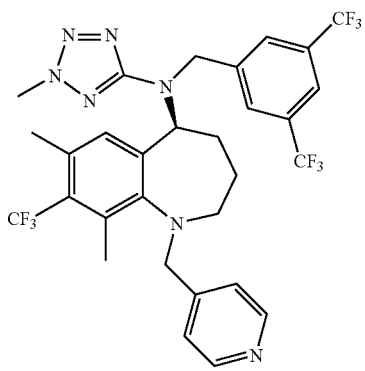

Prepare the title compound by essentially following the procedure described in Example 148, Step 3 by replacing cyclopropanecarboxaldehyde with pyridine-4-carbaldehyde and 1,2-dichloroethane with acetonitrile. MS (ES+): 658 (M+H).

Example 152

Synthesis of (S)-(3,5-Bis-trifluoromethyl-benzyl)-(1-ethyl-7,9-dimethyl-8-trifluoromethyl-2,3,4,5-tetrahydro-1H-benzo[b]azepin-5-yl)-(2-methyl-2H-tetrazol-5-yl)-amine

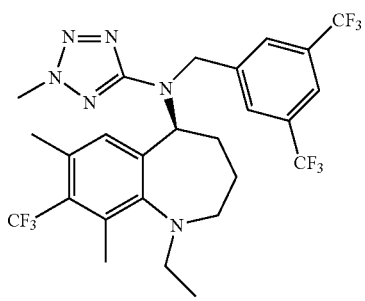

Prepare the title compound by essentially following the procedure described in Example 148, Step 3 by replacing cyclopropanecarboxaldehyde with acetaldehyde. MS (ES+): 595 (M+H).

Example 153

Synthesis of (S)-(4-{5-[(3,5-Bis-trifluoromethyl-benzyl)-(2-methyl-2H-tetrazol-5-yl)-amino]-7,9-dimethyl-8-trifluoromethyl-2,3,4,5-tetrahydro-benzo[b]azepin-1-ylmethyl}-cyclohexyl)-acetic acid

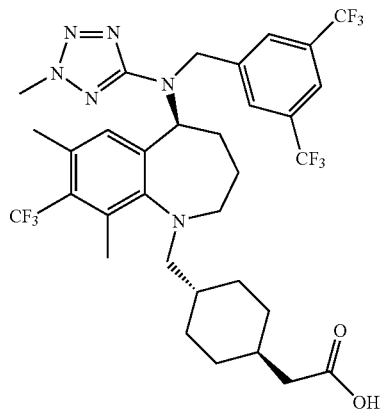

Step 1. Preparation of (S)-(4-{5-[(3,5-Bis-trifluoromethyl-benzyl)-(2-methyl-2H-tetrazol-5-yl)-amino]-7,9-dimethyl-8-trifluoromethyl-2,3,4,5-tetrahydro-benzo[b]azepin-1-ylmethyl}-cyclohexyl)-acetic acid methyl ester

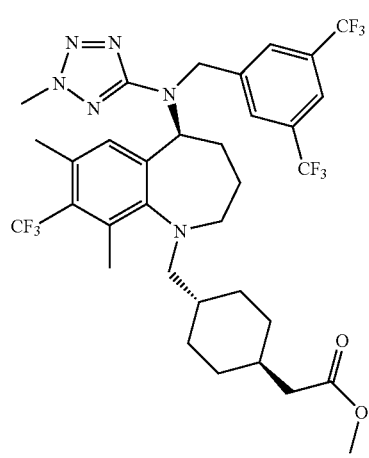

Prepare the title compound by essentially following the procedure described in Example 148, Step 3 by replacing cyclopropanecarboxaldehyde with (4-formyl-cyclohexyl)-acetic acid methyl ester. MS (ES+): 735 (M+H).

Step 2. Preparation of (S)-(4-{5-[(3,5-Bis-trifluoromethyl-benzyl)-(2-methyl-2H-tetrazol-5-yl)-amino]-7,9-dimethyl-8-trifluoromethyl-2,3,4,5-tetrahydro-benzo[b]azepin-1-ylmethyl}-cyclohexyl)-acetic acid

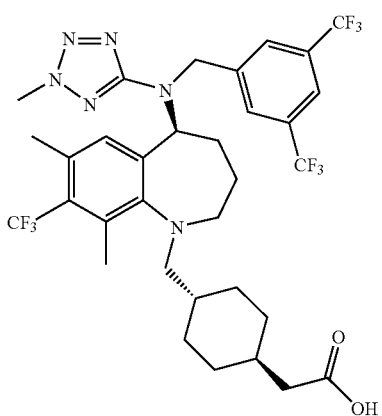

Heat the mixture of (S)-(4-{5-[(3,5-Bis-trifluoromethyl-benzyl)-(2-methyl-2H-tetrazol-5-yl)-amino]-7,9-dimethyl-8-trifluoromethyl-2,3,4,5-tetrahydro-benzo[b]azepin-1-ylmethyl}-cyclohexyl)-acetic acid methyl ester (0.0950 g, 0.129 mmol) in 5.0 N NaOH (1 mL) and methanol (2 mL) under reflux for 2 h. Evaporate the solvents and re-dissolve in water (10 mL). Adjust to pH=7 by adding 2.0 N HCl. Extract with ethyl acetate (2×10 mL). Combine organic layers, dry over anhydrous sodium sulfate and filter. Remove the solvent under reduced pressure. Chromatograph the residue over silica gel, eluting with ethyl acetate/hexanes (0-100%), to provide the title compound as a white foam (0.0620 g, 67%). MS (ES+): 721 (M+H); 719 (M−H).

Example 154

Synthesis of (S)-5-{5-[(3,5-Bis-trifluoromethyl-benzyl)-(2-methyl-2H-tetrazol-5-yl)-amino]-7,9-dimethyl-8-trifluoromethyl-2,3,4,5-tetrahydro-benzo[b]azepin-1-yl}-3,3-dimethyl-pentanoic acid

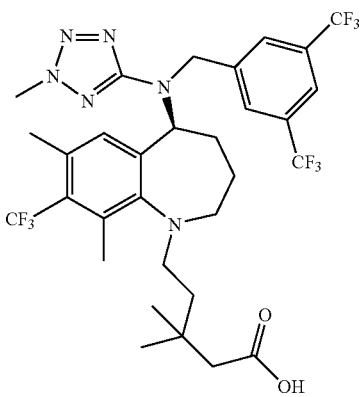

Step 1. Preparation of (S)-5-{5-[(3,5-Bis-trifluoromethyl-benzyl)-(2-methyl-2H-tetrazol-5-yl)-amino]-7,9-dimethyl-8-trifluoromethyl-2,3,4,5-tetrahydro-benzo[b]azepin-1-yl}-3,3-dimethyl-pentanoic acid methyl ester

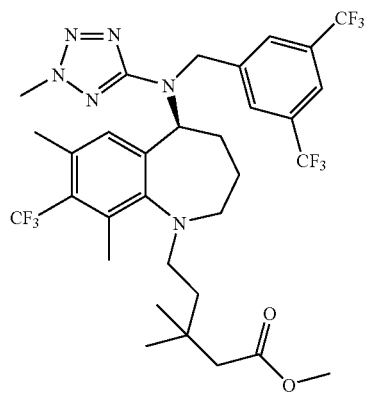

Prepare the title compound by essentially following the procedure described in Example 148, Step 3 by replacing cyclopropanecarboxaldehyde with 3,3-Dimethyl-5-oxo-pentanoic acid methyl ester. MS (ES+): 709 (M+H).

Step 2. Preparation of (S)-5-{5-[(3,5-Bis-trifluoromethyl-benzyl)-(2-methyl-2H-tetrazol-5-yl)-amino]-7,9-dimethyl-8-trifluoromethyl-2,3,4,5-tetrahydro-benzo[b]azepin-1-yl}-3,3-dimethyl-pentanoic acid

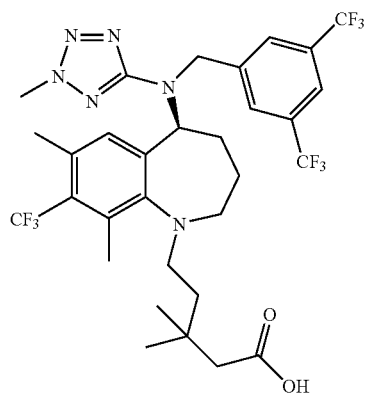

Heat the mixture of (S)-5-{5-[(3,5-Bis-trifluoromethyl-benzyl)-(2-methyl-2H-tetrazol-5-yl)-amino]-7,9-dimethyl-8-trifluoromethyl-2,3,4,5-tetrahydro-benzo[b]azepin-1-yl}-3,3-dimethyl-pentanoic acid methyl ester (0.120 g, 0.169 mmol) in 5.0 N NaOH (1 mL) and methanol (5 mL) under reflux for 2 h. Evaporate the solvents and re-dissolve in water (10 mL). Adjust to pH=4 by adding 4.0 N HCl. Extract with ethyl acetate (2×10 mL). Combine the organic layers, dry over anhydrous sodium sulfate and filter. Remove the solvent under reduced pressure. Chromatograph the residue over silica gel, eluting with ethyl acetate/hexanes (0-100%), to provide the title compound as white foam (0.104 g, 88%). MS (ES+): 695 (M+H); 693 (M−H).

Example 155

Synthesis of (S)-{5-[(3,5-Bis-trifluoromethyl-benzyl)-(2-methyl-2H-tetrazol-5-yl)-amino]-7,9-dimethyl-8-trifluoromethyl-2,3,4,5-tetrahydro-benzo[b]azepin-1-yl}-oxo-acetic acid methyl ester

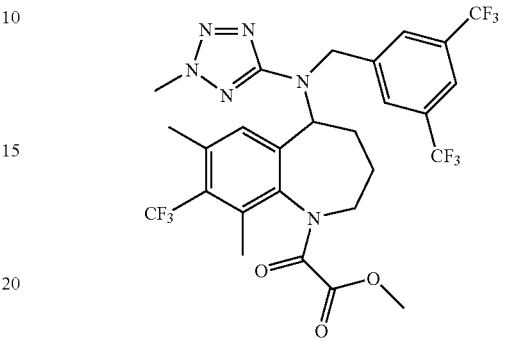

Dissolve (S)-(3,5-Bis-trifluoromethyl-benzyl)-(7,9-dimethyl-8-trifluoromethyl-2,3,4,5-tetrahydro-1H-benzo[b]azepin-5-yl)-(2-methyl-2H-tetrazol-5-yl)-amine (Example 148, Step 2) (0.200 g, 0.353 mmol) in dichloromethane (4 mL), cool the solution down with an ice-water bath. Add pyridine (0.143 mL, 1.77 mmol) followed by chloro-oxo-acetic acid methyl ester (0.162 mL, 1.77 mmol) dropwise. Warm up the reaction to room temperature and stir overnight. Dilute the reaction mixture with more dichloromethane (10 mL), and wash with aqueous NaHCO₃ (10 mL). Extract back the aqueous layer with dichloromethane (10 mL). Combine the organic layers, dry over anhydrous sodium sulfate and filter. Remove the solvent under reduced pressure. Chromatograph the residue over silica gel, eluting with ethyl acetate/hexanes (0-30%), to provide the title compound (0.187 g, 81%). MS (ES+): 653 (M+H).

Example 156

Synthesis of (S)-5-{5-[(3,5-Bis-trifluoromethyl-benzyl)-(2-methyl-2H-tetrazol-5-yl)-amino]-7,9-dimethyl-8-trifluoromethyl-2,3,4,5-tetrahydro-benzo[b]azepin-1-yl}-5-oxo-pentanoic acid methyl ester

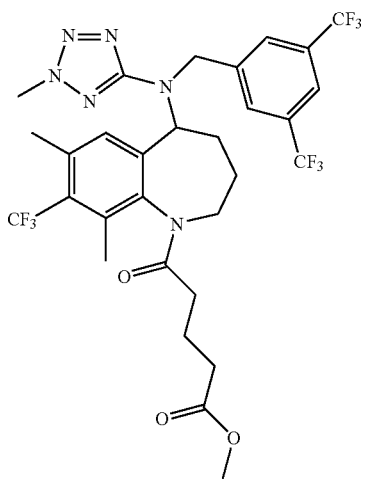

Prepare the title compound by essentially following the procedure described in Example 155 by replacing chloro-oxo-acetic acid methyl ester with 4-chlorocarbonyl-butyric acid methyl ester. MS (ES+): 695 (M+H).

Example 157

Synthesis of (S)-2-{5-[(3,5-Bis-trifluoromethyl-benzyl)-(2-methyl-2H-tetrazol-5-yl)-amino]-7,9-dimethyl-8-trifluoromethyl-2,3,4,5-tetrahydro-benzo[b]azepin-1-yl}-ethanol

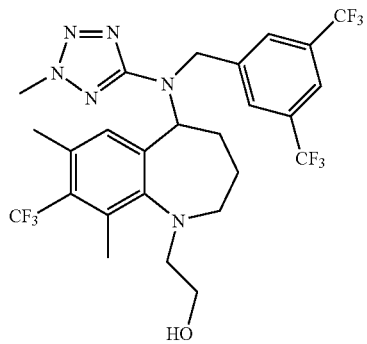

Prepare the title compound by essentially following the procedures described in Example 33, by replacing (3,5-Bis-trifluoromethyl-benzyl)-(2-methyl-2H-tetrazol-5-yl)-(7-methyl-8-trifluoromethyl-2,3,4,5-tetrahydro-1H-benzo[b]azepin-5-yl)-amine with (3,5-Bis-trifluoromethyl-benzyl)-(7,9-dimethyl-8-trifluoromethyl-2,3,4,5-tetrahydro-1H-benzo[b]azepin-5-yl)-(2-methyl-2H-tetrazol-5-yl)-amine. MS (ES+): 611 (M+H).

Example 158

Synthesis of (S)-[2-(2-Amino-ethyl)-2H-tetrazol-5-yl]-(3,5-bis-trifluoromethyl-benzyl)-(1-cyclopropylmethyl-7,9-dimethyl-8-trifluoromethyl-2,3,4,5-tetrahydro-1H-benzo[b]azepin-5-yl)-amine

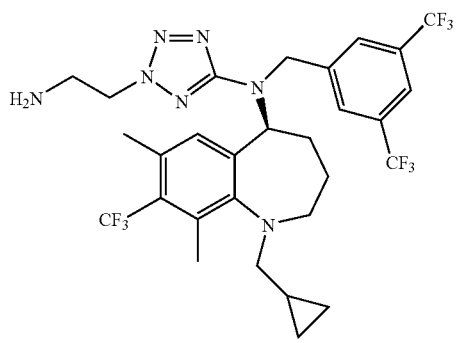

Step 1. Preparation of (S)-2-(2-{5-[(3,5-Bis-trifluoromethyl-benzyl)-(7,9-dimethyl-8-trifluoromethyl-2,3,4,5-tetrahydro-1H-benzo[b]azepin-5-yl)-amino]-tetrazol-2-yl}-ethyl)-isoindole-1,3-dione

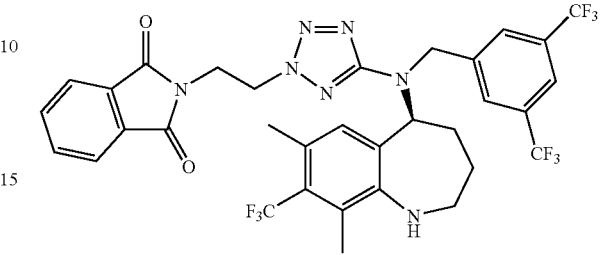

Prepare the title compound by essentially following the procedure described in Example 148, Step 1 and 2, by replacing (3,5-bis-trifluoromethyl-benzyl)-(2-methyl-2H-tetrazol-5-yl)-(7-methyl-8-trifluoromethyl-2,3,4,5-tetrahydro-1H-benzo[b]azepin-5-yl)-amine with 2-(2-{5-[(3,5-bis-trifluoromethyl-benzyl)-(7-methyl-8-trifluoromethyl-2,3,4,5-tetrahydro-1H-benzo[b]azepin-5-yl)-amino]-tetrazol-2-yl}-ethyl)-isoindole-1,3-dione (Example 126, Step 2). MS (ES+): 726 (M+H).

Step 2. Preparation of (S)-2-(2-{5-[(3,5-Bis-trifluoromethyl-benzyl)-(1-cyclopropylmethyl-7,9-dimethyl-8-trifluoromethyl-2,3,4,5-tetrahydro-1H-benzo[b]azepin-5-yl)-amino]-tetrazol-2-yl}-ethyl)-isoindole-1,3-dione

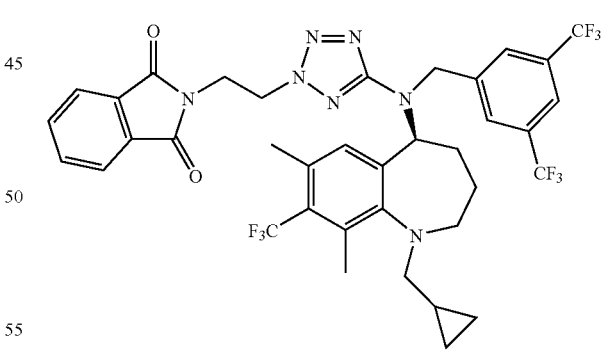

Prepare the title compound by essentially following the procedure described in Example 148, Step 3, by replacing (S)-(3,5-Bis-trifluoromethyl-benzyl)-(7,9-dimethyl-8-trifluoromethyl-2,3,4,5-tetrahydro-1H-benzo[b]azepin-5-yl)-(2-methyl-2H-tetrazol-5-yl)-amine with (S)-2-(2-{5-[(3,5-Bis-trifluoromethyl-benzyl)-(7,9-dimethyl-8-trifluoromethyl-2,3,4,5-tetrahydro-1H-benzo[b]azepin-5-yl)-amino]-tetrazol-2-yl}-ethyl)-isoindole-1,3-dione. MS (ES+): 780 (M+H).

Step 3. Preparation of (S)-[2-(2-Amino-ethyl)-2H-tetrazol-5-yl]-(3,5-bis-trifluoromethyl-benzyl)-(1-cyclopropylmethyl-7,9-dimethyl-8-trifluoromethyl-2,3,4,5-tetrahydro-1H-benzo[b]azepin-5-yl)-amine

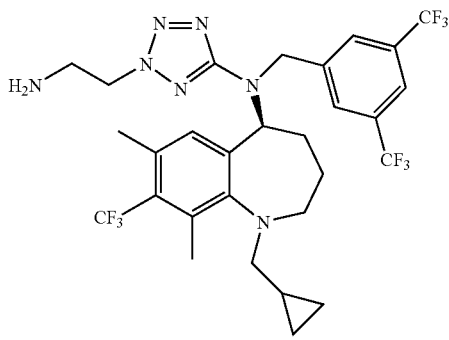

Heat the mixture of (S)-2-(2-{5-[(3,5-Bis-trifluoromethyl-benzyl)-(1-cyclopropylmethyl-7,9-dimethyl-8-trifluoromethyl-2,3,4,5-tetrahydro-1H-benzo[b]azepin-5-yl)-amino]-tetrazol-2-yl}-ethyl)-isoindole-1,3-dione (0.175 g, 0.224 mmol) and hydrazine hydrate (0.1 ml) in methanol (2.0 mL) at 60° C. overnight. Cool down to room temperature. Remove the precipitate by filtration and evaporate the solvent to provide the title compound (0.143 g, 98%). MS (ES+): 650 (M+H).

Example 159

Synthesis of (S)-tert-butyl 4-{5-[(3,5-bistrifluoromethylbenzyl)-(2-methyl-2H-tetrazol-5-yl)amino]-7,9-dimethyl-8-trifluoromethyl-2,3,4,5-tetrahydrobenzo[b]azepin-1-ylmethyl}-piperidine-1-carboxylate

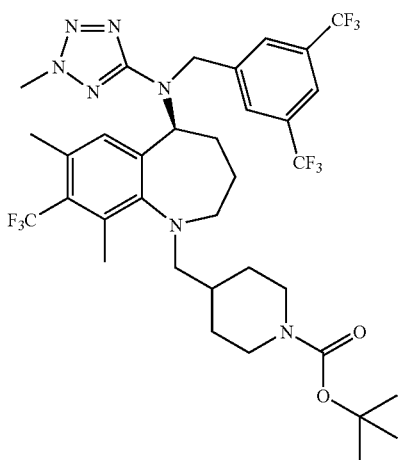

Add sodium triacetoxyborohydride (0.374 g, 1.76 mmol) portionwise to a solution of (S)-(3,5-bistrifluoromethylbenzyl)-(7,9-dimethyl-8-trifluoromethyl-2,3,4,5-tetrahydro-1H-benzo[b]azepin-5-yl)-(2-methyl-2H-tetrazol-5-yl)-amine (Example 148, Step 2) (0.250 g, 0.441 mmol), tert-butyl-4-formylpiperidine-1-carboxylate (0.282 g, 1.32 mmol) and glacial acetic acid (0.2 mL) in 1,2-dichloroethane (3 mL) at room temperature under an atmosphere of nitrogen and stir for 24 h. Quench the reaction with saturated sodium bicarbonate (5 mL) and dilute with dichloromethane (15 mL). Separate the layers and wash the organic layer with saturated sodium bicarbonate and brine (20 mL each). Dry the organic layer over sodium sulfate, filter and remove the solvent under reduced pressure. Purify the residue using flash column chromatography on silica gel, eluting with hexanes/ethyl acetate (80:20), to provide the title compound as a white crushable foam (0.272 g, 81%). $^1$H NMR (CDCl$_3$, 500 MHz) δ 0.87-1.14 (m, 3H), 1.24-1.34 (m, 1H), 1.45 (s, 9H), 1.61-1.97 (m, 7H), 2.30-2.33 (m, 6H), 2.65-2.75 (m, 2H), 2.86-2.89 (m, 2H), 2.95-3.11 (m, 1H), 3.25-3.28 (m, 1H), 4.13 (s, 3H), 4.81-4.88 (m, 1H), 5.21 (br s, 1H), 5.60 (br s, 1H), 6.57 (s, 1H), 7.77 (s, 3H); ESI MS m/z 764 [C$_{35}$H$_{42}$F$_9$N$_7$O$_2$+H]$^+$.

Example 160

Synthesis of (S)-(3,5-bistrifluoromethylbenzyl)-(7,9-dimethyl-1-piperidin-4-ylmethyl-8-trifluoromethyl-2,3,4,5-tetrahydro-1H-benzo[b]azepin-5-yl)-(2-methyl-2H-tetrazol-5-yl)-amine

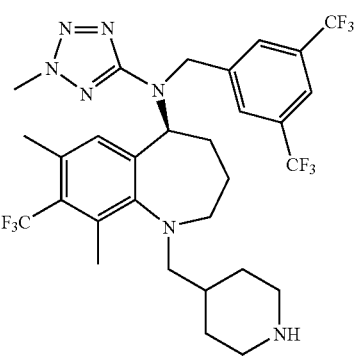

Add trifluoroacetic acid (1.7 mL) slowly to a solution of (S)-tert-butyl 4-{5-[(3,5-bistrifluoromethylbenzyl)-(2-methyl-2H-tetrazol-5-yl)amino]-7,9-dimethyl-8-trifluoromethyl-2,3,4,5-tetrahydrobenzo[b]azepin-1-ylmethyl}-piperidine-1-carboxylate (Example 159) (0.251 g, 0.329 mmol) in dichloromethane (4 mL) at 0° C. under an atmosphere of nitrogen and stir for 4.5 h. Pour the reaction into saturated sodium bicarbonate (25 mL) and dilute with dichloromethane (15 mL). Separate the layers and extract the aqueous layer with dichloromethane (10 mL). Combine the organic layers, wash with saturated sodium bicarbonate (25 mL), dry over sodium sulfate, filter and remove the solvent under reduced pressure. Purify the residue using flash column chromatography on silica gel, eluting with dichloromethane/methanol/concentrated ammonium hydroxide (90:10:1), to provide the title compound as a white solid (0.101 g, 46%): $^1$H NMR (CDCl$_3$, 500 MHz) δ 1.01-1.11 (m, 2H), 1.47-1.66 (m, 3H), 1.73-1.95 (m, 5H), 2.34 (s, 6H), 2.55-2.60 (m, 2H), 2.84-2.87 (m, 2H), 2.98-3.09 (m, 3H), 3.25 (br s, 1H), 4.13 (m, 3H), 4.73-4.96 (m, 1H), 5.12 (br s, 1H), 5.56 (br s, 1H), 6.58 (s, 1H), 7.77 (s, 3H); ESI MS m/z 664 [C$_{30}$H$_{34}$F$_9$N$_7$+H]$^+$.

Example 161

Synthesis of (S)-(3,5-bistrifluoromethylbenzyl)-[7,9-dimethyl-1-(1-methylpiperidin-4-ylmethyl)-8-trifluoromethyl-2,3,4,5-tetrahydro-1H-benzo[b]azepin-5-yl]-(2-methyl-2H-tetrazol-5-yl)-amine

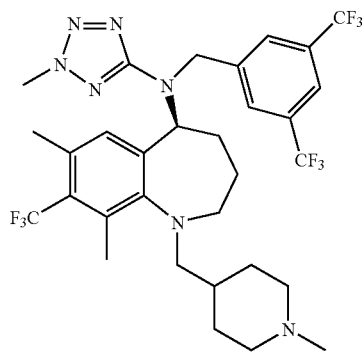

Add glacial acetic acid (0.25 mL) over 25 minutes to a solution of (S)-(3,5-bistrifluoromethylbenzyl)-(7,9-dimethyl-1-piperidin-4-ylmethyl-8-trifluoromethyl-2,3,4,5-tetrahydro-1H-benzo[b]azepin-5-yl)-(2-methyl-2H-tetrazol-5-yl)-amine (Example 160) (0.038 g, 0.057 mmol), 37% aqueous formaldehyde (0.014 mL, 0.189 mmol) and sodium cyanoborohydride (0.011 g, 0.172 mmol) in acetonitrile (2.5 mL) at room temperature under an atmosphere of nitrogen and stir for 18 h. Dilute the reaction with dichloromethane (20 mL) and wash with 2 N sodium hydroxide and brine (10 mL each). Dry the organic layer over sodium sulfate, filter and remove the solvent under reduced pressure. Purify the residue using flash column chromatography on silica gel, eluting with dichloromethane/methanol/concentrated ammonium hydroxide (90:10:1), to provide the title compound as a white crushable foam (0.028 g, 72%). $^1$H NMR (CDCl$_3$, 500 MHz) δ 1.15-1.70 (m, 4H), 1.83-2.06 (m, 7H), 2.33-2.35 (m, 9H), 2.76-3.03 (m, 5H), 3.24 (br s, 1H), 4.13 (m, 3H), 4.80-4.87 (m, 1H), 5.14 (br s, 1H), 5.58 (br s, 1H), 6.58 (m, 1H), 7.77-7.78 (m, 3H); ESI MS m/z 678 [C$_{31}$H$_{36}$F$_9$N$_7$+H]$^+$.

Example 162

Synthesis of (S)-(3,5-Bis-trifluoromethyl-benzyl)-(2-methyl-2H-tetrazol-5-yl)-(5-pyridin-4-ylmethyl-3,5,6,7,8,9-hexahydro-1H-2-oxa-5-aza-cyclohepta[f]inden-9-yl)-amine Hydrochloride

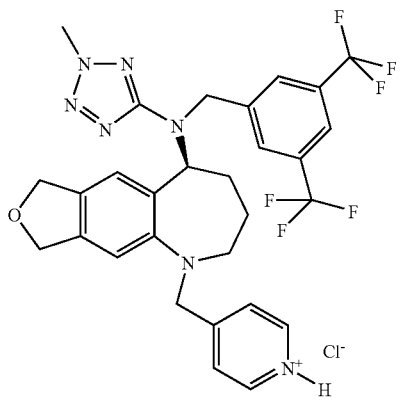

To a solution of (S)-(3,5-Bis-trifluoromethyl-benzyl)-(2-methyl-2H-tetrazol-5-yl)-(5-pyridin-4-ylmethyl-3,5,6,7,8,9-hexahydro-1H-2-oxa-5-aza-cyclohepta[f]inden-9-yl)-amine (Example 103) in diethyl ether, add HCl as a 1.0 M solution in diethyl ether. Remove solvent under a slow stream of nitrogen followed by vacuum to obtain the title compound as an off white solid. MS (ES+): 580 (M+H).

Example 163

Synthesis of (S)-[2-(2-Amino-ethyl)-2H-tetrazol-5-yl]-(3,5-bis-trifluoromethyl-benzyl)-(5-thiazol-2-ylmethyl-3,5,6,7,8,9-hexahydro-1H-2-oxa-5-aza-cyclohepta[f]inden-9-yl)-amine

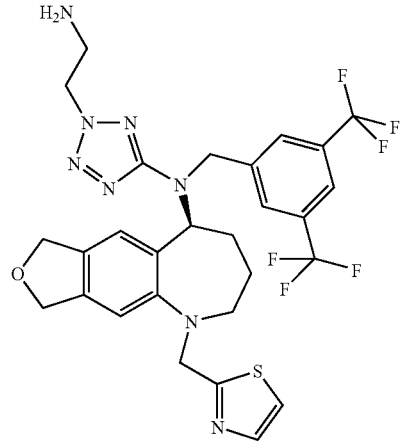

Prepare the title compound by essentially following the procedures described in the synthesis of (S)-[2-(2-Amino-ethyl)-2H-tetrazol-5-yl]-(5-benzyl-3,5,6,7,8,9-hexahydro-1H-2-oxa-5-aza-cyclohepta[f]inden-9-yl)-(3,5-bis-trifluoromethyl-benzyl)-amine (Example 107) starting with (S)-2-(2-{5-[(3,5-Bis-trifluoromethyl-benzyl)-(3,5,6,7,8,9-hexahydro-1H-2-oxa-5-aza-cyclohepta[f]inden-9-yl)-amino]-tetrazol-2-yl}-ethyl)-isoindole-1,3-dione (Example 107, Step 1) and replacing benzaldehyde with thiazole-2-carbaldehyde in Example 107, Step 2. MS (ES+): 637 (M−H).

Example 164

Synthesis of (S)-1-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-yl}-2-ethyl-butan-1-one

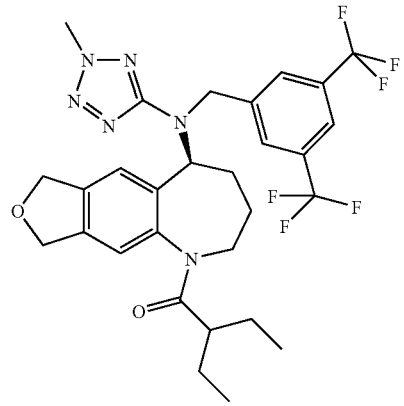

Add pyridine (0.35 mmol) followed by 2-ethyl-butyryl chloride (0.35 mmol) to a solution of (S)-(3,5-Bis-trifluoromethyl-benzyl)-(3,5,6,7,8,9-hexahydro-1H-2-oxa-5-aza-cyclohepta[f]inden-9-yl)-(2-methyl-2H-tetrazol-5-yl)-amine (Example 73, Step 7) (0.17 mmol) in dichloromethane (3 mL). After stirring at room temperature for 14 h, dilute the reaction with dichloromethane (10 mL) followed by water (10 mL). Separate the organic phase and wash the aqueous with dichloromethane (2×10 mL). Dry the combined organics over sodium sulfate, filter, and remove solvent in vacuo. Chromatograph the crude product over silica gel using ethyl acetate/hexane (10-50%) to elute to obtain the title compound as a colorless foam. MS (ES+): 611 (M+H).

Example 165

Synthesis of (S)-(4-{9-[(3,5-Bis-trifluoromethyl-benzyl)-(2-methyl-2H-tetrazol-5-yl)-amino]-4-methyl-1,3,6,7,8,9-hexahydro-2-oxa-5-aza-cyclohepta[f]inden-5-ylmethyl}-cyclohexyl)-acetic acid

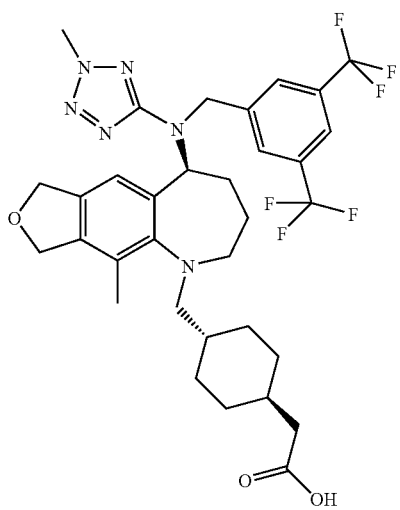

Step 1. Preparation of (S)-(3,5-Bis-trifluoromethyl-benzyl)-(4-bromo-3,5,6,7,8,9-hexahydro-1H-2-oxa-5-aza-cyclohepta[f]inden-9-yl)-(2-methyl-2H-tetrazol-5-yl)-amine

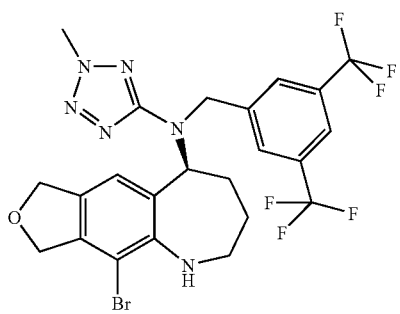

To a solution of (S)-(3,5-Bis-trifluoromethyl-benzyl)-(3,5,6,7,8,9-hexahydro-1H-2-oxa-5-aza-cyclohepta[f]inden-9-yl)-(2-methyl-2H-tetrazol-5-yl)-amine (Example 73, Step 7) (2.64 mmol) in chloroform (20 mL), add N-bromosuccinamide (2.9 mmol) along with sodium bicarbonate (5.28 mmol). After stirring the mixture at room temperature for 20 minutes, add water (20 mL) and dilute the mixture with dichloromethane (20 mL). Separate the organics and wash the aqueous with dichloromethane (2×10 mL). Dry the combined organics over sodium sulfate, filter, and remove solvent under vacuum. Chromatograph the crude intermediate over silica gel eluting with ethyl acetate/hexane to obtain the title compound as an off white solid. MS (ES+): 593 (M+H).

Step 2. Preparation of (S)-(3,5-Bis-trifluoromethyl-benzyl)-(4-methyl-3,5,6,7,8,9-hexahydro-1H-2-oxa-5-aza-cyclohepta[f]inden-9-yl)-(2-methyl-2H-tetrazol-5-yl)-amine

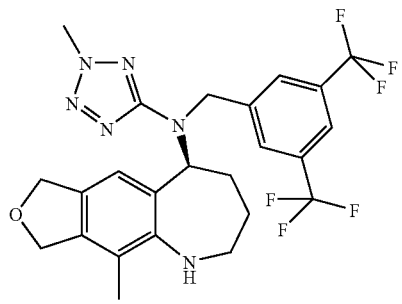

To a solution of (S)-(3,5-Bis-trifluoromethyl-benzyl)-(4-bromo-3,5,6,7,8,9-hexahydro-1H-2-oxa-5-aza-cyclohepta[f]inden-9-yl)-(2-methyl-2H-tetrazol-5-yl)-amine (2.16 mmol) in dioxane (150 mL), add bis(diphenylphosphinoferrocene)palladium(II) chloride (0.22 mmol) followed by cesium fluoride (9.32 mmol) and methylboronic acid (6.48 mmol). Heat the mixture under nitrogen to 95° C. After heating for 2 h, cool the reaction mixture to room temperature and dilute with ethyl acetate (50 mL) and water (50 mL). Separate the organics and wash the aqueous with ethyl acetate (2×20 mL). Dry the combined organics over sodium sulfate, filter, and remove the solvent under vacuum. Chromatograph the crude product over silica gel, eluting with ethyl acetate/hexane (10-45%) to obtain the title compound as an off white solid. MS (ES+): 527 (M+H).

Step 3. Preparation of (S)-(4-{9-[(3,5-Bis-trifluoromethyl-benzyl)-(2-methyl-2H-tetrazol-5-yl)-amino]-4-methyl-1,3,6,7,8,9-hexahydro-2-oxa-5-aza-cyclohepta[f]inden-5-ylmethyl}-cyclohexyl)-acetic acid methyl ester

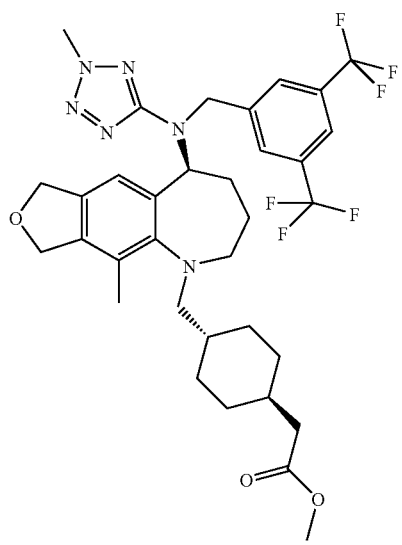

Prepare the title compound by essentially following the procedures described in the synthesis of (S)5-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-ylmethyl}-thiophene-2-carboxylic acid (Example 102), starting with (S)-(3,5-Bis-trifluoromethyl-benzyl)-(4-methyl-3,5,6,7,8,9-hexahydro-1H-2-oxa-5-aza-cyclohepta[f]inden-9-yl)-(2-methyl-2H-tetrazol-5-yl)-amine and replacing 5-formyl-thiophene-2-carboxylic acid with (4-formyl-cyclohexyl)-acetic acid methyl ester.

Step 4. Synthesis of (4-{9-[(3,5-Bis-trifluoromethyl-benzyl)-(2-methyl-2H-tetrazol-5-yl)-amino]-4-methyl-1,3,6,7,8,9-hexahydro-2-oxa-5-aza-cyclohepta[f]inden-5-ylmethyl}-cyclohexyl)-acetic acid

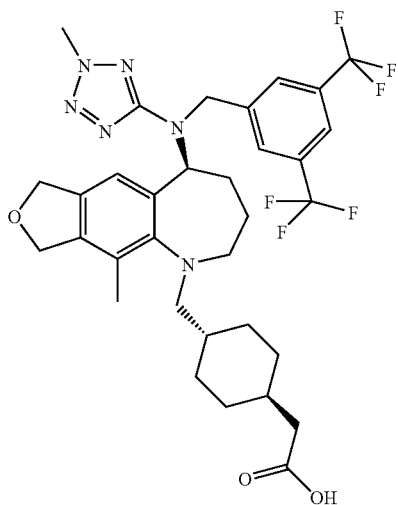

To a solution of (S)-(4-{9-[(3,5-Bis-trifluoromethyl-benzyl)-(2-methyl-2H-tetrazol-5-yl)-amino]-4-methyl-1,3,6,7,8,9-hexahydro-2-oxa-5-aza-cyclohepta[f]inden-5-ylmethyl}-cyclohexyl)-acetic acid methyl ester (0.15 mmol) in methanol (5 mL), add 5 N sodium hydroxide (3 mL). Heat the mixture to 60° C. for 2 h, then cool to room temperature and dilute with water (20 mL). Neutralize the reaction with 5M HCl and extract the organics with ethyl acetate (3×10 mL). Dry the combined organics over sodium sulfate, filter, and remove the solvent under vacuum. Chromatograph the product over silica gel, eluting with ethyl acetate/hexane (10-70%) to obtain the title compound as a colorless foam. MS (ES+): 681 (M+H).

Example 166

Synthesis of (S)-4-{9-[(3,5-Bis-trifluoromethyl-benzyl)-(2-methyl-2H-tetrazol-5-yl)-amino]-4-methyl-1,3,6,7,8,9-hexahydro-2-oxa-5-aza-cyclohepta[f]inden-5-ylmethyl}-benzoic acid

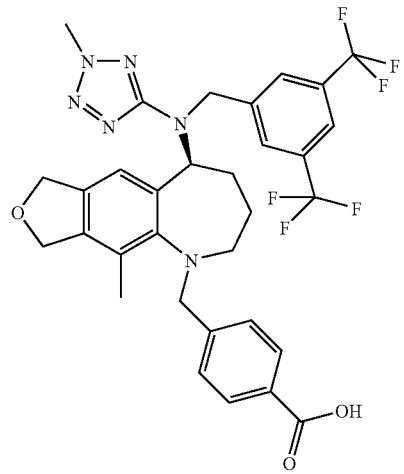

Prepare the title compound by essentially following the procedures described in the synthesis of (S)-(4-{9-[(3,5-Bis-trifluoromethyl-benzyl)-(2-methyl-2H-tetrazol-5-yl)-amino]-4-methyl-1,3,6,7,8,9-hexahydro-2-oxa-5-aza-cyclohepta[f]inden-5-ylmethyl}-cyclohexyl)-acetic acid (Example 165), starting with (S)-(3,5-Bis-trifluoromethyl-benzyl)-(4-methyl-3,5,6,7,8,9-hexahydro-1H-2-oxa-5-aza-cyclohepta[f]inden-9-yl)-(2-methyl-2H-tetrazol-5-yl)-amine and replacing (4-formyl-cyclohexyl)-acetic acid methyl ester with 4-formyl-benzoic acid methyl ester in Example 165, step 3. MS (ES+): 661 (M+H).

Example 167

Synthesis of (S)-5-{9-[(3,5-Bis-trifluoromethyl-benzyl)-(2-methyl-2H-tetrazol-5-yl)-amino]-4-methyl-1,3,6,7,8,9-hexahydro-2-oxa-5-aza-cyclohepta[f]inden-5-ylmethyl}-thiophene-2-carboxylic acid

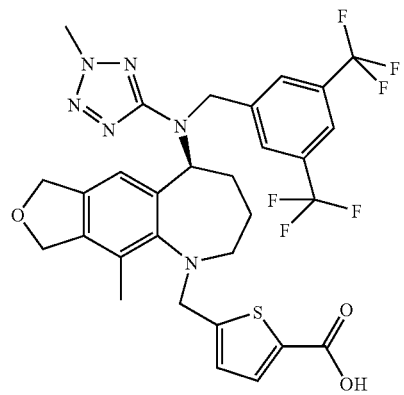

Prepare the title compound by essentially following the procedures described in the synthesis of (S)-(4-{9-[(3,5-Bistrifluoromethyl-benzyl)-(2-methyl-2H-tetrazol-5-yl)-amino]-4-methyl-1,3,6,7,8,9-hexahydro-2-oxa-5-aza-cyclohepta[f]inden-5-ylmethyl}-cyclohexyl)-acetic acid (Example 165), starting with (S)-(3,5-Bis-trifluoromethyl-benzyl)-(4-methyl-3,5,6,7,8,9-hexahydro-1H-2-oxa-5-aza-cyclohepta[f]inden-9-yl)-(2-methyl-2H-tetrazol-5-yl)-amine and replacing (4-formyl-cyclohexyl)-acetic acid methyl ester with 5-Formyl-thiophene-2-carboxylic acid in Example 165, Step 3. MS (ES+): 665 (M−H).

Example 168

Synthesis of (S)-(3,5-Bis-trifluoromethyl-benzyl)-(4-methyl-5-pyridin-3-ylmethyl-3,5,6,7,8,9-hexahydro-1H-2-oxa-5-aza-cyclohepta[f]inden-9-yl)-(2-methyl-2H-tetrazol-5-yl)-amine

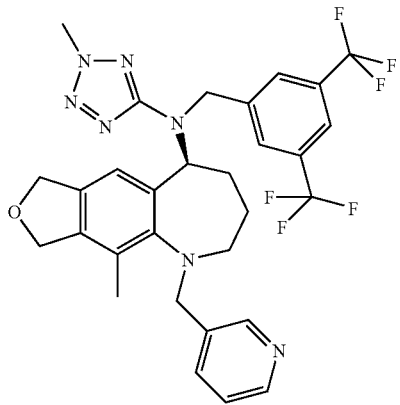

Prepare the title compound by essentially following the procedures described in the synthesis of (S)5-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-ylmethyl}-thiophene-2-carboxylic acid (Example 102), starting with (S)-(3,5-Bis-trifluoromethyl-benzyl)-(4-methyl-3,5,6,7,8,9-hexahydro-1H-2-oxa-5-aza-cyclohepta[f]inden-9-yl)-(2-methyl-2H-tetrazol-5-yl)-amine (Example 165, Step 2) and replacing 5-formyl-thiophene-2-carboxylic acid with pyridine-3-carbaldehyde. MS (ES+): 618 (M+H).

Example 169

Synthesis of (S)-(3,5-Bis-trifluoromethyl-benzyl)-(5-cyclopropylmethyl-4-methyl-3,5,6,7,8,9-hexahydro-1H-2-oxa-5-aza-cyclohepta[f]inden-9-yl)-(2-methyl-2H-tetrazol-5-yl)-amine

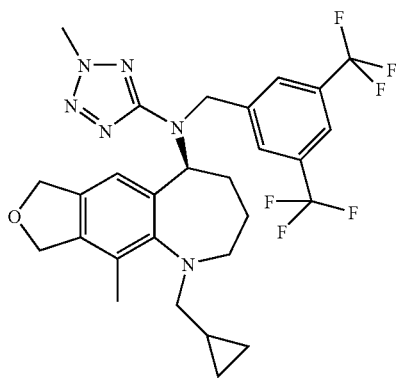

Prepare the title compound by essentially following the procedures described in the synthesis of (S)5-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-ylmethyl}-thiophene-2-carboxylic acid (Example 102), starting with (S)-(3,5-Bis-trifluoromethyl-benzyl)-(4-methyl-3,5,6,7,8,9-hexahydro-1H-2-oxa-5-aza-cyclohepta[f]inden-9-yl)-(2-methyl-2H-tetrazol-5-yl)-amine (Example 165, Step 2) and replacing 5-formyl-thiophene-2-carboxylic acid with cyclopropanecarboxaldehyde. MS (ES+): 581 (M+H).

Example 170

Synthesis of (S)-(3,5-Bis-trifluoromethyl-benzyl)-(5-cyclopentylmethyl-4-methyl-3,5,6,7,8,9-hexahydro-1H-2-oxa-5-aza-cyclohepta[f]inden-9-yl)-(2-methyl-2H-tetrazol-5-yl)-amine

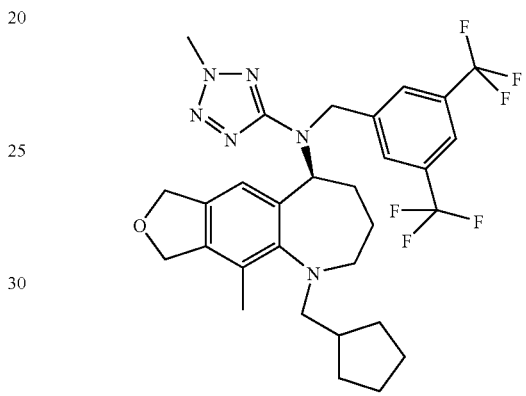

Prepare the title compound uby essentially following the procedures described in the synthesis of (S)5-{9-[(3,5-Bis-trifuoromethyl-benzyl)-(2-methyl-2H-tetrazol-5-yl)-amino]-1,3,6,7,8,9-hexahydro-2-oxa-5-aza-cyclohepta[f]inden-5-ylmethyl}-thiophene-2-carboxylic acid (Example 102), starting with (S)-(3,5-Bis-trifluoromethyl-benzyl)-(4-methyl-3,5,6,7,8,9-hexahydro-1H-2-oxa-5-aza-cyclohepta[f]inden-9-yl)-(2-methyl-2H-tetrazol-5-yl)-amine (Example 165, Step 2) and replacing 5-formyl-thiophene-2-carboxylic acid with cyclopentanecarboxaldehyde. MS (ES+): 609 (M+H).

Example 171

Synthesis of (S)-(3,5-Bis-trifluoromethyl-benzyl)-(5-cyclobutylmethyl-4-methyl-3,5,6,7,8,9-hexahydro-1H-2-oxa-5-aza-cyclohepta[f]inden-9-yl)-(2-methyl-2H-tetrazol-5-yl)-amine

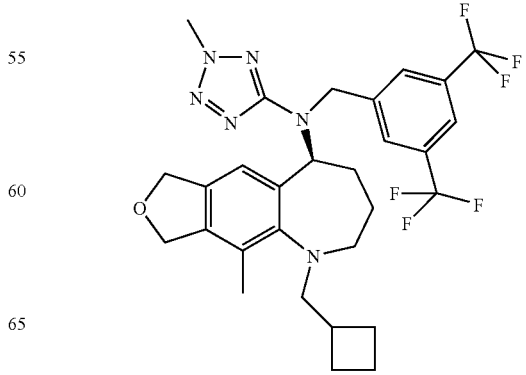

Prepare the title compound by essentially following the procedures described in the synthesis of (S)-5-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-ylmethyl}-thiophene-2-carboxylic acid (Example 102), starting with (S)-(3,5-Bis-trifluoromethyl-benzyl)-(4-methyl-3,5,6,7,8,9-hexahydro-1H-2-oxa-5-aza-cyclohepta[f]inden-9-yl)-(2-methyl-2H-tetrazol-5-yl)-amine (Example 165, Step 2) and replacing 5-formyl-thiophene-2-carboxylic acid with cyclobutanecarboxaldehyde. MS (ES+): 595 (M+H).

Example 172

Synthesis of (S)-(3,5-Bis-trifluoromethyl-benzyl)-(5-cyclobutyl-4-methyl-3,5,6,7,8,9-hexahydro-1H-2-oxa-5-aza-cyclohepta[f]inden-9-yl)-(2-methyl-2H-tetrazol-5-yl)-amine

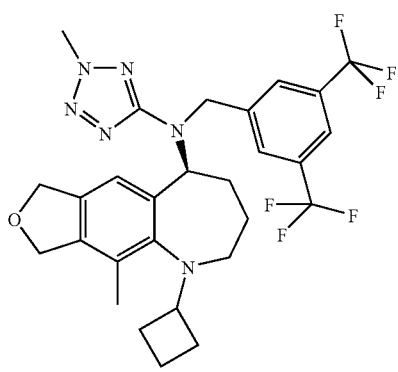

Prepare the title compound by essentially following the procedures described in the synthesis of (S)5-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-ylmethyl}-thiophene-2-carboxylic acid (Example 102), starting with (S)-(3,5-Bis-trifluoromethyl-benzyl)-(4-methyl-3,5,6,7,8,9-hexahydro-1H-2-oxa-5-aza-cyclohepta[f]inden-9-yl)-(2-methyl-2H-tetrazol-5-yl)-amine (Example 165, Step 2) and replacing 5-formyl-thiophene-2-carboxylic acid with cyclobutanone. MS (ES+): 581 (M+H).

Example 173

Synthesis of (S)-(3,5-Bis-trifluoromethyl-benzyl)-[4-methyl-5-(tetrahydro-pyran-4-yl)-3,5,6,7,8,9-hexahydro-1H-2-oxa-5-aza-cyclohepta[f]inden-9-yl]-(2-methyl-2H-tetrazol-5-yl)-amine

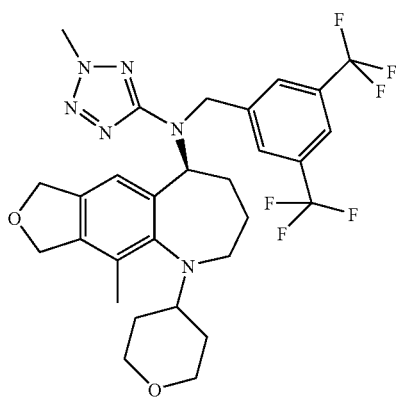

Prepare the title compound by essentially following the procedures described in the synthesis of (S)5-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-ylmethyl}-thiophene-2-carboxylic acid (Example 102), starting with (S)-(3,5-Bis-trifluoromethyl-benzyl)-(4-methyl-3,5,6,7,8,9-hexahydro-1H-2-oxa-5-aza-cyclohepta[f]inden-9-yl)-(2-methyl-2H-tetrazol-5-yl)-amine (Example 165, Step 2) and replacing 5-formyl-thiophene-2-carboxylic acid with tetrahydro-pyran-4-one. MS (ES+): 611 (M+H).

Example 174

Synthesis of (S)-(3-Chloro-5-trifluoromethyl-benzyl)-(5-cyclopropylmethyl-4-methyl-3,5,6,7,8,9-hexahydro-1H-2-oxa-5-aza-cyclohepta[f]inden-9-yl)-(2-methyl-2H-tetrazol-5-yl)-amine

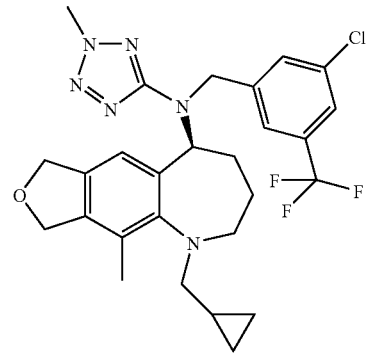

Step 1. Preparation of (S)-(3-Chloro-5-trifluoromethyl-benzyl)-(3,5,6,7,8,9-hexahydro-1H-2-oxa-5-aza-cyclohepta[f]inden-9-yl)-(2-methyl-2H-tetrazol-5-yl)-amine

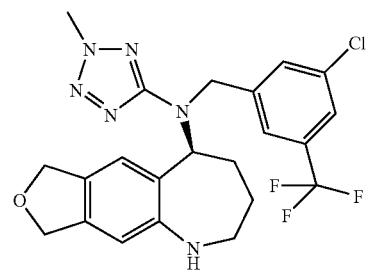

Prepare the title compound by essentially following the procedures described for the preparation of (S)-(3,5-Bis-trifluoromethyl-benzyl)-(3,5,6,7,8,9-hexahydro-1H-2-oxa-5-aza-cyclohepta[f]inden-9-yl)-(2-methyl-2H-tetrazol-5-yl)-amine (Example 73) by replacing 3-Chloro-5-trifluoromethyl-benzaldehyde for 3,5-bis-trifluoromethylbenzaldehyde in Example 73, Step 4. MS (ES+): 579 (M+H).

Step 2. Preparation of (S)-(3-Chloro-5-trifluoromethyl-benzyl)-(4-methyl-3,5,6,7,8,9-hexahydro-1H-2-oxa-5-aza-cyclohepta[f]inden-9-yl)-(2-methyl-2H-tetrazol-5-yl)-amine

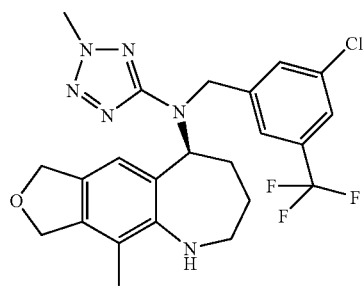

Prepare the title compound by essentially following the procedures described in the preparation of (S)-(3,5-Bis-trifluoromethyl-benzyl)-(4-methyl-3,5,6,7,8,9-hexahydro-1H-2-oxa-5-aza-cyclohepta[f]inden-9-yl)-(2-methyl-2H-tetrazol-5-yl)-amine (Example 165 Steps 1 and 2), starting with (S)-(3-Chloro-5-trifluoromethyl-benzyl)-(3,5,6,7,8,9-hexahydro-1H-2-oxa-5-aza-cyclohepta[f]inden-9-yl)-(2-methyl-2H-tetrazol-5-yl)-amine. MS (ES+): 491 (M−H).

Step 3. Preparation of (S)-(3-Chloro-5-trifluoromethyl-benzyl)-(5-cyclopropylmethyl-4-methyl-3,5,6,7,8,9-hexahydro-1H-2-oxa-5-aza-cyclohepta[f]inden-9-yl)-(2-methyl-2H-tetrazol-5-yl)-amine

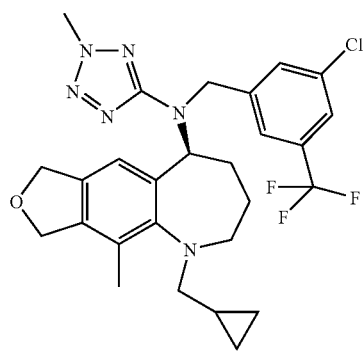

Prepare the title compound by essentially following the procedures described in the synthesis of (S)5-{9-[(3,5-Bis-trifluoromethyl-benzyl)-(2-methyl-2H-tetrazol-5-yl)-amino]-1,3,6,7,8,9-hexahydro-2-oxa-5-aza-cyclohepta[f]inden-5-ylmethyl}-thiophene-2-carboxylic acid (Example 102), starting with (S)-(3-Chloro-5-trifluoromethyl-benzyl)-(4-methyl-3,5,6,7,8,9-hexahydro-1H-2-oxa-5-aza-cyclohepta[f]inden-9-yl)-(2-methyl-2H-tetrazol-5-yl)-amine and replacing 5-formyl-thiophene-2-carboxylic acid with cyclopropane carboxyaldehyde. MS (ES+): 547 (M+H).

Example 175

Synthesis of (S)-4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-cyclohexanecarboxylic acid

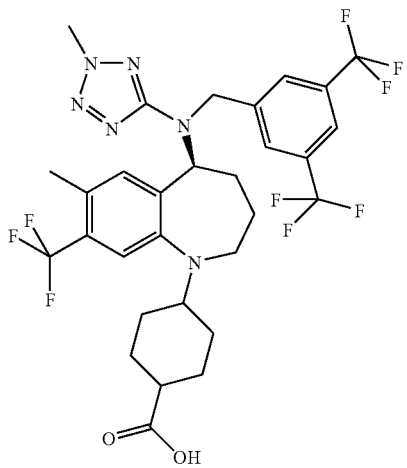

Step 1. Preparation of (S)-4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-cyclohexanecarboxylic acid ethyl ester

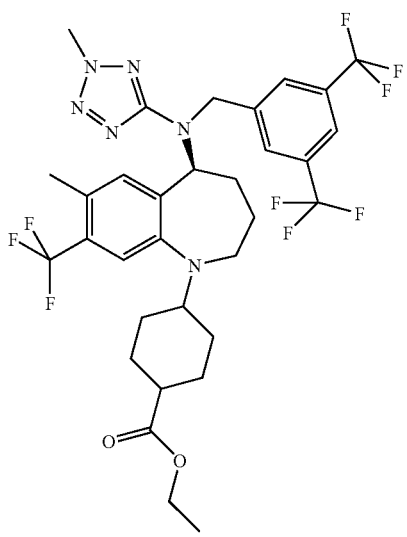

Prepare the title compound by essentially following the procedures described in the synthesis of (S)-(3,5-Bistrifluoromethylbenzyl)-(1-cyclopentylmethyl-7-methyl-8-trifluoromethyl-2,3,4,5-tetrahydro-1H-benzo[b]azepin-5-yl)-(2-methyl-2H-tetrazol-5-yl)amine (Example 3 step 19) by replacing cyclopentanecarboxaldehyde with 4-oxo-cyclohexanecarboxylic acid ethyl ester. Isolate the title compound by chromatography over silica gel, eluting with ethyl acetate/hexane. MS (ES+): 707 (M+H).

Step 2. Preparation of (S)-4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-cyclohexanecarboxylic acid

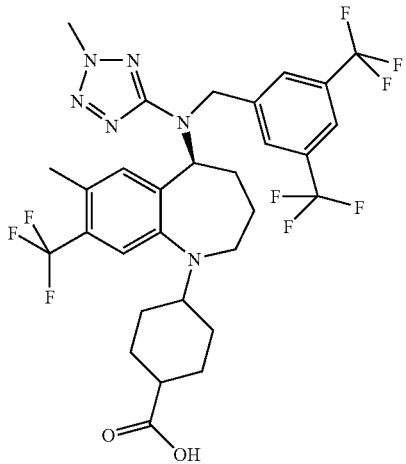

To a solution of (S)-4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-cyclohexanecarboxylic acid ethyl ester (0.14 mmol) in methanol (5 mL), add 5N sodium hydroxide (14 mmol). After heating the mixture at 60° C. for 2 h, cool to room temperature and dilute with water (20 mL). Neutralize the mixture using 5M HCl and extract the organics using ethyl actate (3×5 mL). Dry the combined organics over sodium sulfate, filter, and remove the solvent under vacuum. Chromatograph the crude product over silica gel, eluting with methanol/dichloromethane (0-5%) to obtain the separated cis and trans isomers. MS (ES+): 679 (M+H).

Example 176

Synthesis of (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid 4-carboxy-cyclohexyl ester

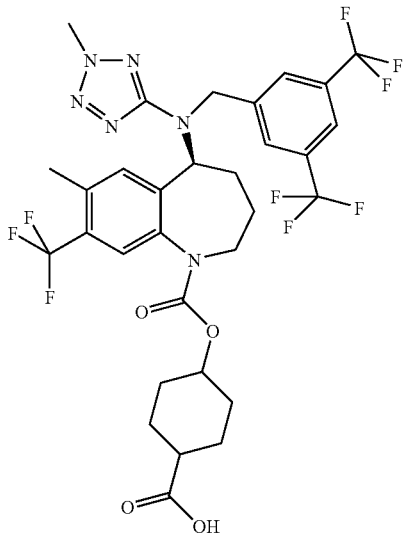

Step 1. Preparation of (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid 4-methoxycarbonyl-cyclohexyl ester

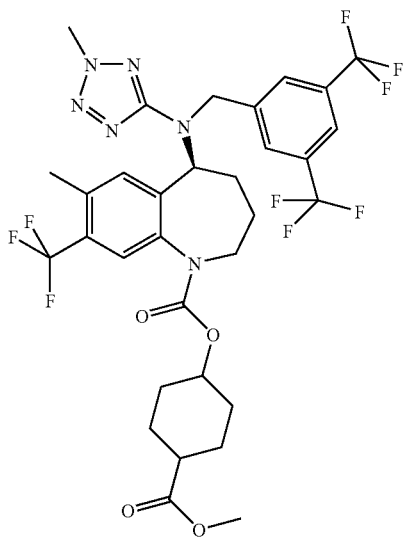

Prepare the title compound by essentially following the procedures described in the synthesis of (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid 1-ethyl-propyl ester (Example 18), by replacing pentan-3-ol with 4-hydroxy-cyclohexanecarboxylic acid methyl ester. MS (ES+): 737 (M+H).

Step 2. Preparation of (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid 4-carboxy-cyclohexyl ester

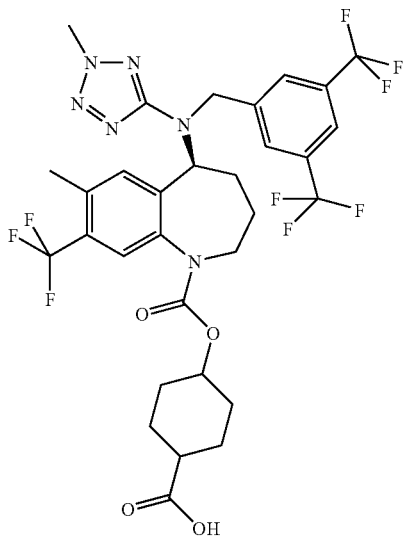

To a solution of (S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid 4-methoxycarbonyl-cyclohexyl ester (0.14 mmol) in methanol (5 mL), add 5N sodium hydroxide (14 mmol). After heating the mixture at 60° C. for 2 h, cool to room temperature and dilute with water (20 mL). Neutralize the mixture using 5M HCl and extract the organics using ethyl actate (3×5 mL). Dry the combined organics over sodium sulfate, filter, and remove the solvent under vacuum. Chromatograph the crude product over silica gel, eluting with methanol/dichloromethane (0-5%) to obtain the separated cis and trans isomers. MS (ES+): 723 (M+H).

Example 177

Synthesis of (S)-9-[(3,5-Bis-trifluoromethyl-benzyl)-(2-methyl-2H-tetrazol-5-yl)-amino]-2,2-difluoro-6,7,8,9-tetrahydro-1,3-dioxa-5-aza-cyclohepta[f]indene-5-carboxylic acid tert-butyl ester

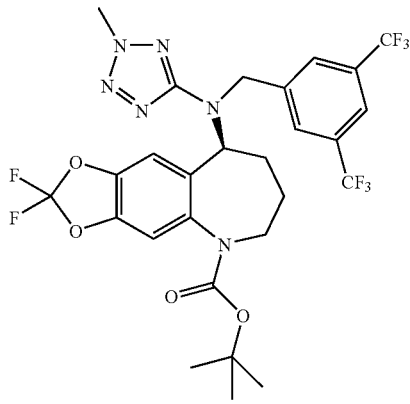

Prepare the title compound by essentially following the procedures described in the synthesis of (S)-(3,5-Bistrifluoromethylbenzyl)-(1-cyclopentylmethyl-7-methyl-8-trifluoromethyl-2,3,4,5-tetrahydro-1H-benzo[b]azepin-5-yl)-(2-methyl-2H-tetrazol-5-yl)amine (Example 3, Steps 1-3) (alternative preparation of methyl-2-(N-isoproposycarbonyl)amino-5-methyl-4-trifluoromethylbezoate) starting with 2,2-difluoro-benzo[1,3]dioxol-5-ylamine and then proceeding with Example 3, Steps 6-17. MS (ES+): 543 (M+H).

Example 178

Synthesis of (S)-(3,5-Bis-trifluoromethyl-benzyl)-(5-cyclopentylmethyl-2,2-difluoro-6,7,8,9-tetrahydro-5H-1,3-dioxa-5-aza-cyclohepta[f]inden-9-yl)-(2-methyl-2H-tetrazol-5-yl)-amine

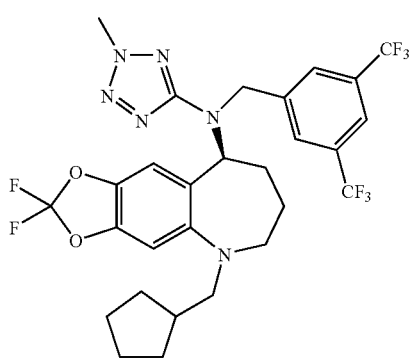

Prepare the title compound by essentially following the procedures described in the synthesis of (S)-(3,5-Bistrifluoromethylbenzyl)-(1-cyclopentylmethyl-7-methyl-8-trifluoromethyl-2,3,4,5-tetrahydro-1H-benzo[b]azepin-5-yl)-(2-methyl-2H-tetrazol-5-yl)amine (Example 3, Steps 18-19) by replacing (S)-tert-butyl 5-[(3,5-bistrifluoromethylbenzyl)-(2-methyl-2H-tetrazol-5-yl)amino]-7-methyl-8-trifluoromethyl-2,3,4,5-tetrahydrobenzo[b]azepine-1-carboxylate with (S)-9-[(3,5-Bis-trifluoromethyl-benzyl)-(2-methyl-2H-tetrazol-5-yl)-amino]-2,2-difluoro-6,7,8,9-tetrahydro-1,3-dioxa-5-aza-cyclohepta[f]indene-5-carboxylic acid tert-butyl ester (Example 177). MS (ES+): 525 (M+H).

Example 179

Synthesis of (S)-5-(3-fluoro-5-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid tert-butyl ester

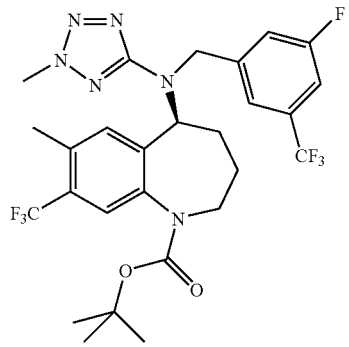

Step 1. Preparation of (S)-5-(3-fluoro-5-trifluoromethyl-benzylamino)-7-methyl-8-trifluoromethyl-2,3,4,5-tetrahydro-benzo[b]azepine-1-carboxylic acid tert-butyl ester

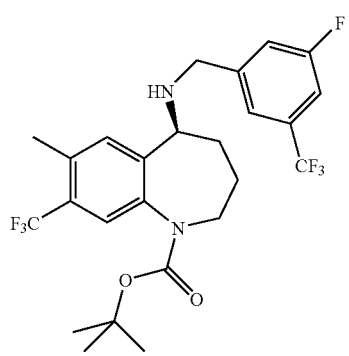

Add sodium triacetoxyborohydride (0.40 g, 1.89 mmol) to a mixture of 3-fluoro-5-trifluoromethyl benzaldehyde (0.096 mL, 0.69 mmol), acetic acid (0.030 mL, 0.625 mmol)) and (S)-tert-Butyl 5-amino-7-methyl-8-trifluoromethyl-2,3,4,5-tetrahydrobenzo[b]azepine-1-carboxylate (Example 3, Step 13) (0.215 g, 0.63 mmol) in dichloroethane (3.0 mL). Stir the mixture at room temperature under an atmosphere of nitrogen for 20 h. Add a saturated solution of sodium bicarbonate, separate the layers and extract the aqueous layer with dichloromethane. Dry the combined organic layers over anhydrous sodium sulfate, filter, and remove the solvent under reduced pressure. Purify the residue by flash chromatography, eluting with hexanes/ethyl acetate (gradient eluent, 0-30% ethyl acetate in hexane), to afford the title compound (0.32 g, 98%). MS (ES+): 521 (M+H).

Step 2. Preparation of (S)-5-[cyano-(3-fluoro-5-trifluoromethyl-benzylamino)-7-methyl-8-trifluoromethyl-2,3,4,5-tetrahydro-benzo[b]azepine-1-carboxylic acid tert-butyl ester

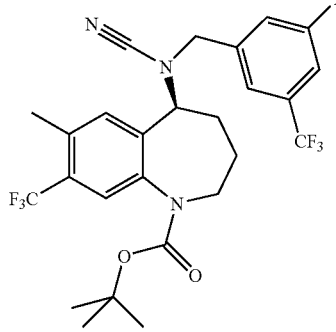

Add cyanogen bromide (0.20 g, 1.88 mmol) followed by N,N-diisopropyl ethylamine (0.43 mL, 2.48 mmol) to a solution of (S)-5(3-fluoro-5-trifluoromethyl acid tert-butyl ester (0.32 g, 0.62 mmol) in THF (2 mL). After stirring at 65° C. for 12 h remove the solvent under vacuum. Dilute with ether (20 mL), wash with water, brine, dry and concentrate under reduced pressure. Chromatograph the product over silica gel, eluting with ethyl acetate/hexane (gradient eluent, 0-50% ethyl acetate in hexane) to obtain the title compound (0.32 g, 91%). MS (ES+): 546 (M+H).

Step 3. Preparation of (S)-5-(3-fluoro-5-trifluoromethyl-benzyl)-(1H-tetrazol-5-yl)-amino]-7-methyl-8-trifluoromethyl-2,3,4,5-tetrahydro-benzo[b]azepine-1-carboxylic acid tert-butyl ester

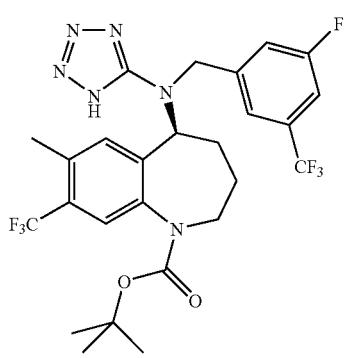

Prepare the title compound by stirring (S)-5-[cyano-(3-fluoro-5-trifluoromethyl-benzylamino)-7-methyl-8-trifluoromethyl-2,3,4,5-tetrahydro-benzo[b]azepine-1-carboxylic acid tert-butyl ester (0.31 g, 0.57 mmol) with sodium azide (0.11 g, 1.70 mmol) and triethylamine hydrochloride (0.31 g, 2.28 mmol) in anhydrous toluene (3 mL) and heat at 110° C. for 16 h. Dilute the cooled mixture with water and 0.1N HCl to bring the pH to 6-7 and extract with EtOAc (3×15 mL). Combine the organic layers and wash with water and brine, dry over sodium sulfate, filter, and concentrate under reduced pressure to give a residue. Purify the residue by chromatography (elution with 5% methanol in EtOAc) to afford the title compound (0.27 g, 81%). MS (ES+): 589 (M+H).

Step 4. Preparation of (S)-5(3-fluoro-5-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid tert-butyl ester

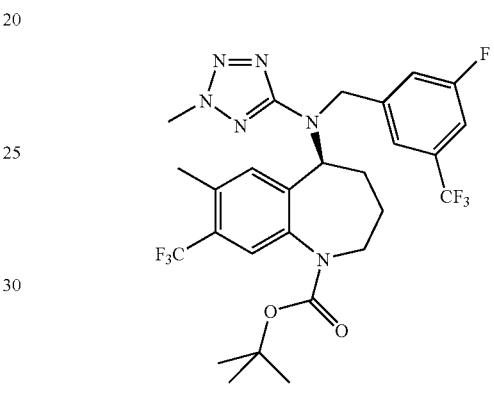

To a solution of (S)-5-(3-fluoro-5-trifluoromethyl-benzyl)-(1H-tetrazol-5-yl)-amino]-7-methyl-8-trifluoromethyl-2,3,4,5-tetrahydro-benzo[b]azepine-1-carboxylic acid tert-butyl ester (0.19 g, 0.32 mmol) and methanol (0.065 mL, 1.61 mmol) in dichloromethane (2 mL) at room temperature, under nitrogen atmosphere, add in one portion triphenyl phosphine (0.084 g, 0.32 mmol) followed by addition of DEAD (0.06 mL, 0.32 mmol). Allow the reaction mixture to stir at room temperature overnight. Remove the solvent under reduced pressure. Purify the residue by flash chromatography, eluting with hexanes/ethyl acetate (elution with 30% EtOAc in hexane), to afford the title compound (0.18 g, 93%). MS (ES+): 503 (M⁺-Boc+H).

Examples 180-185

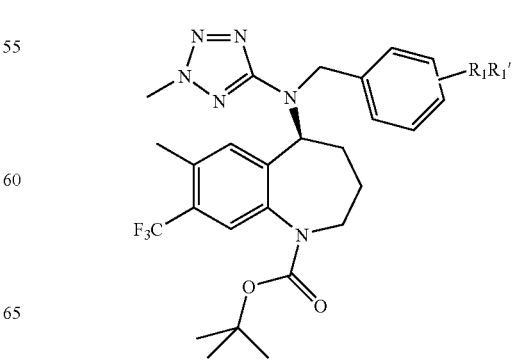

Prepare Examples 180-185, in the table below, by essentially following the procedure describe in the synthesis of (S)-5(3-fluoro-5-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid tert-butyl ester (Example 179, Steps 1-4), by replacing 3-fluoro-5-trifluoromethyl benzaldehyde in Step 1 with the appropriate reagent.

| Example # | Reagent | MS (ES+) |
|---|---|---|
| Example 180 | 3,5-dichloro benzaldehyde | 585 (M + H) |
| Example 181 | 3-trifluoromethoxy benzaldehyde | 601 (M + H) |
| Example 182 | 2-fluoro-3-chloro-5-trifluoromethyl benzaldehyde | 635 (M − H) |

-continued
| Example # | Reagent | MS (ES+) |
|---|---|---|
| Example 183 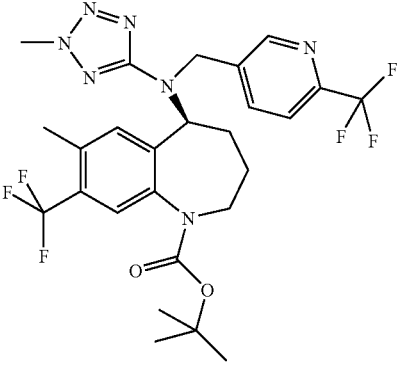 | 4-trifluoromethyl-3-pyridine carboxaldehyde | 608 (M + Na) |
| Example 184 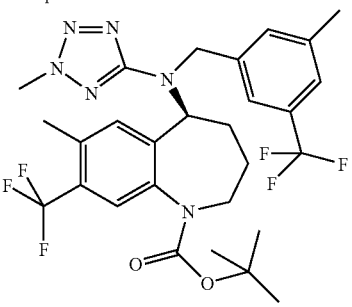 | 3-methyl-5-trifluoromethyl benzaldehyde | 499 (M − Boc + H) |
| Example 185 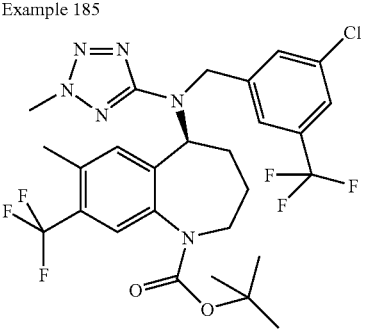 | 3-chloro-5-trifluoromethyl benzaldehyde | 519 (M − Boc + H) |

Example 186

Synthesis of (S)-(3-fluoro-5-trifluoromethyl-benzyl)-(7-methyl-1-pyridin-4-ylmethyl-8-trifluoromethyl-2,3,4,5-tetrahydro-1H-benzo[b]azepin-5-yl)-(2-methyl-2H-tetrazol-5-yl)-amine

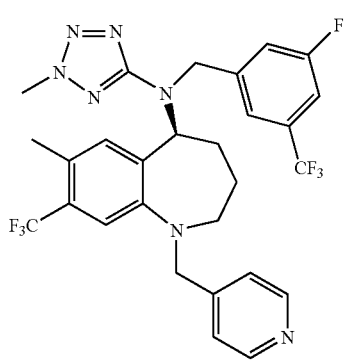

Step 1. Preparation of (S)-(3-fluoro-5-trifluoromethyl-benzyl)-(2-methyl-2H-tetrazol-5-yl)-(7-methyl-8-trifluoromethyl-2,3,4,5-tetrahydro-1H-benzo[b]azepine-5-yl)-amine

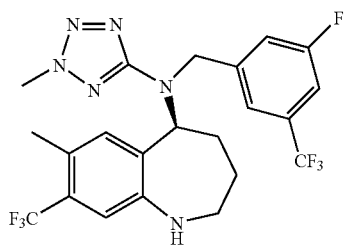

Add trifluoroacetic acid (0.37 mL) to a solution of (S)-5-(3-fluoro-5-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid tert-butyl ester (Example 179, Step 4) (0.14 g, 0.24 mmol) in methylene chloride (2 mL) at room temperature under nitrogen. Stir the reaction for 1 h and pour the mixture into saturated aqueous sodium bicarbonate solution (20 mL). Extract the mixture with methylene chloride (2×20 mL) and wash the combined organic extracts with brine (50 mL), dry over anhydrous sodium sulfate and filter. Remove the solvent under reduced pressure to provide the title compound as a colorless oil. Purify the residue by column chromatography on silica gel, eluting with ethyl acetate/hexanes (0-30%), to provide the title compound (0.12 g, 98%). MS (ES+): 503 (M+H).

Step 2. Preparation of (S)-(3-fluoro-5-trifluoromethyl-benzyl)-(7-methyl-1-pyridin-4-ylmethyl-8-trifluoromethyl-2,3,4,5-tetrahydro-1H-benzo[b]azepin-5-yl)-(2-methyl-2H-tetrazol-5-yl)-amine

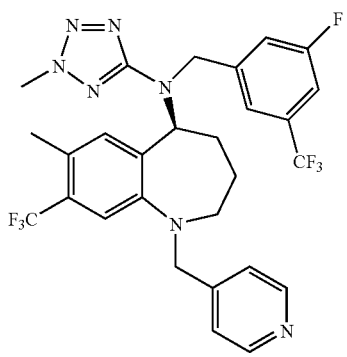

Add pyridine-4-carboxaldehyde (0.065 mL, 0.69 mmol) to a solution of (S)-(3-fluoro-5-trifluoromethyl-benzyl)-(2-methyl-2H-tetrazol-5-yl)-(7-methyl-8-trifluoromethyl-2,3,4,5-tetrahydro-1H-benzo[b]azepine-5-yl)-amine (0.12 g, 0.23 mmol) in 1,2-dichloroethane (10 mL) and acetic acid (0.02 mL) at room temperature under nitrogen and stir for 5 min. Add sodium triacetoxy borohydride (0.29 g, 1.38 mmol) and stir for 12 h. Dilute the mixture with methylene chloride (30 mL) and wash with saturated aqueous sodium bicarbonate solution (2×10 mL). Extract the combined aqueous washes with methylene chloride (20 mL) and wash the combined organic extracts with brine (20 mL) and dry over anhydrous sodium sulfate. Remove the solvents under reduced pressure and purify by silica gel column (gradient eluent, 0-5% MeOH in ethyl acetate) to give the title compound (0.12 g, 87%). MS (ES+): 594 (M+H).

Example 187

Synthesis of (S)-(3,5-Dichloro-benzyl)-(7-methyl-1-pyridin-4-ylmethyl-8-trifluoromethyl-2,3,4,5-tetrahydro-1H-benzo[b]azepin-5-yl)-(2-methyl-2H-tetrazol-5-yl)-amine

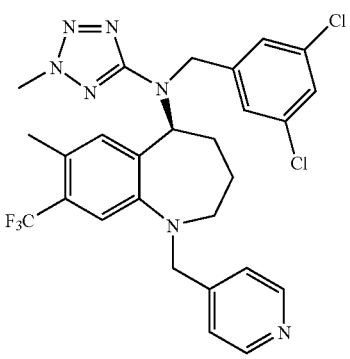

Prepare the title compound by essentially following the procedures described in the synthesis of (S)-(3-fluoro-5-trifluoromethyl-benzyl)-(7-methyl-1-pyridin-4-ylmethyl-8-trifluoromethyl-2,3,4,5-tetrahydro-1H-benzo[b]azepin-5-yl)-(2-methyl-2H-tetrazol-5-yl)-amine (Example 186) by replacing (S)-5(3-fluoro-5-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid tert-butyl ester with (S)-5-[(3,5-Dichloro-benzyl)-(2-methyl-2H-tetrazol-5-yl)-amino]-7-methyl-8-trifluoromethyl-2,3,4,5-tetrahydro-benzo[b]azepine-1-carboxylic acid tert-butyl ester (Example 180) in Example 186, Step 1. MS (ES+): 576 (M+H).

Example 188

Synthesis of (S)-(7-Methyl-1-pyridin-4-ylmethyl-8-trifluoromethyl-2,3,4,5-tetrahydro-1H-benzo[b]azepin-5-yl)-(2-methyl-2H-tetrazol-5-yl)-(3-trifluoromethoxy-benzyl)-amine

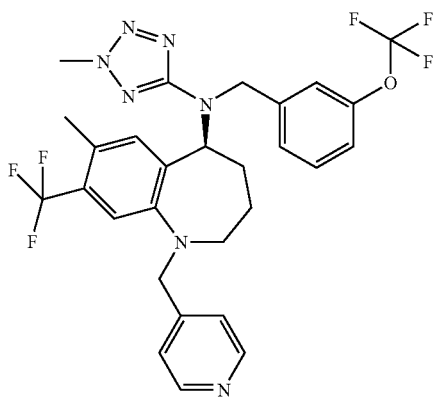

Prepare the title compound by essentially following the procedures described in the synthesis of (S)-(3-fluoro-5-trifluoromethyl-benzyl)-(7-methyl-1-pyridin-4-ylmethyl-8-trifluoromethyl-2,3,4,5-tetrahydro-1H-benzo[b]azepin-5-yl)-(2-methyl-2H-tetrazol-5-yl)-amine (Example 186) by replacing (S)-5(3-fluoro-5-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid tert-butyl ester with (S)-7-Methyl-5-[(2-methyl-2H-tetrazol-5-yl)-(3-trifluoromethoxy-benzyl)-amino]-8-trifluoromethyl-2,3,4,5-tetrahydro-benzo[b]azepine-1-carboxylic acid tert-butyl ester (Example 181) in Example 186, Step 1. MS (ES+): 592 (M+H).

Example 189

Synthesis of (S)-(7-Methyl-1-pyridin-4-ylmethyl-8-trifluoromethyl-2,3,4,5-tetrahydro-1H-benzo[b]azepin-5-yl)-(2-methyl-2H-tetrazol-5-yl)-(6-trifluoromethyl-pyridin-3-ylmethyl)-amine

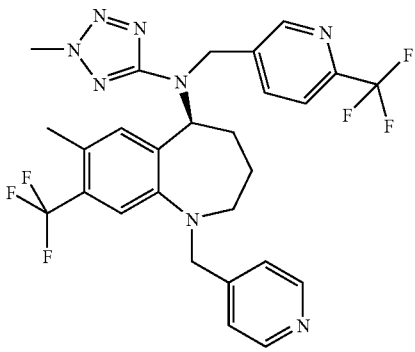

Prepare the title compound by essentially following the procedure described in the synthesis of (S)-(3-fluoro-5-trifluoromethyl-benzyl)-(7-methyl-1-pyridin-4-ylmethyl-8-trifluoromethyl-2,3,4,5-tetrahydro-1H-benzo[b]azepin-5-yl)-(2-methyl-2H-tetrazol-5-yl)-amine (Example 186) by replacing (S)-5(3-fluoro-5-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid tert-butyl ester with (S)-7-Methyl-5-[(2-methyl-2H-tetrazol-5-yl)-(6-trifluoromethyl-pyridin-3-ylmethyl)-amino]-8-trifluoromethyl-2,3,4,5-tetrahydro-benzo[b]azepine-1-carboxylic acid tert-butyl ester (Example 183) in Example 186, Step 1. MS (ES+): 577 (M+H).

Example 190

Synthesis of (S)-(7-Methyl-1-pyridin-4-ylmethyl-8-trifluoromethyl-2,3,4,5-tetrahydro-1H-benzo[b]azepin-5-yl)-(2-methyl-2H-tetrazol-5-yl)-(3-methyl-5-trifluoromethyl-benzyl)-amine

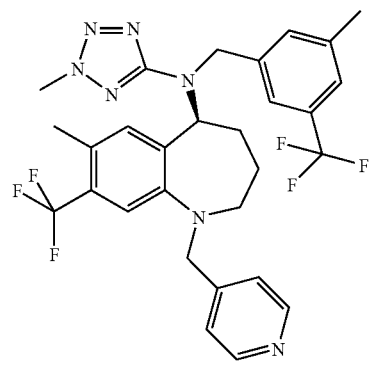

Prepare the title compound by essentially following the procedure described in the synthesis of (S)-(3-fluoro-5-trifluoromethyl-benzyl)-(7-methyl-1-pyridin-4-ylmethyl-8-trifluoromethyl-2,3,4,5-tetrahydro-1H-benzo[b]azepin-5-yl)-(2-methyl-2H-tetrazol-5-yl)-amine (Example 186) by replacing (S)-5(3-fluoro-5-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid tert-butyl ester with (S)-7-Methyl-5-[(2-methyl-2H-tetrazol-5-yl)-(3-methyl-5-trifluoromethyl-benzyl)-amino]-8-trifluoromethyl-2,3,4,5-tetrahydro-benzo[b]azepine-1-carboxylic acid tert-butyl ester (Example 184) in Example 186, Step 1. MS (ES+): 590 (M+H).

Example 191

Synthesis of (S)-(3-Chloro-5-trifluoromethyl-benzyl)-(7-methyl-1-pyridin-4-ylmethyl-8-trifluoromethyl-2,3,4,5-tetrahydro-1H-benzo[b]azepin-5-yl)-(2-methyl-2H-tetrazol-5-yl)-amine

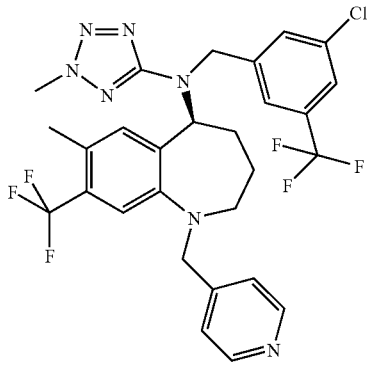

Prepare the title compound by essentially following the procedure described in the synthesis of (S)-(3-fluoro-5-trifluoromethyl-benzyl)-(7-methyl-1-pyridin-4-ylmethyl-8-trifluoromethyl-2,3,4,5-tetrahydro-1H-benzo[b]azepin-5-yl)-(2-methyl-2H-tetrazol-5-yl)-amine (Example 186) by replacing (S)-5(3-fluoro-5-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid tert-butyl ester with (S)-5-[(3-Chloro-5-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid tert-butyl ester (Example 185) in Example 186, Step 1. MS (ES+): 610 (M+H).

Example 192

Synthesis of (S)-4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-benzonitrile

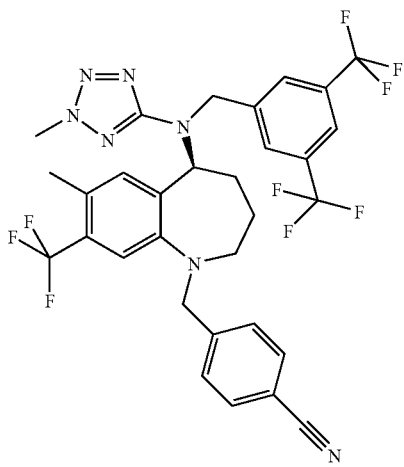

Prepare the title compound by essentially following the procedure described in the synthesis of (S)-(3,5-bistrifluoromethylbenzyl)-(1-cyclopentylmethyl-7-methyl-8-trifluoromethyl-2,3,4,5-tetrahydro-1H-benzo[b]azepin-5-yl)-(2-methyl-2H-tetrazol-5-yl)amine (Example 3, Step 19) by replacing cyclopentanecarboxaldehyde with 4-cyanobenzaldehyde. MS (ES+): 668 (M+H).

Example 193

Synthesis of (S)-(3,5-Bis-trifluoromethyl-benzyl)-(2-methyl-2H-tetrazol-5-yl)-{7-methyl-1-[4-(1H-tetrazol-5-yl)-benzyl]-8-trifluoromethyl-2,3,4,5-tetrahydro-1H-benzo[b]azepin-5-yl}-amine

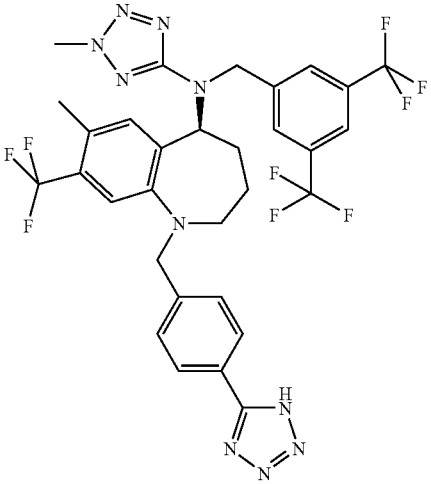

Heat a mixture of (S)-4-{5-[(3,5-bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-benzonitrile (Example 192) (0.13 g, 0.19 mmol), sodium azide (0.04 g, 0.60 mmol) and triethylamine hydrochloride (0.08 g, 0.60 mmol) in anhydrous toluene (5 mL) at 110° C. under nitrogen for 20 h. Dilute the cooled mixture with ethyl acetate (50 mL) and wash with aqueous 0.1N HCl (10 mL) and brine (10 mL). Dry over anhydrous sodium sulfate. Filter and remove the solvent under reduced pressure. Purify the residue by column chromatography on silica gel, eluting with MeOH/EtOAc (0-20%), to provide the title compound (0.12 g, 82%). MS (ES+): 711 (M+H).

Example 194

Synthesis of (S)-2-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-benzonitrile

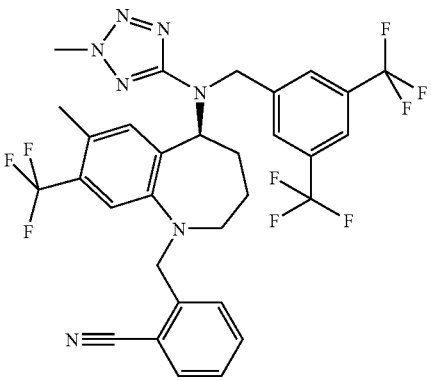

Prepare the title compound by essentially following the procedure described in the synthesis of (S)-(3,5-bistrifluoromethylbenzyl)-(1-cyclopentylmethyl-7-methyl-8-trifluoromethyl-2,3,4,5-tetrahydro-1H-benzo[b]azepin-5-yl)-(2-methyl-2H-tetrazol-5-yl)amine (Example 3, Step 19) by replacing cyclopentanecarboxaldehyde with 2-cyanobenzaldehyde. MS (ES+): 668 (M+H).

Example 195

Synthesis of (S)-3-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-benzonitrile

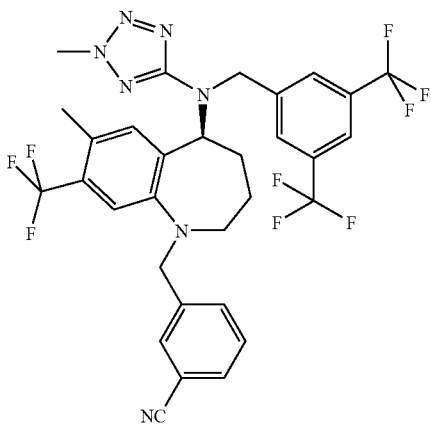

Prepare the title compound by essentially following the procedure described in the synthesis of (S)-(3,5-bistrifluoromethylbenzyl)-(1-cyclopentylmethyl-7-methyl-8-trifluoromethyl-2,3,4,5-tetrahydro-1H-benzo[b]azepin-5-yl)-(2-methyl-2H-tetrazol-5-yl)amine (Example 3, Step 19) by replacing cyclopentanecarboxaldehyde with 3-cyanobenzaldehyde. MS (ES+): 668 (M+H).

Example 196

Synthesis of (S)-(3-Chloro-5-trifluoromethyl-benzyl)-(1-cyclopropylmethyl-7-methyl-8-trifluoromethyl-2,3,4,5-tetrahydro-1H-benzo[b]azepin-5-yl)-(2-methyl-2H-tetrazol-5-yl)-amine

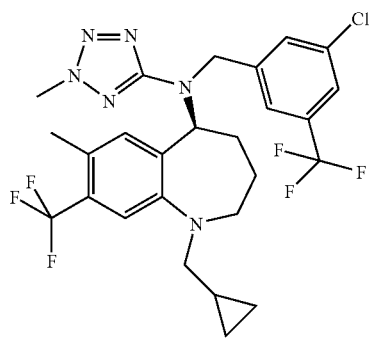

Prepare the title compound by essentially following the procedures described in the synthesis of (S)-(3-Chloro-5-trifluoromethyl-benzyl)-(7-methyl-1-pyridin-4-ylmethyl-8-trifluoromethyl-2,3,4,5-tetrahydro-1H-benzo[b]azepin-5-yl)-(2-methyl-2H-tetrazol-5-yl)-amine (Example 191) by replacing pyridine-4-carboxaldehyde with cyclopropane carboxaldehyde. MS (ES+): 573 (M+H).

Example 197

Synthesis of (S)-(4-{5-[(3-Chloro-5-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-cyclohexyl)-acetic acid

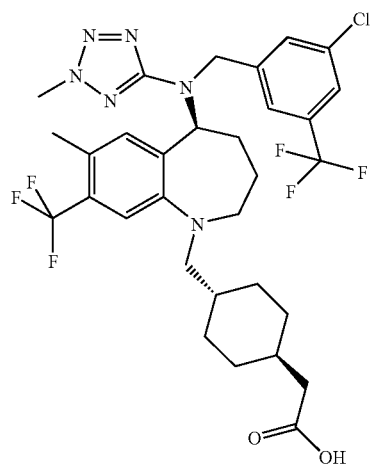

Step 1. Preparation of (S)-(4-{5-[(3-Chloro-5-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-cyclohexyl)-acetic acid methyl ester

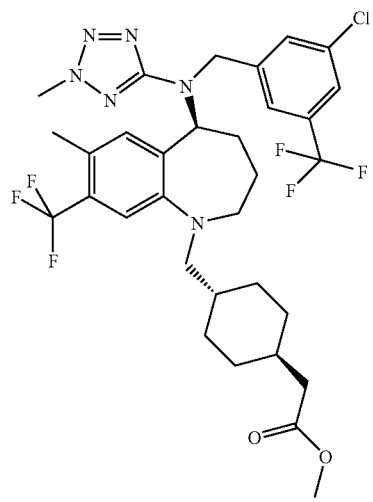

Prepare the title compound by essentially following the procedure described in the synthesis of (S)-(3-Chloro-5-trifluoromethyl-benzyl)-(7-methyl-1-pyridin-4-ylmethyl-8-trifluoromethyl-2,3,4,5-tetrahydro-1H-benzo[b]azepin-5-yl)-

(2-methyl-2H-tetrazol-5-yl)-amine (Example 191) by replacing pyridine-4-carboxaldehyde with (4-formyl-cyclohexyl)acetic acid methyl ester. MS (ES+): 687 (M+H).

Step 2. Preparation of (S)-(4-{5-[(3-Chloro-5-trifluoromethyl-benzyl)-(2-methyl-2 H-tetrazol-5-yl)-amino]-7-methyl-8-trifluoromethyl-2,3,4,5-tetrahydro-benzo[b]azepin-1-ylmethyl}-cyclohexyl)-acetic acid

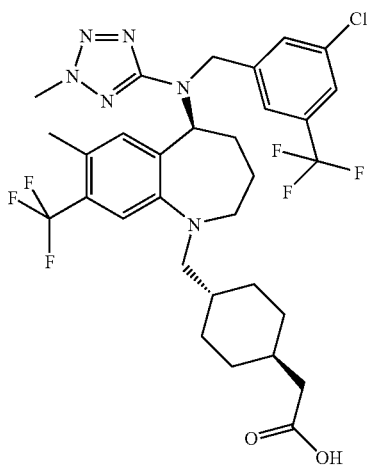

To a solution of (S)-(4-{5-[(3-Chloro-5-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-cyclohexyl)-acetic acid methyl ester (0.1 mmol) in methanol (1 mL), add 4N sodium hydroxide (0.4 mL). Heat the mixture at 60° C. for 3 h. Dilute the cooled mixture with water and 1N HCl to bring the pH to 6-7 and extract with CH₂Cl₂ (3×15 mL). Combine the organic layers and wash with water and brine, dry over sodium sulfate, filter, and concentrate under reduced pressure to give a residue. Purify the residue by chromatography (elution with 5%-20% methanol in EtOAc) to afford the title compound. MS (ES+): 673 (M+H).

Example 198

Synthesis of (S)-4-{7-Methyl-5-[(2-methyl-2H-tetrazol-5-yl)-(3-methyl-5-trifluoromethyl-benzyl)-amino]-8-trifluoromethyl-2,3,4,5-tetrahydro-benzo[b]azepin-1-yl}-cyclohexanecarboxylic acid

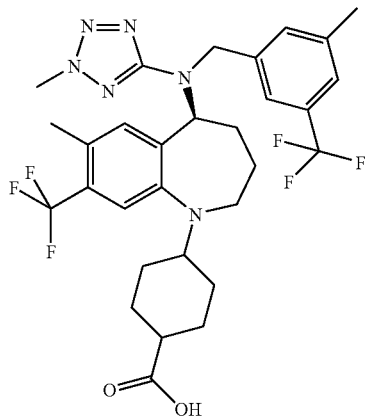

Prepare the title compound by essentially following the procedure described in the synthesis of (S)-4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-cyclohexanecarboxylic acid (Example 175) by replacing (S)-(3,5-Bistrifluoromethylbenzyl)-(1-cyclopentylmethyl-7-methyl-8-trifluoromethyl-2,3,4,5-tetrahydro-1H-benzo[b]azepin-5-yl)-(2-methyl-2H-tetrazol-5-yl)amine with (S)-(2-Methyl-2H-tetrazol-5-yl)-(3-methyl-5-trifluoromethyl-benzyl)-(7-methyl-8-trifluoromethyl-2,3,4,5-tetrahydro-1H-benzo[b]azepin-5-yl)-amine in Example 175, Step 1. MS (ES+): 639 (M+H).

Example 199

Synthesis of (S)-(3-chloro-5-trifluoromethyl-benzyl)-(7,9-dimethyl-1-pyridin-4-ylmethyl-8-trifluoromethyl-2,3,4,5-tetrahydro-1H-benzo[b]azepin-5-yl)-(2-methyl-2H-tetrazol-5-yl)-amine

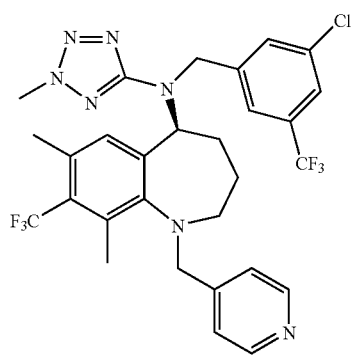

Step 1. Preparation of (S)-(2-Methyl-2H-tetrazol-5-yl)-(3-methyl-5-trifluoromethyl-benzyl)-(7-methyl-8-trifluoromethyl-2,3,4,5-tetrahydro-1H-benzo[b]azepin-5-yl)-amine

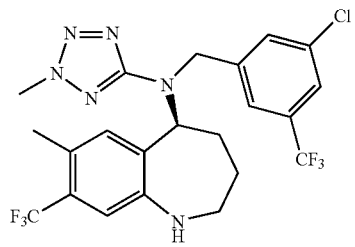

Prepare the title compound by essentially following the procedure described in the synthesis of (S)-(3-fluoro-5-trifluoromethyl-benzyl)-(2-methyl-2H-tetrazol-5-yl)-(7-methyl-8-trifluoromethyl-2,3,4,5-tetrahydro-1H-benzo[b]azepine-5-yl)-amine (Example 186, Step 1) by replacing (S)-5-(3-fluoro-5-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid tert-butyl ester with (S)-5-[(3-Chloro-5-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid tert-butyl ester (Example 185). MS (ES+): 519 (M+H).

Step 2. Preparation of (S)-(9-bromo-7-methyl-8-trifluoromethyl-2,3,4,5-tetrahydro-1H-benzo[b]azepin-5-yl)-(3-chloro-5-trifluoromethyl-benzyl)-(2-methyl-2H-tetrazol-5-yl)-amine

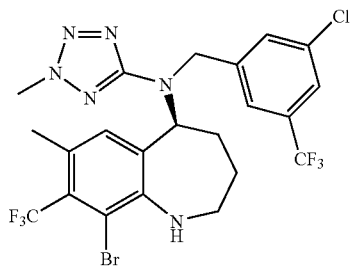

Stir (S)-(3-chloro-5-trifluoromethyl-benzyl)-(2-methyl-2H-tetrazol-5-yl)-(7-methyl-8-trifluoromethyl-2,3,4,5-tetrahydro-1H-benzo[b]azepine-5-yl)-amine (0.53 g, 1.02 mmol) with N-bromosuccinimide (0.22 g, 1.22 mmol) in acetic acid (2 mL) at room temperature for 2 h. Evaporate the solvent under reduced pressure. Dilute the residue with water and neutralize with saturated NaHCO₃ and extract with EtOAc (3×25 mL). Combine the organic layers and wash with water and brine, dry over sodium sulfate, filter, and concentrate under reduced pressure to give a residue. Purify the residue by flash chromatography, eluting with hexane/ethyl acetate (5-40% EtOAc in hexane), to provide the title compound (0.49 g, 83%). MS (ES+): 599 (M+H).

Step 3. Preparation of (S)-(3-chloro-5-trifluoromethyl-benzyl)-(7,9-dimethyl-8-trifluoromethyl-2,3,4,5-tetrahydro-1H-benzo[b]azepin-5-yl)-(2-methyl-2H-tetrazol-5-yl)-amine Add a solution of (S)-(9-bromo-7-methyl-8-trifluoromethyl-2,3,4,5-tetrahydro-1H-benzo[b]azepin-5-yl)-(3-chloro-5-trifluoromethyl-benzyl)-(2-methyl-2H-tetrazol-5-yl)-amine (0.39 g, 0.65 mmol) in dioxane (5 mL) to a mixture of methylboronic acid (0.12 g, 1.96 mmol), palladium diphenylphosphinoferrocene dichloride (0.05 g, 0.06 mmol), and cesium fluoride (0.35 g, 2.32 mmol), then purge with nitrogen and stir for 15 min. at room temperature, then at 100° C. for 4 h. After completion, cool the reaction to room temperature, dilute with ethyl acetate (50 mL) and wash with water and brine (10 mL each). Dry the organic layer over sodium sulfate, filter, and remove the solvent under reduced pressure. Purify the residue using flash column chromatography on silica gel, eluting with hexanes/ethyl acetate (0-30% EtOAc in hexane), to provide the title compound as a white solid (0.32 g, 90%). MS (ES+): 533 (M+H).

Step 4. Preparation of (S)-(3-chloro-5-trifluoromethyl-benzyl)-(7,9-dimethyl-1-pyridin-4-ylmethyl-8-trifluoromethyl-2,3,4,5-tetrahydro-1H-benzo[b]azepin-5-yl)-(2-methyl-2H-tetrazol-5-yl)-amine

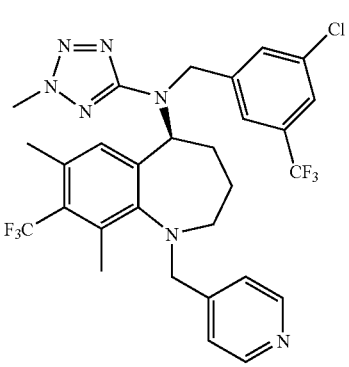

Prepare the title compound by essentially following the procedure described in the synthesis of (S)-(3-fluoro-5-trifluoromethyl-benzyl)-(7-methyl-1-pyridin-4-ylmethyl-8-trifluoromethyl-2,3,4,5-tetrahydro-1H-benzo[b]azepin-5-yl)-(2-methyl-2H-tetrazol-5-yl)-amine (Example 186, Step 2) by using (S)-(3-chloro-5-trifluoromethyl-benzyl)-(7,9-dimethyl-8-trifluoromethyl-2,3,4,5-tetrahydro-1H-benzo[b]azepin-5-yl)-(2-methyl-2H-tetrazol-5-yl)-amine (0.08 g, 0.15 mmol) and pyridine-4-carboxaldehyde (0.045 mL, 0.45 mmol) in dichloroethane (2 mL) at room temperature for 15 h to afford the title compound. Purification by silica gel column (gradient eluent, 0-5% MeOH in ethyl acetate) provides the title compound (0.09 g, 91%). MS (ES+): 624 (M+H).

Example 200

Synthesis of (S)-(3-Chloro-5-trifluoromethyl-benzyl)-(1-cyclopropylmethyl-7,9-dimethyl-8-trifluoromethyl-2,3,4,5-tetrahydro-1H-benzo[b]azepin-5-yl)-(2-methyl-2H-tetrazol-5-yl)-amine

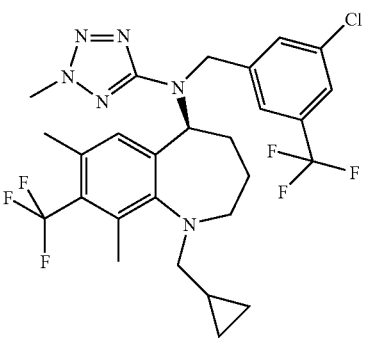

Prepare the title compound by essentially following the procedure described in the synthesis of (S)-(3-chloro-5-trifluoromethyl-benzyl)-(7,9-dimethyl-1-pyridin-4-ylmethyl-8-trifluoromethyl-2,3,4,5-tetrahydro-1H-benzo[b]azepin-5-yl)-(2-methyl-2H-tetrazol-5-yl)-amine (Example 199) by replacing pyridine-4-carboxaldehyde with cyclopropane carboxaldehyde. MS (ES+): 587 (M+H).

Example 201

Synthesis of (S)-(4-{5-[(3-Chloro-5-trifluoromethyl-benzyl)-(2-methyl-2H-tetrazol-5-yl)-amino]-7,9-dimethyl-8-trifluoromethyl-2,3,4,5-tetrahydro-benzo[b]azepin-1-ylmethyl}-cyclohexyl)-acetic acid

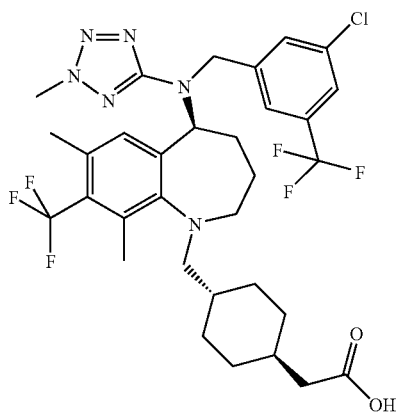

Step 1. Preparation of (S)-(4-{5-[(3-Chloro-5-trifluoromethyl-benzyl)-(2-methyl-2 H-tetrazol-5-yl)-amino]-7,9-dimethyl-8-trifluoromethyl-2,3,4,5-tetrahydro-benzo[b]azepin-1-ylmethyl}-cyclohexyl)-acetic acid methyl ester

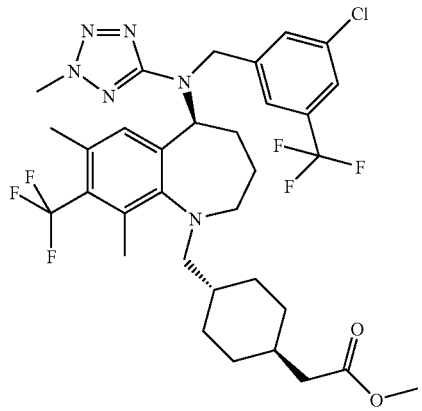

Prepare the title compound by essentially following the procedure described in the synthesis of (S)-(3-chloro-5-trifluoromethyl-benzyl)-(7,9-dimethyl-1-pyridin-4-ylmethyl-8-trifluoromethyl-2,3,4,5-tetrahydro-1H-benzo[b]azepin-5-yl)-(2-methyl-2H-tetrazol-5-yl)-amine (Example 199) by replacing pyridine-4-carboxaldehyde with (4-formyl-cyclohexyl)-acetic acid methyl ester. MS (ES+): 701 (M+H).

Step 2. Preparation of (S)-(4-{5-[(3-Chloro-5-trifluoromethyl-benzyl)-(2-methyl-2 H-tetrazol-5-yl)-amino]-7,9-dimethyl-8-trifluoromethyl-2,3,4,5-tetrahydro-benzo[b]azepin-1-ylmethyl}-cyclohexyl)-acetic acid

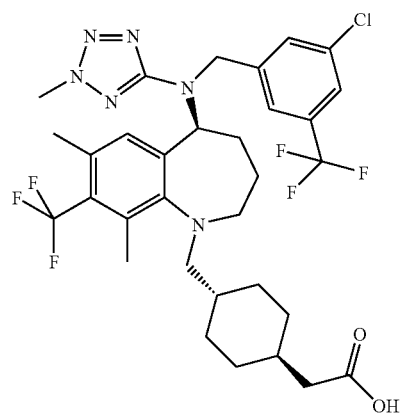

To a solution of (S)-(4-{5-[(3-Chloro-5-trifluoromethyl-benzyl)-(2-methyl-2H-tetrazol-5-yl)-amino]-7,9-dimethyl-8-trifluoromethyl-2,3,4,5-tetrahydro-benzo[b]azepin-1-ylmethyl}-cyclohexyl)-acetic acid methyl ester (0.1 mmol) in methanol (1 mL), add 4N sodium hydroxide (0.5 mL). Heat the mixture at 60° C. for 3 h. Dilute the cooled mixture with water and 1N HCl to bring the pH to 6-7 and extract with $CH_2Cl_2$ (3×15 mL). Combine the organic layers, dry over sodium sulfate, filter, and concentrate under reduced pressure to give a residue. Purify the residue by chromatography (elution with 5%-10% methanol in EtOAc) to afford the title compound. MS (ES+): 687 (M+H).

Example 202

Synthesis of (S)-4-{5-[(3,5-Bis-trifluoromethyl-benzyl)-(2-methyl-2H-tetrazol-5-yl)-amino]-7,9-dimethyl-8-trifluoromethyl-2,3,4,5-tetrahydro-benzo[b]azepin-1-ylmethyl}-benzoic acid

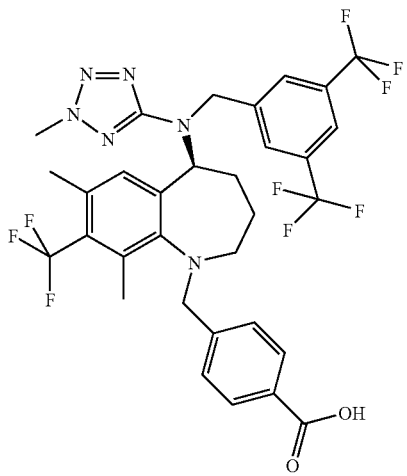

Step 1. Preparation of (S)-4-{5-[(3,5-bis-trifluoromethyl-benzyl)-(2-methyl-2H-tetrazol-5-yl)-amino]-7,9-dimethyl-8-trifluoromethyl-2,3,4,5-tetrahydro-benzo[b]azepin-1-ylmethyl}-benzoic acid methyl ester

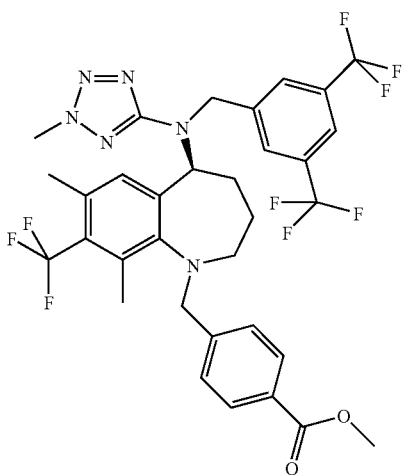

Prepare the title compound by essentially following the procedure described in the synthesis of (S)-(3-fluoro-5-trifluoromethyl-benzyl)-(7-methyl-1-pyridin-4-ylmethyl-8-trifluoromethyl-2,3,4,5-tetrahydro-1H-benzo[b]azepin-5-yl)-(2-methyl-2H-tetrazol-5-yl)-amine (Example 186, Step 2) by replacing (S)-(3-fluoro-5-trifluoromethyl-benzyl)-(2-methyl-2H-tetrazol-5-yl)-(7-methyl-8-trifluoromethyl-2,3,4,5-tetrahydro-1H-benzo[b]azepine-5-yl)-amine with (S)-(3,5-Bis-trifluoromethyl-benzyl)-(7,9-dimethyl-8-trifluoromethyl-2,3,4,5-tetrahydro-1H-benzo[b]azepin-5-yl)-(2-methyl-2H-tetrazol-5-yl)-amine (Example 148, Step 2) and pyridine-4-carboxaldehyde with 4-formyl methyl benzoate. MS (ES+): 715 (M+H).

Step 2. Preparation of (S)-4-{5-[(3,5-Bis-trifluoromethyl-benzyl)-(2-methyl-2H-tetrazol-5-yl)-amino]-7,9-dimethyl-8-trifluoromethyl-2,3,4,5-tetrahydro-benzo[b]azepin-1-ylmethyl}-benzoic acid

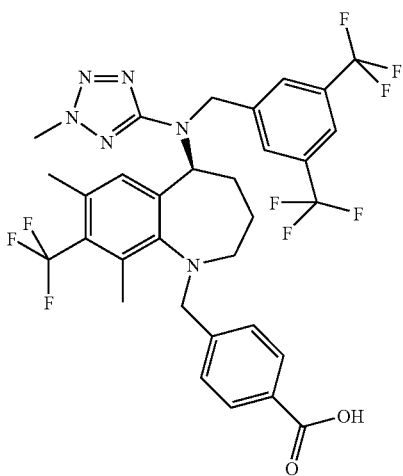

To a solution of (S)-4-{5-[(3,5-Bis-trifluoromethyl-benzyl)-(2-methyl-2H-tetrazol-5-yl)-amino]-7,9-dimethyl-8-trifluoromethyl-2,3,4,5-tetrahydro-benzo[b]azepin-1-ylmethyl}-benzoic acid methyl ester (0.1 mmol) in methanol (1 mL), add 4N sodium hydroxide (0.5 mL). Heat the mixture at 60° C. for 3 h. Dilute the cooled mixture with water and 1N HCl to bring the pH to 6-7 and extract with $CH_2Cl_2$ (3×15 mL). Combine the organic layers, dry over sodium sulfate, filter, and concentrate under reduced pressure to give a residue. Purify the residue by chromatography (elution with 5% methanol in EtOAc) to afford the title compound. MS (ES+): 701 (M+H).

Example 203

Synthesis of (S)-3-{5-[(3,5-Bis-trifluoromethyl-benzyl)-(2-methyl-2H-tetrazol-5-yl)-amino]-7,9-dimethyl-8-trifluoromethyl-2,3,4,5-tetrahydro-benzo[b]azepin-1-ylmethyl}-benzoic acid

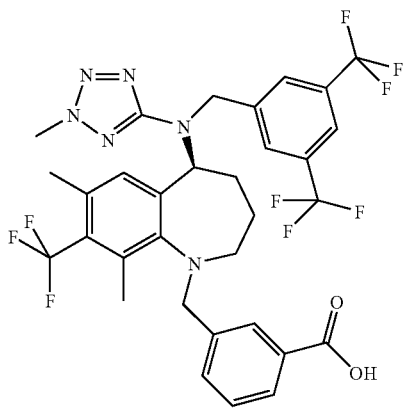

Prepare the title compound by essentially following the procedure described in the synthesis of (S)-4-{5-[(3,5-Bis-trifluoromethyl-benzyl)-(2-methyl-2H-tetrazol-5-yl)-amino]-7,9-dimethyl-8-trifluoromethyl-2,3,4,5-tetrahydro-benzo[b]azepin-1-ylmethyl}-benzoic acid (Example 202) by replacing 4-formyl methyl benzoate with 3-formyl methyl benzoate in Example 202, Step 1. MS (ES+): 701 (M+H).

Example 204

Synthesis of (S)-4-{5-[(3,5-Bis-trifluoromethyl-benzyl)-(2-methyl-2H-tetrazol-5-yl)-amino]-7,9-dimethyl-8-trifluoromethyl-2,3,4,5-tetrahydro-benzo[b]azepin-1-yl}-butyric acid

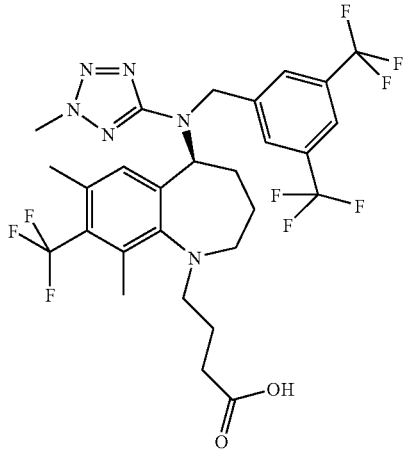

Prepare the title compound by essentially following the procedure described in the synthesis of (S)-4-{5-[(3,5-Bis-trifluoromethyl-benzyl)-(2-methyl-2H-tetrazol-5-yl)-amino]-7,9-dimethyl-8-trifluoromethyl-2,3,4,5-tetrahydro-benzo[b]azepin-1-ylmethyl}-benzoic acid (Example 202) by replacing 4-formyl methyl benzoate with succinic semialdehyde in Example 202, Step 1. MS (ES+): 653 (M+H).

Example 205

Synthesis of (S)-4-{5-[(3,5-Bis-trifluoromethyl-benzyl)-(2-methyl-2H-tetrazol-5-yl)-amino]-7,9-dimethyl-8-trifluoromethyl-2,3,4,5-tetrahydro-benzo[b]azepin-1-ylmethyl}-benzonitrile

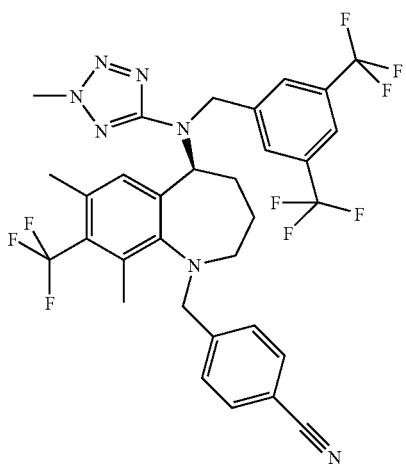

Prepare the title compound by essentially following the procedure described in the synthesis of (S)-(3-fluoro-5-trifluoromethyl-benzyl)-(7-methyl-1-pyridin-4-ylmethyl-8-trifluoromethyl-2,3,4,5-tetrahydro-1H-benzo[b]azepin-5-yl)-(2-methyl-2H-tetrazol-5-yl)-amine (Example 186, Step 2) by replacing (S)-(3-fluoro-5-trifluoromethyl-benzyl)-(2-methyl-2H-tetrazol-5-yl)-(7-methyl-8-trifluoromethyl-2,3,4,5-tetrahydro-1H-benzo[b]azepine-5-yl)-amine with (S)-(3,5-Bis-trifluoromethyl-benzyl)-(7,9-dimethyl-8-trifluoromethyl-2,3,4,5-tetrahydro-1H-benzo[b]azepin-5-yl)-(2-methyl-2H-tetrazol-5-yl)-amine (Example 148, Step 2) and pyridine-4-carboxaldehyde with 4-cyanobenzaldehyde. MS (ES+): 682 (M+H).

Example 206

Synthesis of (S)-(3,5-Bis-trifluoromethyl-benzyl)-{7,9-dimethyl-1-[4-(1H-tetrazol-5-yl)-benzyl]-8-trifluoromethyl-2,3,4,5-tetrahydro-1H-benzo[b]azepin-5-yl}-(2-methyl-2H-tetrazol-5-yl)-amine

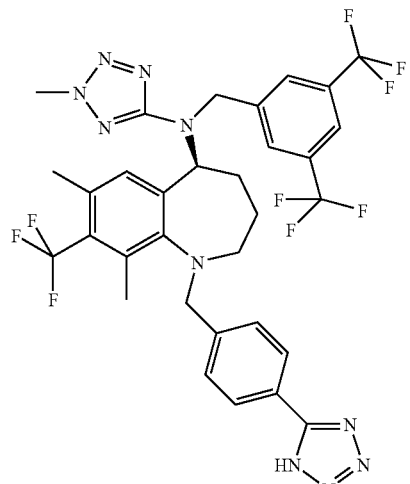

Prepare the title compound by essentially following the procedure described in the synthesis of (S)-(3,5-Bis-trifluoromethyl-benzyl)-(2-methyl-2H-tetrazol-5-yl)-{7-methyl-1-[4-(1H-tetrazol-5-yl)-benzyl]-8-trifluoromethyl-2,3,4,5-tetrahydro-1H-benzo[b]azepin-5-yl}-amine (Example 193). MS (ES+): 725 (M+H).

We claim:
1. A compound of a formula below:

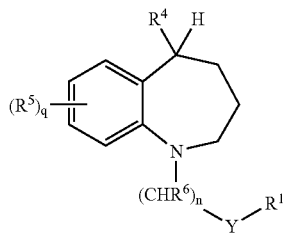

wherein
n is 0, 1, 2, or 3;
q is 1, 2, or 3;
Y is a bond or C=O;
$R^1$ is aryl, $C_1$-$C_6$ alkylaryl, $C_3$-$C_8$ cycloalkyl, $C_1$-$C_6$ alkylcycloalkyl or $C_0$-$C_6$ alkylCOOR$^{11}$, wherein each cycloalkyl and aryl is optionally substituted with $C_0$-$C_6$ alkylCOOR$^{11}$;
$R^4$ is a group represented by the formula —NR$^{4a}$R$^{4b}$ wherein;
$R^{4a}$ is a tetrazolyl optionally substituted with $C_1$-$C_6$ alkyl; and
$R^{4b}$ is benzyl optionally substituted with 1-3 groups independently selected from $C_1$-$C_6$ alkyl or $C_1$-$C_6$ haloalkyl;
$R^5$ is individually selected from hydrogen, $C_1$-$C_6$ alkyl, or $C_1$-$C_6$ haloalkyl;

R⁶ is hydrogen;
R¹¹ is hydrogen or $C_1$-$C_6$ alkyl;
or a pharmaceutically acceptable salt thereof.

2. The compound of claim 1 wherein q is 2 and each R⁵ is methyl.

3. The compound of claim 1 wherein:
q is 2 or 3;
Y is a bond;
R¹ is $C_3$-$C_8$ cycloalkyl, optionally substituted with $C_0$-$C_6$ alkylCOOR¹¹;
R⁴ᵃ is 2-methyl-2H-tetrazol-5-yl;
R₄ᵦ is 3,5-bis-trifluoromethyl-benzyl;
R⁵ each individually is methyl or trifluoromethyl;
or a pharmaceutically acceptable salt thereof.

4. The compound of claim 3 wherein:
R¹ is cyclohexyl optionally substituted with $C_0$-$C_6$ alkyl-COOR¹¹;
or a pharmaceutically acceptable salt thereof.

5. A compound according to claim 1, or a pharmaceutically acceptable salt thereof, wherein n is 0 or 1 and q is 2 or 3.

6. A compound according to claim 1, or a pharmaceutically acceptable salt thereof, wherein n is 0, Y is C(O), and R¹ is $C_0$-$C_6$ alkylcycloalkyl or $C_0$-$C_6$ alkylaryl wherein each cycloalkyl and aryl is optionally substituted with $C_0$-$C_3$ alkyl COOH or C(O)O$C_1$-$C_3$ alkyl.

7. A compound according to claim 1, or a pharmaceutically acceptable salt thereof, wherein n is 0, Y is a bond, and R¹ is $C_0$-$C_6$ alkylcycloalkyl, $C_0$-$C_6$ alkylaryl, or $C_1$-$C_6$ alkylCO₂R¹¹ wherein each cycloalkyl, and aryl is optionally substituted with $C_0$-$C_3$ alkylCOOH.

8. A compound according to claim 1 selected from:
(S)-(3,5-Bistrifluoromethylbenzyl)-(1-cyclopentylmethyl-7-methyl-8-trifluoromethyl-2,3,4,5-tetrahydro-1H-benzo[b]azepin-5-yl)-(2-methyl-2H-tetrazol-5-yl) amine,
(S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid isopropyl ester,
(S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid tert-butyl ester,
(S)-5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepine-1-carboxylic acid 1-ethyl-2-methyl-propyl ester,
(4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-cyclohexyl)-acetic acid,
(S)-5-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-3,3-dimethyl-pentanoic acid,
(+/−)-isopropyl 5-[(3,5-bistrifluoromethyl-benzyl)-(2-methyl-2H-tetrazol-5-yl)-amino]-9-methyl-8-trifluormethyl-2,3,4,5-tetrahydrobenzo[b]azepine-1-carboxylate,
(S)-isopropyl 5-[(3,5-bistrifluoromethyl-benzyl)-(2-methyl-2H-tetrazol-5-yl)-amino]-8,9-dimethyl-2,3,4,5-tetrahydrobenzo[b]azepine-1-carboxylate,
(S)-4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-benzoic acid methyl ester,
(S)-4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-benzoic acid,
(S)-3-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-benzoic acid methyl ester,
(S)-3-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-benzoic acid,
(S)-4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-benzoic acid,
(S)-(3,5-Bis-trifluoromethyl-benzyl)-(1-cyclopropylmethyl-7-methyl-8-trifluoromethyl-2,3,4,5-tetrahydro-1H-benzo[b]azepin-5-yl)-(2-methyl-2H-tetrazol-5-yl)-amine,
(S)-4-{5-[(3,5-Bis-trifluoromethyl-benzyl)-(2-methyl-2H-tetrazol-5-yl)-amino]-7-ethyl-8-trifluoromethyl-2,3,4,5-tetrahydro-benzo[b]azepin-1-ylmethyl}-benzoic acid,
(S)-5-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-2-methyl-propionic acid ethyl ester,
(S)-(1-Benzyl-7-methyl-8-trifluoromethyl-2,3,4,5-tetrahydro-1H-benzo[b]azepin-5-yl)-(3,5-bis-trifluoromethyl-benzyl)-(2-methyl-2H-tetrazol-5-yl)-amine,
(S)-(4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-phenyl)-acetic acid,
(S)-4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-butyric acid,
(S)-3-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-2-methyl-propionic acid,
(S)-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-acetic acid,
(S)-Acetic acid 2-{5-[(3,5-bis-trifluoromethyl-benzyl)-(2-methyl-2H-tetrazol-5-yl)-amino]-7-methyl-8-trifluoromethyl-2,3,4,5-tetrahydro-benzo[b]azepin-1-yl}-ethyl ester,
and pharmaceutically acceptable salts, thereof.

9. A method of treating dyslipidemia in a mammal comprising administering a therapeutically effective composition comprising a compound according to claim 1, or a pharmaceutically acceptable salt thereof, to said mammal.

10. A method of treating atherosclerosis in a mammal comprising administering a therapeutically effective composition comprising a compound according to claim 1, or a pharmaceutically acceptable salt thereof, to said mammal.

11. A pharmaceutical composition comprising a compound according to claim 1, or a pharmaceutically acceptable salt thereof, and at least one of: a carrier, diluent, and excipient.

12. A method of raising plasma HDL-cholesterol in a mammal comprising administering a therapeutically effective dose of a compound according to claim 1, or a pharmaceutically acceptable salt thereof, to said mammal.

* * * * *